(12) United States Patent
Ogawa et al.

(10) Patent No.: US 6,913,797 B1
(45) Date of Patent: Jul. 5, 2005

(54) DECAHYDRONAPHTHALENE DERIVATIVE

(75) Inventors: Shinji Ogawa, Ohmiya (JP); Hiroyuki Ohnishi, Urawa (JP); Yutaka Nagashima, Ageo (JP); Sadao Takehara, Sakura (JP); Makoto Negishi, Tokyo (JP); Haruyoshi Takatsu, Tokyo (JP); Gerwald Grahe, Berlin (DE); Rainer Bruno Frings, Berlin (DE); Christine Fugger, Berlin (DE); Cornelia Pithart, Berlin (DE)

(73) Assignee: Dainippon Ink and Chemicals, Inc., Tokyo (JP)

(*) Notice: Subject to any disclaimer, the term of this patent is extended or adjusted under 35 U.S.C. 154(b) by 0 days.

(21) Appl. No.: 09/763,531

(22) PCT Filed: Aug. 23, 1999

(86) PCT No.: PCT/JP99/04511

§ 371 (c)(1),
(2), (4) Date: Feb. 23, 2001

(87) PCT Pub. No.: WO00/10952

PCT Pub. Date: Mar. 2, 2000

(30) Foreign Application Priority Data

Aug. 24, 1998 (JP) ............................................. 10-237187
Feb. 5, 1999 (JP) ............................................. 11-029015

(51) Int. Cl.$^7$ ..................... C07C 43/225; C07D 317/72
(52) U.S. Cl. ..................................................... 428/1.1
(58) Field of Search .................... 428/1.1; 252/299.61, 252/299.62, 299.63; 549/333; 568/374; 570/183, 187

(56) References Cited

U.S. PATENT DOCUMENTS

| 4,432,885 A | 2/1984 | Petrzilka et al. |
| 4,434,073 A | 2/1984 | Sucrow et al. |
| 5,238,600 A | 8/1993 | Kelly |
| 5,907,005 A | 5/1999 | Shimizu |

FOREIGN PATENT DOCUMENTS

| DE | 31 50312 A1 | 7/1982 |
| DE | 31 48448 A1 | 7/1983 |
| EP | 0 047 817 A2 | 3/1982 |
| EP | 0 344 557 A2 | 12/1989 |
| GB | 2-112 387 A | 7/1983 |
| JP | 57-130929 | 8/1982 |
| JP | 59-141527 | 8/1984 |
| JP | 64-74270 | 3/1989 |
| JP | 2-25440 | 1/1990 |
| JP | 7-310048 | 11/1995 |

OTHER PUBLICATIONS

D. R. Dodds et al.; Journal of The Chemical Society, No. 18, Sep. 15, 1982. See PCT search report.
J. B. Jones et al.; Canada Journal of Chemistry, vol. 65, No. 10, pp. 2397–2404, 1987. See PCT search report.
Principles of Organic Synthesis, 3$^{rd}$ Edition, 640–643, 1993.
Wolfgang Sucrow et al. "Flüssig–kristalline 2–Cyclohexyl-decaline"; Chemische Berichte, Verlag Chemie CMBH; vol. 118, No. 8, 1985, pp. 3350–3356.

*Primary Examiner*—Shean C. Wu
(74) *Attorney, Agent, or Firm*—Armstrong, Kratz, Quintos, Hanson, & Brooks, LLP

(57) ABSTRACT

The present invention discloses a decahydronaphthalene derivative represented by general formula (I):

$$R\text{-}\left(\!\left\langle A\right\rangle\text{-}L\right)_m\text{-}\left\langle\text{decalin}\right\rangle\text{-}\left(M\text{-}\left\langle B\right\rangle\right)_n\text{-}Z \quad (I)$$

a liquid crystal composition in which it is contained, and a liquid crystal device in which it is used. The novel decahydronaphthalene derivative of the present invention can be produced industrially extremely easily as shown in the examples, and by adding a small amount to a base liquid crystal, it is possible to have effects that expand the nematic phase temperature range, thereby improving its various characteristics as a nematic liquid crystal. Moreover, the novel decahydronaphthalene derivative of the present invention also has superior co-solubility with base liquid crystals generally used at present. Thus, it is suitable for various types of liquid crystal devices requiring a wide operating temperature range, and is extremely useful as a liquid crystal material.

23 Claims, No Drawings

DECAHYDRONAPHTHALENE DERIVATIVE

TECHNICAL FIELD

The present invention relates to a decahydronaphthalene derivative, which is a novel liquid crystal compound, and a liquid crystal composition containing said derivative. This derivative is useful as a liquid crystal material for electrooptical liquid crystal display, and has a wide temperature range in particular.

BACKGROUND ART

Liquid crystal display elements have come to be used in not only clocks and calculators, but also in various types of measuring instruments, automobile instrument panels, word processors, Personal Digital Assistants, printers, computers and televisions. Typical examples of liquid crystal display methods include TN (twisted nematic) types, STN (super twisted nematic) types, DS (dynamic scattering) types, GH (guest host) types and FLC (ferroelectric liquid crystal) types. In addition, multiplex driving instead of the conventional static driving has become the most common type of driving method. Moreover, simple matrix types, and more recently, active matrix types, have come into practical use.

Liquid crystal materials are required to have various characteristics to accommodate these display and driving methods. Although a wide temperature range is extremely important in nearly all cases, this includes that in which the nematic phase upper limit temperature ($T_{N-I}$) is sufficiently high, and the melting point ($T_{C-N}$) or the smectic-nematic transition temperature ($T_{S-N}$) is sufficiently low.

In addition, co-solubility with other liquid crystal compounds and versatile liquid crystal compositions is also important. If this co-solubility was defective, it became necessary to mix extremely many kinds of liquid crystal compounds in order to avoid the risk of precipitation and phase separation, making compound preparation extremely bothersome and making increased costs unavoidable.

In addition, a sufficiently low driving voltage is also an important characteristic in many cases, and it is necessary for the threshold voltage ($V_{th}$) to be low in order to accomplish this.

In addition, rapid response is also an equally important characteristic, and the viscosity of the liquid crystal is required to be as low as possible in order to accomplish this.

In addition, birefringence (Δn) is also an important characteristic. Although various values are required according to the display method, a low value is frequently required in the case of liquid crystal devices having a large cell thickness for easy manufacturing.

Although an extremely large number of liquid crystal compounds have been synthesized in the past in order to satisfy these requirements, not all of the problems were able to be solved. Thus, there is a need for a liquid crystal compound having superior characteristics with respect to each of the above requirements.

In general, liquid crystal compounds are formed from a central skeleton (core) portion and side groups (side chains and polar groups). There are numerous known examples of the ring structure that composes the core portion, such as a 1,4-phenylene group (which may be substituted with fluorine) and trans-1,4-cyclohexylene group, as well as heterocyclic aromatics such as a pyridine-2,5-diyl group and pyrimidne-2,5-diyl group, and saturated heterocyclic rings such as a dioxane-trans-1,4-diyl group and piperidine-1,4-diyl group. However, this ring structure is practically limited to a 1,4-phenylene group (which may be substituted with fluorine), trans-1,4-cyclohexylene group and a small number of heterocyclic aromatics. However, liquid crystal compounds composed of these ring structures alone are currently unable to adequately accommodate the characteristics required of increasingly sophisticated liquid crystal compounds.

Since compounds containing a trans-2,6-trans-decahydronaphthalene group are saturated rings that do not contain hetero atoms such as oxygen atoms or nitrogen atoms, in addition to being expected to demonstrate superior stability, they are also expected to improve liquid crystal properties. However, there have been few examples of trans-2,6-trans-decahydronaphthalene derivatives reported thus far (W. Sucrow and H. Wolter, Chimia, 36, 460 (1982); Mol. Cryst. Liq. Cryst., 95, 63 (1983)), and hardly anything is known regarding their characteristics.

DISCLOSURE OF THE INVENTION

The problem to be solved by the present invention is to provide a novel liquid crystal composition in the form of a decahydronaphthalene derivative, and to provide a liquid crystal composition suitable for STN or TFT driving that uses any of these derivatives, has a wide nematic phase temperature range, has a low birefringence, and is able to be driven at a low voltage and respond rapidly.

In order to solve the above problems, the present invention provides a novel liquid crystal compound in the form of a decahydronaphthalene derivative represented by general formula (I).

Invention 1: A compound represented by general formula (I):

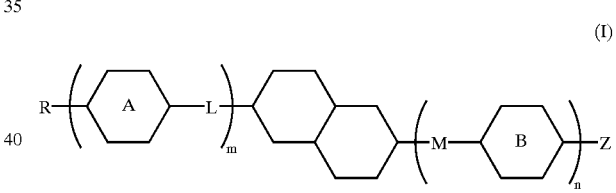

(wherein, R and Z may be substituted with a halogen and represent alkyl groups or alkoxy groups having 1–16 carbon atoms, alkenyl groups having 2–16 carbon atoms, alkenyloxy groups having 3–16 carbon atoms, alkyl groups having 1–12 carbon atoms substituted with an alkoxy group having 1–10 carbon atoms, hydrogen atoms, fluorine atoms, chlorine atoms, trifluoromethoxy groups, difluoromethoxy groups, trifluoromethyl groups, 2,2,2-trifluoroethoxy groups, cyano groups, cyanato groups, hydroxy groups or carboxy groups, m and n may be the same or different and respectively and independently represent an integer of 0–2, m+n 3, L and M may be the same or different and respectively and independently represent —CH₂CH₂—, —CH(CH₃)CH₂—, —CH₂CH(CH₃)—, —CH₂O—, —OCH₂—, —CF₂O—, —OCF₂—, —COO—, —OCO—, —CH=CH—, —CF=CF—, —C C—, —O(CH₂)₃—, —(CH₂)₃O—, —(CH₂)₄— or a single bond, rings A and B when present may be the same or different and respectively and independently represent a trans-1,4-cyclohexylene group in which one CH₂ group or more than one non-adjacent CH₂ groups in the group may be replaced by —O— or —S—, a 1,4-phenylene group in which one CH₂ group or more than one non-adjacent CH₂ groups in the group may be replaced by —N=, a 1,4-cyclohexenylene group, 1,4- bicyclo(2,2,2)octylene group, piperidine-1,4-diyl group, naphthalene-2,6-diyl group, trans-decahydronaphthalene-trans-2,6-diyl group or 1,2,3,4-tetrahydronaphthalene-2,6-diyl group, and although these may be substituted with a cyano group or halogen, in the case m or n represents 2, at least one of the two L or M present represents a single bond; provided that the following cases are excluded:

1. case in which m and n represent 0, R represents a non-substituted alkyl group, and Z represents a non-substituted alkyl group or cyano group;
2. case in which either m or n represents 1, the other of m or n represents 0, ring A or ring B when present represents a 1,4-cyclohexylene group, L or M when present represents a single bond, R or Z bonded to a decahydronaphthalene ring represents a non-substituted alkyl group, and R or Z bonded to a 1,4-cyclohexylene group represents a non-substituted alkyl group, alkoxy group or alkenyloxy group;
3. case in which either m or n represents 1, the other m or n represents 0, ring A or ring B when present represents a 1,4-cyclohexylene group, L when present represents —OCO— or M when present represents —COO—, R or Z bonded to a decahydronaphthalene ring represents a non-substituted alkyl group, and R or Z bonded to a 1,4-cyclohexylene group represents a non-substituted alkyl group or cyano group;
4. case in which either m or n represents 1, the other m or n represents 0, ring A or ring B when present represents a non-substituted 1,4-phenylene group, L when present represents —OCO— or M when present represents —COO—, L or M when present represents a single bond, R or Z bonded to a decahydronaphthalene ring represents an alkyl group, and R or Z bonded to a 1,4-phenylene group represents a non-substituted alkyl group, alkoxy group or cyano group;
5. case in which either m or n represents 1, the other m or n represents 0, ring A or ring B when present represents a non-substituted 1,4-phenylene group, L or M when present represents a single bond, R or Z bonded to a decahydronaphthalene ring represents a non-substituted alkoxy group, and R or Z bonded to a 1,4-phenylene group represents a non-substituted alkyl group;
6. case in which either m or n represents 1, the other m or n represents 0, ring A or ring B when present represents a trans-decahydronaphthalene-trans-2,6-diyl group, L when present represents —OCO—, M when present represents —COO— or L or M when present represent a single bond, and R and Z represent non-substituted alkoxy groups;
7. case in which either m or n represents 1, the other m or n represents 0, ring A or ring B when present represents a non-substituted naphthalene-2,6-diyl group, L when present represents —OCO— or M when present represents —COO—, R or Z bonded to a decahydronaphthalene ring represents a non-substituted alkyl group, and R or Z bonded to a naphthalene-2,6-diyl group represents a non-substituted alkyl group, bromine atom or cyano group, or the case in which R or Z bonded to a decahydronaphthalene ring represents a non-substituted alkoxy group, and R or Z bonded to a naphthalene-2,6-diyl group represents a non-substituted alkyl group or cyano group;
8. case in which n represents 2, m represents 0, R represents a non-substituted alkyl group, M when present adjacent to a decahydronaphthalene ring represents —COO—, at least one of rings B present represents a non-substituted 1,4-phenylene group, and Z represents a non-substituted alkyl group or bromine atom, or the case in which at least one of rings B present represents a pyrimidine-2,5-diyl group, and Z represents a non-substituted alkyl group, alkoxy group or cyano group;
9. case in which m and n represent 1, ring A represents a trans-decahydronaphthalene-trans-2,6-diyl group or a 1,4-cyclohexylene group, ring B represents a non-substituted 1,4-phenylene group or 1,4-cyclohexylene group, L represents a single bond, M represents —COO—, —OCO—, —CH$_2$O— or —OCH$_2$—, and R and Z represent non-substituted alkyl groups; and, applying similarly to compounds equivalent to the above using combinations of the abbreviations).

Invention 2: A compound described in Invention 1 wherein, ring A and ring B when present respectively and independently represent a 1,4-phenylene group, naphthalene-2,6-diyl group, 1,2,3,4-tetrahydronaphthalene-2,6-diyl group, trans-1,4-cyclohexylene group or decahydronaphthalene-2,6-diyl group that may be substituted with fluorine atom(s).

Invention 3: A compound described in Invention 1 wherein, ring A or ring B when present respectively and independently represent a 1,4-phenylene group or trans-1,4-cyclohexylene group that may be substituted with fluorine atom(s).

Invention 4: A compound described in Invention 1 wherein, L and M when present represent —CH$_2$CH$_2$—, —CH$_2$O—, —OCH$_2$—, —CF$_2$O—, —OCF$_2$—, —COO—, —OCO—, —CF=CF— or a single bond.

Invention 5: A compound described in Invention 1 wherein, L or M represents a single bond.

Invention 6: A compound described in Invention 1 wherein, L and M represent single bonds.

Invention 7: A compound described in Invention 1 wherein, 1≦m+n≦2.

Invention 8: A compound described in Invention 1 wherein, R represents an alkyl group, alkoxy group, alkenyl group or alkenyloxy group having 1–12 carbon atoms.

Invention 9: A compound described in Invention 1 wherein Z represents a halogen atom or an alkyl group, alkoxy group, alkenyl group, alkenyloxy group or cyano group having 1–12 carbon atoms.

Invention 10: A compound described in Invention 1 wherein, R represents an alkyl group or alkenyl group having 1–12 carbon atoms, m represents 1, n represents 1, ring A represents a trans-1,4-cyclohexylene group, ring B represents a 3-fluoro-1,4-phenylene group or 3,5-difluoro-1,4-phenylene group, L and M represent single bonds, and Z represents a fluorine atom, chlorine atom, trifluoromethoxy group, difluoromethoxy group, trifluoromethyl group, 2,2,2-trifluoroethoxy group or cyano group.

Invention 11: A compound described in Invention 1 wherein, R represents an alkyl group or alkenyl group having 1–12 carbon atoms, m represents 0, n represents 1, ring B represents a 3-fluoro-1,4-phenylene group or 3,5-difluoro-1,4-phenylene group, M represents a single bond and Z represents a fluorine atom, chlorine atom, trifluoromethoxy group, difluoromethoxy group, trifluoromethyl group, 2,2,2-trifluoroethoxy group or cyano group.

Invention 12: A compound described in Invention 1 wherein, R and Z represent alkyl groups or alkenyl groups having 1–12 carbon atoms, m and n represent 1, rings A and B represent 1,4-phenylene groups or trans-1,4-cyclohexylene groups, and L and M represent single bonds.

Invention 13: A compound described in Invention 1 wherein, R and Z represent alkyl groups or alkenyl groups having 1–12 carbon atoms, at least one of R or Z represents an alkenyl group, m represents 1, n represents 0, rings A and B represent 1,4-phenylene groups or trans-1,4-cyclohexylene groups, and L represents a single bond.

Invention 14: A compound represented by general formula (II):

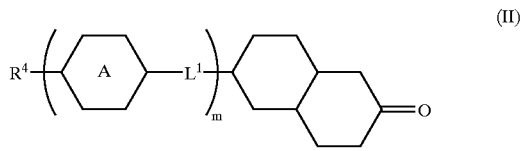

(II)

(wherein, $R^4$ represents an alkyl group, alkoxy group, alkenyl group, alkenyloxy group or alkoxyalkyl group, $L^1$ represents —CH$_2$CH$_2$—, —CH(CH$_3$)CH$_2$—, —CH$_2$CH(CH$_3$)—, —CH$_2$O—, —OCH$_2$—, —CF$_2$O—, —OCF$_2$—, —COO—, —OCO—, —CH=CH—, —CF=CF—, —C≡C—, —O(CH$_2$)$_3$—, —(CH$_2$)$_3$O—, —(CH$_2$)$_4$— or a single bond, $R^4$ represents an alkenyl group, alkenyloxy group or alkoxyalkyl group when $L^1$ represents a single bond, ring A and m are the same as defined in general formula (I), and the decahydronaphthalene ring has a trans form).

Invention 15: A production method of general formula (II) described in Invention 14 including: reducing a compound represented by general formula (II-A):

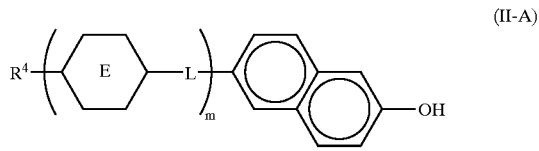

(II-A)

(wherein, $R^4$ is the same as previously defined in general formula (II), ring E represents a 1,4-phenylene group or trans-1,4-cyclohexylene group, L and m are the same as previously defined in general formula (I), and the decahydronaphthalene ring has a trans form), and oxidizing the hydroxyl group as necessary.

Invention 16: A compound represented by general formula (V-1) or general formula (V-2):

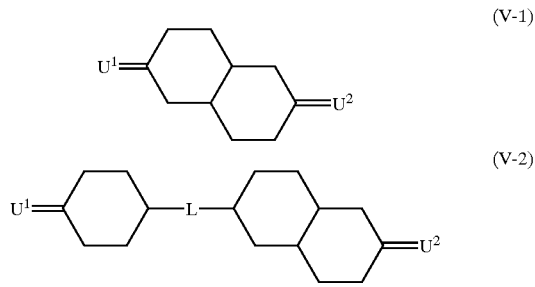

(V-1)

(V-2)

(wherein, $U^1$ and $U^2$ respectively and independently represent an oxygen atom or the following structure:

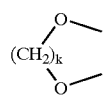

(wherein, k represents an integer from 1 to 7), L is the same as previously defined in general formula (I), and the decahydronaphthalene ring has a trans form).

Invention 17: A production method of general formula (V-1) or general formula (V-2) described in Invention 16 including: converting a compound represented by general formula (V-1A) or general formula (V-2A):

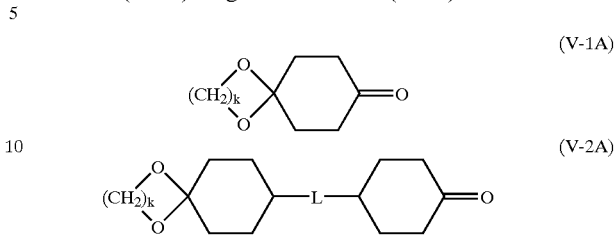

(V-1A)

(V-2A)

(wherein, k is the same as previously defined in general formula (V-1) or general formula (V-2), and L is the same as previously defined in general formula (I)) into an enamine using a secondary amine, and reacting it with methyl vinyl ketone to obtain a compound represented by general formula (V-1B) or general formula (V-2B)

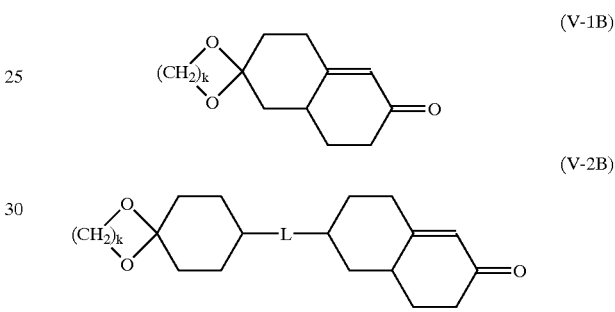

(V-1B)

(V-2B)

(wherein, k is the same as previously defined in general formula (V-1) or general formula (V-2), and L is the same as previously defined in general formula (I)) followed by reductive hydrogenation.

Invention 18: A production method of general formula (V-1) described in Invention 16 including: reducing a compound represented by formula (V-1C):

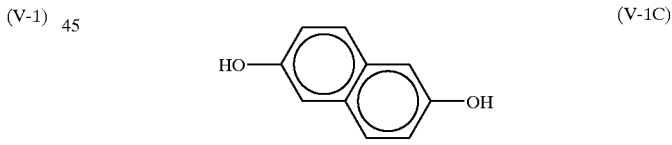

(V-1C)

oxidizing the hydroxyl groups as necessary, and protecting the carbonyl groups as necessary.

Invention 19: A production method of general formula (V-2) described in Invention 16 including: reducing a compound represented by general formula (V-2C):

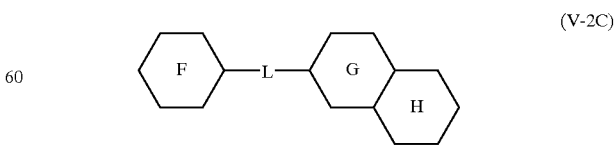

(V-2C)

(wherein, although ring G represents a cyclohexane ring or benzene ring, a single bond(s) of the cyclohexane ring may be replaced by double bond(s), and although rings F and H respectively and independently represent the following structures:

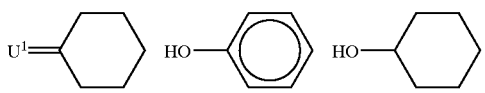

wherein, $U^1$ is the same as previously defined in general formula (V-1) or general formula (V-2)), a single bond(s) of the cyclohexane ring may be replaced by double bond(s)), oxidizing the hydroxyl group as necessary, and further protecting the carbonyl group as necessary.

Invention 20: A production method of general formula (V-1a):

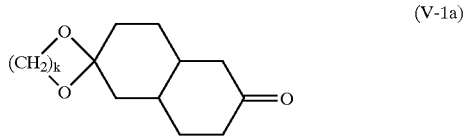

(V-1a)

(wherein, k is the same as previously defined in general formula (V-1) or general formula (V-2)), which is one of the structures of general formula (V-1) described in Invention 16, including monoacetalation of a compound represented by general formula (V-1D):

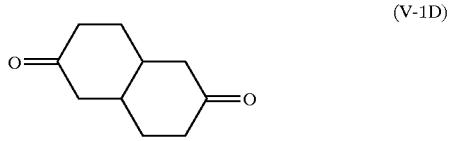

(V-1D)

Invention 21: A liquid crystal composition containing a compound described in any of Inventions 1 through 13.

Invention 22: A liquid crystal device having for its constituent feature the liquid crystal composition described in Invention 21.

Invention 23: An active matrix drive, liquid crystal device that uses the liquid crystal composition described in Invention 21.

Invention 24: A super twisted nematic liquid crystal device that uses the liquid crystal composition described in Invention 21.

BEST MODE FOR CARRYING OUT THE INVENTION

The following provides a detailed explanation of the present invention. A compound of general formula (I) provided in the present invention is preferably of the form described below.

In general formula (I), although R and Z represent alkyl groups or alkoxy groups having 1–16 carbon atoms, alkenyl groups having 2–16 carbon atoms, alkenyloxy groups having 3–16 carbon atoms, alkyl groups having 1–12 carbon atoms substituted with alkoxy group(s) having 1–10 carbon atoms, hydrogen atoms, fluorine atoms, chlorine atoms, trifluoromethoxy groups, difluoromethoxy groups, trifluoromethyl groups, 2,2,2-trifluoroethoxy groups, cyano groups, cyanato groups, hydroxyl groups or carboxyl groups, which may be substituted with halogen(s), a straight chain alkyl group having 1–12 carbon atoms or a straight chain alkenyl group having 2–12 carbon atoms is preferable, a straight chain alkyl group having 1–7 carbon atoms or a straight chain alkenyl group having 2–7 carbon atoms is more preferable, and the following structures are particularly preferable for R in the case of a straight chain alkenyl group:

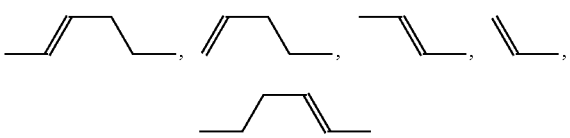

(wherein, the right side is linked to a ring); a structure similar to that in R is preferable for Z in the case the dielectric anisotropy of the compound is near 0 or negative, and a fluorine atom, chlorine atom, trifluoromethoxy group, difluoromethoxy group, trifluoromethyl group, 2,2,2-trifluoroethoxy group or cyano group is preferable, a fluorine atom, trifluoromethoxy group or cyano group is more preferable, and a fluorine atom or cyano group is particularly preferable for Z in the case the dielectric anisotropy of the compound is positive. Although m and n respectively and independently represent an integer from 0 to 2 and satisfy $m+n \leq 3$, they are preferably respectively and independently 0 or 1, and more preferably satisfy $1 \leq m+n \leq 2$. Ring A and ring B when present may be the same or different, represent a trans-1,4-cyclohexylene group wherein one $CH_2$ group or more than one adjacent $CH_2$ groups in the group may be replaced by —O— or —S—, or a 1,4-phenylene group, 1,4-cyclohexenylene group, 1,4-bicylo(2,2,2)octylene group, piperidine-1,4-diyl group, naphthalene-2,6-diyl group, trans-decahydronaphthalene-trans-2,6-diyl group or 1,2,3,4-tetrahydronaphthalene-2,6-diyl group wherein one CH group or more than one adjacent CH groups in the group may be replaced by —N═, and although these may be substituted with a cyano group or halogen, a 1,4-phenylene group or trans-1,4-cyclohexylene group that may be substituted with halogen is preferable, a trans-1,4-cyclohexylene group is more preferable for ring A, and a 1,4-phenylene group, 3-fluoro-1,4-phenylene group, 3,5-difluoro-1,4-phenylene group or trans-1,4-cyclohexylene group is more preferable for ring B. Although L and M when present may be the same or different, and represent —$CH_2CH_2$—, —CH($CH_3$)$CH_2$—, —$CH_2CH(CH_3)$—, —$CH_2O$—, —$OCH_2$—, —$CF_2O$—, —$OCF_2$—, —COO—, —OCO—, —CH═CH—, —CF═CF—, —C≡C—, —O($CH_2$)$_3$—, —($CH_2$)$_3O$—, —($CH_2$)$_4$— or a single bond, —$CH_2CH_2$— or a single bond is preferable for L while a single bond is particularly preferable, and —COO—, —OCO—, —$CH_2CH_2$—, —C≡C— or a single bond is preferable for M, while a single bond is particularly preferable.

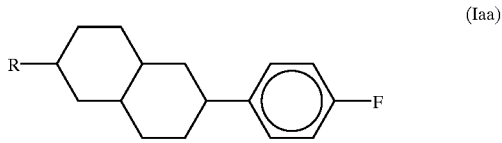

(Iaa)

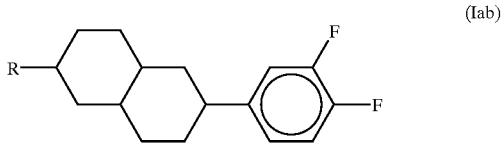

(Iab)

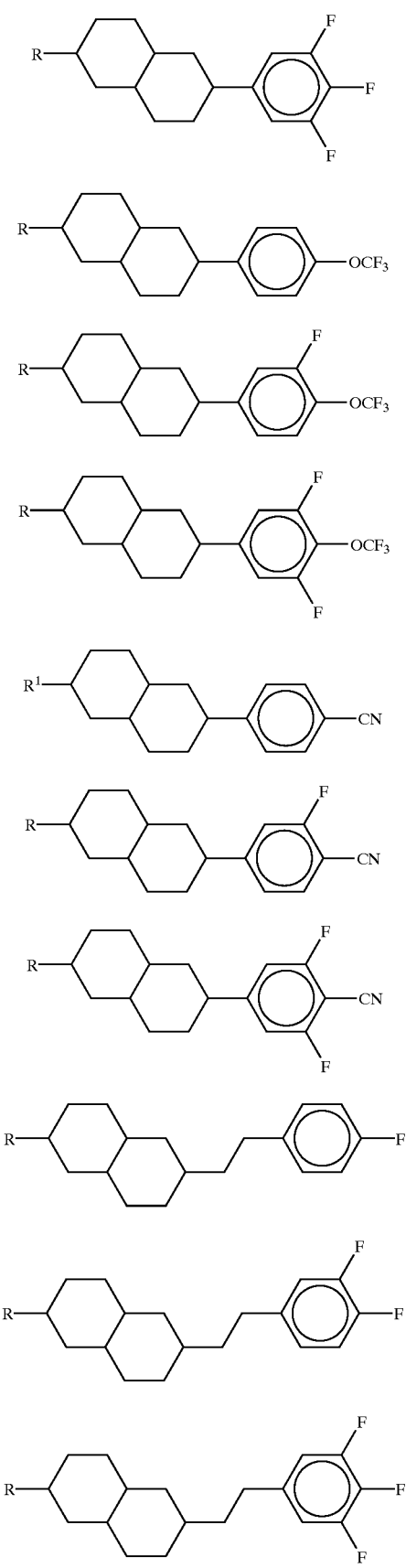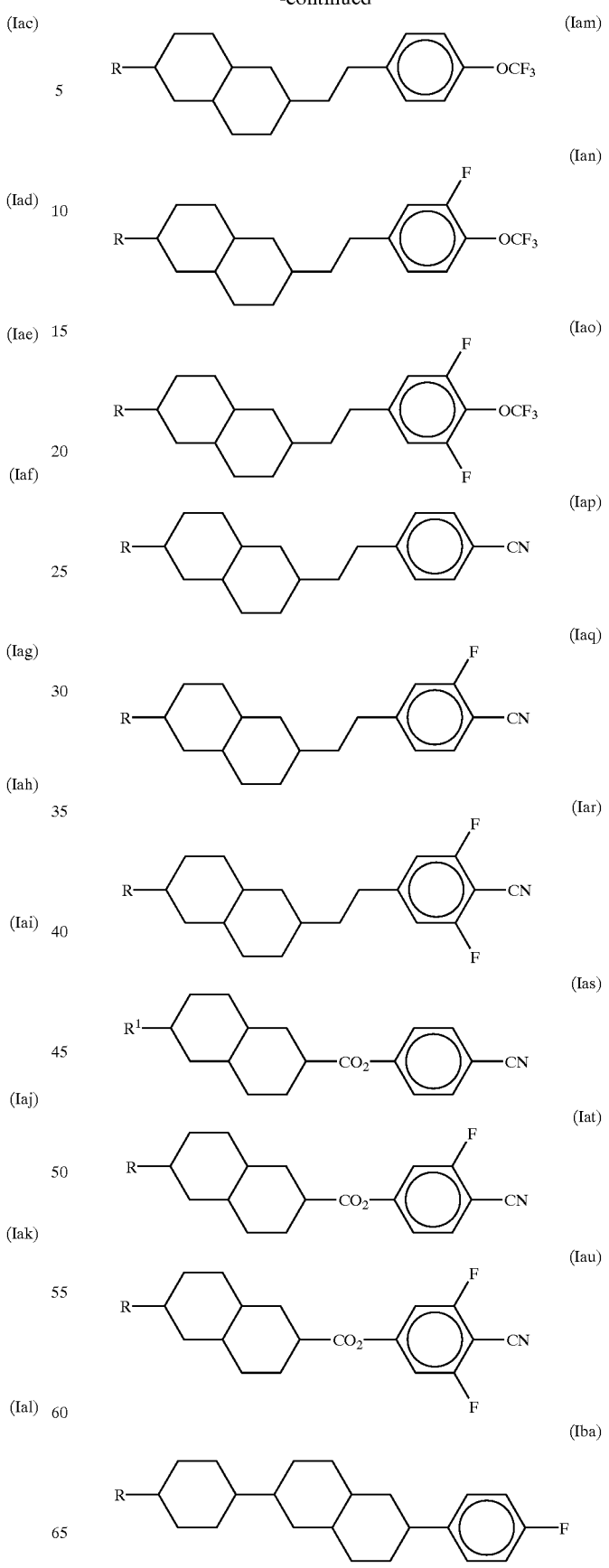

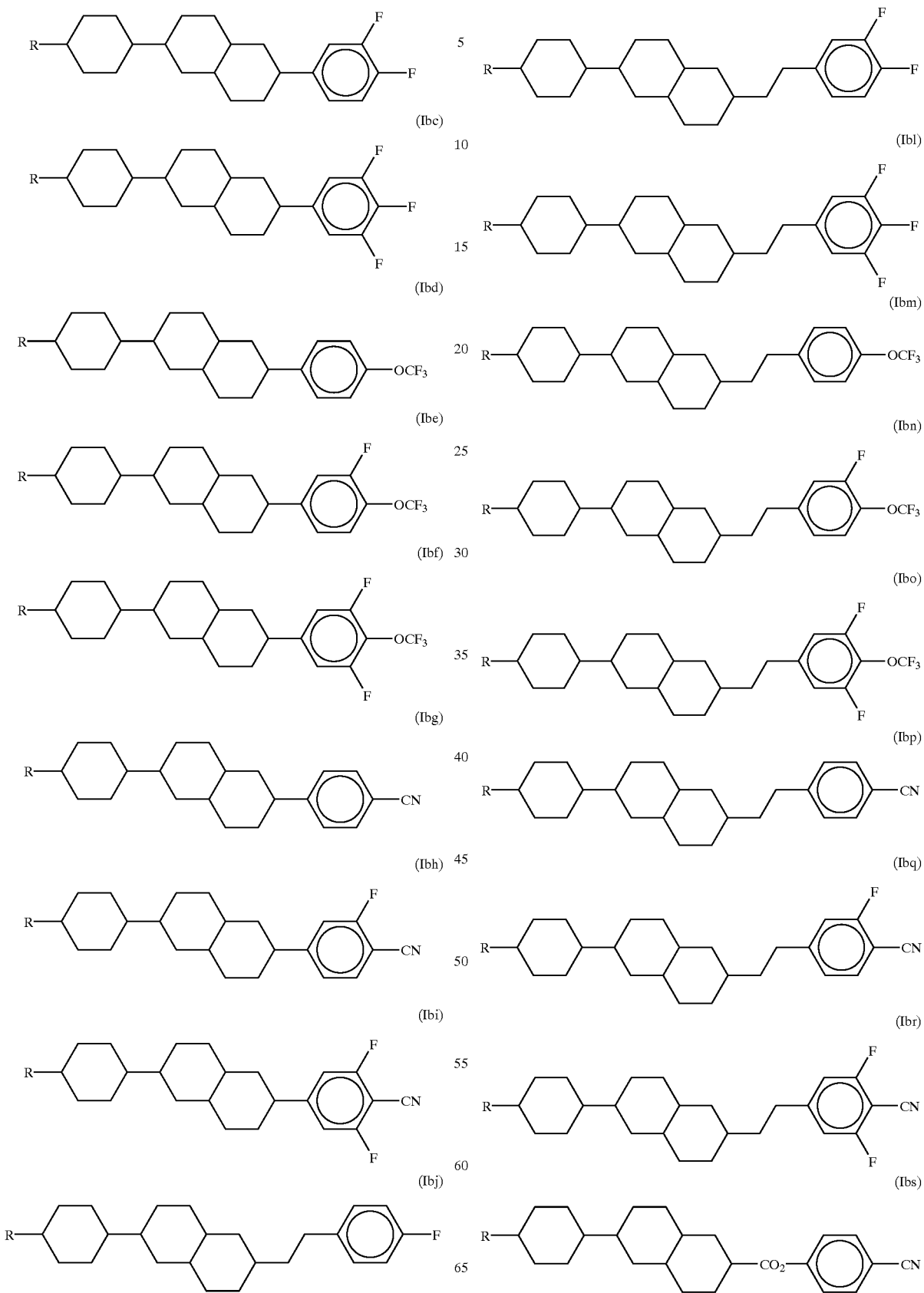

(Ibt)
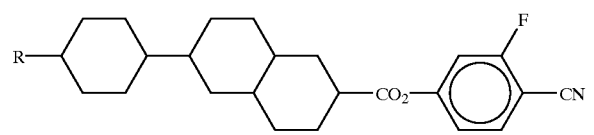
(Ibu)
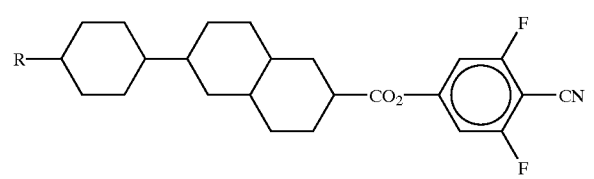
(Ica)
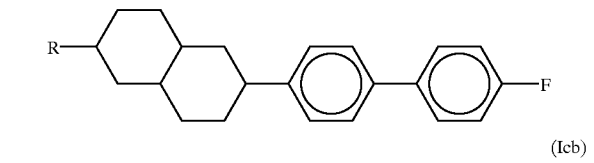
(Icb)
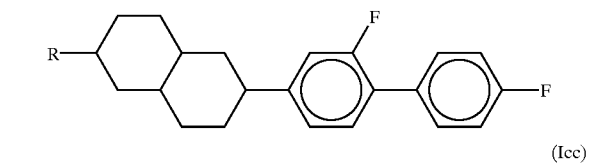
(Icc)
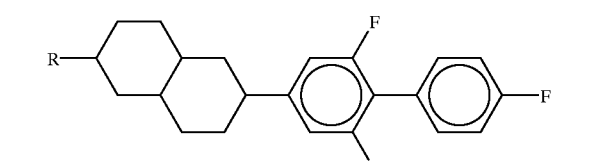
(Icd)
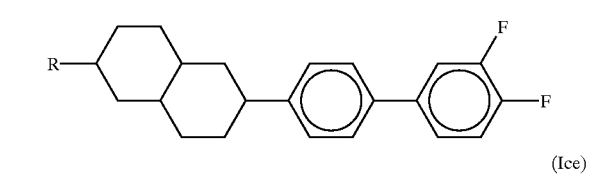
(Ice)
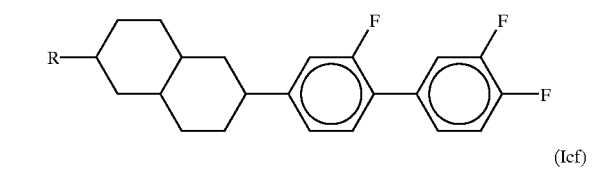
(Icf)
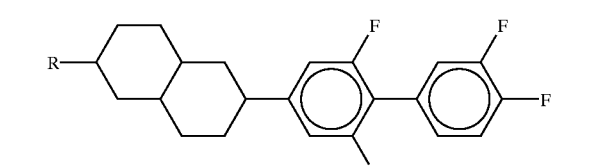
(Icg)
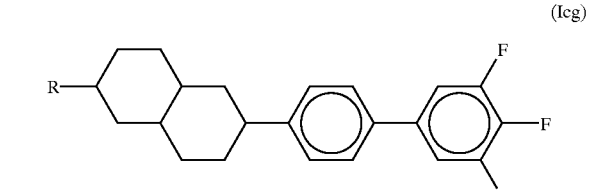
(Ich)
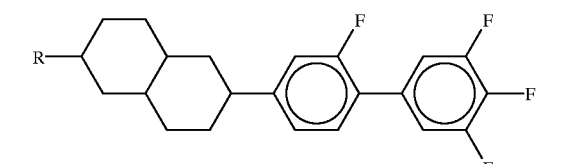
(Ici)
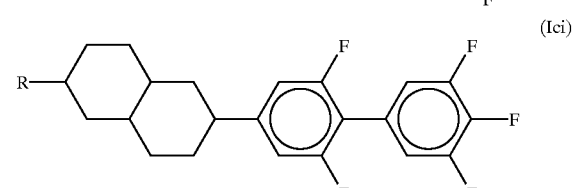
(Icj)
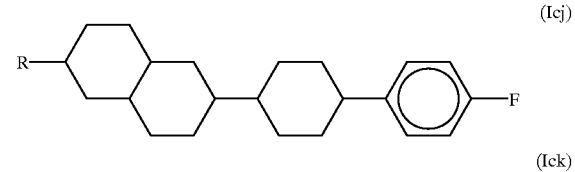
(Ick)
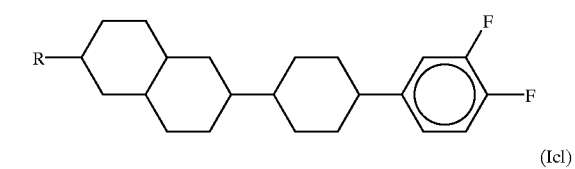
(Icl)
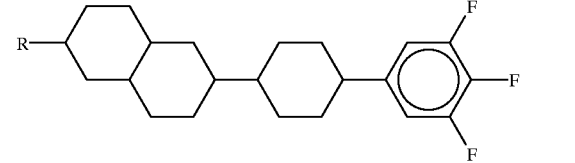
(Icm)
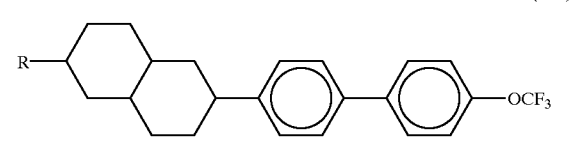
(Icn)
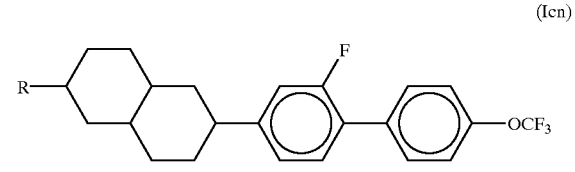
(Ico)
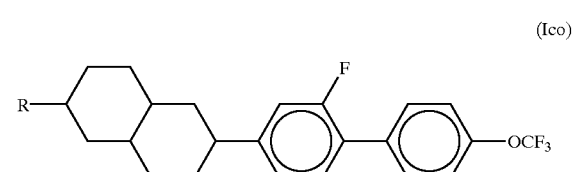
(Icp)
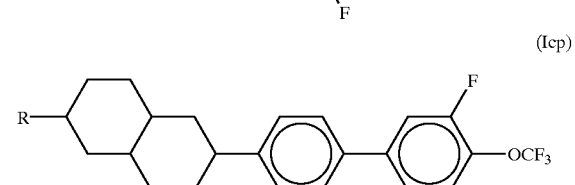

(Icq)
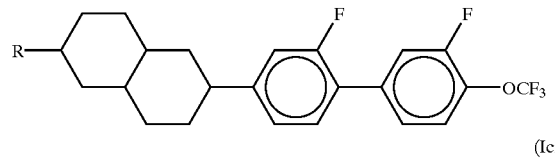
(Icr)
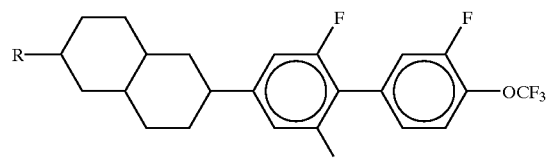
(Ics)
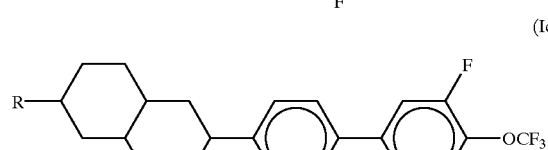
(Ict)
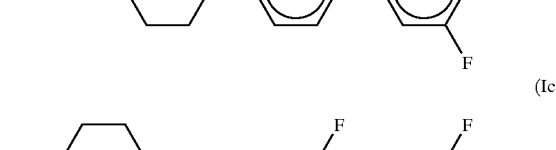
(Icu)
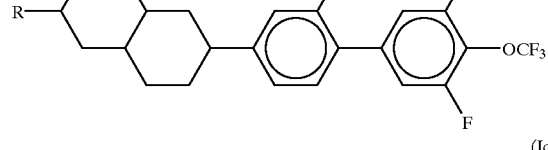
(Icv)
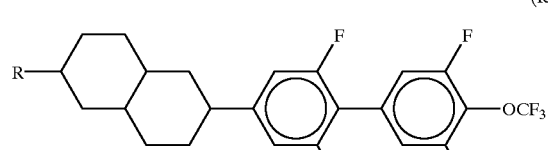
(Icw)
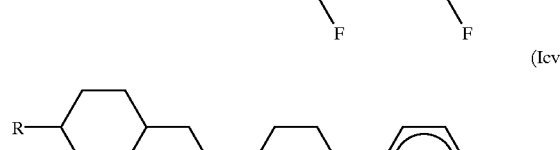
(Icx)
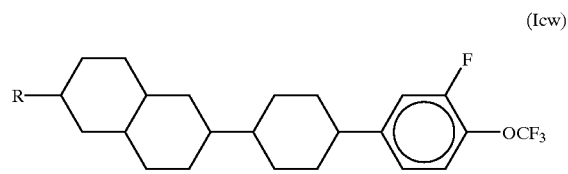
(Ide)
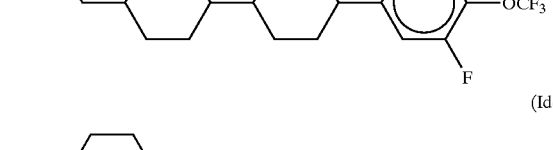
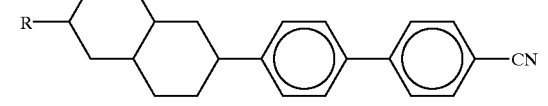
(Idb)
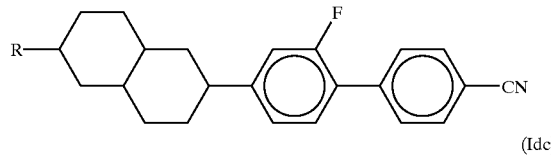
(Idc)
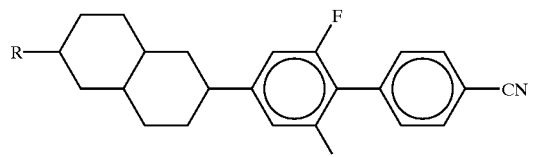
(Idd)
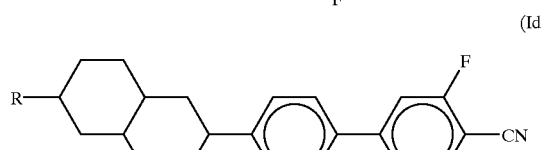
(Ide)
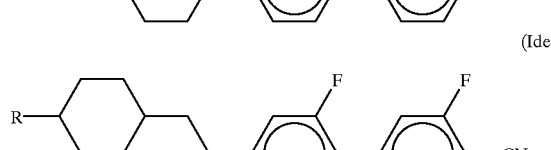
(Idf)
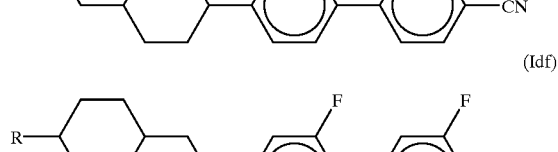
(Idg)
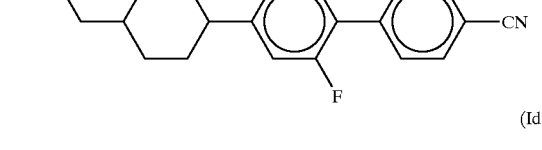
(Idh)
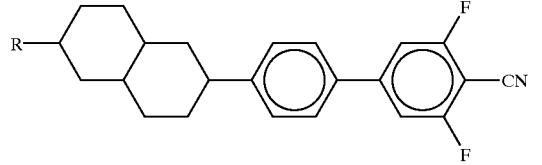
(Idi)
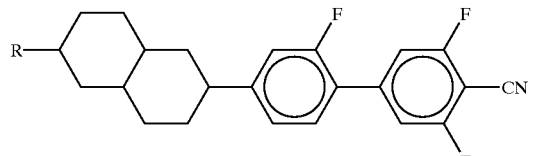
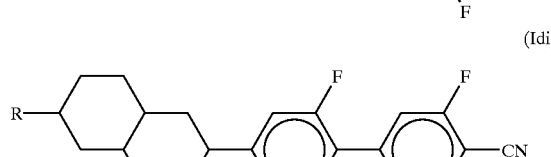
(Idj)
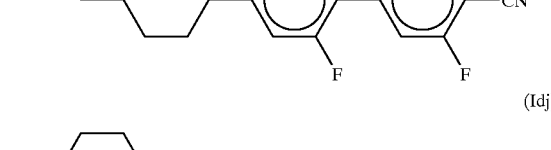
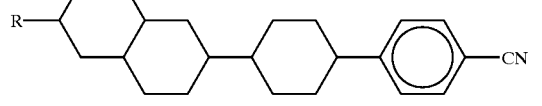

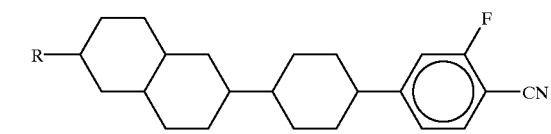
(Idk)
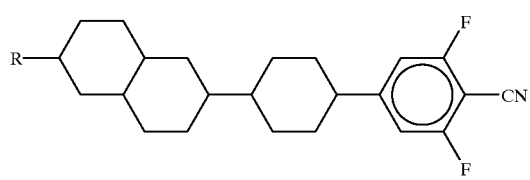
(Idl)
(Idm)
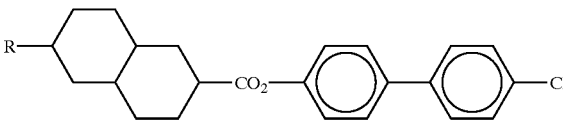
(Idn)
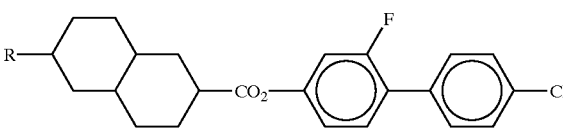
(Ido)
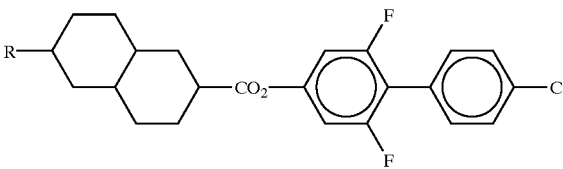
(Idp)
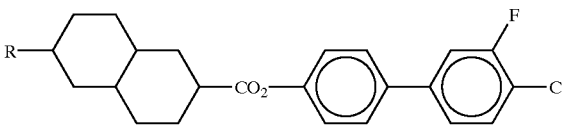
(Idq)
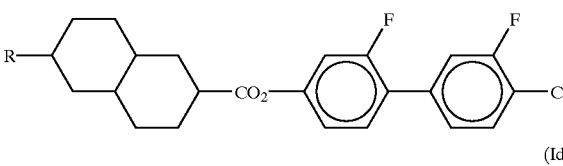
(Idr)
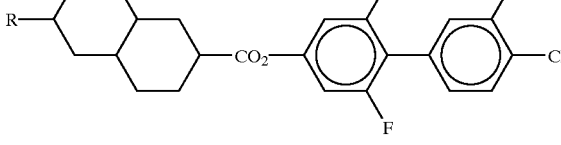
(Ids)
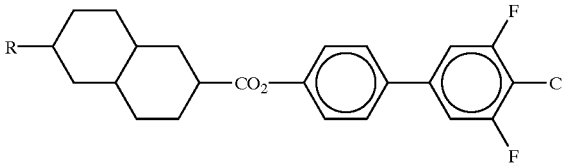
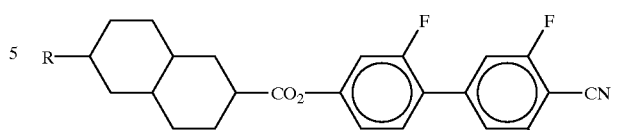
(Idt)
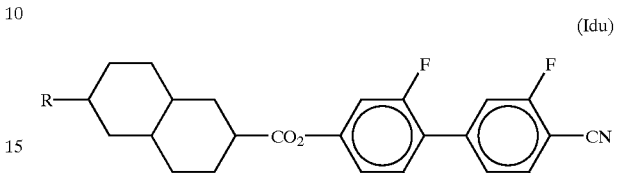
(Idu)
(Idv)
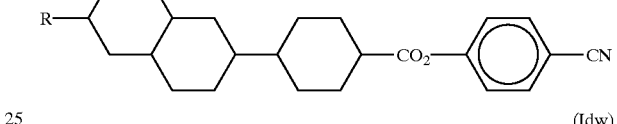
(Idw)
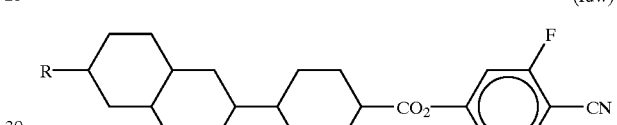
(Idx)
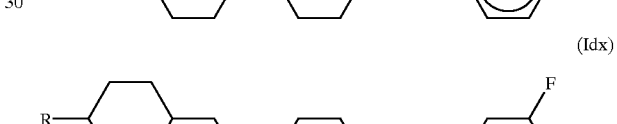
(Iea)
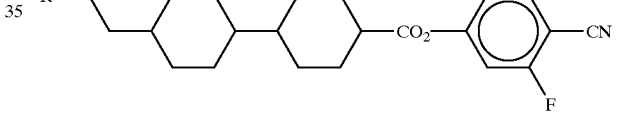
(Ieb)
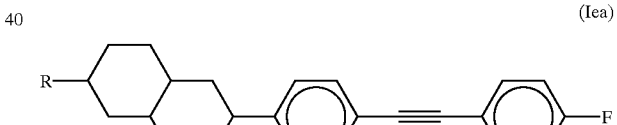
(Iec)
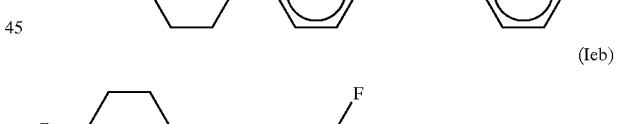
(Ied)
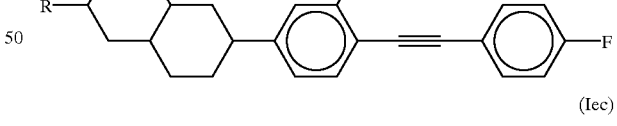
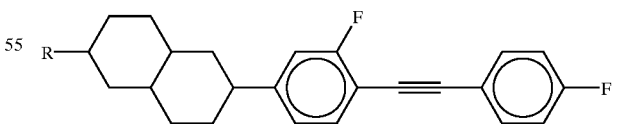
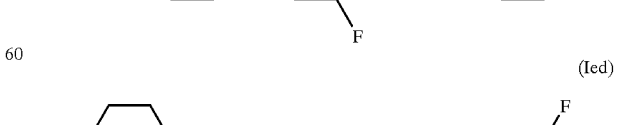
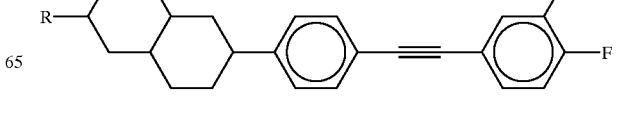

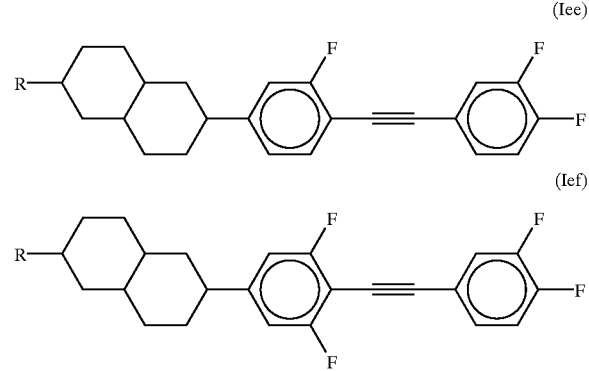
(Iee)
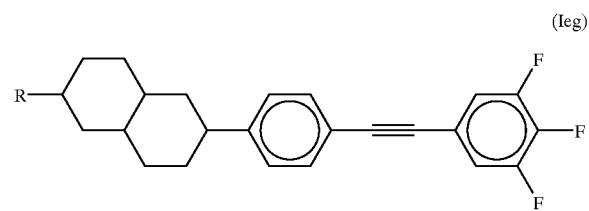
(Ief)
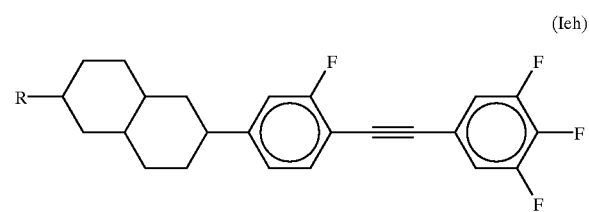
(Ieg)
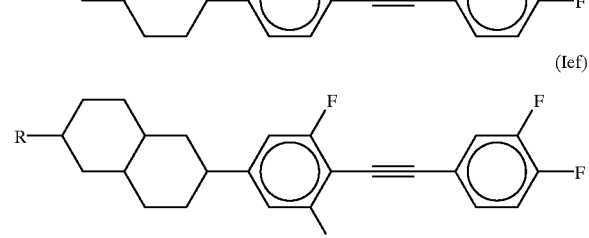
(Ieh)
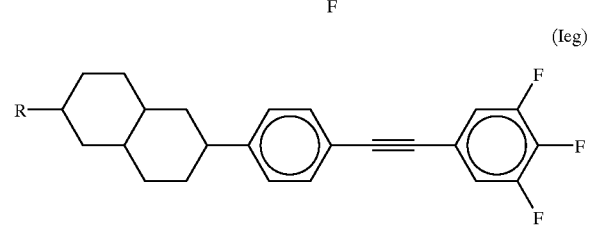
(Iei)
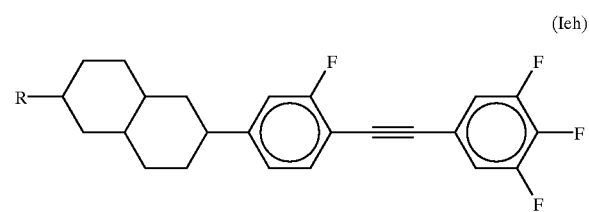
(Iej)
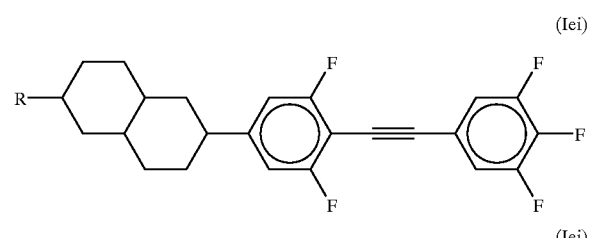
(Iek)
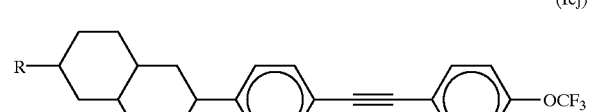
(Iel)
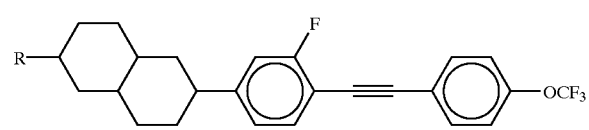
(Iem)
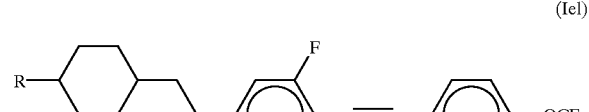
(Ien)
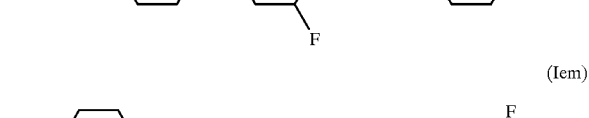
(Ieo)
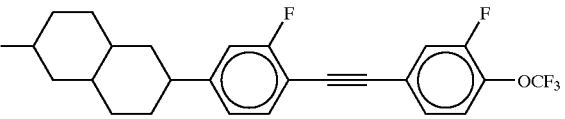
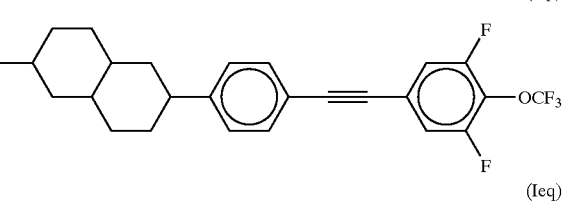
(Iep)
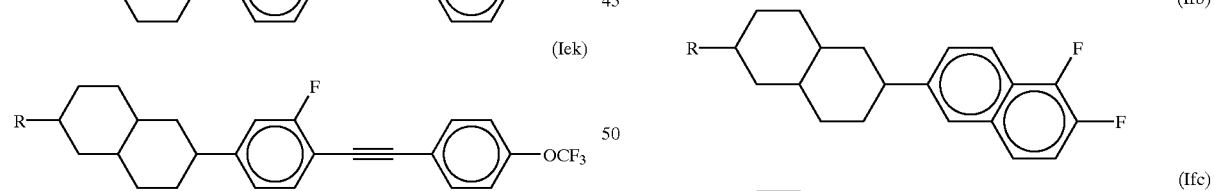
(Ieq)
(Ier)
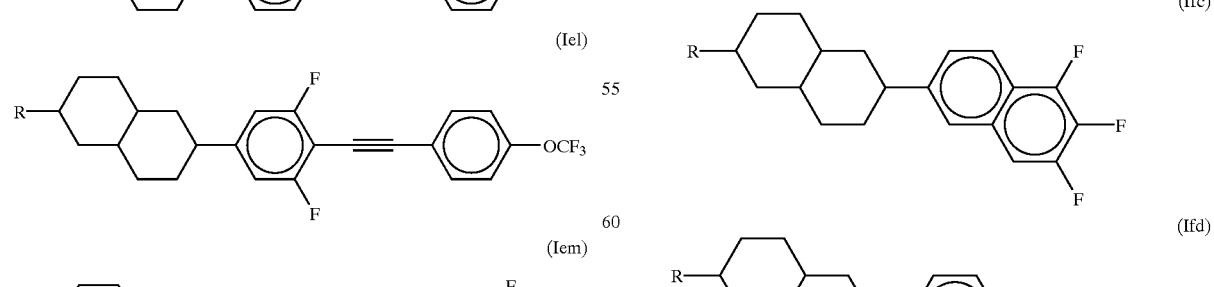
(Ifa)
(Ifb)
(Ifc)
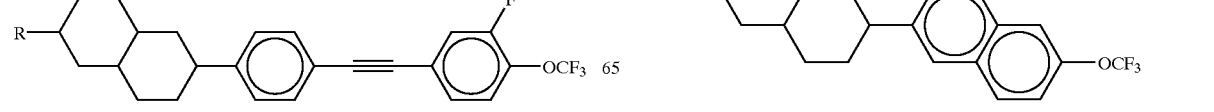
(Ifd)

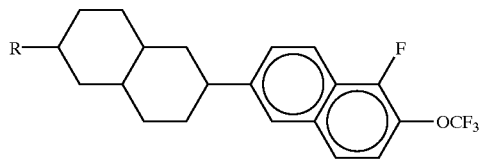 (Ife)
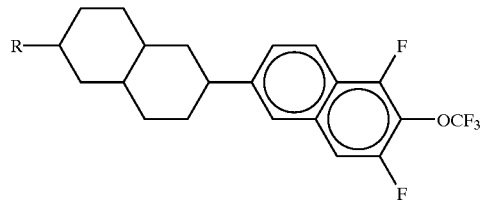 (Iff)
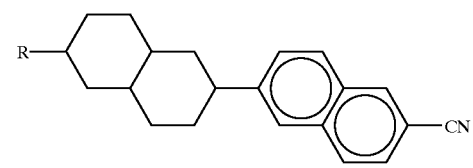 (Ifg)
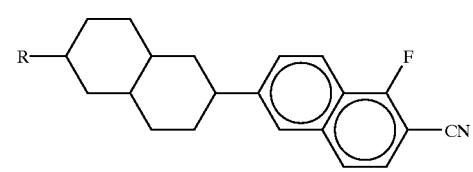 (Ifh)
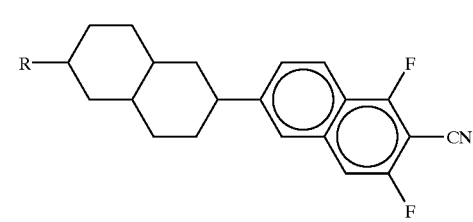 (Ifi)
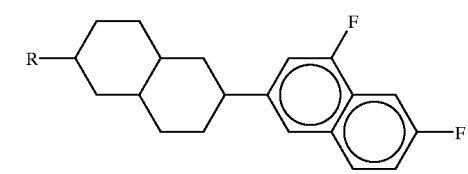 (Ifj)
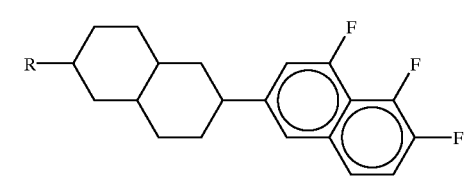 (Ifk)
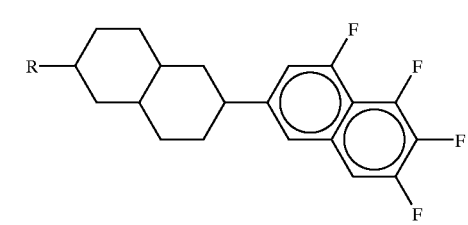 (Ifl)
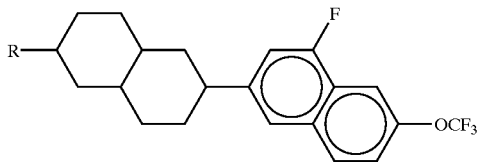 (Ifm)
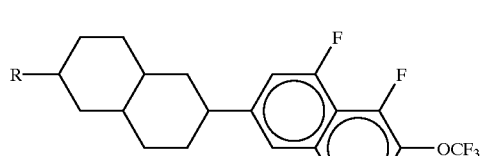 (Ifn)
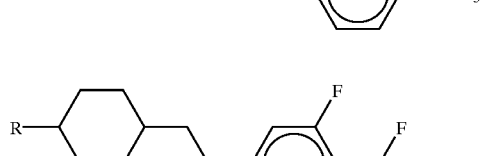 (Ifo)
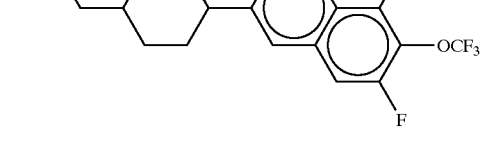 (Ifp)
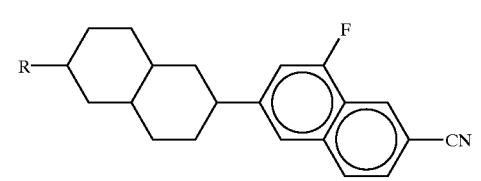 (Ifq)
 (Ifr)
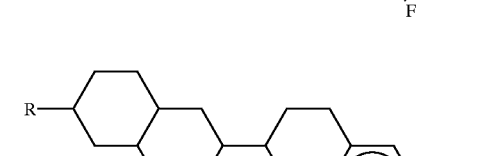 (Iga)
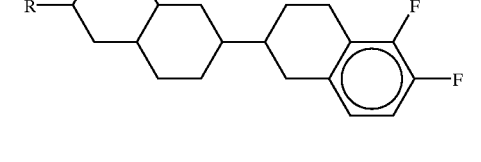 (Igb)

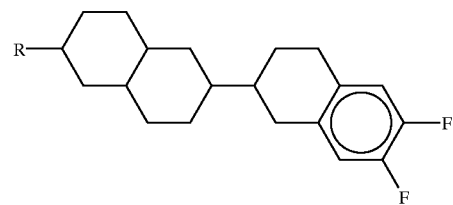
(Igc)
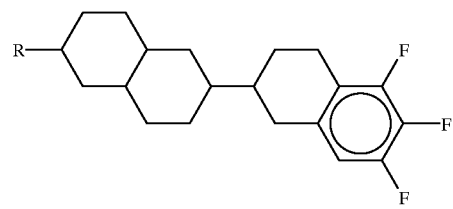
(Igd)
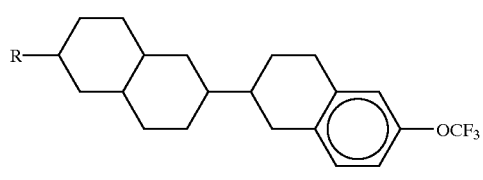
(Ige)
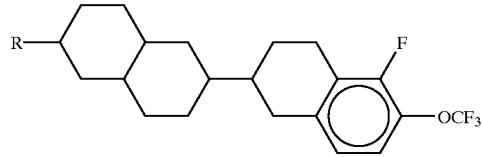
(Igf)
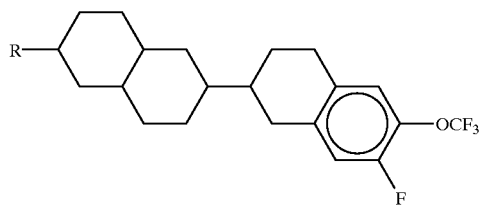
(Igg)
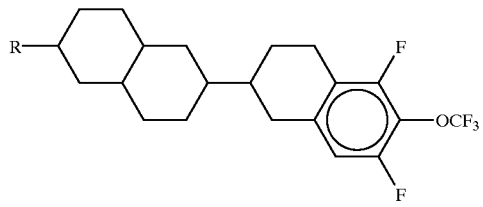
(Igh)
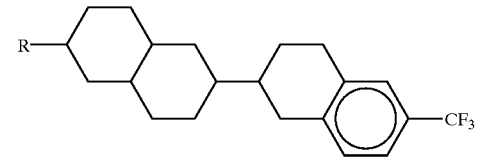
(Igi)
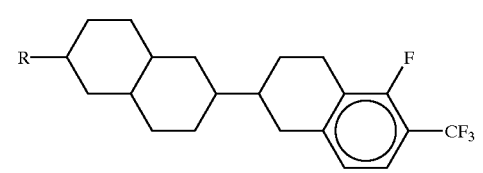
(Igj)
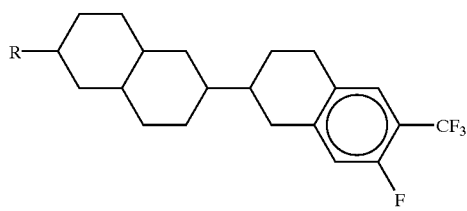
(Igk)
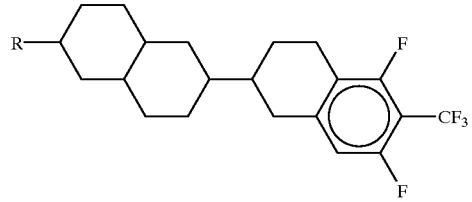
(Igl)
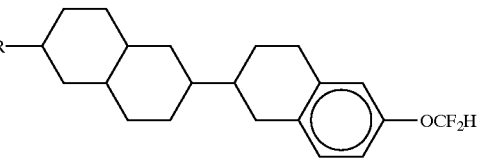
(Igm)
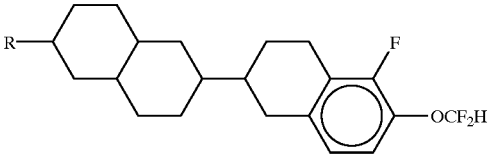
(Ign)
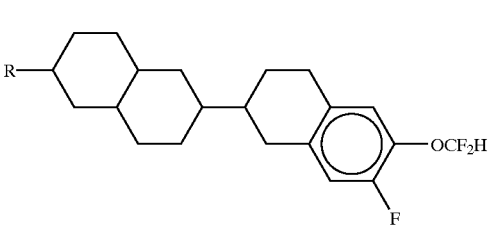
(Igo)
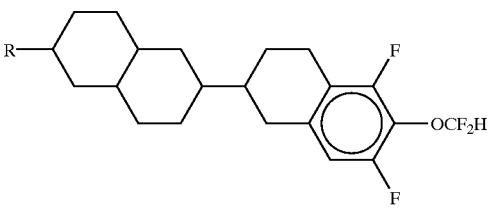
(Igp)
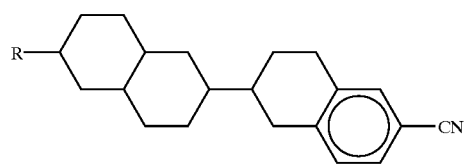
(Igq)
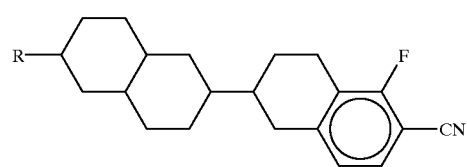
(Igr)

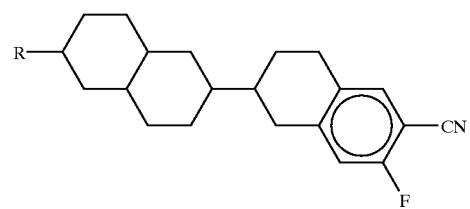
(Igs)
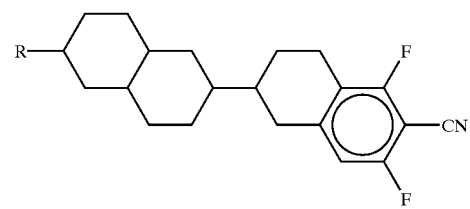
(Igt)
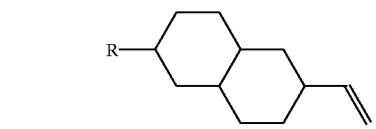
(Ina)
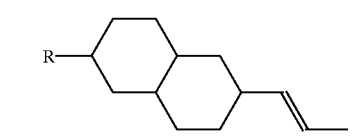
(Inb)
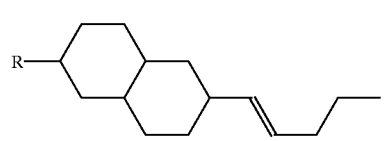
(Inc)
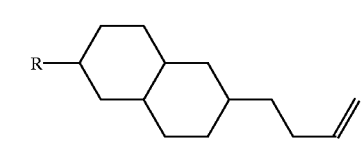
(Ind)
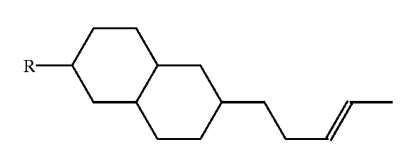
(Ine)
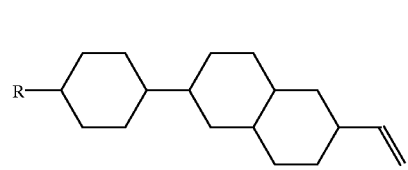
(Inf)
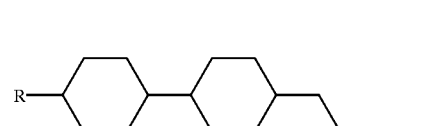
(Ing)
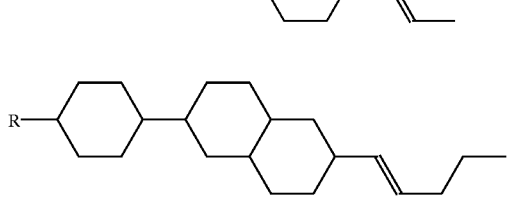
(Inh)
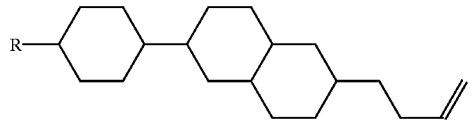
(Ini)
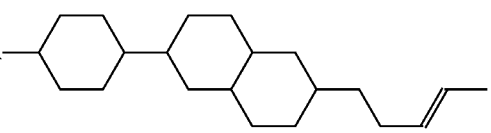
(Inj)
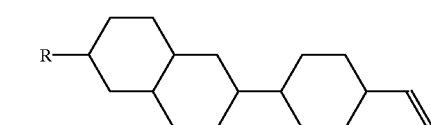
(Ink)
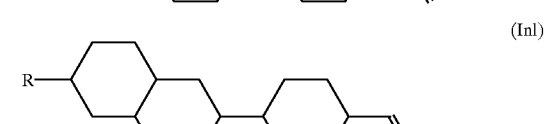
(Inl)
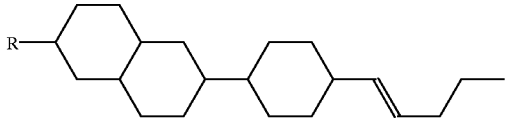
(Inm)
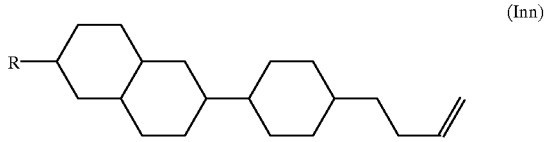
(Inn)
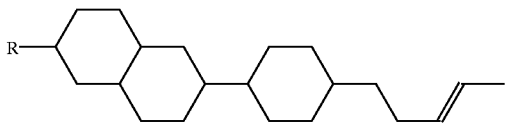
(Ino)
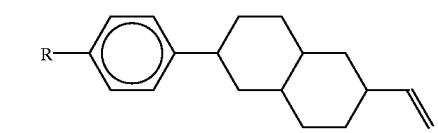
(Ioa)
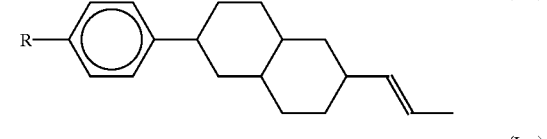
(Iob)
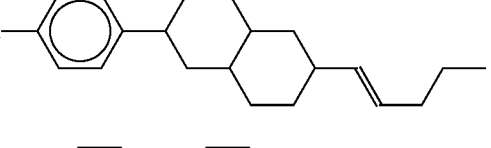
(Ioc)
(Iod)

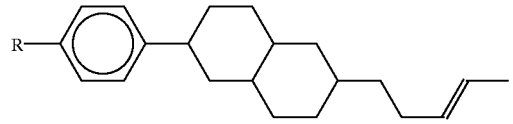
(Ioe)
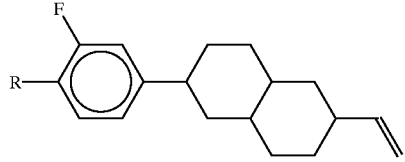
(Iof)
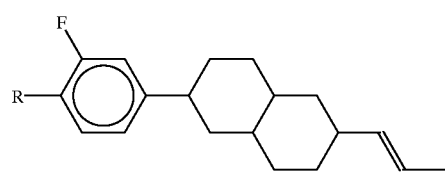
(Iog)
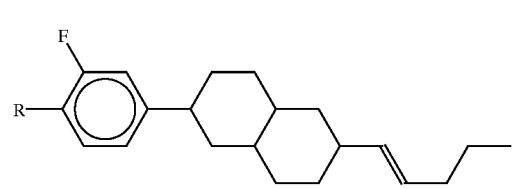
(Ioh)
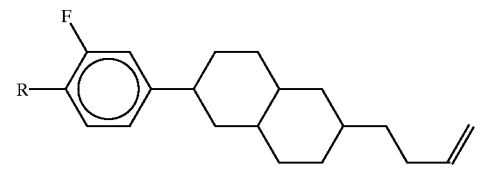
(Ioi)
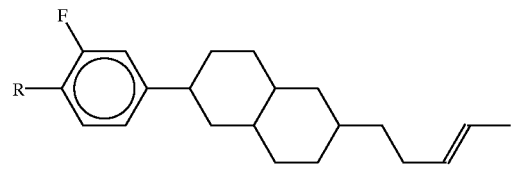
(Ioj)
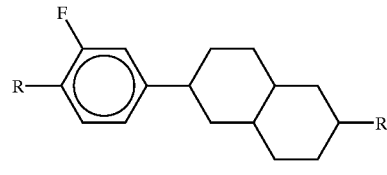
(Iok)
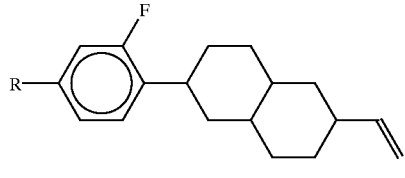
(Iol)
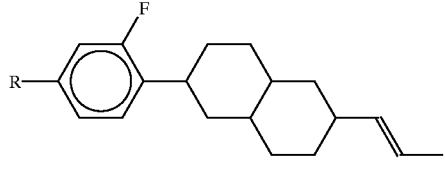
(Iom)
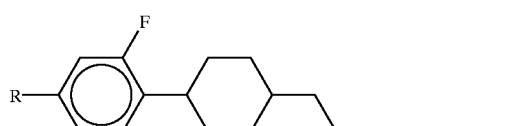
(Ion)
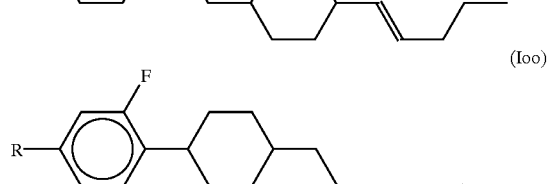
(Ioo)
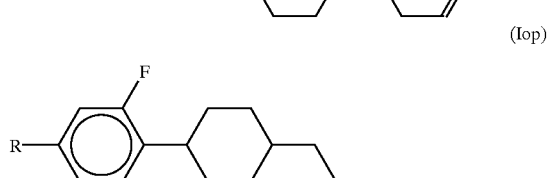
(Iop)
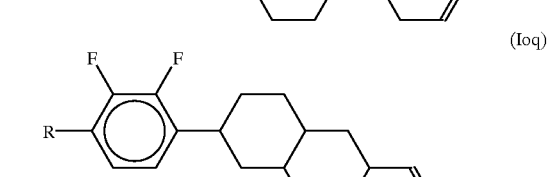
(Ioq)
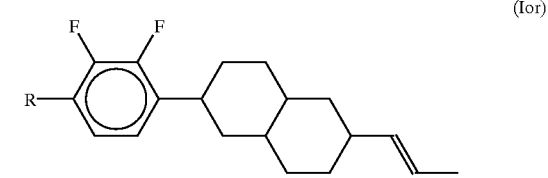
(Ior)
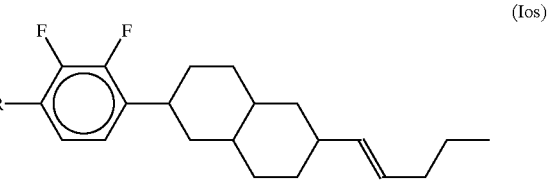
(Ios)
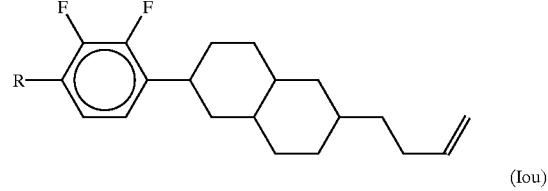
(Iot)
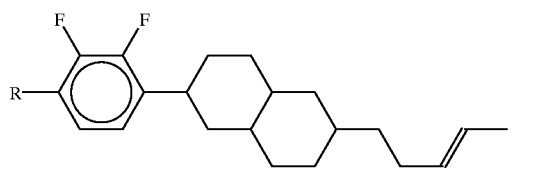
(Iou)
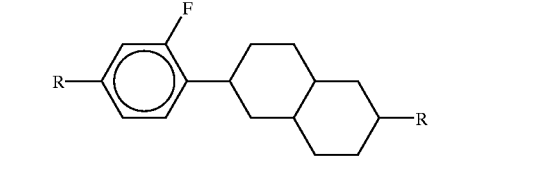
(Iov)

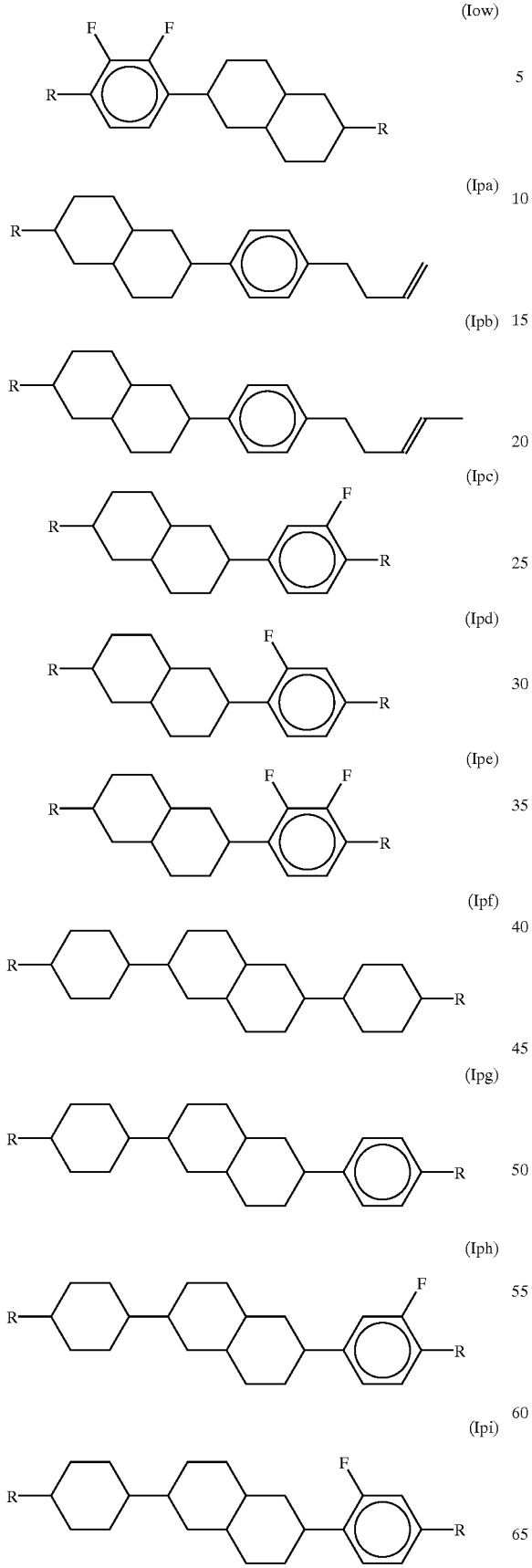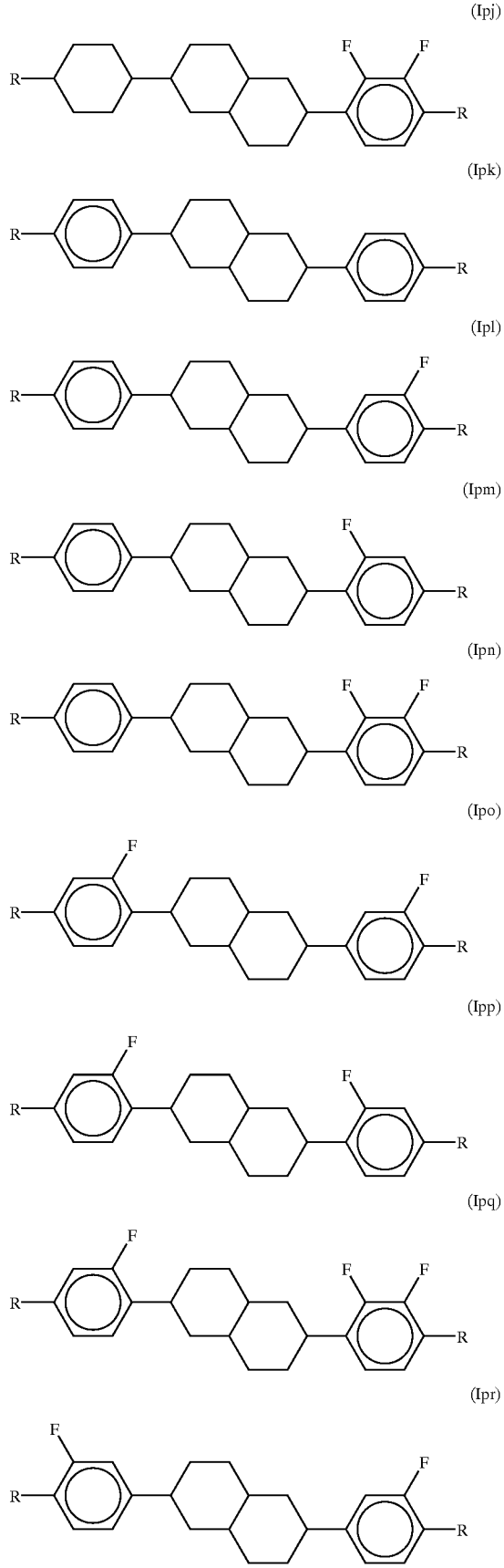

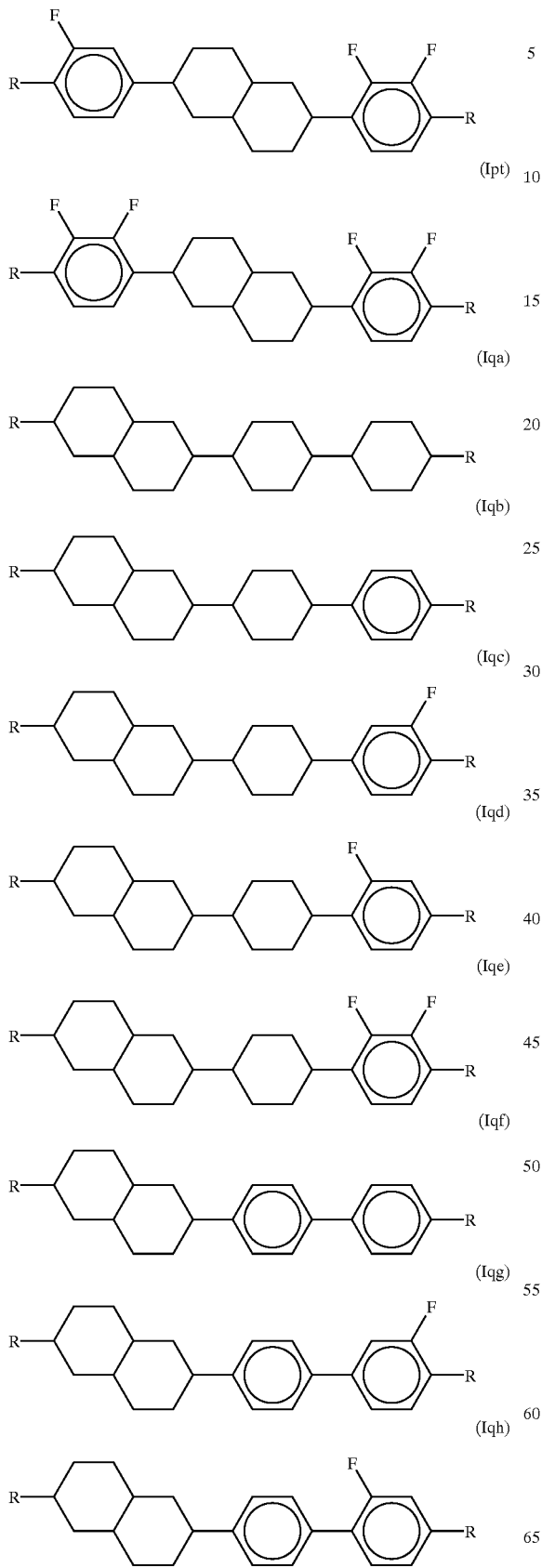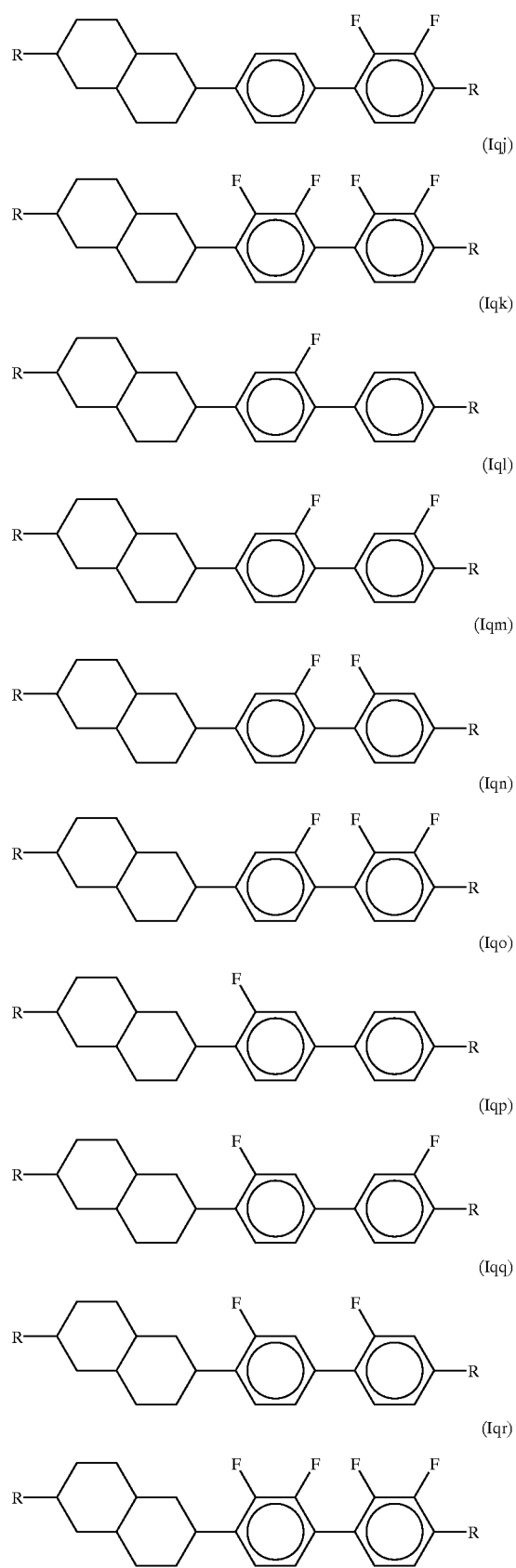

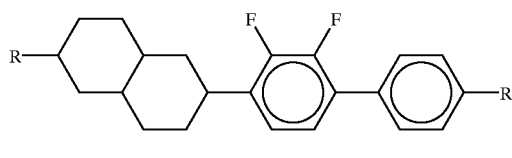
(Iqs)
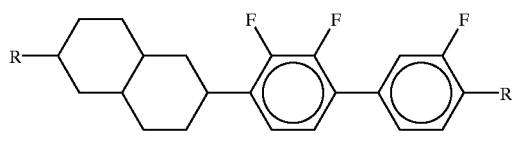
(Iqt)
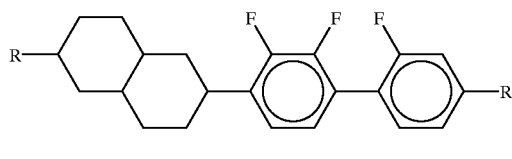
(Iqt)
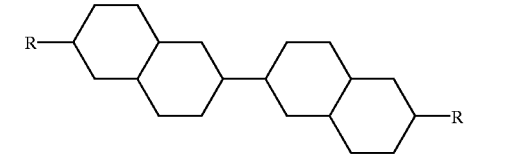
(Ira)
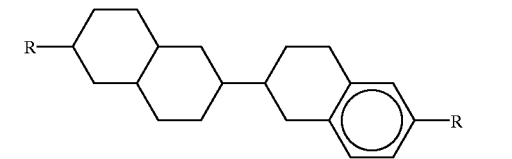
(Irb)
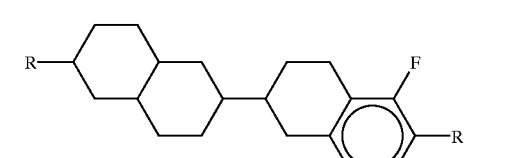
(Irc)
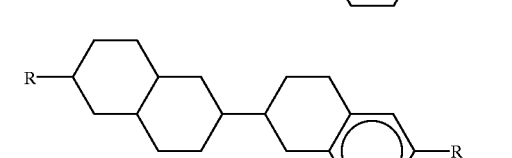
(Ird)
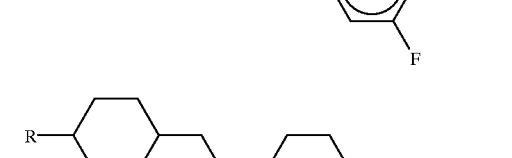
(Ire)
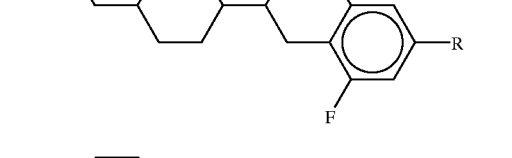
(Irf)
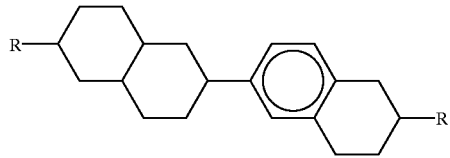
(Irg)
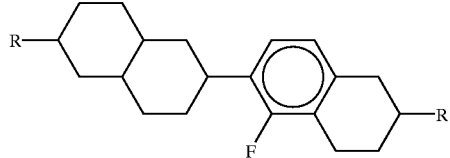
(Irh)
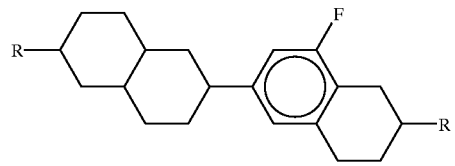
(Iri)
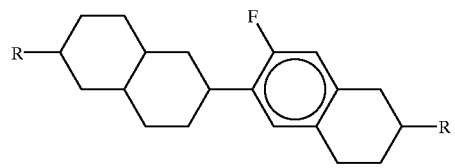
(Irj)
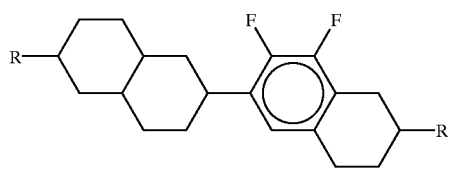
(Irk)
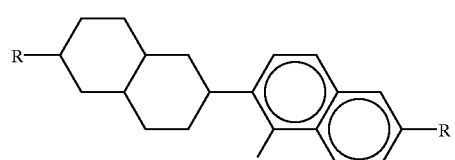
(Irl)
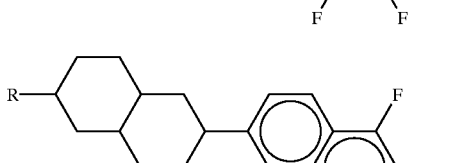
(Irm)
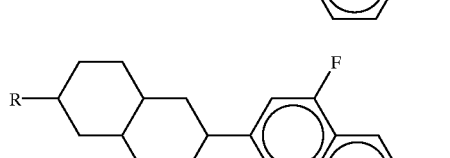
(Irn)
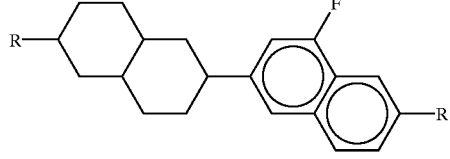
(Iro)

(Irp)
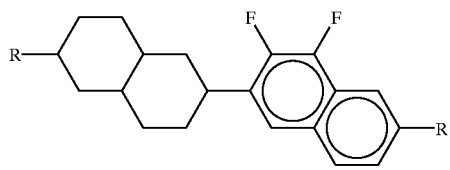

(Irq)
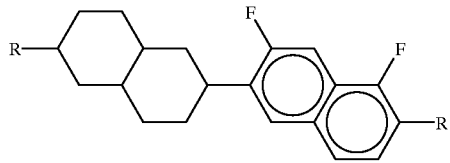

(Irr)
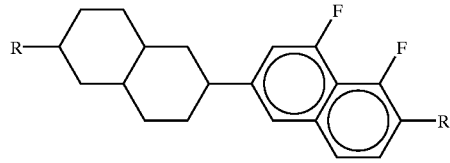

(Irs)
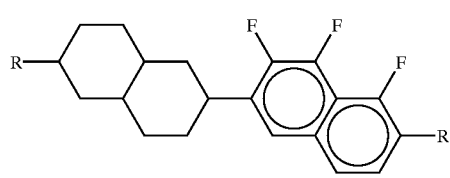

(Irt)
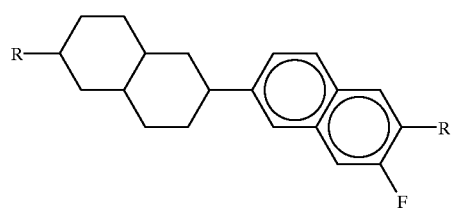

(Iru)
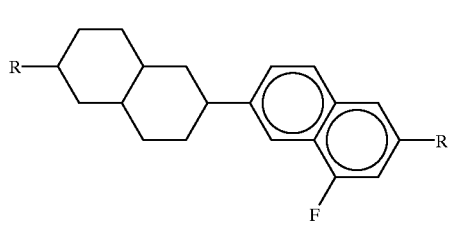

(Irv)
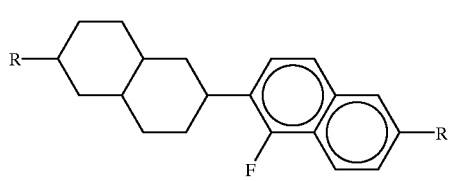

(Irw)
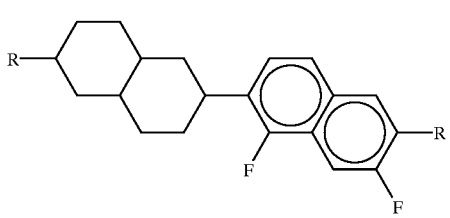

(Irx)
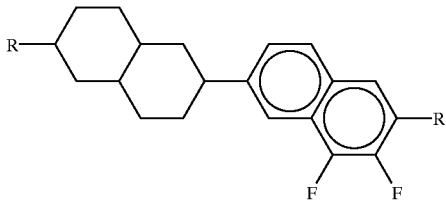

(Iry)
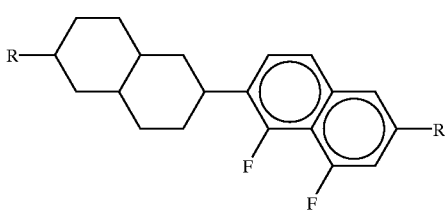

(wherein, although R is the same as previously defined in formula (I), a straight chain alkyl group having 1–7 carbon atoms or a straight chain alkenyl group of the structure shown below is preferable, and although $R^1$ represents an alkenyl group having 2–16 carbon atoms, the following structure is preferable):

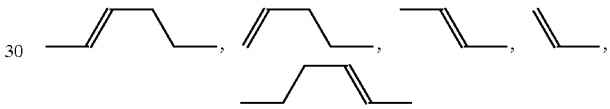

(wherein, the right side is linked to a ring).

The following forms are particularly preferable for the compound of general formula (V-1) or general formula (V-2) provided in the present invention:

(V-1a)
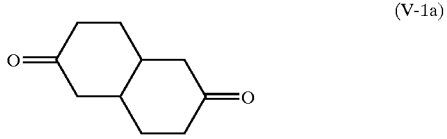

(V-1b)
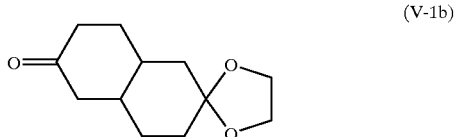

(V-1c)
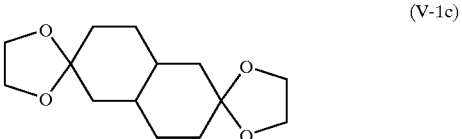

(V-1d)
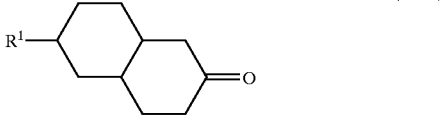

(wherein, $R^1$ is the same as previously defined, and the decahydronaphthalene ring represents the trans form); and,

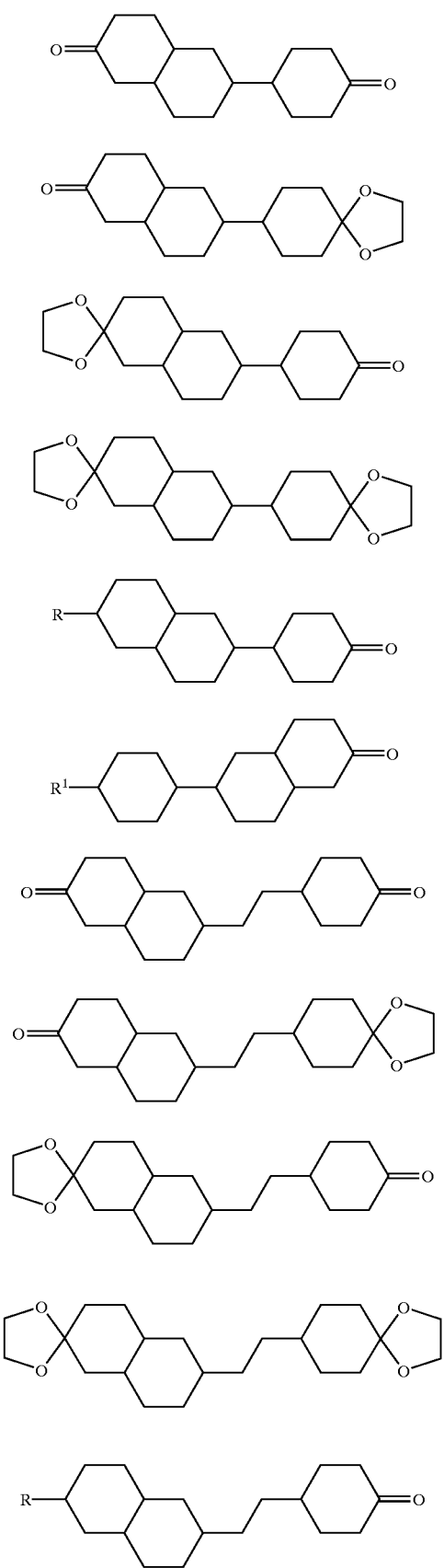

(wherein, although R is the same as previously defined in formula (I), a straight chain alkyl group having 1–7 carbon atoms or a straight chain alkenyl group having the following structure is preferable, R is the same as previously defined, and the decahydronaphthalene ring represents the trans form).

A compound of general formula (I) can be produced based on the steps indicated below. In addition, the production method of the compound of general formula (I) is not limited to the production examples described below.

1. Synthesis of General Formula (I)—1

1-1 Synthesis of General Formula (Iaf) from General Formula (Iaa) and General Formula (Ibf) from General Formula (Iba) in which R is an Alkyl Group, Alkoxy Group or Alkoxyalkyl Group After reacting a decahydronaphthalene derivative represented by general formula (IIa):

(wherein, $R^2$ represents an alkyl group, alkoxy group or alkoxyalkyl group, ring A, m and L are the same as previously defined in general formula (I), and the decahydronaphthalene ring has a trans form) with organometallic reagent (III):

wherein, $Z^1$ represents an alkyl group, alkoxy group, alkyl group substituted with an alkoxy group, hydrogen atom, fluorine atom, chlorine atom, trifluoromethoxy group, difluoromethoxy group, trifluoromethyl group or 2,2,2-trifluoroethoxy group, $Z^2$, $Z^3$ and $Z^4$ respectively and independently represent a hydrogen atom, fluorine atom or chlorine atom, W represents MgX (wherein, X represents a chlorine atom, bromine atom or iodine atom), a metal atom such as Li, $B(OH)_2$ or $SiF(CH_3)_2$, and these can be easily prepared from the corresponding halogenated benzene derivative), by dehydrating in the presence of acid catalyst, octahydronaphthalene derivative (IV):

(IV)

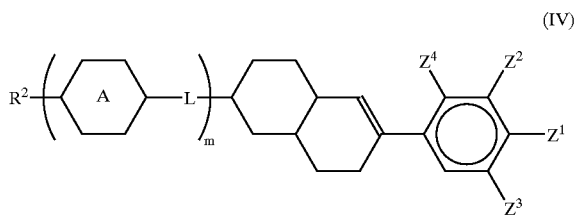

(wherein, $R^2$, L, $Z^1$, $Z^2$, $Z^3$, $Z^4$, ring A and m are the same as previously defined, and the 9,10 positions of the octahydronaphthalene ring have trans forms) is obtained. By hydrogenating the double bond of the octahydronaphthalene ring and isomerizing in the presence of alkaline catalyst as necessary, (IA-1), which includes general formula (Iaf) from general formula (Iaa) and general formula (Ibf) from general formula (Iba):

(IA-1)

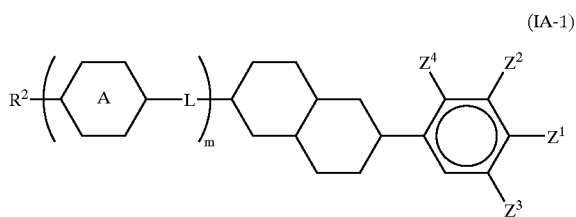

(wherein, $R^2$, L, $Z^1$, $Z^2$, $Z^3$, $Z^4$, ring A and m are the same as previously defined, and decahydronaphthalene ring has a trans form) can be produced.

1-2 Synthesis of General Formula (Iaf) from General Formula (Iaa) and General Formula (Ibf) from General Formula (Iba) in which R is an Alkenyl Group After reacting a decahydronaphthalene derivative represented by formula (V-1b) or general formula (V-2b):

(V-1b)

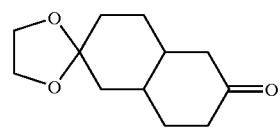

(V-2b)

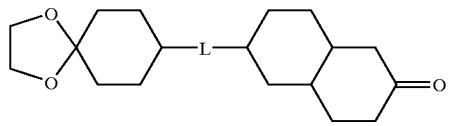

(wherein, L is the same as previously defined in general formula (I), and the decahydronaphthalene ring has a trans form) with organometallic reagent (III), by dehydrating in the presence of acid catalyst and re-converting to acetal, general formula (VIa) or general formula (Vib):

(VIa)

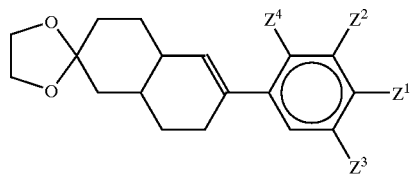

(VIb)

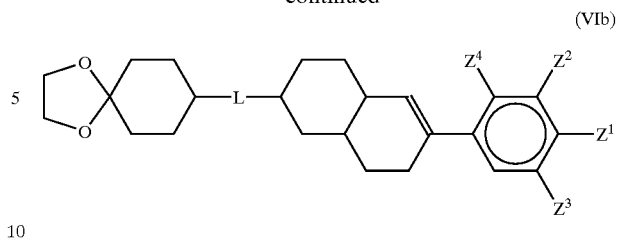

(wherein, L, $Z^1$, $Z^2$, $Z^3$ and $Z^4$ are the same as previously defined, and the 9,10 positions of the octahydronaphthalene ring have trans forms) is obtained. After hydrogenating the double bond of the octahydronaphthalene ring and isomerizing in the presence of alkaline catalyst as necessary followed by deacetalization, general formula (VIIa) or general formula (VIIb):

(VIIa)

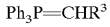

(VIIb)

(wherein, L, $Z^1$, $Z^2$, $Z^3$ and $Z^4$ are the same as previously defined, and the 9,10 positions of the octahydronaphthalene ring have trans forms) is obtained. After then reacting this with Wittig's reagent (VIII), $$Ph_3P=CHOCH_3 \quad (VIII)$$

it was acid hydrolyzed and isomerized to the trans form using base followed by repeating reaction of (VIII) and acid hydrolysis to obtain alkanal derivative (IX):

(IX)

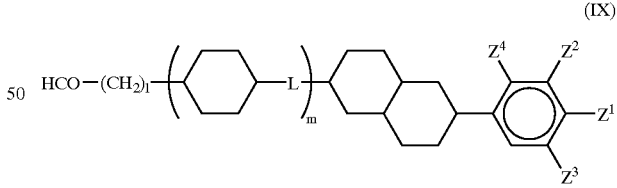

(wherein l represents an integer of 0 or greater, m, L, $Z^1$, $Z^2$, $Z^3$ and $Z^4$ are the same as previously defined, and the decahydronaphthalene ring has a trans form). After reacting this with general formula (X):

$$Ph_3P=CHR^3 \quad (X)$$

(wherein, $R^3$ represents a hydrogen atom or alkyl group that may be substituted with one or more fluorine atoms or alkoxy groups), by isomerizing the double bond to the trans conformation using a benzene sulfinate and so forth as necessary, decahydronaphthalene derivative (IA-2), in which R of general formula (Iaf) from general formula (Iaa)

and general formula (Ibf) from general formula (Iba) represents an alkenyl group:

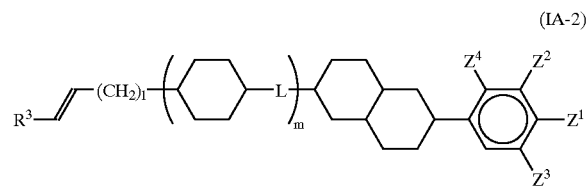
(IA-2)

(wherein, l represents an integer of 0 or greater, $R^3$, m, L, $Z^1$, $Z^2$, $Z^3$ and $Z^4$ are the same as previously defined, and the decahydronaphthalene ring has a trans form), can be produced. In addition, by reducing alkanal derivative (IX) to obtain an alcohol derivative and then converting this to an alkoxide followed by reacting the alkyl halide, a compound can be produced wherein, in general formula (I), n is 1, ring C is a 1,4-phenylene group, and R is an alkoxy group, etc.

1-3 Synthesis of General Formula (Iao) from General Formula (Iaj) and General Formula (Ibo) from General Formula (Ibj)

After reacting Wittig's reagent (VIII) with general formula (IIa), by acid hydrolyzing, isomerizing to the trans form using base, again reacting with (VIII) and repeating acid hydrolysis, and reacting general formula (III) with alkanal derivative (XI):

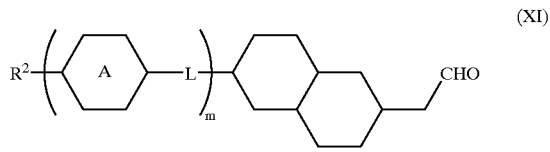
(XI)

(wherein, $R^2$, L, ring A and m are the same as previously defined, and the decahydronaphthalene ring has a trans form), followed by dehydrating in the presence of acid catalyst, decahydronaphthalene derivative (XII):

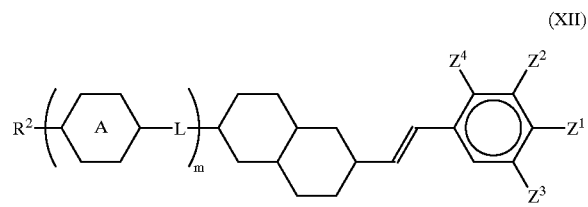
(XII)

(wherein, $R^2$, L, $Z^1$, $Z^2$, $Z^3$, $Z^4$, ring A and m are the same as previously defined, and the decahydronaphthalene ring has a trans form) is obtained. By hydrogenating the double bond, (IA-3), which includes general formula (Iao) from general formula (Iaj) and general formula (Ibo) from general formula (Ibj):

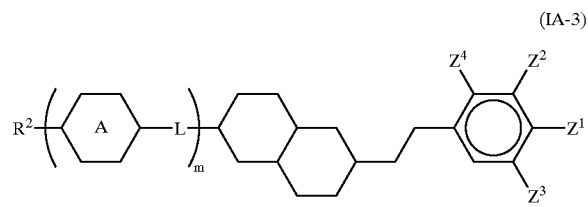
(IA-3)

(wherein, $R^2$, L, $Z^1$, $Z^2$, $Z^3$, $Z^4$, ring A and m are the same as previously defined, and the decahydronaphthalene ring has a trans form) can be produced.

1-4 Synthesis of General Formula (Iai) from General Formula (Iag), General Formula (Iar) from General Formula (Iap), General Formula (Ibi) from General Formula (Ibg) and General Formula (Ibr) from General Formula (Ibp)

After either direct bromination or iodination or lithionation with alkyl lithium of a phenyldecahydro-naphthalene derivative represented by general formula (XIII) for which the synthesis method has already been described:

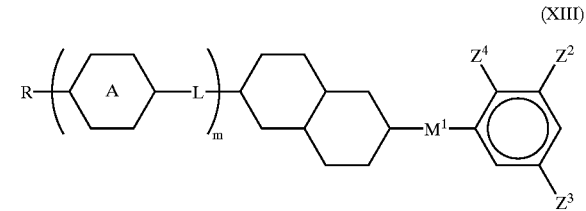
(XIII)

(wherein, R, L, $Z^2$, $Z^3$, $Z^4$, ring A and m are the same as previously defined, $M^1$ represents a single bond or an alkylene group having 1–4 carbon atoms, and the decahydronaphthalene ring has a trans form), by reacting with bromine or iodine, decahydronaphthalene derivative (XIV):

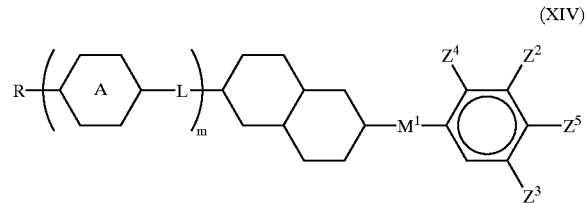
(XIV)

(wherein, $Z^5$ represents a halogen atom such as bromine or iodine, R, L, $Z^2$, $Z^3$, $Z^4$, ring A and m are the same as previously defined, $M^1$ represents a single bond or alkylene group having 1–4 carbon atoms, and the decahydronaphthalene ring has a trans form) can be produced.

Organometallic reagent (XV):

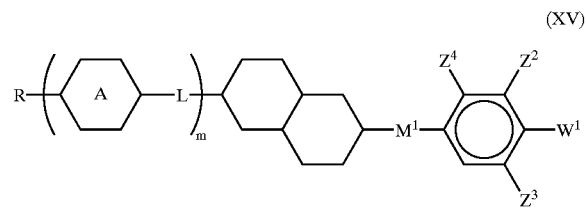
(XV)

(wherein, $W^1$ represents a metal such as MgBr, MgI or Li or a metal-containing group, R, L, $Z^2$, $Z^3$, $Z^4$, ring A and m are the same as previously defined, $M^1$ represents a single bond or an alkylene group having 1–4 carbon atoms, and the decahydronaphthalene ring has a trans form) is produced by reacting a metal such as magnesium with general formula (XIV) or by converting general formula (XIII) to the transmetal using an organometallic reagent such as alkyl lithium. By reacting this with carbon dioxide, a benzoic acid derivative represented by general formula (XVI):

(XVI)

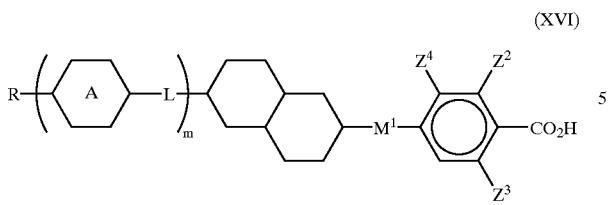

(wherein, R, L, $Z^2$, $Z^3$, $Z^4$, ring A and m are the same as previously defined, $M^1$ represents a single bond or an alkylene group having 1–4 carbon atoms, and the decahydronaphthalene ring has a trans form) is obtained. After converting this to an acid halide with a halogenating agent such as thionyl halide, by reacting with ammonia to convert an acid amide and then dehydrating, general formula (IA-4), which includes general formula (Iai) from general formula (Iag), general formula (Iar) from general formula (Iap), general formula (Ibi) from general formula (Ibg) and general formula (Ibr) from general formula (Ibp):

(IA-4)

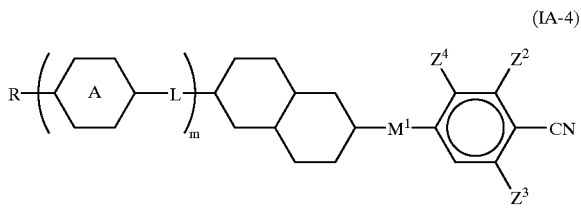

(wherein, R, L, $Z^2$, $Z^3$, $Z^4$, ring A and m are the same as previously defined, $M^1$ represents a single bond or an alkenyl group having 1–4 carbon atoms, and the decahydronaphthalene ring has a trans form) can be produced.

1-5 Production of General Formula (Iau) from General Formula (Ias) and General Formula (Ibu) from General Formula (Ibs)

After acid chloridation of general formula (XVIII):

(XVIII)

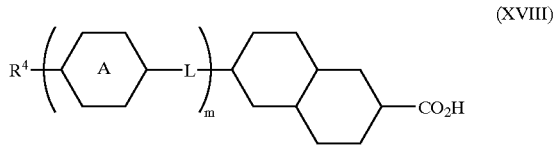

(wherein, $R^4$ represents an alkyl group, alkenyl group, alkoxy group or alkoxyalkyl group, L, ring A and m are the same as previously defined, and the decahydronaphthalene ring has a trans form), obtained by reacting an oxidant such as silver oxide with general formula (XVII) obtained in the production process of general formula (XI) for which the production method has been already described:

(XVII)

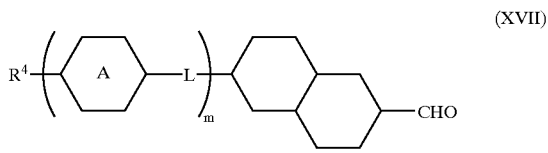

(wherein, $R^4$ represents an alkyl group, alkenyl group, alkoxy group or alkoxyalkyl group, L, ring A and m are the same as previously defined, and the decahydronaphthalene ring has a trans form), by reacting with a compound of general formula (XIX):

(XIX)

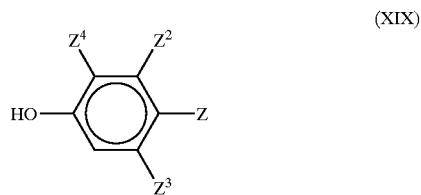

(wherein, Z is the same as previously described in general formula (I), and $Z^2$, $Z^3$ and $Z^4$ are the same as previously defined), general formula (IA-5), which includes general formula (Iau) from general formula (Ias) and general formula (Ibu) from general formula (Ibs):

(IA-5)

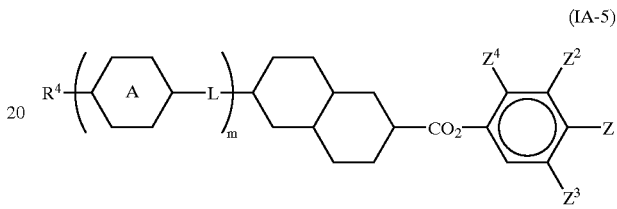

(wherein, $R^4$, L, $Z^2$ $Z^3$, $Z^4$, ring A and m are the same as previously defined, Z is the same as previously described in general formula (I), and the decahydronaphthalene ring has a trans form), can be produced.

1-6 Production from General Formula (Ici) from General Formula (Ica) and General Formula (Icu) from General Formula (Icm)

General formula (IA-6), which includes general formula (Ici) from general formula (Ida) and general formula (Icu) from general formula (Icm):

(IA-6)

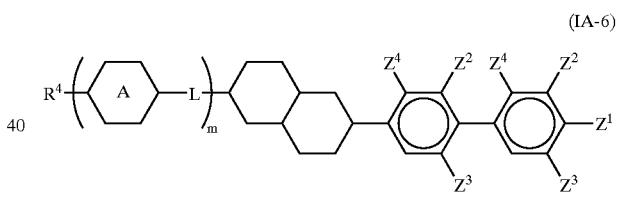

(wherein, $R^4$, L, $Z^1$, $Z^2$, $Z^3$, $Z^4$, ring A and m are the same as previously defined, $Z^2$, $Z^3$ and $Z^4$ may be the same or different, and the decahydronaphthalene ring has a trans form), can be produced by reacting general formula (III) with general formula (XIV), for which the production method has already been described, in the presence of transition metal catalyst.

1-7 Synthesis of General Formula (Idi) from General Formula (Ida)

General formula (IA-7), which includes general formula (Idi) from general formula (Ida):

(IA-7)

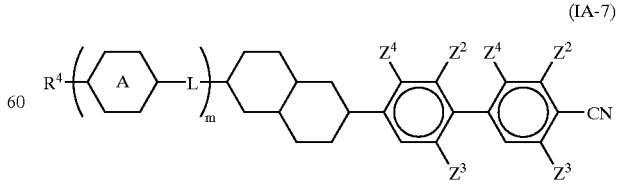

(wherein, $R^4$, L, $Z^1$, $Z^2$ $Z^3$ $Z^4$ ring A and m are the same as previously defined, $Z^2$, $Z^3$ and $Z^4$ may be the same or different, and the decahydronaphthalene ring has a trans form), can be produced using the method described in 1-4 and a phenyldecahydronaphthalene derivative represented by general formula (IA-6a) for which the synthesis method has already been described:

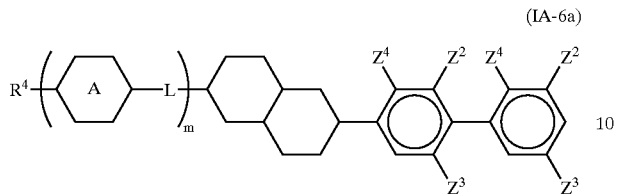

(IA-6a)

(wherein, $R^4$, L, $Z^1$, $Z^2$, $Z^3$, $Z^4$, ring A and m are the same as previously defined, $Z^2$, $Z^3$ and $Z^4$ may be the same or different, and the decahydronaphthalene ring has a trans form).

1-8 Production of General Formula (Idu) from General Formula (Idm)

By converting general formula (XVIII), for which the production method has already been described, into an acid chloride followed by reacting with a compound of general formula (XX):

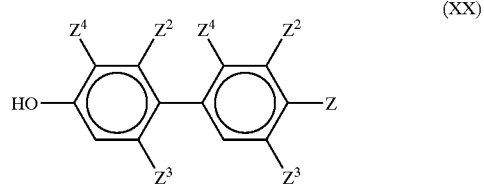

(XX)

(wherein, Z, $Z^2$, $Z^3$, $Z^4$, ring A and m are the same as previously defined, and the plurality of $Z^2$, $Z^3$ and $Z^4$ may be the same or different), general formula (IA-8), which includes general formula (Idu) from general formula (Idm):

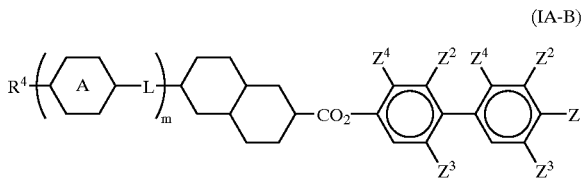

(IA-B)

(wherein, $R^4$, L, Z, $Z^2$, $Z^3$, $Z^4$, ring A and m are the same as previously defined, the plurality of $Z^2$, $Z^3$ and $Z^4$ may be the same or different, and the decahydronaphthalene ring has a trans form) can be produced.

1-9 Production of General Formula (Ier) from General Formula (Iea)

General formula (IA-9), which includes general formula (Icr) from general formula (Ica):

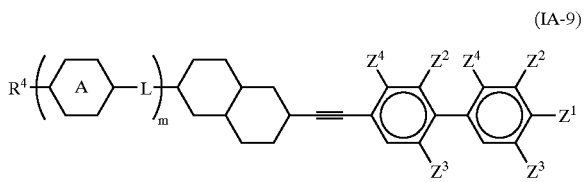

(IA-9)

(wherein, $R^4$, L, $Z^1$, $Z^2$, $Z^3$, $Z^4$, ring A and m are the same as previously defined, the plurality of $Z^2$, $Z^3$ and $Z^4$ may be the same or different, and the decahydronaphthalene ring has a trans form), can be produced by reacting general formula (XXI):

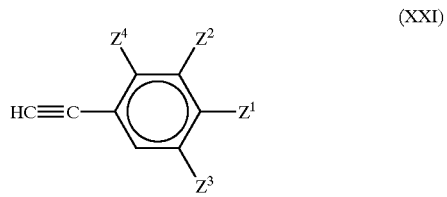

(XXI)

(wherein, $Z^1$, $Z^2$, $Z^3$ and $Z^4$ are the same as previously defined) with general formula (XIV), for which the production method has already been described, in the presence of transition metal catalyst.

1-10 Production of General Formula (Iff) from General Formula (Ifa), General Formula (Ifo) from General Formula (Ifj) and General Formula (Iry) from General Formula (Irm)

After reacting an organometallic reagent (XXII)

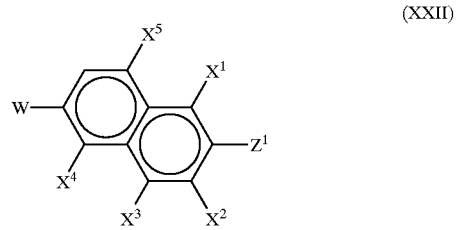

(XXII)

(wherein, $X^1$, $X^2$, $X^3$, $X^4$ and $X^5$ respectively and independently represent a hydrogen atom, fluorine atom or chlorine atom, and W and $Z^1$ are the same as previously defined) with a decahydronaphthalene derivative represented by general formula (IIa), by then dehydrating in the presence of acid catalyst, hydrogenating the double bond of the octahydronaphthalene ring, and isomerizing in the presence of alkaline catalyst as necessary, (IA-10), which includes general formula (Iff) from general formula (Ifa), general formula (Ifo) from general formula (Ifj) and general formula (Iry) from general formula

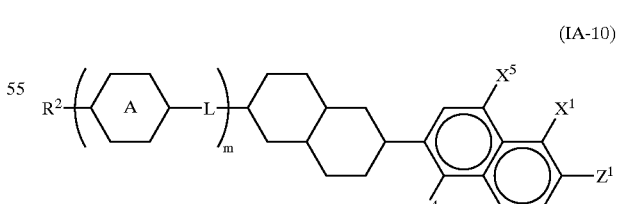

(IA-10)

(wherein, $R^2$, L, $X^1$, $X^2$, $X^3$, $X^4$, $X^5$, $Z^1$, ring A and m are the same as previously defined, and the decahydronaphthalene ring has a trans form), can be produced.

1-11 Synthesis of General Formula (Ifi) from General Formula (Ifg) and General Formula (Ifr) from General Formula (Ifp)

After demethoxyating general formula (XXIII), for which the synthesis method has already been described:

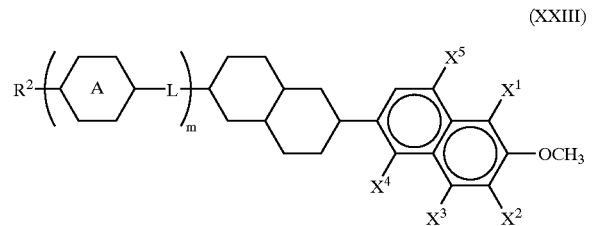
(XXIII)

(wherein, $R^2$, L, $X^1$, $X^2$, $X^3$, $X^4$, $X^5$, ring A and m are the same as previously defined, and the decahydronaphthalene ring has a trans form) using hydrobromic acid and so forth to obtain phenol derivative (XXIV):

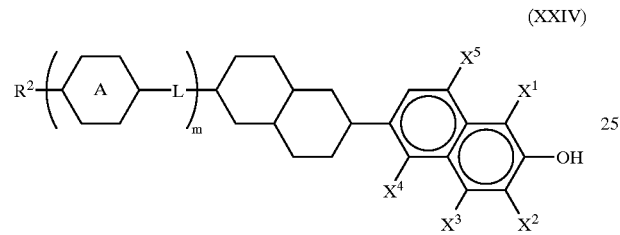
(XXIV)

(wherein, $R^2$, L, $X^1$, $X^2$, $X^3$, $X^4$, $X^5$, ring A and m are the same as previously defined, and the decahydronaphthalene ring has a trans form), and converting to an elimination group by allowing p-toluene sulfonyl chloride or trifluoromethane sulfonic acid anhydride to act on this, by reacting with potassium cyanate and so forth in the presence of transition metal catalyst, general formula (IA-11), which includes general formula (Ifi) from general formula (Ifg) and general formula (Ifr) from general formula (Ifp):

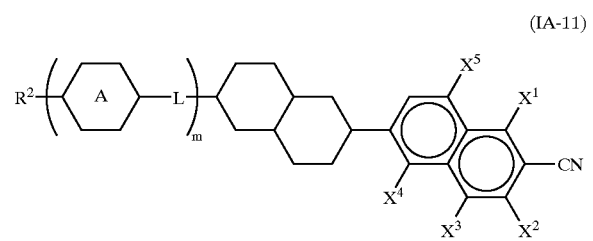
(IA-11)

(wherein, $R^2$, L, $X^1$, $X^2$, $X^3$, $X^4$, $X^5$, ring A and m are the same as previously defined, and the decahydronaphthalene ring has a trans form), can be produced. Here, a palladium complex or nickel complex is preferable for the transition metal catalyst.

1-12 Synthesis of General Formula (Igp) from General Formula (Iga)

After reducing decahydronaphthalene derivative (II) to obtain alcohol derivative (XXV):

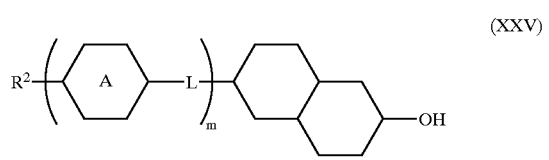
(XXV)

(wherein, $R^2$, L, ring A and m are the same as previously defined, and the decahydronaphthalene ring has a trans form), by either reacting this with a halogenating agent, p-toluene sulfonyl chloride or trifluoromethane sulfonic acid anhydride, a compound represented by general formula (XXVI):

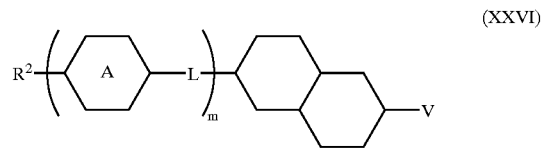
(XXVI)

(wherein, V represents a bromine or iodine halogen atom or an elimination group such as a p-toluene sulfonyloxy group or a trifluoromethane sulfonyloxy group, $R^2$, L, ring A and m are the same as previously defined, and the decahydronaphthalene ring has a trans form) is obtained. By then reacting this compound with a metal such as magnesium or alkyl lithium and so forth, organometallic reagent (XXVII):

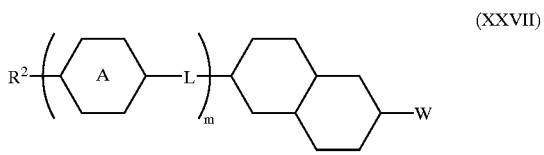
(XXVII)

(wherein, W, $R^2$, L, ring A and m are the same as previously defined, and the decahydronaphthalene ring has a trans form) is prepared, and after reacting this with 1,2,3,4-tetrahydronaphthalene-2-one derivative (XXVIII):

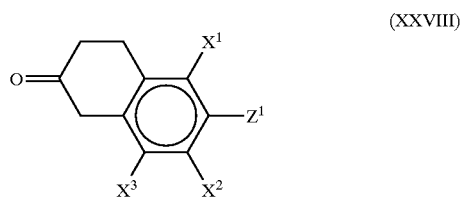
(XXVIII)

(wherein, $X^1$, $X^2$, $X^3$ and $Z^1$ are the same as previously defined), by dehydrating in the presence of acid catalyst to obtain 1,2-dihydronaphthalene derivative followed by hydrogenating the double bond of the 1,2-dihydronaphthalene ring, general formula (IA-12), which includes general formula (Igp) from general formula (Iga):

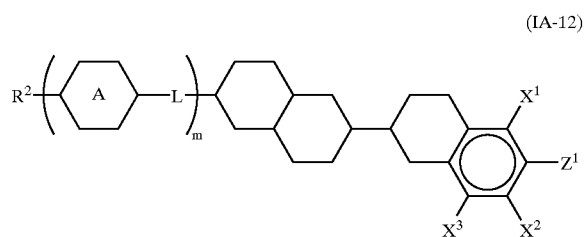
(IA-12)

(wherein, $R^2$, L, $X^1$, $X^2$, $X^3$, $Z^1$, ring A and m are the same as previously defined, and the decahydronaphthalene ring has a trans form), can be produced.

1-13 Synthesis of General Formula (Igt) from General Formula (Igq)

General formula (IA-13), which includes general formula (Igt) from general formula (Igq):

(IA-13)

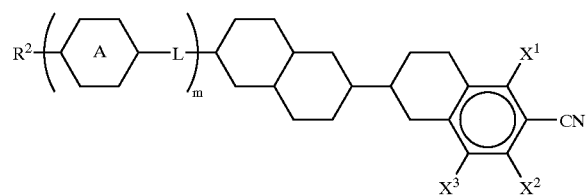

(wherein, $R^2$, L, $X^1$, $X^2$, $X^3$, ring A and m are the same as previously defined, and the decahydronaphthalene ring has a trans form), can be produced by using the method described in 1-4 and a phenyldecahydronaphthalene derivative represented by general formula (IA-12a), for which the synthesis method has already been described:

(IA-12a)

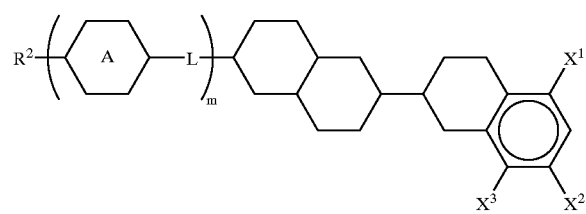

(wherein, $R^2$, L, $X^1$, $X^2$, $X^3$, ring A and m are the same as previously defined, and the decahydronaphthalene ring has a trans form).

1-14 Synthesis of General Formula (Icl) from General Formula (Icj) and General Formula (Icx) from General Formula (Icv)

After reacting organometallic reagent (XXVII) with formula (XXIX):

(XXIX)

by preparing general formula (XXX):

(XXX)

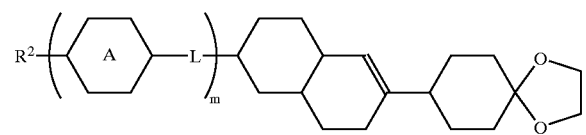

(wherein, $R^2$, L, ring A and m are the same as previously defined, and the octahydronaphthalene ring has a trans form) by dehydrating in the presence of acid catalyst, hydrogenating the double bond and removing the protection of the carbonyl groups under acidic conditions, general formula (XXXI):

(XXXI)

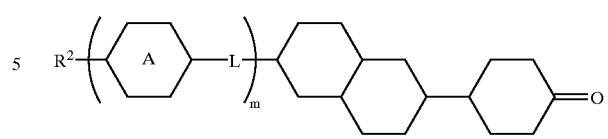

(wherein, $R^2$, L, ring A and m are the same as previously defined, and the octahydronaphthalene ring has a trans form) is obtained. After reacting this with organometallic reagent (III), by dehydrating in the presence of acid catalyst, hydrogenating the double bond of the octahydronaphthalene ring and isomerizing in the presence of alkaline catalyst as necessary, (IA-14), which includes general formula (Icl) from general formula (Icj) and general formula (Icx) from general formula (Icv):

(IA-14)

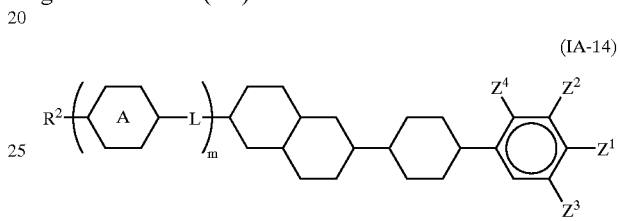

(wherein, $R^2$, L, $Z^1$, $Z^2$, $Z^3$, $Z^4$, ring A and m are the same as previously defined, and the decahydronaphthalene ring has a trans form) can be produced.

1-15 Synthesis of General Formula (Idl) from General Formula (Idj)

General formula (IA-15), which includes general formula (Idl) from general formula (Idj):

(IA-15)

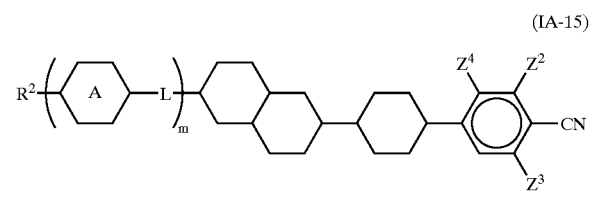

(wherein, $R^2$, L, $Z^2$, $Z^3$, $Z^4$, ring A and m are the same as previously defined, and the decahydronaphthalene ring has a trans form), can be produced using the method described in 1-4 and a phenyldecahydronaphthalene derivative represented by general formula (IA-14a), for which the synthesis method has already been described:

(IA-14a)

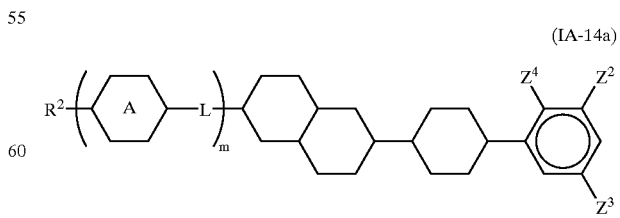

(wherein, $R^2$, L, $Z^2$, $Z^3$, $Z^4$, ring A and m are the same as previously defined, and the decahydronaphthalene ring has a trans form).

1-16 Synthesis of General Formula (Idx) from General Formula (Idv)

With the exception of using for the raw material a phenol derivative that can be produced from general formula (XXXI) or general formula (IA-1), for which the synthesis methods have already been described, general formula (IA-16), which includes general formula (Idx) from general formula (Idv):

(IA-16)

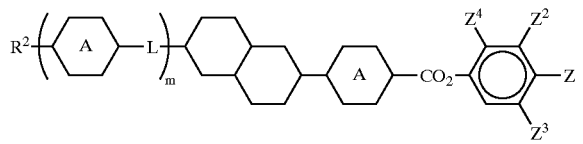

(wherein, $R^2$, L, $Z^2$, $Z^3$, $Z^4$, Z, ring A and m are the same as previously defined, the plurality of A may be the same or different, and the decahydronaphthalene ring has a trans form) can be produced using the method described in 1-5.

2. Synthesis of General Formula (I)—2

2-1 Synthesis of General Formula (Inj) from General Formula (Ina)

After reacting Wittig's reagent (VIII) with general formula (IIa), by hydrolyzing and isomerizing to the trans form using base and then repeating reaction with (VIII) and hydrolysis, alkanal derivative (L):

(L)

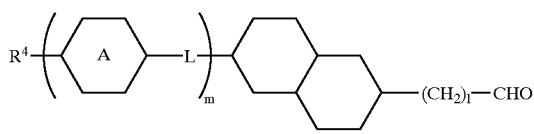

(wherein, l represents an integer of 0 or greater, $R^4$, L, ring A and m are the same as previously defined, and the decahydronaphthalene ring has a trans form) is obtained. After reacting this with general formula (X), by isomerizing the double bond to the trans conformation by allowing benzene sulfinic acid to act on the product as necessary, (IB-1), which includes general formula (Inj) from general formula (Ina):

(IB-1)

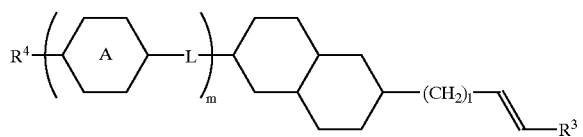

(wherein, l represents an integer of 0 or greater, $R^4$, $R^3$, L, ring A and m are the same as previously defined, and the decahydronaphthalene ring has a trans form), can be produced. In addition, after reducing alkanal derivative (XXIX) or general formula (IIa) to obtain an alcohol derivative and converting this to an alkoxide, by reacting with alkyl halide, a compound in which n=0 and Z is an alkoxy group and so forth in general formula (I) can also be produced.

2-2 Synthesis of General Formula (Ino) from General Formula (Ink)

(IB-2), which includes general formula (Inj) from general formula (Ina):

(IB-2)

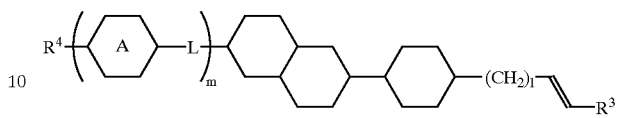

(wherein, $R^3$, $R^4$, L, ring A, l and m are the same as previously defined, and the decahydronaphthalene ring has a trans form), can be produced in the same manner as 2-1 with the exception of using general formula (XXXI) as the raw material. In addition, after reducing the alkanal derivative or general formula (XXXI) to obtain an alcohol derivative and converting this to an alkoxide in the same manner as 2-1, by reacting with alkyl halide, a compound in which Z is an alkoxy group and so forth in general formula (I) can be produced. Furthermore, an alkenyl form of general formula (XXXI) can also be produced according to 1-2.

2-3 Synthesis of General Formula (Iow) from General Formula (Ioa), General Formula (Ipe) from General Formula (Ipa), General Formula (Ipi) from General Formula (Ipg) and General Formula (Iqe) from General Formula (Iqb) General formula (XXXII):

(XXXII)

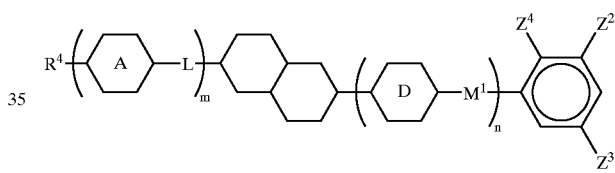

(wherein, ring A, $R^4$, m, n, L, $M^1$, $Z^2$, $Z^3$ and $Z^4$ are the same as previously defined, ring D represents a 1,4-phenylene group or trans-1,4-cyclohexylene group, and the decahydronaphthalene ring has a trans form), which can be produced by the above methods or their combinations, can be obtained. An organometallic reagent is then produced that is prepared by directly iodinating or brominating this, or lithionating with alkyl lithium, and allowing the bromine or iodine to react, followed by reacting with a metal such as magnesium or transmetalating using an organometallic reagent such as alkyl lithium. By then allowing this to react with dimethylformamide (DMF), general formula (XXXIII):

(XXXIII)

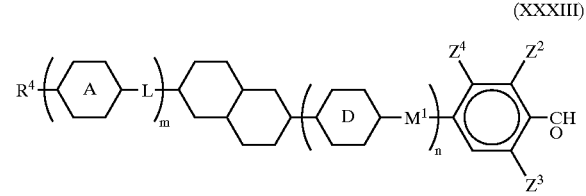

(wherein, ring A, ring D, $R^4$, m, n, L, $M^1$, $Z^2$, $Z^3$ and $Z^4$ are the same as previously defined, and the decahydronaphthalene ring has a trans form) is produced. After allowing Wittig's reagent (VIII) to react with this, by hydrolyzing and isomerizing to the trans form using base, and then repeating reaction with (VIII) and hydrolysis, alkanal derivative (XXXIV):

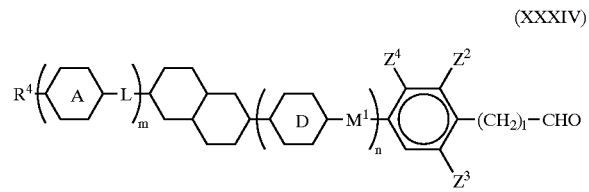
(XXXIV)

(wherein, ring A, ring D, $R^4$, l, m, n, L, $M^1$, $Z^2$, $Z^3$ and $Z^4$ are the same as previously defined, and the decahydronaphthalene ring has a trans form) is obtained. After reacting general formula (X) with this, by isomerizing the double bond to the trans conformation by allowing benzene sulfinic acid to act on this as necessary, general formula (IB-3), which includes general formula (Iow) from general formula (Ioa), general formula (Ipe) from general formula (Ipa), general formula (Ipi) from general formula (Ipg) and general formula (Iqe) from general formula (Iqb):

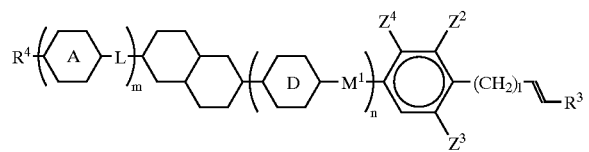
(IB-3)

(wherein, ring A, ring D, $R^3$, $R^4$, l, m, n, L, $M^1$, $Z^2$, $Z^3$ and $Z^4$ are the same as previously defined, and the decahydronaphthalene ring has a trans form), can be produced. In addition, after reducing alkanal derivative (XXXIV) to obtain an alcohol derivative and converting this to an alkoxide, by reacting with alkyl halide, a compound can also be produced in which R is an alkoxy group and so forth. Furthermore, the production method of a compound that does not contain an alkenyl group has been previously described.

2-4 Synthesis of General Formula (Ira) from General Formula (Ipf)

General formula (IB-4), which includes general formula (Ipf) and general formula (Ira):

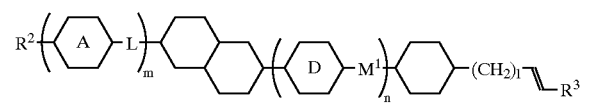
(IB-4)

(wherein, ring A, ring D, $R^3$, $R^2$, m, n, 1, L and $M^1$ are the same as previously defined, and the decahydronaphthalene ring has a trans form), can be produced by the same method as 2-1 using general formula (XXXV):

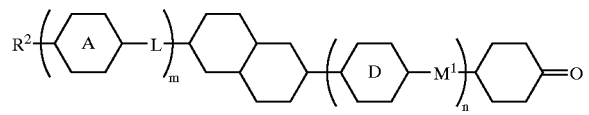
(XXXV)

(wherein, ring A, ring D, $R^2$, L, m, n and $M^1$ are the same as previously defined, and the decahydronaphthalene ring has a trans form), which can be produced according to the method of 1-13 and 1-14.

2-5 Synthesis of General Formula (Ipt) from General Formula (Ipk)

After reacting the following compound:

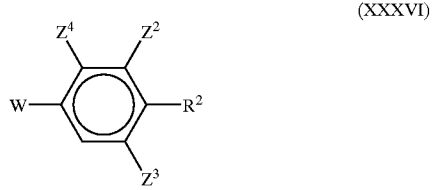
(XXXVI)

(wherein, $R^2$, $Z^2$, $Z^3$, $Z^4$ and W are the same as previously defined) with general formula (VIIa) or general formula (VIIb), by dehydrating in the presence of acid catalyst, hydrogenating the double bond of general formula (XXXVIIa) or general formula (XXXVIIb):

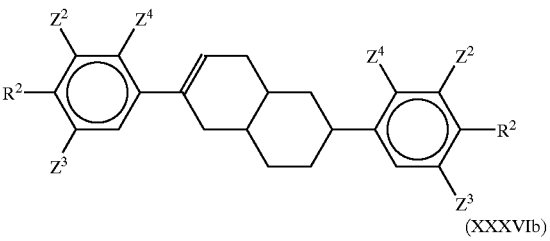
(XXXVIa)

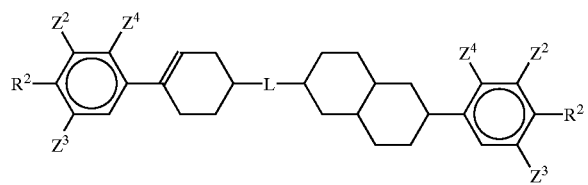
(XXXVIb)

(wherein, $R^2$, $Z^2$, $Z^3$, $Z^4$ and L are the same as previously defined, the plurality of $R^2$, $Z^2$, $Z^3$ and $Z^4$ may be the same or different, and the decahydronaphthalene ring has a trans form) and isomerizing in the presence of alkaline catalyst as necessary, general formula (IB-5), which includes general formula (Ipt) from general formula (Ipk):

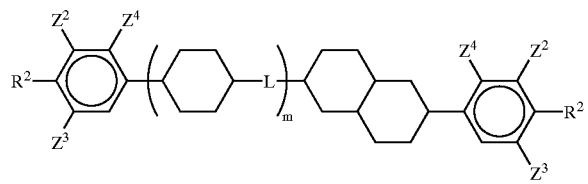
(IB-5)

(wherein, m, $R^2$, $Z^2$, $Z^3$, $Z^4$ and L are the same as previously defined, the plurality of $R^2$, $Z^2$, $Z^3$ and $Z^4$ may be the same or different, and the decahydronaphthalene ring has a trans form), can be produced.

2-6 Production of General Formula (Iqi) from General Formula (Iqf) and General Formula (Iqt) from General Formula (Iqk)

General formula (IB-6), which includes general formula (Iqi) from general formula (Iqf) and general formula (Iqt) from general formula (Iqk):

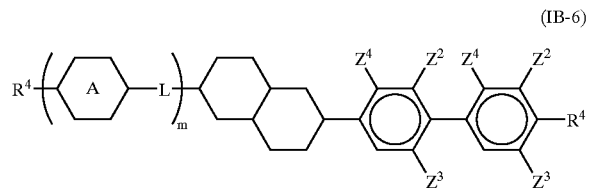
(IB-6)

(wherein, $R^4$, L, $Z^2$, $Z^3$, $Z^4$, ring A and m are the same as previously defined, the plurality of $Z^2$, $Z^3$, $Z^4$ and $R^4$ may be the same or different, and the decahydronaphthalene ring has a trans form), can be produced by reacting general formula (XXXVI) with general formula (XIV), for which the production method has already been described, in the presence of a transition metal catalyst.

2-7 Synthesis of General Formula (Irf) from General Formula (Ira)

After reacting organometallic reagent (XXVII) with general formula (IIa) or general formula (XXVIII), by dehydrating in the presence of acid catalyst and then hydrogenating the double bond, general formula (IB-7), which includes general formula (Igp) from general formula (Iga):

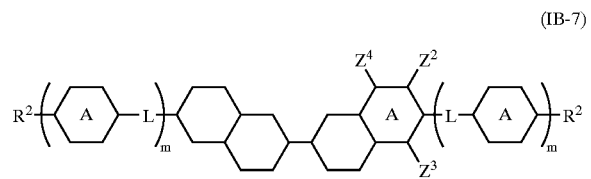
(IB-7)

(wherein, $R^2$, L, $Z^2$, $Z^3$, $Z^4$, ring A and m are the same as previously defined, and the decahydronaphthalene ring has a trans form), can be produced.

2-8 Synthesis of General Formula (Irk) from General Formula (Irg)

After reacting the following compound:

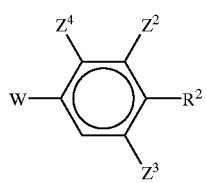
(XXXVI)

(wherein, $R^2$, $Z^2$, $Z^3$, $Z^4$ and W are the same as previously defined) with general formula (XXXI), by dehydrating in the presence of acid catalyst, hydrogenating the double bond of general formula (XXXIX):

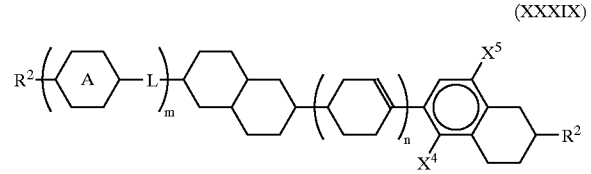
(XXXIX)

(wherein, ring A, m, n, L, $X^4$ and $X^5$ are the same as previously defined, the plurality of $R^2$ may be the same or different, and the decahydronaphthalene ring has a trans form), and isomerizing in the presence of alkaline catalyst as necessary, general formula (IB-8), which includes general formula (Irk) from general formula (Irg):

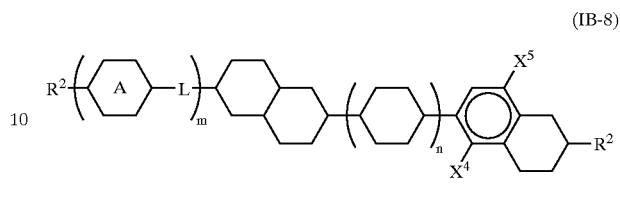
(IB-8)

(wherein, ring A, m, n, L, $X^4$ and $X^5$ are the same as previously defined, the plurality of $R^2$ may be the same or different, and the decahydronaphthalene ring has a trans form), can be produced.

3. Synthesis of General Formula (I)—3

3-1 By reacting a phenyl lithium reagent represented by general formula (XVa):

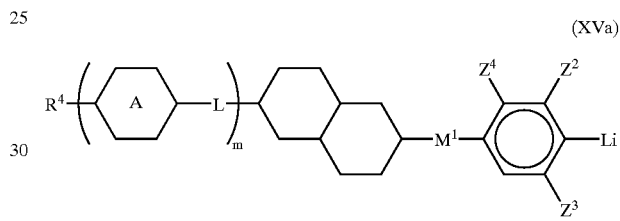
(XVa)

(wherein, $R^4$, L, $Z^2$, $Z^3$, $Z^4$, ring A, $M^1$ and m are the same as previously defined, and the decahydronaphthalene ring has a trans form) with a phenyltrifluoroethylene derivative represented by general formula (XL):

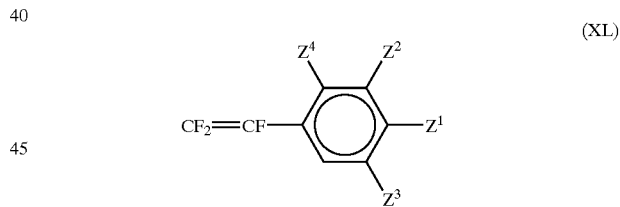
(XL)

(wherein, $Z^1$, $Z^2$, $Z^3$ and $Z^4$ are the same as previously defined) and de-protecting the protective groups as necessary, general formula (IC-1):

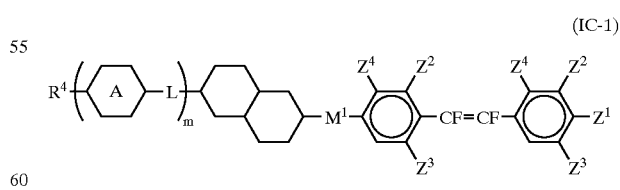
(IC-1)

(wherein, $R^4$, L, $Z^1$, $Z^2$, $Z^3$, $Z^4$, ring A, $M^1$ and m are the same as previously defined, the plurality of $Z^2$, $Z^3$ and $Z^4$ may be the same or different, the steric form of the double bonds represents the trans form, and the decahydronaphthalene ring has a trans form) can be produced.

3-2 By reacting a thiocarboxylate-O-ester represented by general formula (XLI):

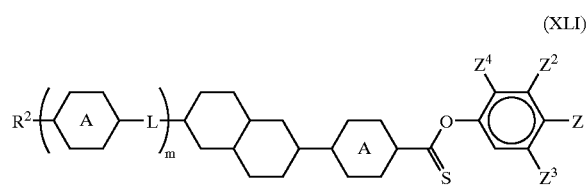
(XLI)

(wherein, $R^2$, L, Z, $Z^2$, $Z^2$, $Z^4$, ring A and m are the same as previously defined, the plurality of rings A may be the same or different, and the decahydronaphthalene ring has a trans form) with a fluorinating agent such as DAST, and de-protecting the protective groups as necessary, general formula (IC-2):

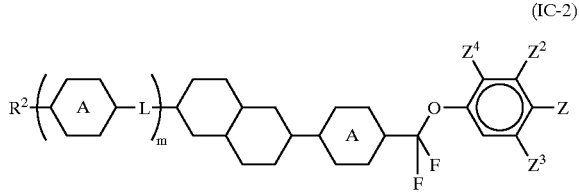
(IC-2)

(wherein, $R^2$, L, $Z^2$ $Z^3$ $Z^4$, Z, ring A and m are the same as previously defined, the plurality of rings A may be the same or different, and the decahydronaphthalene ring has a trans form) can be produced.

Here, thiocarboxylate-O-ester can be produced by reacting the corresponding carboxylate ester (IA-16) with Lawesson's reagent.

3-3 General formula (IC-3):

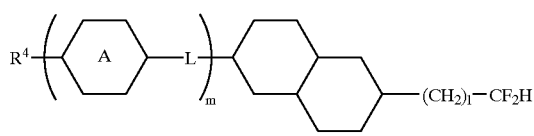
(IC-3)

(wherein, l is an integer of 0 or greater, $R^4$, L, ring A and m are the same as previously defined, and the decahydronaphthalene ring has a trans form) can be produced by reacting sodium chlorodifluoroacetate with an alkanal derivative (L) to overheating.

4. Synthesis of General Formula (I) Intermediates
4-1 Synthesis of General Formula (II)
After reacting general formula (XLIII):

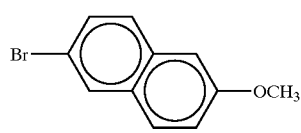
(XLIII)

with general formula (XLIV):

(XLIV)

(wherein, $R^4$, W and m are the same as previously defined) in the presence of a transition metal catalyst, by de-protecting the resulting general formula (XLV):

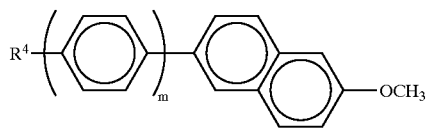
(XLV)

(wherein, $R^4$ and m are the same as previously defined), general formula (XLVI):

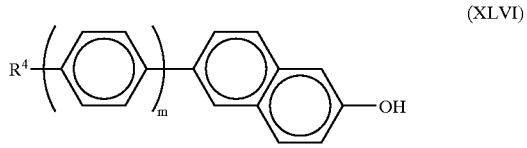
(XLVI)

(wherein, $R^4$ and m are the same as previously defined) is obtained. By then hydrogenating the aromatic rings of this compound, general formula (XLVII):

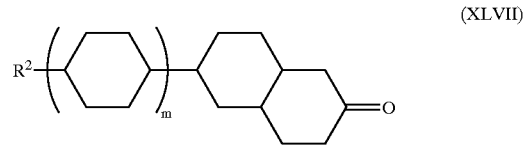
(XLVII)

(wherein, $R^2$ and m are the same as previously defined) can be produced. In addition, after reacting general formula (XLVIII):

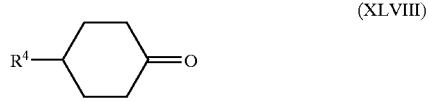
(XLVIII)

wherein, $R^4$ is the same as previously defined, with general formula (XLIIIa):

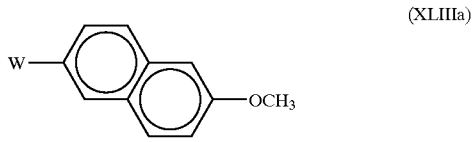
(XLIIIa)

(wherein, W is the same as previously defined) and dehydrating, general formula (XLIX):

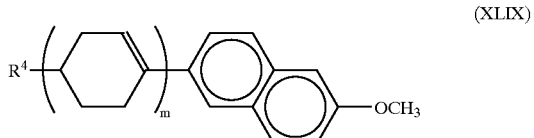
(XLIX)

(wherein, $R^4$ and m are the same as previously defined) is obtained. General formula (XLVII) can also be produced by hydrogenating this compound.

4-2 Synthesis of General Formula (V-1)

Formula (V-1D) is obtained by hydrogenating formula (V-1C). General formula (V-1):

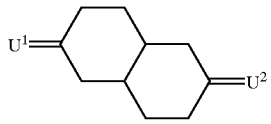
(V-1)

(wherein, $U^1$ and $U^2$ are the same as previously defined) can be produced by acetalation of the carbonyl groups followed by isolation of the diketone, monoacetal and diacetal.

4-3 Synthesis of General Formula (V-2) General formula (LII):

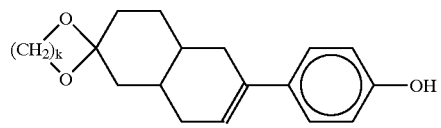
(LII)

(wherein, k is the same as previously defined) is obtained by reacting general formula (XLIV) with general formula (V-1A), dehydrating, de-protecting the resulting compound and reacetalization. General formula (V-2) in which L is a single bond can then be produced by hydrogenating the aromatic ring of this compound and oxidizing or acetalating as necessary. In addition, general formula (LI):

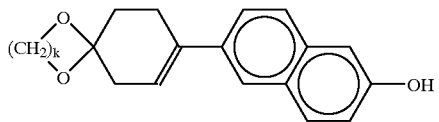
(LI)

(wherein, k is the same as previously defined) is obtained by reacting general formula (XLIIIa) with general formula (V-1A), dehydrating, de-protecting the resulting compound and reacetalization. General formula (V-2) in which L is a single bond can then be produced by hydrogenating the aromatic rings of this compound and oxidizing or acetalating as necessary. Furthermore, in cases when L is not a single bond, general formula (LIII) or general formula (LIV):

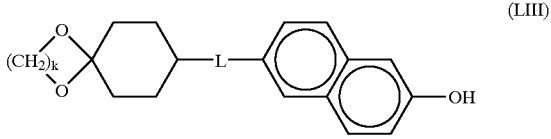
(LIII)

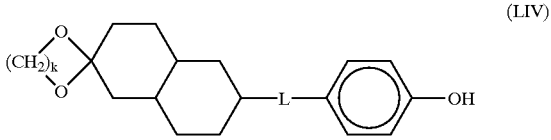
(LIV)

(wherein, k and L are the same as previously defined) is obtained in accordance with the method described above. This compound can be obtained by hydrogenating using the method described above.

Specific examples of typical examples of compound (I) of the present invention produced in this manner are summarized in Table 1.

TABLE 1

Compound 1 Represented by General Formula (I):

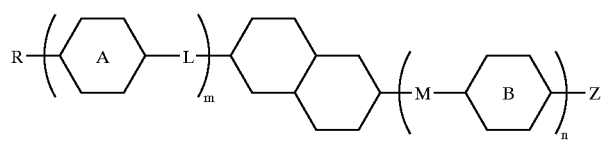
(I)

| Compound | Formula | Phase transition temperature (° C.) |
|---|---|---|
| I-1 | n-C$_3$H$_7$—[structure]—F | C 52 (N 46) I |
| I-2 | n-C$_3$H$_7$—[structure]—F, F | oil |
| I-3 | n-C$_3$H$_7$—[structure]—F, F, F | C 46 I |

TABLE 1-continued

Compound 1 Represented by General Formula (I):

$$R-\left(\!\!\begin{array}{c}\bigcirc\!\!\!\!\bigcirc\\A\end{array}\!\!-L\right)_{\!m}\!\!\!\!\bigcirc\!\!\!\!\bigcirc\!\!\!\!\left(\!\!M-\!\!\bigcirc\!\!\!\!\bigcirc\!\!\!\!\right)_{\!n}\!\!\!-Z \quad (I)$$

| Compound | Formula | Phase transition temperature (° C.) |
|---|---|---|
| I-4 | n-C$_3$H$_7$–[decalin]–[phenyl]–OCF$_3$ | C 47 I |
| I-5 | CH$_2$=CHCH$_2$–[decalin]–[phenyl(3,4-diF)]–F | — |
| I-6 | CH$_3$CH=CH–[decalin]–[phenyl(3,4,5-triF)] | — |
| I-7 | CH$_2$=CHCH(CH$_3$)CH$_2$–[cyclohexyl(CH$_3$)]–[phenyl]–OCF$_3$ | — |
| I-8 | n-C$_3$H$_7$–[decalin]–CH$_2$CH$_2$–[phenyl(3,4,5-triF)] | — |

(In the table, C indicates the crystal phase, N the nematic phase, and I an isotropic liquid.)

TABLE 2

Compound 2 Represented by General Formula (I):

$$R-\left(\!\!\begin{array}{c}\bigcirc\!\!\!\!\bigcirc\\A\end{array}\!\!-L\right)_{\!m}\!\!\!\!\bigcirc\!\!\!\!\bigcirc\!\!\!\!\left(\!\!M-\!\!\bigcirc\!\!\!\!\bigcirc\!\!\!\!\right)_{\!n}\!\!\!-Z \quad (I)$$

| Compound | Formula | Phase transition temperature (° C.) |
|---|---|---|
| I-9 | n-C$_3$H$_7$–[decalin]–[phenyl(3-F)]–CN | — |

TABLE 2-continued
Compound 2 Represented by General Formula (I):
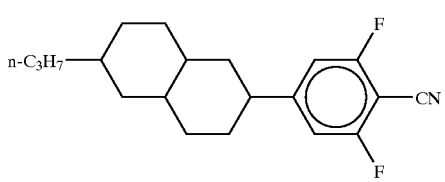
| Compound | Formula | Phase transition temperature (° C.) |
|---|---|---|
| I-10 | 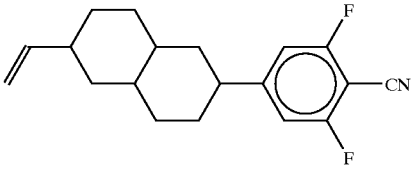 | C 86 (N 18) I |
| I-11 | 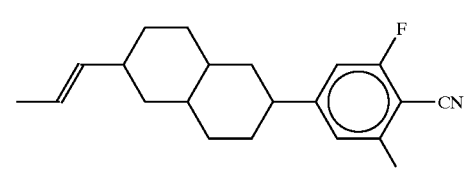 | C 80 N 129 I |
| I-12 | 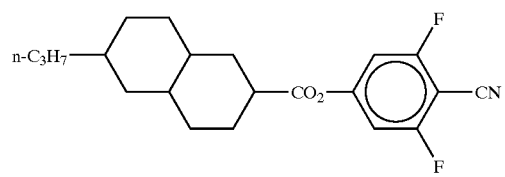 | C 88 I |
| I-13 | 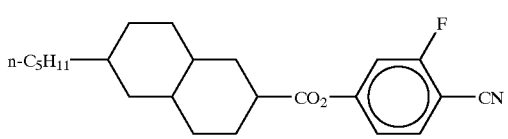 | — |
| I-14 | | — |

TABLE 2-continued
Compound 2 Represented by General Formula (I):
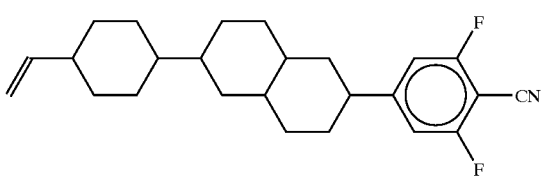
| Compound | Formula | Phase transition temperature (° C.) |
|---|---|---|
| I-15 | 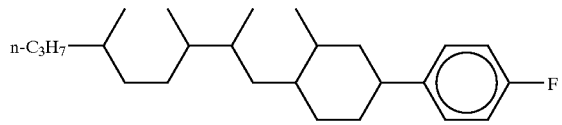 | — |
(In the table, C indicates the crystal phase, N the nematic phase, and I an isotropic liquid.)
TABLE 3
Compound 3 Represented by General Formula (I):
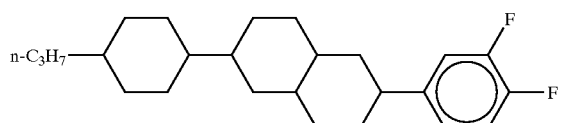
| Compound | Formula | Phase transition temperature (° C.) |
|---|---|---|
| I-16 | 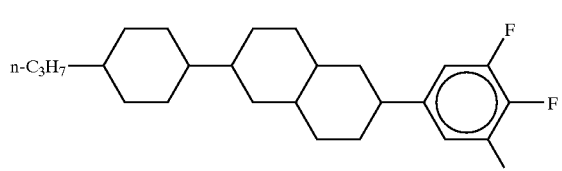 | C 102 N 220 I |
| I-17 | | C 62 N 188 I |
| I-18 | | C 76 N 141 I |
| I-19 | | C 94 N 215 I |

TABLE 3-continued

Compound 3 Represented by General Formula (I):

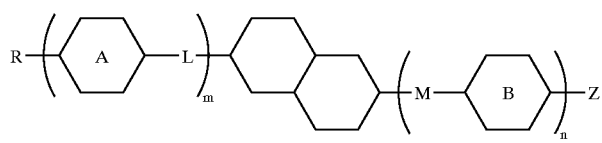

| Compound | Formula | Phase transition temperature (° C.) |
|---|---|---|
| I-20 | n-C$_5$H$_{11}$—[decalin]—[phenyl]—[phenyl(F,F,F)] | — |
| I-21 | n-C$_3$H$_7$—[decalin]—[phenyl(F,F)]—[phenyl(F,F)] | C 96 N 107 I |

(In the table, C indicates the crystal phase, N the nematic phase, and I an isotropic liquid.)

TABLE 4

Compound 4 Represented by General Formula (I):

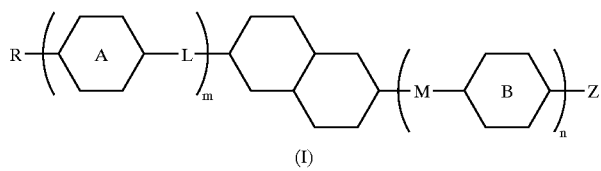

| Compound | Formula | Phase transition temperature (° C.) |
|---|---|---|
| I-22 | [allyl]—[decalin]—[allyl] | oil |
| I-23 | [vinyl]—[decalin]—[cyclohexyl]—n-C$_3$H$_7$ | C 24 N 115 I |
| I-24 | [propenyl]—[decalin]—[cyclohexyl]—n-C$_3$H$_7$ | C 67 N 139 I |

TABLE 4-continued

Compound 4 Represented by General Formula (I):

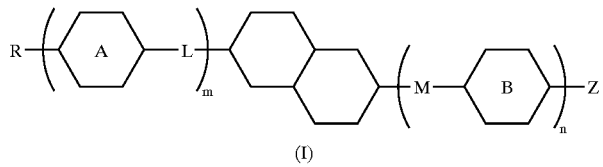

(I)

| Compound | Formula | Phase transition temperature (° C.) |
|---|---|---|
| I-25 | | C 30 N 99 I |
| I-26 | | — |
| I-27 | | — |
| I-28 | | — |

(In the table, C indicates the crystal phase, N the nematic phase, and I an isotropic liquid.)

Since many of the compounds represented by general formula (I) exhibit superior co-solubility with other liquid crystal materials, they can be suitably used as materials for liquid crystal display cells in the state of a mixture with other liquid crystal compounds. Although the compound of (I) can be used in any of the various display methods previously described, they are suited for use in simple matrix driving or active matrix driving TN display elements and STN display elements.

In this manner, although compositions provided by the present invention contain at least one type of compound represented by general formula (I) as their first component for as preferable typical examples of nematic liquid crystal compounds that can be used by mixing with a compound represented by general formula (I), they particularly preferably contain at least one type of the second to fourth components indicated below as other components.

Namely, the second component is a so-called fluorine-based (halogen-based) p type liquid crystal compound that is composed of the compounds indicated in general formulas (A1) through (A3) below.

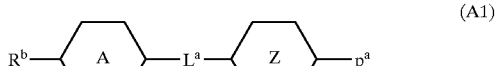 (A1)

 (A2)

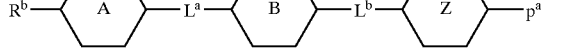 (A3)

In the above formulas, $R^b$ represents an alkyl group having 1–12 carbon atoms, these may have a straight chain or methyl or ethyl branched structure, a 3–6 membered ring structure, any arbitrary —$CH_2$— present in the group may be replaced by —O—, —CH=CH—, —CH=CF—, —CF=CH—, —CF=CF— or —C≡C—, and any arbitrary hydrogen atom present in the group may be substituted with a fluorine atom or trifluoromethoxy group. However, a straight chain alkyl group having 2–7 carbon atoms, straight chain 1-alkenyl group having 2–7 carbon atoms, straight chain 3-alkenyl group having 4–7 carbon atoms and an alkyl group having 1–5 carbon atoms in which the terminal is substituted with an alkoxyl group having 1–3 carbon atoms are preferable. In addition, the compound may have optical activity or be a racemic mixture in the case asymmetric carbons are formed as a result of branching.

Rings A, B and C respectively and independently represent a trans-1,4-cyclohexylene group, trans-decahydronaphthalene-trans-2,6-diyl group, 1,4-phenylene group that may be substituted with one or more fluorine atoms, naphthalene-2,6-diyl group that may be substituted with one or more fluorine atoms, tetrahydronaphthalene-2,6-diyl group that may be substituted with one or more fluorine atoms, 1,4-cyclohexenylene group that may be substituted with a fluorine atom, 1,3-dioxane-trans-2,5-diyl group, pyrimidine-2,5-diyl group or pyridine-2,5-diyl group. However, a trans-1,4-cyclohexylene group, trans-decahydronaphthalene-trans-2,6-diyl group, naphthalene-2,6-diyl group that may be substituted with a fluorine atom, or 1,4-phenylene group that may be substituted with 1 or 2 fluorine atoms is preferable. In particular, it is preferable that ring A be a trans-1,4-cyclohexylene group in the case ring B is a trans-1,4-cyclohexylene group or trans-decahydronaphthalene-trans-2,6-diyl group, and it is preferable that rings B and A be trans-1,4-cyclohexylene groups in the case ring C is a trans-1,4-cyclohexylene group or trans-decahydronaphthalene-trans-2,6-diyl group. In addition, it is preferable that ring A be a trans-1,4-cyclohexylene group in (A3).

$L^a$, $L^b$ and $L^c$ are connecting groups that respectively and independently represent a single bond, ethylene group (—CH$_2$CH$_2$—), 1,2-propylene group (—CH(CH$_3$)CH$_2$— and —CH$_2$CH(CH$_3$)—), 1,4-butylene group, —COO—, —OCO—, —OCF$_2$—, —CF$_2$O—, —CH=CH—, —CH=CF—, —CF=CH—, —CF=CF—, —C≡C— or —CH=NN=CH—. However, a single bond, ethylene group, 1,4-butylene group, —COO—, —OCF$_2$—, —CF$_2$O—, —CH=CF— or —C≡C— is preferable, and a single bond or ethylene group is particularly preferable. In addition, it is preferable that at least one of these represent a single bond in (A2), and at least two of these represent a single bond in (A3).

Ring Z is an aromatic ring that can be represented by general formulas (La) through (Lc) below.

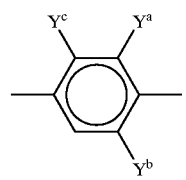

(La)

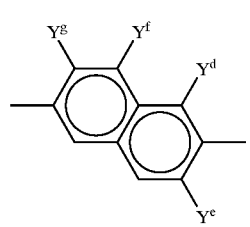

(Lb)

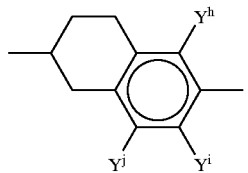

(Lc)

In these formulas, $Y^a$ through $Y^j$ respectively and independently represent a hydrogen atom or fluorine atom. However, it is preferable that at least one of $Y^a$ and $Y^b$ be a fluorine atom in (La), and it is preferable that at least one of $Y^d$ through $Y^f$ be a fluorine atom in (Lb), with $Y^d$ particularly preferably being a fluorine atom.

Terminal group $P^a$ represents a fluorine atom, chlorine atom, trifluoromethoxy group, difluoromethoxy group, trifluoromethyl group or difluoromethyl group, or an alkoxyl group, alkyl group, alkenyl group or alkenyloxy group having 2 or 3 carbon atoms and substituted by a fluorine atom or more than one fluorine atoms. However, a fluorine atom, trifluoromethoxy group or difluoromethoxy group is preferable, and a fluorine atoms is particularly preferable.

In addition, the compounds of general formula (I) of the present invention are excluded in (A2).

The third component is a so-called cyano-based p type liquid crystal compound, and is composed of the compounds indicated with general formulas (B1) through (B3) below.

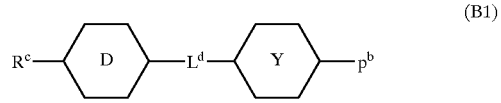

(B1)

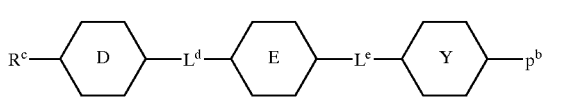

(B2)

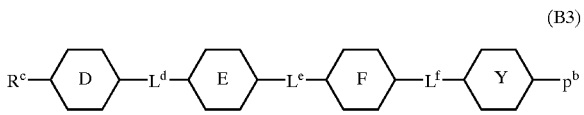

(B3)

In the above formulas, $R^c$ represents an alkyl group having 1–12 carbon atoms, and these may have a straight chain or methyl or ethyl branched structure, a 3–6 membered ring structure, any arbitrary —CH$_2$— present in the group may be replaced by —O—, —CH=CH—, —CH=CF—, —CF=CH—, —CF=CF— or —C≡C—, and any arbitrary hydrogen atom present in the group may be substituted with a fluorine atom or trifluoromethoxy group. However, a straight chain alkyl group having 2–7 carbon atoms, straight chain 1-alkenyl group having 2–7 carbon atoms, straight chain 3-alkenyl group having 4–7 carbon atoms and an alkyl group having 1–5 carbon atoms in which the terminal is substituted with an alkoxyl group having 1–3 carbon atoms are preferable. In addition, the compound may have optical activity or be a racemic mixture in the case asymmetric carbons are formed as a result of branching.

Rings D, E and F respectively and independently represent a trans-1,4-cyclohexylene group, trans-decahydronaphthalene-trans-2,6-diyl group, 1,4-phenylene group that may be substituted with one or more fluorine atoms, naphthalene-2,6-diyl group that may be substituted with one or more fluorine atoms, tetrahydronaphthalene-2,6-diyl group that may be substituted with one or more fluorine atoms, 1,4-cyclohexenylene group that may be substituted with a fluorine atom, 1,3-dioxane-trans-2,5-diyl group, pyrimidine-2,5-diyl group or pyridine-2,5-diyl group. However, a trans-1,4-cyclohexylene group, trans-decahydronaphthalene-trans-2,6-diyl group, naphthalene-2,6-diyl group that may be substituted with a fluorine atom, or 1,4-phenylene group that may be substituted with 1 or 2 fluorine atoms is preferable. In particular, it is preferable that ring D be a trans-1,4-cyclohexylene group in the case ring E is a trans-1,4-cyclohexylene group or trans-decahydronaphthalene-trans-2,6-diyl group, and it is preferable that rings D and E be trans-1,4-cyclohexylene groups in the case ring F is a trans-1,4-cyclohexylene group or trans-decahydronaphthalene-trans-2,6-diyl group. In addition, it is preferable that ring D be a trans-1,4-cyclohexylene group in (B3).

$L^d$, $L^e$ and $L^f$ are connecting groups that respectively and independently represent a single bond, ethylene group (—CH$_2$CH$_2$—), 1,2-propylene group (—CH(CH$_3$)CH$_2$— and —CH$_2$CH(CH$_3$)—), 1,4-butylene group, —COO—, —OCO—, —OCF$_2$—, —CF$_2$O—, —CH=CH—, —CH=CF—, —CF=CH—, —CF=CF—, —C≡C—, —OCH$_2$—, —CH$_2$O— or —CH=NN=CH—. However, a single bond, ethylene group, —COO—, —OCF$_2$—, —CF$_2$O—, —CF=CF— or —C≡C— is preferable, and a single bond, ethylene group or —COO— is particularly preferable. In addition, it is preferable that at least one of these represent a single bond in (B2), and at least two of these represent a single bond in (B3).

Ring Y is an aromatic ring that can be represented by general formulas (Ld) through (Lf) below.

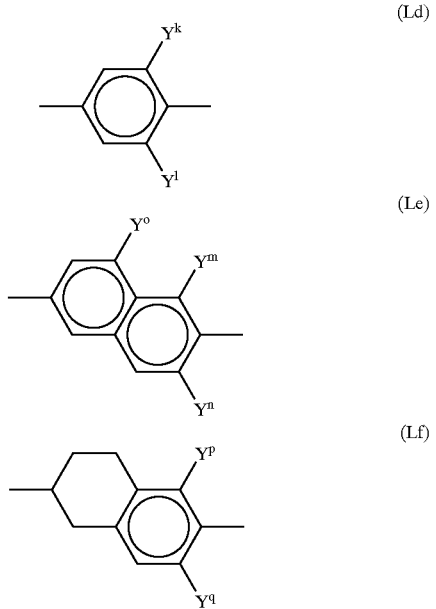

In these formulas, $Y^k$ through $Y^q$ respectively and independently represent a hydrogen atom or fluorine atom. However, $Y^n$ and $Y^o$ are preferably hydrogen atoms in (Le). Although terminal group $P^b$ represents a cyano group (—CN—), cyanato group (—OCN—) or —C≡CCN, a cyano group is preferable.

In addition, the compounds of general formula (I) of the present invention are excluded in (B2).

The fourth component is a non-polar liquid crystal having dielectric anisotropy of near 0, and is composed of the compounds indicated with general formulas (C1) through (C3) below.

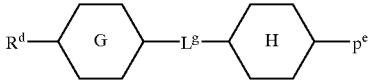

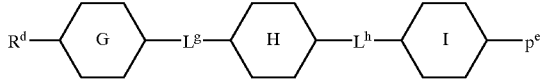

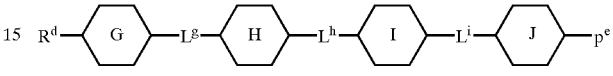

In the above formulas, $R^d$ and $P^e$ respectively and independently represent an alkyl group having 1–12 carbon atoms, and these may have a straight chain or methyl or ethyl branched structure, a 3–6 membered ring structure, any arbitrary —CH$_2$— present in the group may be replaced by —O—, —CH=CH—, —CH=CF—, —CF=CH—, —CF=CF— or —C≡C—, and any arbitrary hydrogen atom present in the group may be substituted with a fluorine atom or trifluoromethoxy group. However, a straight chain alkyl group having 1–7 carbon atoms, straight chain 1-alkenyl group having 2–7 carbon atoms, straight chain 3-alkenyl group having 4–7 carbon atoms and an alkyl group having 1–5 carbon atoms in which the terminal is substituted with an alkoxyl group having 1–3 carbon atoms are preferable. Moreover, it is more preferable that at least one of these represent a straight chain alkyl group having 1–7 carbon atoms, a straight chain 1-alkenyl group having 2–7 carbon atoms, or a straight chain 3-alkenyl group having 4–7 carbon atoms.

Rings G, H, I and J respectively and independently represent a trans-1,4-cyclohexylene group, trans-decahydronaphthalene-trans-2,6-diyl group, 1,4-phenylene group that may be substituted with one or two fluorine atoms, naphthalene-2,6-diyl group that may be substituted with one or more fluorine atoms, tetrahydronaphthalene-2,6-diyl group that may be substituted with one or two fluorine atoms, 1,4-cyclohexenylene group that may be substituted with one or two fluorine atoms, 1,3-dioxane-trans-2,5-diyl group, pyrimidine-2,5-diyl group or pyridine-2,5-diyl group. However, it is preferable that in each compound there be no more than one trans-decahydronaphthalene-trans-2,6-diyl group, naphthalene-2,6-diyl group that may be substituted with one or more fluorine atoms, tetrahydronaphthalene-2,6-diyl group that may be substituted with one or two fluorine atoms, 1,4-cyclohexenylene group that may be substituted with a fluorine atom, 1,3-dioxane-trans-2,5-diyl group, pyrimidine-2,5-diyl group or pyridine-2,5-diyl group, and that the other rings be a trans-1,4-cyclohexylene group or a 1,4-phenylene group that may be substituted with 1 or 2 fluorine atoms or methyl groups.

$L^g$, $L^h$ and $L^i$ are connecting groups that respectively and independently represent a single bond, ethylene group (—CH$_2$CH$_2$—), 1,2-propylene group (—CH(CH$_3$)CH$_2$— and —CH$_2$CH(CH$_3$)—), 1,4-butylene group, —COO—, —OCO—, —OCF$_2$—, —CF$_2$O—, —CH=CH—, —CH=CF—, —CF=CH—, —CF=CF—, —C≡C— or —CH=NN=CH—. However, a single bond, ethylene group, —COO—, —OCF$_2$—, —CF$_2$O—, —CF=CF— or —C≡C— is preferable, and a single bond, ethylene group, 1,4-butylene group, —COO—, —OCO—, —OCF$_2$—, —CF$_2$O—, —CF═CF—, —C—C— or —CH═NN═CH— is particularly preferable. In addition, it is preferable that at least one of these represent a single bond in (C2), and at least two of these represent a single bond in (C3).

In addition, the compounds of general formula (I) of the present invention are excluded in (C2).

More preferable forms in (C1) can be represented by general formulas (C1a) through (C1h) below.

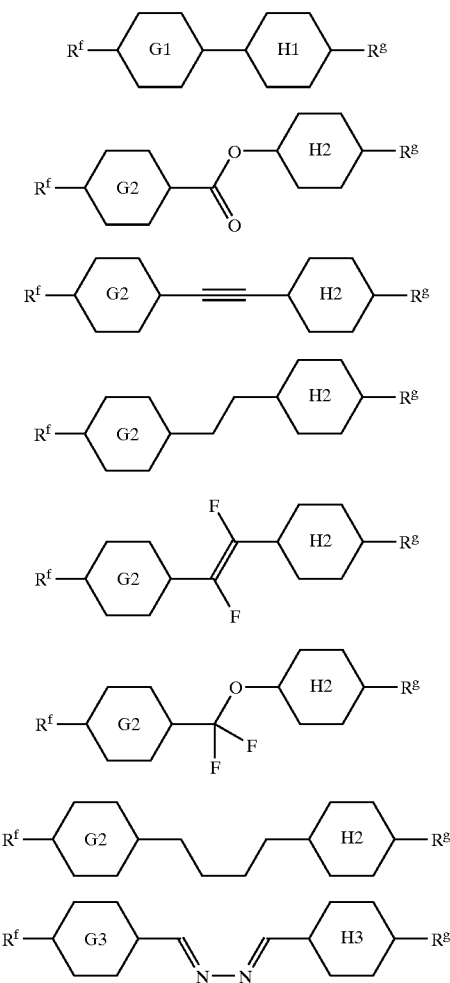

In each of the above formulas, R$^f$ and P$^g$ respectively and independently represent a straight chain alkyl group having 1–7 carbon atoms, straight chain 1-alkenyl group having 2–7 carbon atoms, straight chain 3-alkenyl group having 4–7 carbon atoms, straight chain alkoxyl group having 1–3 carbon atoms or a straight chain alkyl group having 1–5 carbon atoms in which the terminal is substituted with an alkoxyl group having 1–3 carbon atoms. However, at least one of these represents a straight chain alkyl group having 1–7 carbon atoms, straight chain 1-alkenyl group having 2–7 carbon atoms or straight chain 3-alkenyl group having 4–7 carbon atoms. However, in the case rings G1 through G3 are aromatic rings, the case of the corresponding R$^f$ being a 1-alkenyl group or alkoxyl group is excluded, and in the case rings H1 through H3 are aromatic rings, the case of the corresponding R$^9$ being a 1-alkenyl group or alkoxyl group is excluded.

Rings G1 and H1 respectively and independently represent a trans-1,4-cyclohexylene group, trans-decahydronaphthalene-trans-2,6-diyl group, 1,4-phenylene group that may be substituted with one or two fluorine atoms, naphthalene-2,6-diyl group that may be substituted with one or more fluorine atoms, tetrahydronaphthalene-2,6-diyl group that may be substituted with one or two fluorine atoms, 1,4-cyclohexenylene group that may be substituted with one or two fluorine atoms, 1,3-dioxane-trans-2,5-diyl group, pyrimidine-2,5-diyl group or pyridine-2,5-diyl group. However, it is preferable that in each compound there be no more than one trans-decahydronaphthalene-trans-2,6-diyl group, naphthalene-2,6-diyl group that may be substituted with one or more fluorine atoms, tetrahydronaphthalene-2,6-diyl group that may be substituted with one or two fluorine atoms, 1,4-cyclohexenylene group that may be substituted with a fluorine atom, 1,3-dioxane-trans-2,5-diyl group, pyrimidine-2,5-diyl group or pyridine-2,5-diyl group, and that the other rings in this case be a trans-1,4-cyclohexylene group or a 1,4-phenylene group that may be substituted with 1 or 2 fluorine atoms or methyl groups. Rings G2 and H2 respectively and independently represent a trans-1,4-cyclohexylene group, trans-decahydronaphthalene-trans-2,6-diyl group, 1,4-phenylene group that may be substituted with one or two fluorine atoms or methyl groups, naphthalene-2,6-diyl group that may be substituted with one or more fluorine atoms, or tetrahydronaphthalene-2,6-diyl group that may be substituted with one or two fluorine atoms. However, it is preferable that in each compound there be no more than one trans-decahydronaphthalene-trans-2,6-diyl group, naphthalene-2,6-diyl group that may be substituted with one or more fluorine atoms or tetrahydronaphthalene-2,6-diyl group that may be substituted with one or two fluorine atoms, and that the other rings in this case be a trans-1,4-cyclohexylene group or a 1,4-phenylene group that may be substituted with one or two fluorine atoms or methyl groups. Rings G3 and H3 respectively and independently represent a 1,4-phenylene group that may be substituted with one or two fluorine atoms or methyl groups, naphthalene-2,6-diyl group that may be substituted with one or more fluorine atoms or tetrahydronaphthalene-2,6-diyl group that may be substituted with one or two fluorine atoms. However, it is preferable that in each compound there be no more than one naphthalene-2,6-diyl group that may be substituted with one or more fluorine atoms or tetrahydronaphthalene-2,6-diyl group that may be substituted with one or two fluorine atoms.

More preferable forms in (C2) can be represented by general formulas (C2a) through (C2m) below.

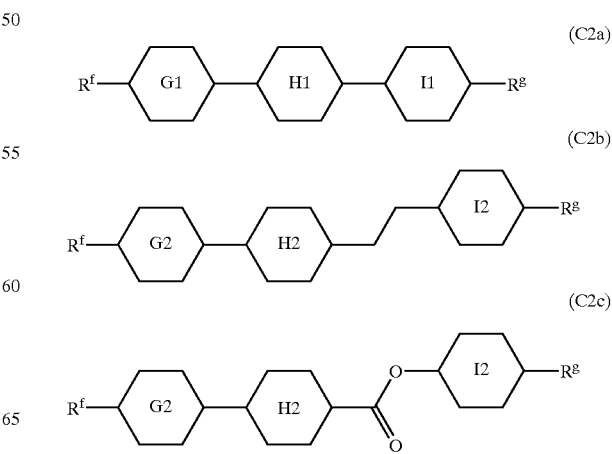

-continued

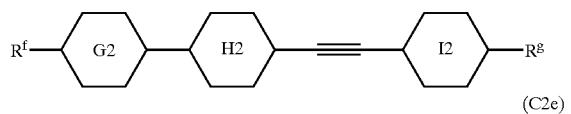
(C2d)

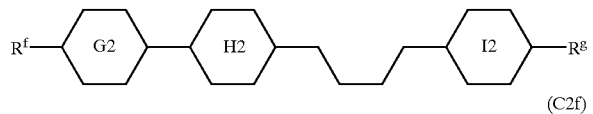
(C2e)

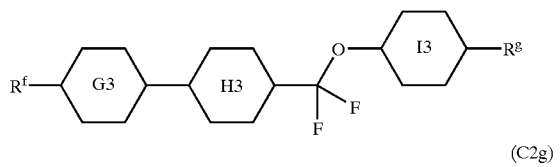
(C2f)

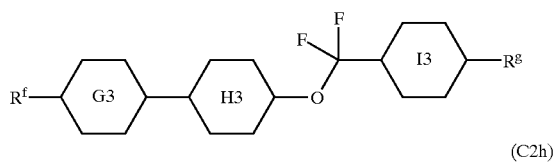
(C2g)

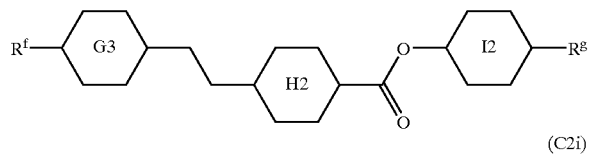
(C2h)

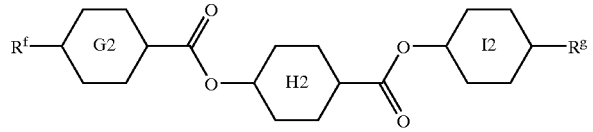
(C2i)

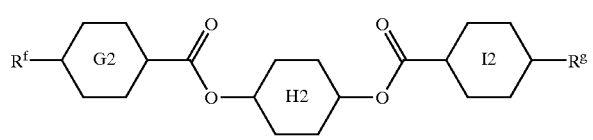
(C2j)

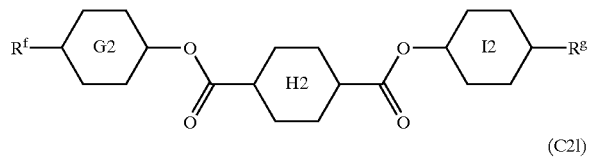
(C2k)

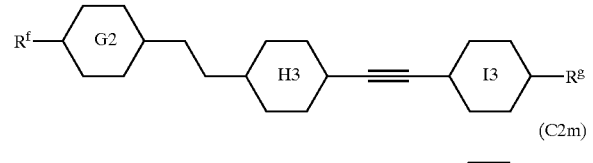
(C2l)

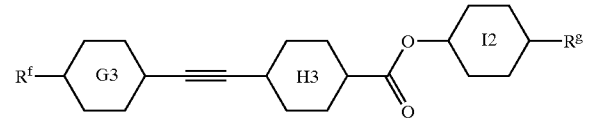
(C2m)

In the above formulas, rings G1, G2, G3, H1, H2 and H3 are the same as previously defined, and ring I1 is the same as ring G1, ring I2 is the same as ring G2 and ring I3 is the same as ring G3. In addition, it is preferable that in each compound there be no more than one trans-decahydronaphthalene-trans-2,6-diyl group, naphthalene-2,6-diyl group that may be substituted with one or more fluorine atoms, tetrahydronaphthalene-2,6-diyl group that may be substituted with one or two fluorine atoms, 1,4-cyclohexenylene group that may be substituted with a fluorine atom, 1,3-dioxane-trans-2,5-diyl group, pyrimidine-2,5-diyl group or pyridine-2,5-diyl group, and that the other rings in this case be a trans-1,4-cyclohexylene group or a 1,4-phenylene group that may be substituted with one or two fluorine atoms or methyl groups.

Next, more preferable forms in (C3) can be represented by general formulas (C3a) through (C3f) below.

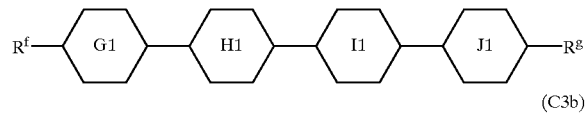
(C3a)

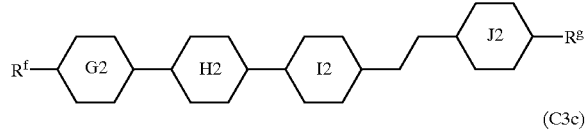
(C3b)

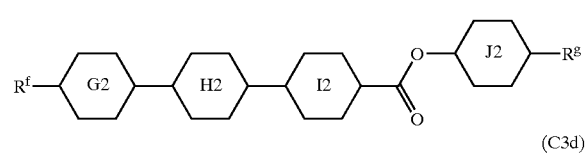
(C3c)

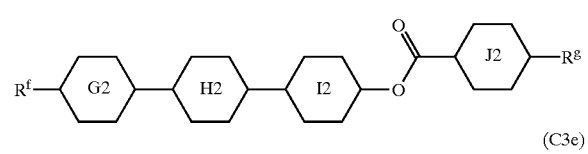
(C3d)

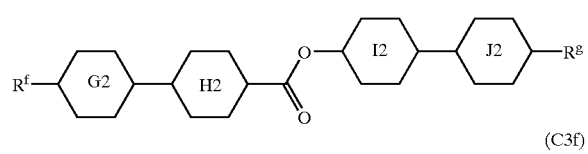
(C3e)

(C3f)

In the above formulas, rings G1, G2, H1, H2, I1 and I2 are the same as previously defined, and ring J1 is the same as ring G1 or ring J2 is the same as ring G2. In addition, it is preferable that in each compound there be no more than one trans-decahydronaphthalene-trans-2,6-diyl group, naphthalene-2,6-diyl group that may be substituted with one or more fluorine atoms, tetrahydronaphthalene-2,6-diyl group that may be substituted with one or two fluorine atoms, 1,4-cyclohexenylene group that may be substituted with a fluorine atom, 1,3-dioxane-trans-2,5-diyl group, pyrimidine-2,5-diyl group or pyridine-2,5-diyl group, and that the other rings in this case be a trans-1,4-cyclohexylene group or a 1,4-phenylene group that may be substituted with one or two fluorine atoms or methyl groups.

EXAMPLES

The present invention will be further described with reference to examples of the present invention shown below. However, the present invention is not limited to these examples.

Example 1

Synthesis of trans-6-propyl-trans-2-(3,4,5-trifluorophenyl)-trans-decahydronaphthalene

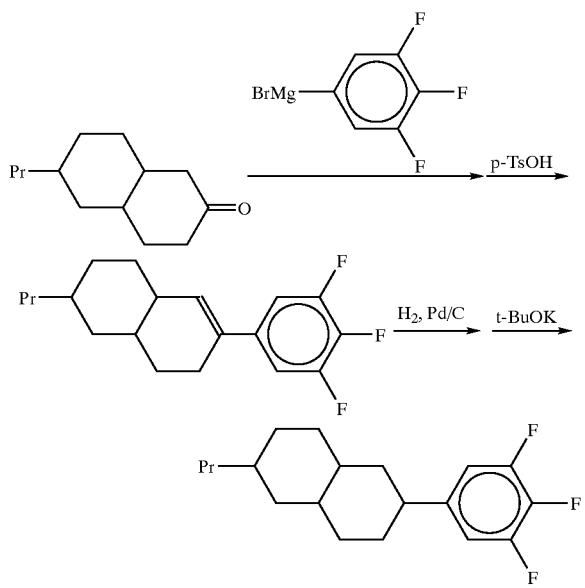

3.6 g of magnesium was suspended in 3.5 ml of tetrahydrofuran (THF), and a 110 ml THF solution of 25.8 g of 1-bromo-3,4,5-trifluorobenzene was added dropwise to the suspension over a period of about 30 minutes at such a rate that the THF was moderately refluxed. After further stirring the mixture for 1 hour, a 6 ml THF solution of 20 g of 6-propyl-trans-decahydro-2-naphthalenone, which was obtained according to the above reference example, was added dropwise over a period of 30 minutes. After further stirring the mixture for 2 hours, 50 ml of 10% hydrochloric acid was added. 100 ml of hexane was added, and the organic phase was separated. The aqueous phase was extracted with 100 ml of hexane, and the extracts were combined with the organic phase. The combined organic phase was rinsed with water, a saturated aqueous solution of sodium hydrogencarbonate, and a saturated saline solution, and dried on anhydrous sodium sulfate. The solvent was evaporated, and 100 ml of toluene and 2.0 g of p-toluenesulfonic acid monohydrate were added. The mixture was heated at 110° C. with stirring while evaporated water was separated and removed. When the evaporation of water was stopped, the temperature was reduced to room temperature. 50 ml of water was added, and the organic phase was separated. The organic phase was rinsed with a saturated aqueous solution of sodium hydrogencarbonate, water and a saturated saline solution, and dried on anhydrous sodium sulfate. The solvent was evaporated, and the whole amount of the residue was dissolved in 200 ml of ethyl acetate. 2.5 g of palladium-carbon (5%, wet) was added, and the mixture was stirred in an autoclave in hydrogen under a pressure of 400 KPa. After stirring for 5 hours at room temperature, the catalyst was removed by way of filtration through celite, and the solvent was evaporated to obtain a trans/cis mixture of trans-6-propyl-2-(3,4,5-trifluorophenyl)-trans-decahydronaphthalene. The whole amount of this mixture was dissolved in 55 ml of N,N-dimethylformamide (DMF). 1 g of potassium t-butoxide was added to the solution, and the mixture was stirred for 5 hours at 70° C. After the mixture was cooled to room temperature, 100 ml of water was added, and extraction was performed twice using 100 ml of hexane. Organic phases were combined, and the combined organic phase was rinsed with a diluted hydrochloric acid, a saturated aqueous solution of sodium hydrogencarbonate, water, and a saturated saline solution, and dried on anhydrous sodium sulfate. The solvent was evaporated, and the residue was purified by silica gel column chromatography (hexane), and recrystallized twice from ethanol to obtain 5 g white crystals of trans-6-propyl-trans-2-(3,4,5-trifluorophenyl)-trans-decahydronaphthalene.

IR(neat)1615, 1530 cm$^{-1}$ $^1$H NMR(Acetone-d$_6$)δ7.4–6.8(m,2H), 2.5–2.8(m,4H), 1.9–0.7(m,18H)

$^{13}$C NMR(Acetone-d$_6$)δ154, 150, 140, 137, 146, 112, 43–34, 21, 15

MS m/z 310, 267, 247, 225, 211, 197, 185, 171, 158, 145, 135, 123, 109, 95, 81, 67, 5 5

The following compounds were prepared in the same manner as mentioned above:

trans-6-propyl-trans-2-(3,5-difluorophenyl)-trans-decahydronaphthalene,
trans-6-propyl-trans-2-(4-fluorophenyl)-trans-decahydronaphthalene,
trans-6-propyl-trans-2-(3,4-difluorophenyl)-trans-decahydronaphthalene,
trans-6-propyl-trans-2-(4-trifluoromethoxyphenyl)-trans-decahydronaphthalene,
trans-6-propyl-trans-2-(3-fluoro-4-trifluoromethoxyphenyl)-trans-decahydronaphthalene,
trans-6-propyl-trans-2-(3,5-difluoro-4-trifluoromethoxyphenyl)-trans-decahydronaphthalene,
trans-6-propyl-trans-2-(4-difluoromethoxyphenyl)-trans-decahydronaphthalene,
trans-6-propyl-trans-2-(3-fluoro-4-difluoromethoxyphenyl)-trans-decahydronaphthalene,
trans-6-propyl-trans-2-(3,5-difluoro-4-difluoromethoxyphenyl)-trans-decahydronaphthalene,
trans-6-propyl-trans-2-(4-chlorophenyl)-trans-decahydronaphthalene,
trans-6-propyl-trans-2-(3-fluoro-4-chlorophenyl)-trans-decahydronaphthalene,
trans-6-propyl-trans-2-(3,5-difluoro-4-chlorophenyl)-trans-decahydronaphthalene,
trans-6-propyl-trans-2-(4-methoxyphenyl)-trans-decahydronaphthalene,
trans-6-propyl-trans-2-(3-fluoro-4-methoxyphenyl)-trans-decahydronaphthalene,
trans-6-propyl-trans-2-(3,5-difluoro-4-methoxyphenyl)-trans-decahydronaphthalene.

Example 2

Synthesis of 6-(trans-4-propylcyclohexyl)-decahydro-2-naphthalenone (2-a) Synthesis of 6-(trans-4-propylcyclohexyl)-4,4a,5,6,7,8-hexahydro-3H-2-naphthalenone

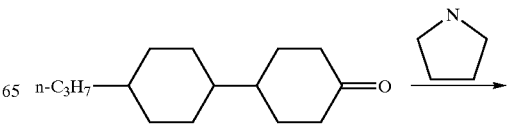

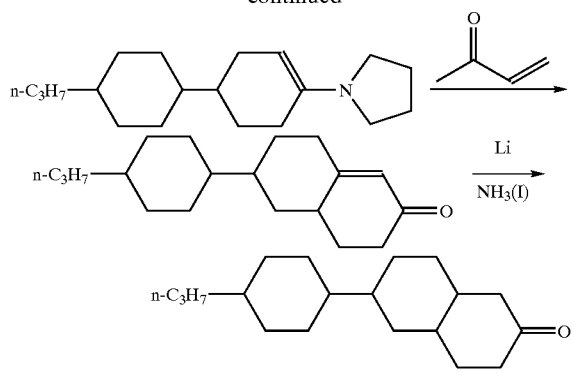

200 g of 4-(trans-4-propylcyclohexyl)cyclohexanone and 135.2 g of pyrrolidine were dissolved in 800 ml of toluene. The solution was heated and stirred for 6 hours while water which is evaporated by azeotropic distillation was removed. Azeotropic distillation of the solution was carried out with toluene so that excessive pyrrolidine was removed, and 1-(4-(trans-4-propylcyclohexyl)-cyclohexen-1-yl)-pyrrolidine was obtained. The product as it was was cooled to room temperature, and 800 ml of toluene was added again. The mixture was cooled in a water bath, and 150 ml toluene solution of 89 ml of methyl vinyl ketone was added dropwise over a period of 2 hours at 20° C. or less. After the dropwise addition was completed, the temperature was increased over a period of 2 hours to reach the reflux temperature. The solution was cooled to room temperature, and a buffer solution of pH 5 which was prepared from B5.2 g of sodium acetate, 104.2 ml of acetic acid, and 104.2 ml of water was added. Reflux was further continued for 5 hours. After the solution was cooled to room temperature, the organic phase was separated and rinsed with water and a saturated saline solution. The organic phase was dried on anhydrous sodium sulfate. The solvent was evaporated, and 313 g of 6-(trans-4-propylcyclohexyl)-4,4a,5,6,7,8-hexahydro-2(3H)-naphthalenone was obtained.

(2-b) Synthesis of 6-(trans-4-propylcyclohexyl)-octahydro-2-naphthalenone 21.8 g of metal lithium was added to 1500 ml of liquid ammonia which is cooled to −40° C. To the mixture, a 1200 ml THF solution of 313 g of 6-(trans-4-propylcyclohexyl)-4,4a,5,6,7,8-hexahydro-2(3H)-naphthalenone which was obtained in (1-a) and 91 g of t-butanol were added dropwise at −35° C. Stirring was carried out for 30 minutes, and 50 g of ammonium chloride was added to stop the reaction. The temperature was gradually raised to evaporate ammonia. 200 ml of saturated aqueous solution of ammonium chloride and 400 ml of toluene were added. The organic phase was separated and rinsed with water and a saturated saline solution. The organic phase was dried on anhydrous sodium sulfate. The solvent was evaporated, and distillation was carried out (bp.=180° C., 0.03 Ps) to obtain 96 g of 6-(trans-4-propylcyclohexyl)-octahydro-2-naphthalenone.

IR(nujol) 1718 cm−1

$^1$H NMR(CDCl$_3$)□2.4–2.2(m,4H), 1.8–1.6(m,5H), 1.4–1.0(m,20H), 0.9(t,3H)

$^{13}$C NMR(CDCl$_3$)□212, 48, 44, 42, 40, 38, 37, 35, 34, 30, 29, 20, 14.

MS m/z 276, 258, 232, 152, 135, 125, 110, 95, 83, 69, 55

The following compounds were prepared in the same manner as mentioned above:

6-(trans-4-methylcyclohexyl)-octahydro-2-naphthalenone,
6-(trans-4-ethylcyclohexyl)-octahydro-2-naphthalenone,
6-(trans-4-butylcyclohexyl)-octahydro-2-naphthalenone,
6-(trans-4-pentylcyclohexyl)-octahydro-2-naphthalenone,
6-(trans-4-hexylcyclohexyl)-octahydro-2-naphthalenone,
6-(trans-4-heptylcyclohexyl)-octahydro-2-naphthalenone.

Example 3

Synthesis of trans-6-(trans-4-propylcyclohexyl)-2-(3,4,5-trifluorophenyl)-trans-decahydronaphthalene

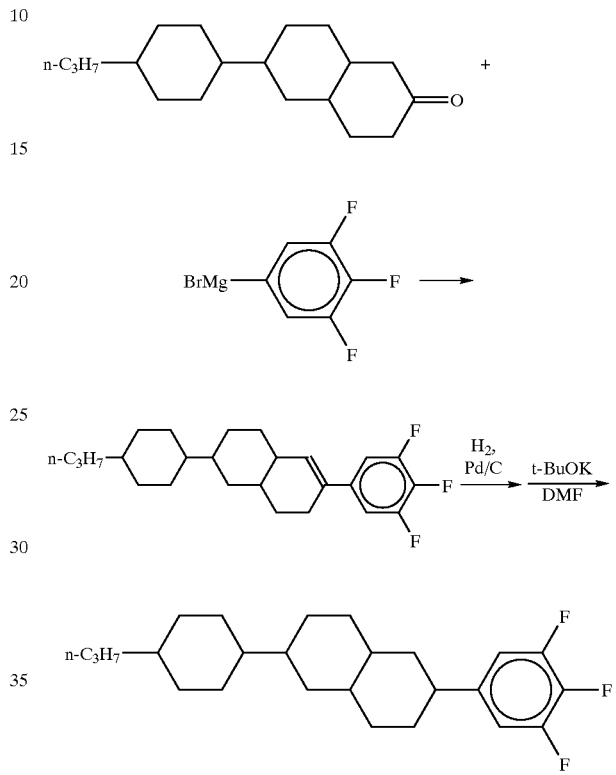

2.1 g of magnesium was suspended in 4 ml of THF, and a 65 ml THF solution of 16.8 g of 1-bromo-3,4,5-trifluorobenzene was added dropwise to the suspension over a period of about 30 minutes at such a rate that the THF was moderately refluxed. After further stirring the mixture for 1 hour, an 80 ml THF solution of 20 g of 6-(trans-4-propylcyclohexyl)-octahydro-2-naphthalenone, which was obtained Example 1, was added dropwise for 30 minutes. After further stirring the mixture for 2 hours, 50 ml of 10% hydrochloric acid was added. 100 ml of hexane was added, and the organic phase was separated. The aqueous phase was extracted with 100 ml of hexane, and the extracts were combined with the organic phase. The combined organic phase was rinsed with water, a saturated aqueous solution of sodium hydrogencarbonate, and a saturated saline solution, and dried on anhydrous sodium sulfate. The solvent was evaporated, and 100 ml of toluene and 2.0 g of p-toluenesulfonic acid monohydrate were added. The mixture was heated at 110° C. with stirring while evaporated water was separated and removed. When the evaporation of water was stopped, the temperature was reduced to room temperature. 50 ml of water was added, and the organic phase was separated. The organic phase was rinsed with a saturated aqueous solution of sodium hydrogencarbonate, water and a saturated saline solution, and dried on anhydrous sodium sulfate. The solvent was evaporated, and the whole amount of the residue was dissolved in 200 ml of ethyl acetate. 2.5 g of palladium-carbon (5%, wet) was added, and the mixture was stirred in an autoclave in hydrogen under a pressure of 400 KPa. After stirring for 5 hours at room temperature, the catalyst was removed by way of filtration through celite, and the solvent was evaporated to obtain a trans/cis mixture of 6-(trans-4-propylcyclohexyl)-2-(3,4,5-trifluorophenyl)-trans-decahydronaphthalene. The whole amount of this mixture was dissolved in 55 ml of N,N-dimethylformamide (DMF). 0.7 g of potassium t-butoxide was added to the solution, and the mixture was stirred for 2 hours at 50° C. After the mixture was cooled to room temperature, 100 ml of water was added, and extraction was performed twice using 100 ml of hexane. Organic phases were combined, and the combined organic phase was rinsed with a diluted hydrochloric acid, a saturated aqueous solution of sodium hydrogencarbonate, water, and a saturated saline solution, and dried on anhydrous sodium sulfate. The solvent was evaporated, and the residue was purified by silica gel column chromatography (hexane), and recrystallized twice from ethanol to obtain 7.2 g white crystals of trans-6-(trans-4-propylcyclohexyl)-2-(3,4,5-trifluorophenyl)-trans-decahydronaphthalene.

IR(nujol)1615, 1533 cm−1

$^1$H NMR(CDCl$_3$)☐7.4–6.8(m,2H), 2.5–2.8(m,4H), 1.9–0.7(m,28H)

$^{13}$C NMR(CDCl$_3$)☐153, 149, 139, 136, 144, 110, 43–34, 20, 14

MS m/z 392, 267, 197, 185, 171, 158, 145, 125, 108, 95, 83, 69, 55

The following compounds were prepared in the same manner as mentioned above:

trans-6-(trans-4-propylcyclohexyl)-trans-2-(3,5-difluorophenyl)-trans-decahydronaphthalene,
trans-6-(trans-4-propylcyclohexyl)-trans-2-(4-fluorophenyl)-trans-decahydronaphthalene,
trans-6-(trans-4-propylcyclohexyl)-trans-2-(3,4-difluorophenyl)-trans-decahydronaphthalene,
trans-6-(trans-4-propylcyclohexyl)-trans-2-(4-trifluoromethoxyphenyl)-trans-decahydronaphthalene,
trans-6-(trans-4-propylcyclohexyl)-trans-2-(3-fluoro-4-trifluoromethoxyphenyl)-trans-decahydronaphthalene,
trans-6-(trans-4-propylcyclohexyl)-trans-2-(3,5-difluoro-4-trifluoromethoxyphenyl)-trans-decahydronaphthalene,
trans-6-(trans-4-propylcyclohexyl)-trans-2-(4-difluoromethoxyphenyl)-trans-decahydronaphthalene,
trans-6-(trans-4-propylcyclohexyl)-trans-2-(3-fluoro-4-difluoromethoxyphenyl)-trans-decahydronaphthalene,
trans-6-(trans-4-propylcyclohexyl)-trans-2-(3,5-difluoro-4-difluoromethoxyphenyl)-trans-decahydronaphthalene,
trans-6-(trans-4-propylcyclohexyl)-trans-2-(4-chlorophenyl)-trans-decahydronaphthalene,
trans-6-(trans-4-propylcyclohexyl)-trans-2-(3-fluoro-4-chlorophenyl)-trans-decahydronaphthalene,
trans-6-(trans-4-propylcyclohexyl)-trans-2-(3,5-difluoro-4-chlorophenyl)-trans-decahydronaphthalene,
trans-6-(trans-4-propylcyclohexyl)-trans-2-(4-methoxyphenyl)-trans-decahydronaphthalene,
trans-6-(trans-4-propylcyclohexyl)-trans-2-(3-fluoro-4-methoxyphenyl)-trans-decahydronaphthalene,
trans-6-(trans-4-propylcyclohexyl)-trans-2-(3,5-difluoro-4-methoxyphenyl)-trans-decahydronaphthalene.

Example 4

Synthesis of trans-6-(3,5-difluorophenyl)-trans-decahydronaphthalene-2-carbaldehyde

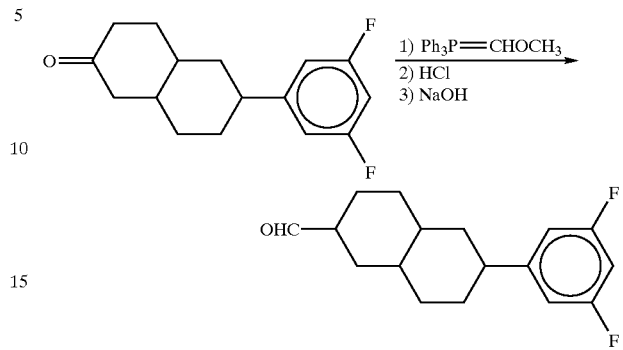

13.5 g of methoxymethyltriphenylphosphonium chloride was suspended in 35 ml of THF. While the suspension was cooled to 10° C. or lower, a 25 ml THF solution of 5.5 g of potassium t-butoxide was added dropwise. While the cooling was further continued, 25 ml THF solution of 8.5 g of 6-(3,5-difluorophenyl)decahydronaphthalen-2-one was added dropwise over a period of 10 minutes. After the temperature was reduced to room temperature and stirring was carried out for 4 hours, water and hexane were added. The organic phase was separated, and rinsed with water. Then, the solvent was evaporated. 10.1 g of the solid substance obtained was dissolved in 50 ml of THF. 50 ml of 10% hydrochloric acid was added, and the mixture was heated under refluxing for 2 hours. The temperature was reduced to room temperature. The organic phase was separated, and the aqueous phase was extracted with ethyl acetate. The organic phases were combined, and the combined organic phase was rinsed with saturated saline solution. The solvent was then evaporated. 10 g of the oily substance obtained was dissolved in 100 ml of methanol. To the solution, which was cooled to 10° C. or lower, 10 ml of 10% aqueous solution of sodium hydroxide was added. After stirring for 2 hours, the temperature was reduced to room temperature. Water was added to the mixture, and the mixture was extracted with ethyl acetate. The organic phase was rinsed with a saturated saline solution, and dried on anhydrous sodium sulfate. The solvent was evaporated, and 10.5 g of trans-6-(3,5-difluorophenyl)-trans-decahydronaphthalene-2-carbaldehyde as an oily substance was obtained.

The following compounds were prepared in the same manner as mentioned above:
trans-6-(4-fluorophenyl)-trans-decahydronaphthalene-2-carbaldehyde,
trans-6-(3,4-difluorophenyl)-trans-decahydronaphthalene-2-carbaldehyde,
trans-6-(3,4,5-trifluorophenyl)-trans-decahydronaphthalene-2-carbaldehyde,
trans-6-(4-trifluoromethoxyphenyl)-trans-decahydronaphthalene-2-carbaldehyde,
trans-6-(3-fluoro-4-trifluoromethoxyphenyl)-trans-decahydronaphthalene-2-carbaldehyde,
trans-6-(3,5-difluoro-4-trifluoromethoxyphenyl)-trans-decahydronaphthalene-2-carbaldehyde,
trans-6-(4-difluoromethoxyphenyl)-trans-decahydronaphthalene-2-carbaldehyde,
trans-6-(3-fluoro-4-difluoromethoxyphenyl)-trans-decahydronaphthalene-2-carbaldehyde, trans-6-(3,5-difluoro-4-difluoromethoxyphenyl)-trans-decahydronaphthalene-2-carbaldehyde,
trans-6-(4-chlorophenyl)-trans-decahydronaphthalene-2-carbaldehyde,
trans-6-(3-fluoro-4-chlorophenyl)-trans-decahydronaphthalene-2-carbaldehyde,
trans-6-(3,5-difluoro-4-chlorophenyl)-trans-decahydronaphthalene-2-carbaldehyde,
trans-6-(4-methoxyphenyl)-trans-decahydronaphthalene-2-carbaldehyde,
trans-6-(3-fluoro-4-methoxyphenyl)-trans-decahydronaphthalene-102-carbaldehyde,
trans-6-(3,5-difluoro-4-methoxyphenyl)-trans-decahydronaphthalene-2-carbaldehyde.

Example 5 trans-6-(3,4-difluorophenyl)-trans-2-(2-formylethyl)decahydronaphthalene

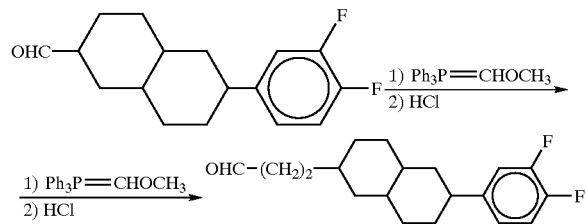

13.5 g of methoxymethyltriphenylphosphonium chloride was suspended in 35 ml of THF. While the suspension was cooled to 10° C. or lower, a 25 ml THF solution of 5.5 g of potassium t-butoxide was added dropwise. While the cooling was further continued, 25 ml THF solution of 10.0 g of trans-6-(3,4-difluorophenyl)-trans-decahydronaphthalene-2-carbaldehyde, which was obtained in a manner similar to that of Example 1, was added dropwise. After the temperature was reduced to room temperature and stirring was carried out for 4 hours, water and hexane were added. The organic phase was separated, and rinsed with water. Then, the solvent was evaporated. 12.0 g of the solid substance obtained was dissolved in 60 ml of THF. 60 ml of 10% hydrochloric acid was further added, and the mixture was heated under refluxing for 2 hours. The temperature was reduced to room temperature. The organic phase was separated, and the aqueous phase was extracted with ethyl acetate. The organic phases were combined, and the combined organic phase was rinsed with saturated saline solution. The solvent was then evaporated. 11.0 g of trans-6-(3,4-difluorophenyl)-trans-decahydronaphthalene-2-carbaldehyde obtained was dissolved in 40 ml of THF. The solution was added again dropwise to a 60 ml THF solution of 13.5 g of methoxymethyltriphenylphosphonium chloride and 5.5 g of potassium t-butoxide, which has been cooled. The temperature was reduced to room temperature. After the mixture was stirred for 4 hours, water and hexane were added, and the organic phase was separated. After the organic phase was rinsed with water, the solvent was evaporated. 13.6 g of the solid substance obtained was dissolved in 70 ml of THF. 70 ml of 10% hydrochloric acid was added to the solution, and the mixture was stirred for 2 hours. The temperature was reduced to room temperature, water was added to the mixture, and the mixture was extracted with ethyl acetate. The organic phase was rinsed with a saturated saline solution, and dried on anhydrous sodium sulfate. The solvent was evaporated, and 12.0 g of trans-6-(3,4-difluorophenyl)-trans-2-(2-formylethyl)decahydronaphthalene as an oily substance was obtained.

The following compounds were prepared in the same manner as mentioned above:
trans-6-(3,5-difluorophenyl)-trans-2-(2-formylethyl)decahydronaphthalene,
trans-6-(4-fluorophenyl)-trans-2-(2-formylethyl)decahydronaphthalene,
trans-6-(3,4,5-trifluorophenyl)-trans-2-(2-formylethyl)decahydronaphthalene,
trans-6-(4-trifluoromethoxyphenyl)-trans-2-(2-formylethyl)decahydronaphthalene,
trans-6-(3-fluoro-4-trifluoromethoxyphenyl)-trans-2-(2-formylethyl)decahydronaphthalene,
trans-6-(3,5-difluoro-4-trifluoromethoxyphenyl)-trans-2-(2-formylethyl)decahydronaphthalene,
trans-6-(4-difluoromethoxyphenyl)-trans-2-(2-formylethyl)decahydronaphthalene,
trans-6-(3-fluoro-4-difluoromethoxyphenyl)-trans-2-(2-formylethyl)decahydronaphthalene,
trans-6-(3,5-difluoro-4-difluoromethoxyphenyl)-trans-2-(2-formylethyl)decahydronaphthalene,
trans-6-(4-chlorophenyl)-trans-2-(2-formylethyl)decahydronaphthalene,
trans-6-(3-fluoro-4-chlorophenyl)-trans-2-(2-formylethyl)decahydronaphthalene,
trans-6-(3,5-difluoro-4-chlorophenyl)-trans-2-(2-formylethyl)decahydronaphthalene,
trans-6-(4-methoxyphenyl)-trans-2-(2-formylethyl)decahydronaphthalene,
trans-6-(3-fluoro-4-methoxyphenyl)-trans-2-(2-formylethyl)decahydronaphthalene,
trans-6-(3,5-difluoro-4-methoxyphenyl)-trans-2-(2-formylethyl)decahydronaphthalene.

Example 6

Synthesis of trans-6-(3,5-difluorophenyl)-trans-2-vinyldecahydronaphthalene

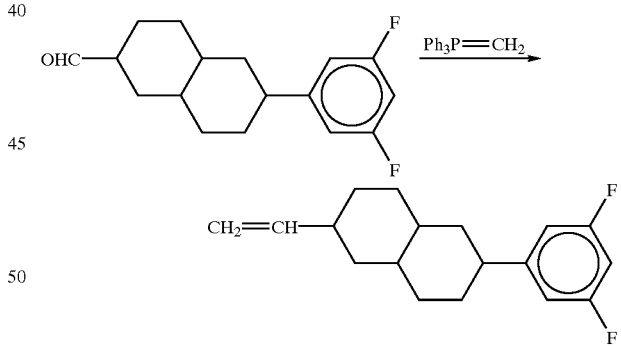

24.4 g of methyltriphenylphosphonium iodide was suspended in 75 ml of THF. While the suspension was cooled to 10° C. or lower, a 40 ml THF solution of 7.6 g of potassium t-butoxide was added dropwise. While the cooling was further continued, 100 ml THF solution of 20.5 g of trans-6-(3,5-difluorophenyl)-trans-decahydronaphthalene-2-carbaldehyde, which was obtained in Example 1, was added dropwise. After the temperature was reduced to room temperature and stirring was carried out for 3 hours, water and hexane were added. The organic phase was separated, rinsed with water, and dried on anhydrous sodium sulfate. Then, the solvent was evaporated. 12.1 g of the oily substance obtained was purified by silica gel column chromatography (hexane), and 4.0 g of trans-6-(3,5-difluorophenyl)-trans-2-vinyldecahydronaphthalene as an oily substance was obtained.

The following compounds were prepared in the same manner as mentioned above:
trans-6-(4-fluorophenyl)-trans-2-vinyldecahydronaphthalene,
trans-6-(3,4-difluorophenyl)-trans-2-vinyldecahydronaphthalene,
trans-6-(3,4,5-trifluorophenyl)-trans-2-vinyldecahydronaphthalene,
trans-6-(4-trifluoromethoxyphenyl)-trans-2-vinyldecahydronaphthalene,
trans-6-(3-fluoro-4-trifluoromethoxyphenyl)-trans-2-vinyldecahydronaphthalene,
trans-6-(3,5-difluoro-4-trifluoromethoxyphenyl)-trans-2-vinyldecahydronaphthalene,
trans-6-(4-difluoromethoxyphenyl)-trans-2-vinyldecahydronaphthalene,
trans-6-(3-fluoro-4-difluoromethoxyphenyl)-trans-2-vinyldecahydronaphthalene,
trans-6-(3,5-difluoro-4-difluoromethoxyphenyl)-trans-2-vinyldecahydronaphthalene,
trans-6-(4-chlorophenyl)-trans-2-vinyldecahydronaphthalene,
trans-6-(3-fluoro-4-chlorophenyl)-trans-2-vinyldecahydronaphthalene,
trans-6-(3,5-difluoro-4-chlorophenyl)-trans-2-vinyldecahydronaphthalene,
trans-6-(4-methoxyphenyl)-trans-2-vinyldecahydronaphthalene,
trans-6-(3-fluoro-4-methoxyphenyl)-trans-2-vinyldecahydronaphthalene,
trans-6-(3,5-difluoro-4-methoxyphenyl)-trans-2-vinyldecahydronaphthalene.

Example 7

Synthesis of trans-6-(3,4,5-trifluorophenyl)-trans-2-(1-propenyl)decahydronaphthalene

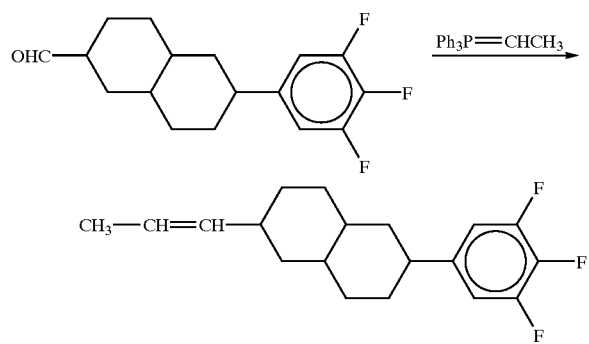

13.4 g of ethyltriphenylphosphonium bromide was suspended in 30 ml of THF. While the suspension was cooled to 10° C. or lower, a 25 ml THF solution of 4.5 g of potassium t-butoxide was added dropwise. While the cooling was further continued, 50 ml THF solution of 10.1 g of trans-6-(3,4,5-trifluorophenyl)-trans-decahydronaphthalene-2-carbaldehyde, which was obtained in a manner similar to that of Example 1, was added dropwise. After the temperature was reduced to room temperature and stirring was carried out for 3 hours, water and hexane were added. The organic phase was separated, rinsed with water, and dried on anhydrous sodium sulfate. Then, the solvent was evaporated. 9.1 g of the oily substance obtained was dissolved in 50 ml of toluene. 2.5 g of sodium benzenesulfinate and 10 ml of 10% hydrochloric acid were added to the solution, and the mixture was heated under refluxing for 20 hours. The temperature was reduced to room temperature. The organic phase was extracted using toluene, rinsed with a saturated aqueous solution of sodium hydrogen carbonate and a saturated saline solution, in sequence, and dried on anhydrous sodium sulfate. Then, the solvent was evaporated. The resultant was purified by silica gel column chromatography (hexane), and recrystallized (in ethanol) to obtain 7.8 g of white solid trans-6-(3,4,5-trifluorophenyl)-trans-2-(1-propenyl)decahydronaphthalene (I-6).

The following compounds were prepared in the same manner as mentioned above:
trans-6-(3,5-difluorophenyl)-trans-2-(1-propenyl)decahydronaphthalene,
trans-6-(4-fluorophenyl)-trans-2-(1-propenyl)decahydronaphthalene,
trans-6-(3,4-difluorophenyl)-trans-2-(1-propenyl)decahydronaphthalene,
trans-6-(4-trifluoromethoxyphenyl)-trans-2-(1-propenyl)decahydronaphthalene,
trans-6-(3-fluoro-4-trifluoromethoxyphenyl)-trans-2-(1-propenyl)decahydronaphthalene,
trans-6-(3,5-difluoro-4-trifluoromethoxyphenyl)-trans-2-(1-propenyl)decahydronaphthalene,
trans-6-(4-difluoromethoxyphenyl)-trans-2-(1-propenyl)decahydronaphthalene,
trans-6-(3-fluoro-4-difluoromethoxyphenyl)-trans-2-(1-propenyl)decahydronaphthalene,
trans-6-(3,5-difluoro-4-difluoromethoxyphenyl)-trans-2-(1-propenyl)decahydronaphthalene,
trans-6-(4-chlorophenyl)-trans-2-(1-propenyl)decahydronaphthalene,
trans-6-(3-fluoro-4-chlorophenyl)-trans-2-(1-propenyl)decahydronaphthalene,
trans-6-(3,5-difluoro-4-chlorophenyl)-trans-2-(1-propenyl)decahydronaphthalene,
trans-6-(4-methoxyphenyl)-trans-2-(1-propenyl)decahydronaphthalene,
trans-6-(3-fluoro-4-methoxyphenyl)-trans-2-(1-propenyl)decahydronaphthalene,
trans-6-(3,5-difluoro-4-methoxyphenyl)-trans-2-(1-propenyl)decahydronaphthalene,
trans-6-(3,4,5-trifluorophenyl)-trans-2-vinyldecahydronaphthalene,
trans-6-(3,5-difluorophenyl)-trans-2-vinyldecahydronaphthalene,
trans-6-(4-fluorophenyl)-trans-2-vinyldecahydronaphthalene,
trans-6-(3,4-difluorophenyl)-trans-2-vinyldecahydronaphthalene,
trans-6-(4-trifluoromethoxyphenyl)-trans-2-vinyldecahydronaphthalene,
trans-6-(3-fluoro-4-trifluoromethoxyphenyl)-trans-2-vinyldecahydronaphthalene,
trans-6-(3,5-difluoro-4-trifluoromethoxyphenyl)-trans-2-vinyldecahydronaphthalene,
trans-6-(4-difluoromethoxyphenyl)-trans-2-vinyldecahydronaphthalene,
trans-6-(3-fluoro-4-difluoromethoxyphenyl)-trans-2-vinyldecahydronaphthalene,
trans-6-(3,5-difluoro-4-difluoromethoxyphenyl)-trans-2-vinyldecahydronaphthalene,
trans-6-(4-chlorophenyl)-trans-2-vinyldecahydronaphthalene, trans-6-(3-fluoro-4-chlorophenyl)-trans-2-vinyldecahydronaphthalene,
trans-6-(3,5-difluoro-4-chlorophenyl)-trans-2-vinyldecahydronaphthalene,
trans-6-(4-methoxyphenyl)-trans-2-vinyldecahydronaphthalene,
trans-6-(3-fluoro-4-methoxyphenyl)-trans-2-vinyldecahydronaphthalene,
trans-6-(3,5-difluoro-4-methoxyphenyl)-trans-2-vinyldecahydronaphthalene,
trans-6-(3,4,5-trifluorophenyl)-trans-2-(1-pentenyl)decahydronaphthalene,
trans-6-(3,5-difluorophenyl)-trans-2-(1-pentenyl)decahydronaphthalene,
trans-6-(4-fluorophenyl)-trans-2-(1-pentenyl)decahydronaphthalene,
trans-6-(3,4-difluorophenyl)-trans-2-(1-pentenyl)decahydronaphthalene,
trans-6-(4-trifluoromethoxyphenyl)-trans-2-(1-pentenyl)decahydronaphthalene,
trans-6-(3-fluoro-4-trifluoromethoxyphenyl)-trans-2-(1-pentenyl)decahydronaphthalene,
trans-6-(3,5-difluoro-4-trifluoromethoxyphenyl)-trans-2-(1-pentenyl)decahydronaphthalene,
trans-6-(4-difluoromethoxyphenyl)-trans-2-(1-pentenyl)decahydronaphthalene,
trans-6-(3-fluoro-4-difluoromethoxyphenyl)-trans-2-(1-pentenyl)decahydronaphthalene,
trans-6-(3,5-difluoro-4-difluoromethoxyphenyl)-trans-2-(1-pentenyl)decahydronaphthalene,
trans-6-(4-chlorophenyl)-trans-2-(1-pentenyl)decahydronaphthalene,
trans-6-(3-fluoro-4-chlorophenyl)-trans-2-(1-pentenyl)decahydronaphthalene,
trans-6-(3,5-difluoro-4-chlorophenyl)-trans-2-(1-pentenyl)decahydronaphthalene,
trans-6-(4-methoxyphenyl)-trans-2-(1-pentenyl)decahydronaphthalene,
trans-6-(3-fluoro-4-methoxyphenyl)-trans-2-(1-pentenyl)decahydronaphthalene,
trans-6-(3,5-difluoro-4-methoxyphenyl)-trans-2-(1-pentenyl)decahydronaphthalene.

Example 8

Synthesis of trans-6-(3,4-difluorophenyl)-trans-2-(3-butenyl)decahydronaphthalene

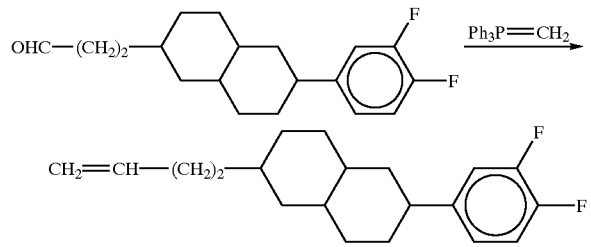

16.5 g of methyltriphenylphosphonium iodide was suspended in a mixture of 17 ml THF and 51 ml toluene. While the suspension was cooled to 10° C. or lower, a 4.6 g of potassium t-butoxide was added. While the cooling was further continued, 20 ml toluene solution of 5.0 g of trans-6-(3,4-difluorophenyl)-trans-2-(2-formylethyl)decahydronaphthalene, which was obtained in Example 2, was added dropwise. After the mixture was stirred for 2 hours, 5 ml of water and then 200 ml of hexane were added, and triphenylphosphine oxide was separated by filtration. The organic phase was separated, rinsed with 100 ml of water and 100 ml of water/methanol mixed solvent (1/2), and dried on anhydrous sodium sulfate. Then, the solvent was evaporated. The oily substance obtained was purified by silica gel column chromatography (hexane) and recrystallized from ethanol to obtain 3.7 g of white solid trans-6-(3,4-difluorophenyl)-trans-2-(3-butenyl)decahydronaphthalene (I-5).

The following compounds were prepared in the same manner as mentioned above:
trans-6-(3,5-difluorophenyl)-trans-2-(3-butenyl)decahydronaphthalene,
trans-6-(4-fluorophenyl)-trans-2-(3-butenyl)decahydronaphthalene,
trans-6-(3,4,5-trifluorophenyl)-trans-2-(3-butenyl)decahydronaphthalene,
trans-6-(4-trifluoromethoxyphenyl)-trans-2-(3-butenyl)decahydronaphthalene,
trans-6-(3-fluoro-4-trifluoromethoxyphenyl)-trans-2-(3-butenyl)decahydronaphthalene,
trans-6-(3,5-difluoro-4-trifluoromethoxyphenyl)-trans-2-(3-butenyl)decahydronaphthalene,
trans-6-(4-difluoromethoxyphenyl)-trans-2-(3-butenyl)decahydronaphthalene,
trans-6-(3-fluoro-4-difluoromethoxyphenyl)-trans-2-(3-butenyl)decahydronaphthalene,
trans-6-(3,5-difluoro-4-difluoromethoxyphenyl)-trans-2-(3-butenyl)decahydronaphthalene,
trans-6-(4-chlorophenyl)-trans-2-(3-butenyl)decahydronaphthalene,
trans-6-(3-fluoro-4-chlorophenyl)-trans-2-(3-butenyl)decahydronaphthalene,
trans-6-(3,5-difluoro-4-chlorophenyl)-trans-2-(3-butenyl)decahydronaphthalene,
trans-6-(4-methoxyphenyl)-trans-2-(3-butenyl)decahydronaphthalene,
trans-6-(3-fluoro-4-methoxyphenyl)-trans-2-(3-butenyl)decahydronaphthalene,
trans-6-(3,5-difluoro-4-methoxyphenyl)-trans-2-(3-butenyl)decahydronaphthalene,
trans-6-(3,4,5-trifluorophenyl)-trans-2-(3-pentenyl)decahydronaphthalene,
trans-6-(3,5-difluorophenyl)-trans-2-(3-pentenyl)decahydronaphthalene,
trans-6-(4-fluorophenyl)-trans-2-(3-pentenyl)decahydronaphthalene,
trans-6-(3,4-difluorophenyl)-trans-2-(3-pentenyl)decahydronaphthalene,
trans-6-(4-trifluoromethoxyphenyl)-trans-2-(3-pentenyl)decahydronaphthalene,
trans-6-(3-fluoro-4-trifluoromethoxyphenyl)-trans-2-(3-pentenyl)decahydronaphthalene,
trans-6-(3,5-difluoro-4-trifluoromethoxyphenyl)-trans-2-(3-pentenyl)decahydronaphthalene,
trans-6-(4-difluoromethoxyphenyl)-trans-2-(3-pentenyl)decahydronaphthalene,
trans-6-(3-fluoro-4-difluoromethoxyphenyl)-trans-2-(3-pentenyl)decahydronaphthalene,
trans-6-(3,5-difluoro-4-difluoromethoxyphenyl)-trans-2-(3-pentenyl)decahydronaphthalene,
trans-6-(4-chlorophenyl)-trans-2-(3-pentenyl)decahydronaphthalene,
trans-6-(3-fluoro-4-chlorophenyl)-trans-2-(3-pentenyl)decahydronaphthalene,
trans-6-(3,5-difluoro-4-chlorophenyl)-trans-2-(3-pentenyl)decahydronaphthalene, trans-6-(4-methoxyphenyl)-trans-2-(3-pentenyl)decahydronaphthalene,
trans-6-(3-fluoro-4-methoxyphenyl)-trans-2-(3-pentenyl)decahydronaphthalene,
trans-6-(3,5-difluoro-4-methoxyphenyl)-trans-2-(3-pentenyl)decahydronaphthalene.

Example 9

Synthesis of trans-2-propyl-trans-6-(3,5-difluoro-4-cyanophenyl)-trans-decahydronaphthalene

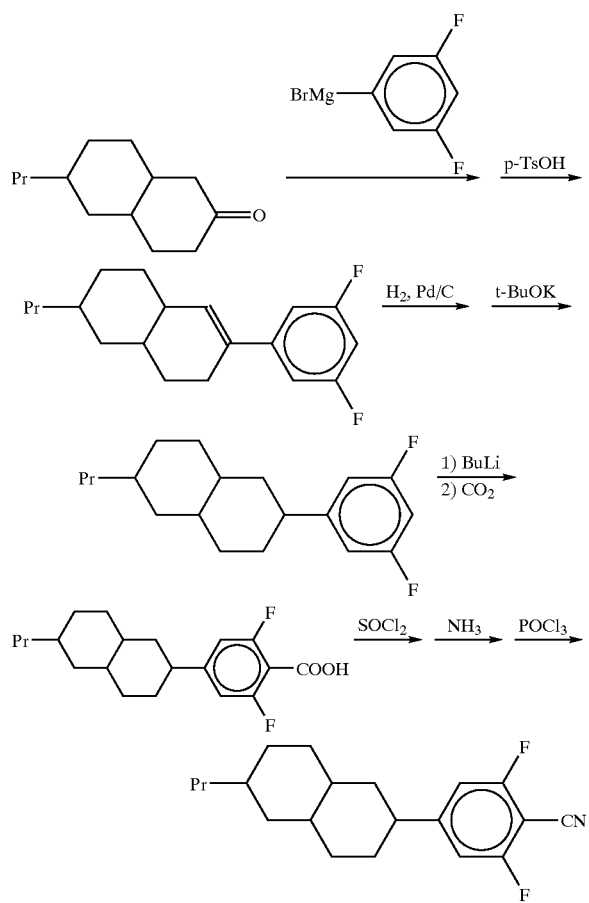

(9-a) Synthesis of trans-2-propyl-trans-6-(3,5-difluorophenyl)-trans-decahydronaphthalene 2.4 g of magnesium was suspended in 5 ml of tetrahydrofuran, and an 80 ml THF solution of 17.6 g of 1-bromo-3,5-difluorobenzene was added dropwise to the suspension over a period of about 30 minutes at such a rate that the THF was moderately refluxed. After further stirring the mixture for 1 hour, an 80 ml THF solution of 20 g of 6-propyloctahydro-2-naphthalenone was added dropwise over a period of 30 minutes. After further stirring the mixture for 2 hours, 80 ml of 10% hydrochloric acid was added. 100 ml of hexane was added, and the organic phase was separated. The aqueous phase was extracted with 100 ml of hexane, and the extracts were combined with the organic phase. The combined organic phase was rinsed with water, a saturated aqueous solution of sodium hydrogencarbonate, and a saturated saline solution, and dried on anhydrous sodium sulfate. The solvent was evaporated, and 105 ml of toluene and 1.7 g of p-toluenesulfonic acid monohydrate were added. The mixture was heated at 110° C. with stirring while evaporated water was separated and removed. When the evaporation of water was stopped, the temperature was reduced to room temperature. 50 ml of water was added, and the organic phase was separated. The organic phase was rinsed with a saturated aqueous solution of sodium hydrogencarbonate, water and a saturated saline solution, and dried on anhydrous sodium sulfate. The solvent was evaporated, and the whole amount of the residue was dissolved in 100 ml of ethyl acetate. 3.0 g of carbon with 5% palladium was added, and the mixture was stirred in an autoclave in hydrogen under a pressure of 400 KPa. After stirring for 5 hours at room temperature, the catalyst was removed by way of filtration through celite, and the solvent was evaporated to obtain a trans/cis mixture of trans-6-propyl-2-(3,5-difluorophenyl)-trans-decahydronaphthalene. The whole amount of this mixture was dissolved in 100 ml of N,N-dimethylformamide (DMF). 2.4 g of potassium t-butoxide was added to the solution, and the mixture was stirred for 5 hours at 70° C. After the mixture was cooled to room temperature, 100 ml of water was added, and extraction was performed twice using 100 ml of toluene. Organic phases were combined, and the combined organic phase was rinsed with 10% hydrochloric acid, a saturated aqueous solution of sodium hydrogencarbonate, water, and a saturated saline solution, and dried on anhydrous sodium sulfate. The solvent was evaporated, and the residue was purified by silica gel column chromatography (hexane), and recrystallized from ethanol to obtain 16.5 g white crystals of trans-6-propyl-trans-2-(3,5-difluorophenyl)-trans-decahydronaphthalene.

(9-b) Synthesis of trans-2-propyl-trans-6-(3,5-difluoro-4-cyanophenyl)-trans-decahydronaphthalene 16.5 of trans-6-propyl-trans-2-(3,5-difluorophenyl)-trans-decahydronaphthalene, which was obtained in (9-a), was dissolved in 70 ml of THF, and the solution was cooled to −78° C. 38.6 ml of 1.6 M butyl lithium-hexane solution was added over a period of 30 minutes in a manner such that the inner temperature does not exceed −50° C. After further stirring for 20 minutes, maintaining the inner temperature under −50° C., carbon dioxide was injected into the mixture. When generation of heat stopped, the temperature was gradually increased to room temperature. 50 ml of water and 50 ml of hexane was added, and the organic phase was separated. The organic phase was rinsed with water and a saturated saline solution, and dried on anhydrous sodium sulfate. The solvent was evaporated, and the whole amount of the residue was dissolved in 170 ml of 1,2-dichloroethane. 8.1 μg of thionyl chloride and 0.1 ml of pyridine were added, and the mixture was stirred for 5 hours. The solvent was evaporated, and the whole amount of the residue was dissolved in 100 ml of dichloromethane. Ammonia gas was injected into the solution while stirring. Two hours later, the solution was filtered. The residue was dissolved in 100 ml of DMF, and 7.9 g of oxalyl chloride was added dropwise. After further stirring for 1 hour, the mixture was poured onto iced water. 100 ml of toluene was added, and the organic phase was separated. The organic phase was rinsed with water, a saturated aqueous solution of sodium hydrogencarbonate, and a saturated saline solution, and dried on anhydrous sodium sulfate. The solvent was evaporated, and the residue was purified by silica gel column chromatography and recrystallized from ethanol to obtain 9 g white crystals of trans-2-propyl-trans-6-(3,5-difluoro-4-cyanophenyl)-trans-decahydronaphthalene.

The following compounds were prepared in the same manner as mentioned above:
trans-2-methyl-trans-6-(3,5-difluoro-4-cyanophenyl)-trans-decahydronaphthalene, trans-2-ethyl-trans-6-(3,5-difluoro-4-cyanophenyl)-trans-decahydronaphthalene,
trans-2-butyl-trans-6-(3,5-difluoro-4-cyanophenyl)-trans-decahydronaphthalene,
trans-2-pentyl-trans-6-(3,5-difluoro-4-cyanophenyl)-trans-decahydronaphthalene,
trans-2-hexyl-trans-6-(3,5-difluoro-4-cyanophenyl)-trans-decahydronaphthalene,
trans-2-heptyl-trans-6-(3,5-difluoro-4-cyanophenyl)-trans-decahydronaphthalene.

Example 10

Synthesis of trans-2-propyl-trans-6-(3-fluoro-4-cyanophenyl)-trans-decahydronaphthalene

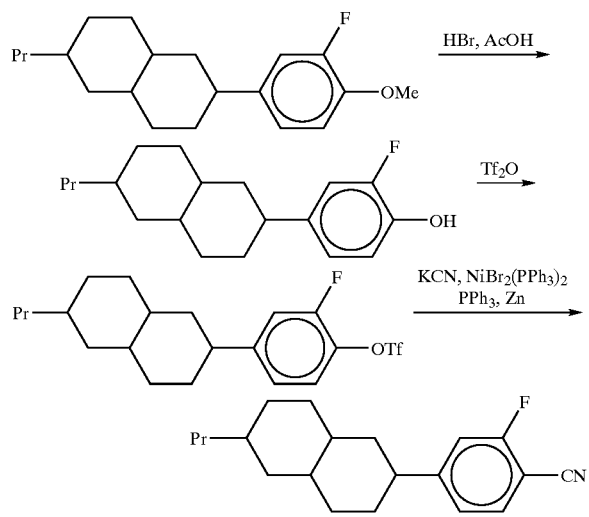

20 g of trans-2-propyl-trans-6-(3-fluoro-4-methoxyphenyl)-trans-decahydronaphthalene (which is a compound obtained in a manner similar to (1-a) except that 1-bromo-3-fluro-4-methoxybenzene was used instead of 1-bromo-3,5-difluorobenzene) was added to a mixture of 100 ml of acetic acid and 100 ml of 48% aqueous solution of hydrobromic acid, and the mixture was heated for 20 hours under refluxing. The temperature was reduced to room temperature. Water and toluene were added to the mixture, and the organic phase was separated. The organic phase was rinsed with a saturated aqueous solution of sodium hydrogencarbonate, water, and a saturated saline solution, and dried on anhydrous sodium sulfate. The solvent was evaporated, and the whole amount of the residue was dissolved in 100 ml of dichloromethane. 19.7 g of trifluromenthanesulfonic anhydride was added to the solution, and the mixture was cooled to 5° C. While the mixture was stirred forcefully, 12 ml of pyridine was added dropwise, and thereafter the mixture was further stirred for 1 hour. Water was added to stop the reaction. The organic phase was separated out, and the aqueous phase was extracted with dichloromethane. Organic phases were combined, and the combined organic phase was rinsed with 10% hydrochloric acid, a saturated aqueous solution of sodium hydrogencarbonate, water, and then a saturated saline solution, and dried on anhydrous sodium sulfate. After the solution was purified by silica gel column chromatography (hexane), the solvent was evaporated. The whole amount of the residue was dissolved in 150 ml of acetonitrile. 1.7 g of dibromobis(triphenylphosphine)nickel(II), 1.4 g of triphenylphosphine, 0.3 g of zinc powder, and 8.5 g of potassium cyanide were added to the solution, and the mixture was heated at 80° C. for 16 hours while stirring. Water was added to stop the reaction. The organic phase was further rinsed with water, and dried on anhydrous sodium sulfate. The solution was purified by silica gel column chromatography (hexane/dichloromethane), and further recrystallized from ethanol to obtain 12.5 g of white solid 5-fluoro-6-cyano-2-(trans-4-propylcyclohexyl)naphthalene.

The following compounds were prepared in the same manner as mentioned above:
trans-2-methyl-trans-6-(3-fluoro-4-cyanophenyl)-trans-decahydronaphthalene,
trans-2-ethyl-trans-6-(3-fluoro-4-cyanophenyl)-trans-decahydronaphthalene,
trans-2-butyl-trans-6-(3-fluoro-4-cyanophenyl)-trans-decahydronaphthalene,
trans-2-pentyl-trans-6-(3-fluoro-4-cyanophenyl)-trans-decahydronaphthalene,
trans-2-hexyl-trans-6-(3-fluoro-4-cyanophenyl)-trans-decahydronaphthalene,
trans-2-heptyl-trans-6-(3-fluoro-4-cyanophenyl)-trans-decahydronaphthalene,
trans-2-vinyl-trans-6-(3-fluoro-4-cyanophenyl)-trans-decahydronaphthalene,
trans-2-(1-propenyl)-trans-6-(3-fluoro-4-cyanophenyl)-trans-decahydronaphthalene,
trans-2-(1-pentenyl)-trans-6-(3-fluoro-4-cyanophenyl)-trans-decahydronaphthalene,
trans-2-(3-butenyl)-trans-6-(3-fluoro-4-cyanophenyl)-trans-decahydronaphthalene,
trans-2-(3-pentenyl)-trans-6-(3-fluoro-4-cyanophenyl)-trans-decahydronaphthalene.

Example 11

Synthesis of trans-6-(4-cyano-3,5-difluorophenyl)-trans-2-(1-propenyl)decahydronaphthalene

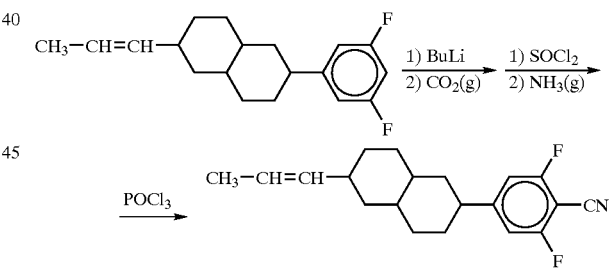

4.8 ml of a 1.5 M hexane solution of n-butyl lithium was added dropwise to a 10 ml THF solution of 1.74 g of trans-6-(3,5-difluorophenyl)-trans-2-(1-propenyl) decahydronaphthalene while cooling the solution to −78° C. After stirring for 10 minutes, carbon dioxide was injected into the mixture until saturation. After the mixture was left to stand until the temperature reached room temperature, 10% hydrochloric acid was added. The organic phase was extracted using ethyl acetate, rinsed with water, and dried on anhydrous magnesium sulfate. Then, the solvent was evaporated. 1.9 g of the solid substance obtained was suspended in 12 ml of 1,2-ethylene dichloride. 1.4 g of thionyl chloride, 0.05 ml of pyridine, and 1 ml of N,N-dimethylformamide (DMF) were added to the suspension, and the mixture was stirred for 1 hour at room temperature. The solvent was evaporated, and the oily substance obtained was dissolved in 50 ml of methylene chloride. Ammonia gas was injected into the solution while cooling the solution to 10° C. or lower until saturation. After stirring for 1 hour at room temperature, the solvent was evaporated. 2.6 g of the solid substance obtained was suspended in 20 ml of DMF. 1.5 ml of phosphorus oxychloride was added to the suspension while cooling the suspension to 10° C. or lower, and the mixture was stirred for 1 hour at room temperature. Water was added to the mixture. The organic phase was extracted using toluene, rinsed with a saturated saline solution, and dried on anhydrous sodium sulfate. Then, the solvent was evaporated. The residue was purified by silica gel column chromatography (hexane), and recrystallized (ethanol) to obtain 0.3 g of white solid trans-6-(4-cyano-3,5-difluorophenyl)-trans-2-(1-propenyl)decahydronaphthalene (I-12).

The following compounds were prepared in the same manner as mentioned above:
trans-2-vinyl-trans-6-(4-cyano-3,5-difluorophenyl)-trans-decahydronaphthalene,
trans-2-(1-propenyl)-trans-6-(4-cyano-3,5-difluorophenyl)-trans-decahydronaphthalene,
trans-2-(1-pentenyl)-trans-6-(4-cyano-3,5-difluorophenyl)-trans-decahydronaphthalene,
trans-2-(3-butenyl)-trans-6-(4-cyano-3,5-difluorophenyl)-trans-decahydronaphthalene,
trans-2-(3-pentenyl)-trans-6-(4-cyano-3,5-difluorophenyl)-trans-decahydronaphthalene.

Example 12

Synthesis of trans-6-propyl-2-[2-(3,4,5-trifluorophenyl)ethyl]-trans-decahydronaphthalene

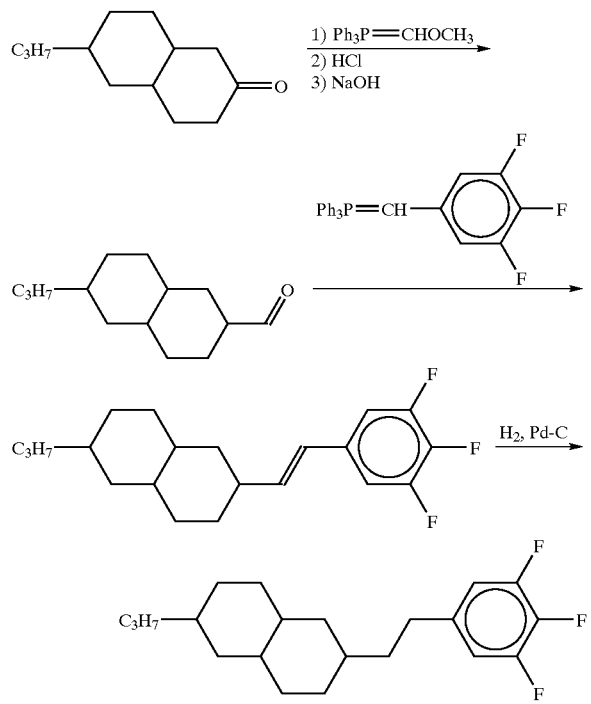

(12-a) Synthesis of 6-propyl-trans-decahydronaphthalene-2-carbaldehyde

A 100 ml THF solution of 24 g of 6-propyl-trans-decahydro-2-naphthalenone was added dropwise to a Wittig reagent prepared from 38 g of methoxymethyltriphenylphosphonium chloride and 14 g of potassium t-butoxide in 200 ml of THF, while the mixture was cooled 10° C. or lower. The temperature was reduced to room temperature. After the mixture was stirred for 4 hours, water and hexane were added. The organic phase was separated and rinsed with water, and the solvent was evaporated. The pale yellow oily substance obtained was dissolved in 180 ml of THF. 180 ml of 10% hydrochloric acid was added to the solution, and the mixture was heated for 3 hours under refluxing. The temperature was reduced to room temperature, the organic phase was separated, and the aqueous phase was extracted with ethyl acetate. Organic phases were combined, the combined organic phase was rinsed with a saturated aqueous solution of sodium hydrogencarbonate, water, and a saturated saline solution, in sequence, and the solvent was evaporated. The pale yellow solid substance obtained was dissolved in 160 ml of methanol. 20 ml of 10% aqueous solution of sodium hydroxide was added to the solution while cooling the solution to 10° C. or lower. After stirring the mixture for 2 hours, the temperature was reduced to room temperature, and the solvent was evaporated. The pale yellow solid substance obtained was rinsed with water, and recrystallized from a hexane solution to obtain 18 g of white solid 6-propyl-trans-decahydronaphthalene-2-carbaldehyde.

(12-b) Synthesis of 2-[2-(3,4,5-trifluorophenyl)ethenyl]-6-propyl-trans-decahydronaphthalene A 90 ml THF solution of 18 g of 6-propyl-trans-decahydronaphthalene-2-carbaldehyde, which was obtained in (12-a), was added dropwise to a Wittig reagent prepared from 49 g of 3,4,5-trifluorobenzyltriphenylphosphonium bromide and 12 g of potassium t-butoxide in 250 ml of THF, while the mixture was cooled to 10° C. or lower. The temperature was reduced to room temperature. After the mixture was stirred for 4 hours, water and hexane were added. The organic phase was separated and rinsed with water, and the solvent was evaporated. The residue was purified by silica gel column chromatography (hexane) to obtain 22 g of 2-[2-(3,4,5-trifluorophenyl)ethenyl]-6-propyl-trans-decahydronaphthalene as a colorless oily substance.

(1-c) Synthesis of trans-6-propyl-2-[2-(3,4,5-trifluorophenyl)ethyl]-trans-decahydronaphthalene 22 g of 2-[2-(3,4,5-trifluorophenyl)ethenyl]-6-propyl-trans-decahydronaphthalene, which was obtained in (12-b), was dissolved in 120 ml of ethyl acetate. 5 g of carbon with 5% palladium was added to the solution. Hydrogenation was carried out at room temperature for 6 hours. The catalyst was removed by way of filtration through celite, and the solvent was evaporated. The residue was purified by silica gel column chromatography (hexane), and recrystallized from ethanol at −70° C. or lower to obtain 6 g of white solid trans-6-propyl-2-[2-(3,4,5-trifluorophenyl)ethyl]-trans-decahydronaphthalene.

The following compounds were prepared in the same manner as mentioned above:
trans-6-propyl-2-[2-(3,5-difluorophenyl)ethyl]-trans-decahydronaphthalene,
trans-6-propyl-2-[2-(4-fluorophenyl)ethyl]-trans-decahydronaphthalene,
trans-6-propyl-2-[2-(3,4-difluorophenyl)ethyl]-trans-decahydronaphthalene,
trans-6-propyl-2-[2-(4-trifluoromethoxyphenyl)ethyl]-trans-decahydronaphthalene,
trans-6-propyl-2-[2-(3-fluoro-4-trifluoromethoxyphenyl)ethyl]-trans-decahydronaphthalene,
trans-6-propyl-2-[2-(3,5-difluoro-4-trifluoromethoxyphenyl)ethyl]-trans-decahydronaphthalene, trans-6-propyl-2-[2-(4-difluoromethoxyphenyl)ethyl]-trans-decahydronaphthalene,
trans-6-propyl-2-[2-(3-fluoro-4-difluoromethoxyphenyl)ethyl]-trans-decahydronaphthalene,
trans-6-propyl-2-[2-(3,5-difluoro-4-difluoromethoxyphenyl)ethyl]-trans-decahydronaphthalene,
trans-6-propyl-2-[2-(4-chlorophenyl)ethyl]-trans-decahydronaphthalene,
trans-6-propyl-2-[2-(3-fluoro-4-chlorophenyl)ethyl]-trans-decahydronaphthalene,
trans-6-propyl-2-[2-(3,5-difluoro-4-chlorophenyl)ethyl]-trans-decahydronaphthalene,
trans-6-propyl-2-[2-(4-methoxyphenyl)ethyl]-trans-decahydronaphthalene,
trans-6-propyl-2-[2-(3-fluoro-4-methoxyphenyl)ethyl]-trans-decahydronaphthalene,
trans-6-propyl-2-[2-(3,5-difluoro-4-methoxyphenyl)ethyl]-trans-decahydronaphthalene.

Example 13

Synthesis of 4-cyano-3-fluorophenyl-6-pentyl-trans-decahydronaphthalene-2-carboxylate (I-14)

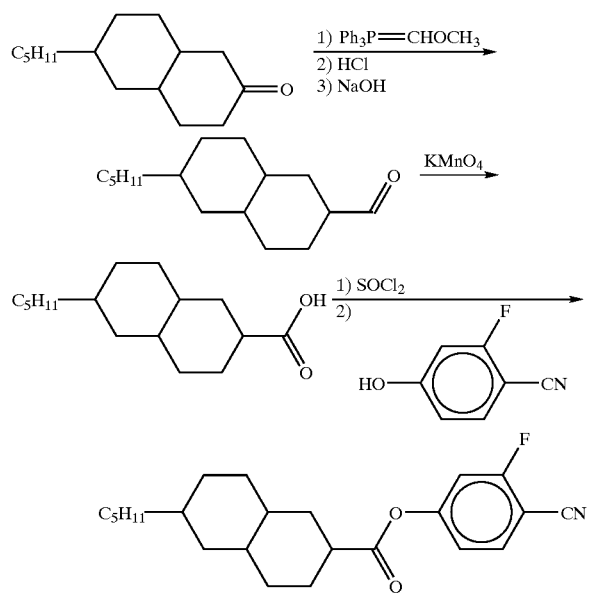

(13-a) Synthesis of 6-pentyl-trans-decahydronaphthalene-2-carbaldehyde

Reaction of 28 g of 6-propyl-trans-decahydro-2-naphthalenone with a Wittig reagent similar to that used in (1-a) was carried out to obtain 19 g of white solid 6-pentyl-trans-decahydronaphthalene-2-carbaldehyde.

(13-b) Synthesis of 6-pentyl-trans-decahydronaphthalene-2-carboxylic acid 19 g of 6-pentyl-trans-decahydronaphthalene-2-carbaldehyde, which was obtained in (13-a), was added dropwise to a 60 ml aqueous solution of 12 g of concentrated sulfuric acid and 6 g of potassium permanganate while the mixture was cooled to 10° C. or lower. After stirring the mixture for 30 minutes at room temperature, water and ethyl acetate were added. The organic phase was separated and rinsed with water, a saturated aqueous solution of sodium hydrogencarbonate, water, and a saturated saline solution, in sequence. After the organic phase was dried on anhydrous sodium sulfate, the solvent was evaporated. The residue was recrystallized from a hexane solution to obtain 8 g white solid 6-pentyl-trans-decahydronaphthalene-2-carboxylic acid.

(13-c) Synthesis of 4-cyano-3-fluorophenyl-6-pentyl-trans-decahydronaphthalene-2-carboxylate 8 g of 6-pentyl-trans-decahydronaphthalene-2-carboxylic acid, which was obtained in (13-b), was dissolved in 40 ml of 1,2-dichloroethane. 5 g of thionyl chloride, 0.1 ml of pyridine, and 5 ml of DMF were added to the solution, and the mixture was heated for 1 hour under refluxing. After excessive thionyl chloride was evaporated, 50 ml of dichloromethane was added, then 4 g of 3-fluoro-4-cyanophenol and 3 g of pyridine were added, and the mixture was stirred for 8 hours at room temperature. 10% hydrochloric acid was added, and the organic phase was separated and rinsed with a saturated aqueous solution of sodium hydrogencarbonate and a saturated saline solution, in sequence, and dried on anhydrous sodium sulfate. After the solvent was evaporated, the residue was purified by silica gel chromatography (hexane/ethyl acetate), and recrystallized from ethanol to obtain 3 g white crystals of 4-cyano-3-fluorophenyl 6-pentyl-trans-decahydronaphthalene-2-carboxylate.

Example 14

Synthesis of 4-cyano-3,5-difluorophenyl 6-propyl-trans-decahydronaphthalene-2-carboxylate (I-13)

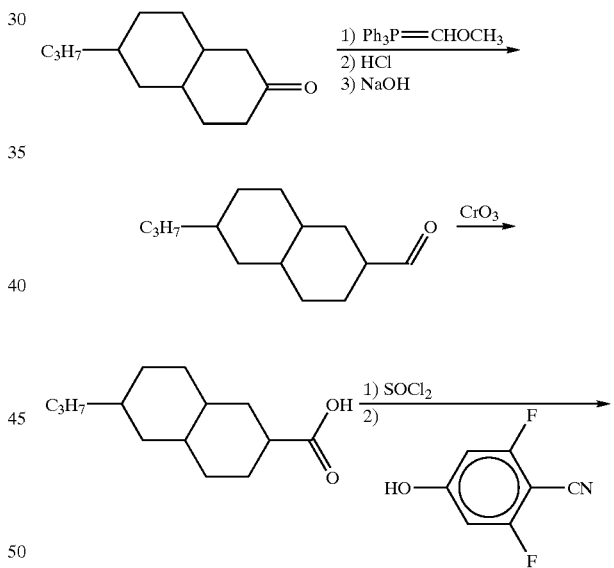

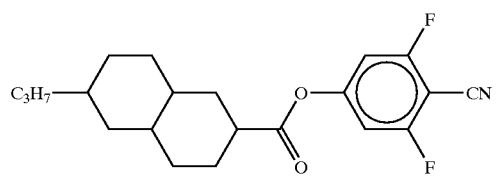

In a manner similar that in (13-c), esterification reaction of 15 g of 6-propyl-trans-decahydronaphthalene-2-carboxylic acid, which was obtained in (13-b), with 11 g of 3,5-difluoro-4-cyanophenol was carried out to obtain 6 g of white solid 4-cyano-3,5-difluorophenyl-6-propyl-trans-decahydronaphthalene-2-carboxylate.

Example 15

Synthesis of 6-(4-vinyl-trans-cyclohexyl)-2-(3,5-difluoro-4-cyanophenyl)-trans-decahydronaphthalene (I-15)

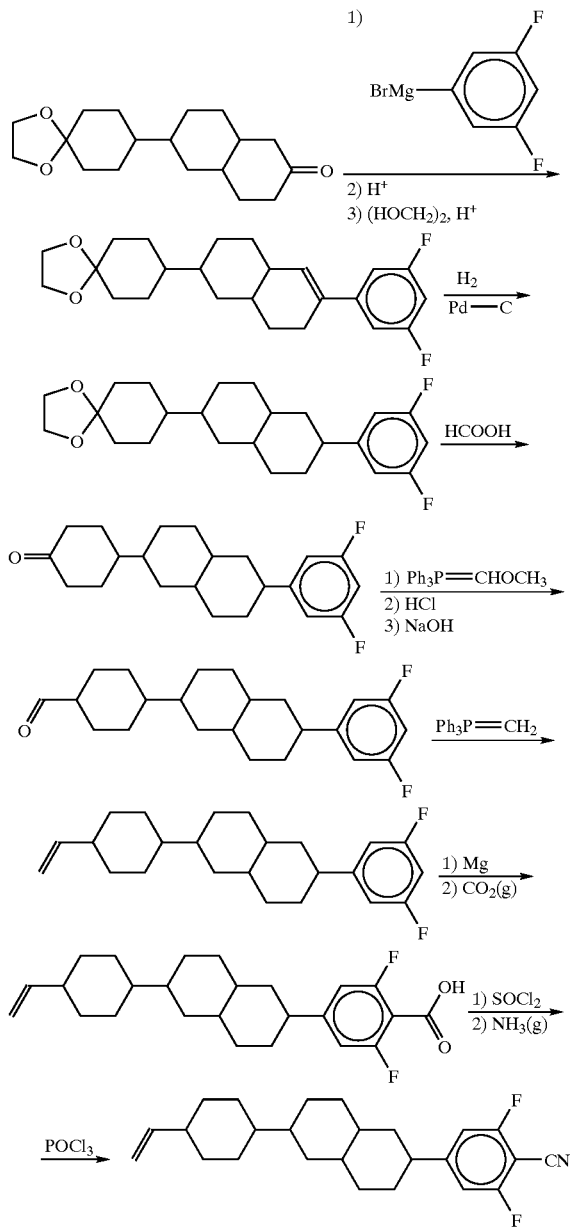

(15-a) Synthesis of 4-[2-(3,5-difluorophenyl)-trans-3,4,4a,5,6,7,8,8a-octahydronaphthalen-6-yl]cyclohexanone ethyleneacetal Reaction of 29 g of 4-[6-oxo-trans-octahydronaphthalen-2-yl]cyclohexanone monoethyleneacetal with a Grignard reagent prepared from 3,5-difluoro-1-bromobenzene was carried out, and dehydration and re-acetalization were carried out to obtain 33 g of pale yellow solid 4-[2-(3,5-difluorophenyl)-trans-3,4,4a,5,6,7,8,8a-octahydronaphthalen-6-yl]cyclohexanone ethyleneacetal.

(15-b) Synthesis of 4-[6-(3,5-difluorophenyl)-trans-decahydronaphthalen-2-yl]cyclohexanone ethyleneacetal Catalytic hydrogenation reduction of 33 g of 4-[2-(3,5-difluorophenyl)-trans-3,4,4a,5,6,7,8,8a-octahydronaphthalen-6-yl]cyclohexanone ethyleneacetal, which was obtained in (15-a), was carried out to obtain 29 g of pale yellow solid 4-[6-(3,5-difluorophenyl)-trans-decahydronaphthalen-2-yl]cyclohexanone ethyleneacetal.

(15-c) Synthesis of 4-[6-(3,5-difluorophenyl)-trans-decahydronaphthalen-2-yl]cyclohexanone Deacetalization of 29 g of 4-[6-(3,5-difluorophenyl)-trans-decahydronaphthalen-2-yl]cyclohexanone ethyleneacetal, which was obtained in (5-b), was carried out to obtain 20 g of pale yellow solid 4-[6-(3,5-difluorophenyl)-trans-decahydronaphthalen-2-yl]cyclohexanone.

(15-d) Synthesis of 4-[6-(3,5-difluorophenyl)-trans-decahydronaphthalen-2-yl]cyclohexylcarbaldehyde Reaction of 20 g of 4-[6-(3,5-difluorophenyl)-trans-decahydronaphthalen-2-yl]cyclohexanone, which was obtained in (5-c), with a Wittig reagent was carried out to obtain 18 g of pale yellow solid 4-[6-(3,5-difluorophenyl)-trans-decahydronaphthalen-2-yl]cyclohexanecarbaldehyde.

(15-e) Synthesis of 6-(3,5-difluorophenyl)-2-(4-vinyl-trans-cyclohexyl)-trans-decahydronaphthalene Reaction of 18 g of 4-[6-(3,5-difluorophenyl)-trans-decahydronaphthalen-2-yl]cyclohexanecarbaldehyde, which was obtained in (15-d), was carried out to obtain 16 g of white solid 6-(3,5-difluorophenyl)-2-(4-vinyl-trans-cyclohexyl)-trans-decahydronaphthalene.

(15-f) Synthesis of 3,5-difluoro-4-[6-(4-vinyl-trans-cyclohexyl)-trans-decahydronaphthalen-2-yl]benzoic acid Reaction of 16 g of 6-(3,5-difluorophenyl)-2-(4-vinyl-trans-cyclohexyl)-trans-decahydronaphthalene, which was obtained in (15-e), with butyl lithium was carried out, and thereafter reaction of the resultant with carbon dioxide was carried out to obtain 16 g of milky-white solid 3,5-difluoro-4-[6-(4-vinyl-trans-cyclohexyl)-trans-decahydronaphthalen-2-yl]benzoic acid.

(15-g) Synthesis of 6-(4-vinyl-trans-cyclohexyl)-2-(3,5-difluoro-4-cyanophenyl)-trans-decahydronaphthalene 16 g of 3,5-difluoro-4-[6-(4-vinyl-trans-cyclohexyl)-trans-decahydronaphthalen-2-yl]benzoic acid, which was obtained in (15-f), was dissolved in 80 ml of 1,2-dichloroethane. 6 g of thionyl chloride, 0.1 ml of pyridine, and 3 ml of DMF were added to the solution, and the mixture was stirred for 6 hours at room temperature. After the solvent and excessive thionyl chloride were evaporated, 120 ml of dichloromethane was added, and ammonia gas was injected while the mixture was cooled to 0° C. When generation of heat stopped, the mixture was stirred for 2 hours at room temperature, and crystals which precipitated were separated by precipitation. The yellow crystals obtained were dissolved in 140 ml of DMF. 11 g of oxalyl chloride was added dropwise to the solution while the mixture was cooled to 0° C. After stirring for 1 hour at room temperature, the mixture was poured onto iced water, and extraction was carried out using toluene. The organic phase was rinsed with water, a saturated aqueous solution of sodium hydrogencarbonate, water, and a saturated saline solution, in sequence, and dried on anhydrous sodium sulfate. The solvent was evaporated, and the residue was purified by silica gel column chromatography (toluene) and recrystallized from ethanol to obtain 3 g white crystals of 6-(4-vinyl-trans-cyclohexyl)-2-(3,5-difluoro-4-cyanophenyl)-trans-decahydronaphthalene.

The following compounds were prepared in the same manner as mentioned above:

6-(trans-1-propenyl)-2-[trans-4-[3,5-difluoro-4-(trans-2-butenyloxy)phenyl]cyclohexyl]-trans-decahydronaphthalene, 6-(trans-3-butenyl)-2-[trans-4-[3,5-difluoro-4-(trans-2-butenyloxy)phenyl]cyclohexyl]-trans-decahydronaphthalene,
6-(trans-3-pentenyl)-2-[trans-4-[3,5-difluoro-4-(trans-2-butenyloxy)phenyl]cyclohexyl]-trans-decahydronaphthalene,
6-(trans-1-pentenyl)-2-[trans-4-[3,5-difluoro-4-(trans-2-butenyloxy)phenyl]cyclohexyl]-trans-decahydronaphthalene.

Example 16

Synthesis of trans-2-[4-(3,4,5-trifluorophenyl)phenyl]-6-pentyl-trans-decahydronaphthalene (I-20)

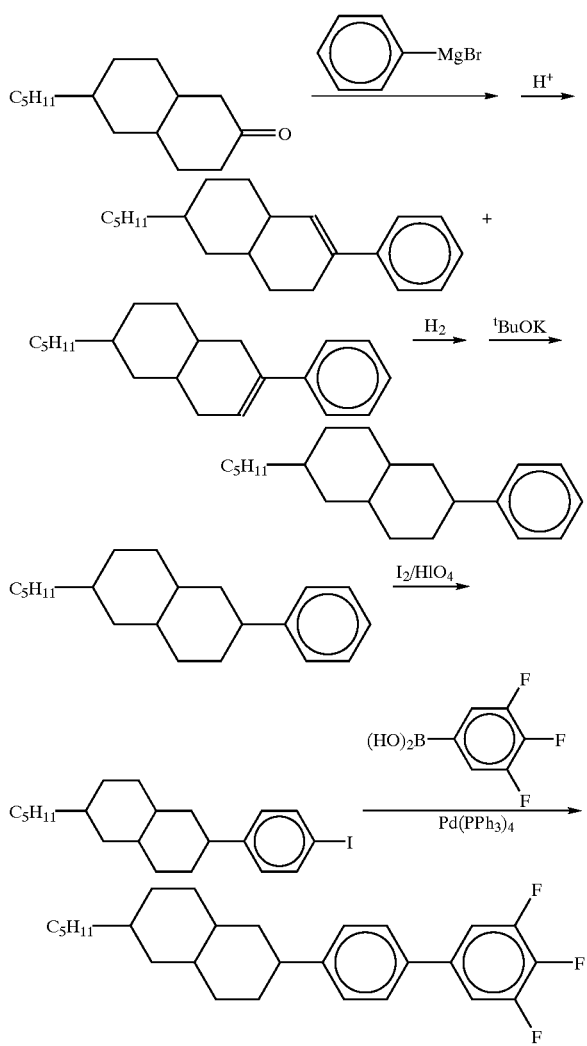

(16-a) Synthesis of trans-2-phenyl-6-pentyl-trans-decahydronaphthalene

To a suspension of 23.6 g of metal magnesium in 90 ml of THF, a 700 ml THF solution of 150 g of bromobenzene was added dropwise to obtain a Grignard reagent. A 400 ml THF solution of 217 g of 6-pentyl-trans-decahydro-2-naphthalenone was added dropwise to the reagent over a period of 30 minutes. After further stirring for 2 hours, 400 ml of 10% hydrochloric acid was added. Then, the organic phase was separated, rinsed with water, and dried on anhydrous magnesium sulfate. Then, the solvent was evaporated. 261 g of the oily substance obtained was dissolved in 800 ml of toluene. 13 g of p-toluenesulfonic acid monohydrate was added to the solution, and the mixture was heated for 4 hours under refluxing using an apparatus equipped with a water separator until evaporation of water stopped. Then, the solution was cooled to room temperature. Water was added to the solution, and the organic phase was separated, rinsed with a saturated saline solution, and dried on anhydrous magnesium sulfate. Then, the solvent was evaporated. 240 g of the oily substance obtained was dissolved in 1 l of ethyl acetate in an autoclave. 24 g of carbon with 5% palladium was added to the solution. Catalytic hydrogenation reduction was carried out for 5 hours at room temperature. Then, the solution was filtered through celite to separate the catalyst, and the solvent was evaporated to obtain 207 g of cis/trans mixture of 2-phenyl-6-pentyl-trans-decahydronaphthalene. The whole amount of this mixture was dissolved in 630 ml of DMF. 45 g of potassium t-butoxide was added to the solution, and the mixture was heated for 2 hours under refluxing. The mixture was cooled to room temperature, water was added to the mixture, and extraction was carried out using hexane. The organic phase was rinsed with a saturated saline solution, and dried on anhydrous sodium sulfate. The solvent was evaporated, and the residue was purified by silica gel column chromatography (hexane) and recrystallized from ethanol to obtain 24 white crystals of trans-2-phenyl-6-pentyl-trans-decahydronaphthalene.

The following compounds were prepared in the same manner as mentioned above:
trans-2-phenyl-6-methyl-trans-decahydronaphthalene,
trans-2-phenyl-6-ethyl-trans-decahydronaphthalene,
trans-2-phenyl-6-propyl-trans-decahydronaphthalene,
trans-2-phenyl-6-butyl-trans-decahydronaphthalene,
trans-2-phenyl-6-hexyl-trans-decahydronaphthalene,
trans-2-phenyl-6-heptyl-trans-decahydronaphthalene,
trans-2-(4-chlorophenyl)-6-methyl-trans-decahydronaphthalene,
trans-2-(4-chlorophenyl)-6-ethyl-trans-decahydronaphthalene,
trans-2-(4-chlorophenyl)-6-propyl-trans-decahydronaphthalene,
trans-2-(4-chlorophenyl)-6-butyl-trans-decahydronaphthalene,
trans-2-(4-chlorophenyl)-6-pentyl-trans-decahydronaphthalene,
trans-2-(4-chlorophenyl)-6-hexyl-trans-decahydronaphthalene,
trans-2-(4-chlorophenyl)-6-heptyl-trans-decahydronaphthalene,
trans-2-(4-methoxyphenyl)-6-methyl-trans-decahydronaphthalene,
trans-2-(4-methoxyphenyl)-6-ethyl-trans-decahydronaphthalene,
trans-2-(4-methoxyphenyl)-6-propyl-trans-decahydronaphthalene,
trans-2-(4-methoxyphenyl)-6-butyl-trans-decahydronaphthalene,
trans-2-(4-methoxyphenyl)-6-pentyl-trans-decahydronaphthalene,
trans-2-(4-methoxyphenyl)-6-hexyl-trans-decahydronaphthalene,
trans-2-(4-methoxyphenyl)-6-heptyl-trans-decahydronaphthalene,
trans-2-(4-hydroxyphenyl)-6-methyl-trans-decahydronaphthalene,
trans-2-(4-hydroxyphenyl)-6-ethyl-trans-decahydronaphthalene,
trans-2-(4-hydroxyphenyl)-6-propyl-trans-decahydronaphthalene, trans-2-(4-hydroxyphenyl)-6-butyl-trans-decahydronaphthalene,
trans-2-(4-hydroxyphenyl)-6-pentyl-trans-decahydronaphthalene,
trans-2-(4-hydroxyphenyl)-6-hexyl-trans-decahydronaphthalene,
trans-2-(4-hydroxyphenyl)-6-heptyl-trans-decahydronaphthalene,
trans-2-[4-(4,4-dimethyl-1,3-oxazolidin-2-yl)phenyl]-6-methyl-trans-decahydronaphthalene,
trans-2-[4-(4,4-dimethyl-1,3-oxazolidin-2-yl)phenyl]-6-ethyl-trans-decahydronaphthalene,
trans-2-[4-(4,4-dimethyl-1,3-oxazolidin-2-yl)phenyl]-6-propyl-trans-decahydronaphthalene,
trans-2-[4-(4,4-dimethyl-1,3-oxazolidin-2-yl)phenyl]-6-butyl-trans-decahydronaphthalene,
trans-2-[4-(4,4-dimethyl-1,3-oxazolidin-2-yl)phenyl]-6-pentyl-trans-decahydronaphthalene,
trans-2-[4-(4,4-dimethyl-1,3-oxazolidin-2-yl)phenyl]-6-hexyl-trans-decahydronaphthalene,
trans-2-[4-(4,4-dimethyl-1,3-oxazolidin-2-yl)phenyl]-6-heptyl-trans-decahydronaphthalene,
trans-2-[3-fluoro-4-(4,4-dimethyl-1,3-oxazolidin-2-yl)phenyl]-6-methyl-trans-decahydronaphthalene,
trans-2-[3-fluoro-4-(4,4-dimethyl-1,3-oxazolidin-2-yl)phenyl]-6-ethyl-trans-decahydronaphthalene,
trans-2-[3-fluoro-4-(4,4-dimethyl-1,3-oxazolidin-2-yl)phenyl]-6-propyl-trans-decahydronaphthalene,
trans-2-[3-fluoro-4-(4,4-dimethyl-1,3-oxazolidin-2-yl)phenyl]-6-butyl-trans-decahydronaphthalene,
trans-2-[3-fluoro-4-(4,4-dimethyl-1,3-oxazolidin-2-yl)phenyl]-6-pentyl-trans-decahydronaphthalene,
trans-2-[3-fluoro-4-(4,4-dimethyl-1,3-oxazolidin-2-yl)phenyl]-6-hexyl-trans-decahydronaphthalene,
trans-2-[3-fluoro-4-(4,4-dimethyl-1,3-oxazolidin-2-yl)phenyl]-6-heptyl-trans-decahydronaphthalene,
trans-2-(3-fluorophenyl)-6-methyl-trans-decahydronaphthalene,
trans-2-(3-fluorophenyl)-6-ethyl-trans-decahydronaphthalene,
trans-2-(3-fluorophenyl)-6-propyl-trans-decahydronaphthalene,
trans-2-(3-fluorophenyl)-6-butyl-trans-decahydronaphthalene,
trans-2-(3-fluorophenyl)-6-pentyl-trans-decahydronaphthalene,
trans-2-(3-fluorophenyl)-6-hexyl-trans-decahydronaphthalene,
trans-2-(3-fluorophenyl)-6-heptyl-trans-decahydronaphthalene,
trans-2-(3,5-difluorophenyl)-6-methyl-trans-decahydronaphthalene,
trans-2-(3,5-difluorophenyl)-6-ethyl-trans-decahydronaphthalene,
trans-2-(3,5-difluorophenyl)-6-propyl-trans-decahydronaphthalene,
trans-2-(3,5-difluorophenyl)-6-butyl-trans-decahydronaphthalene,
trans-2-(3,5-difluorophenyl)-6-pentyl-trans-decahydronaphthalene,
trans-2-(3,5-difluorophenyl)-6-hexyl-trans-decahydronaphthalene,
trans-2-(3,5-difluorophenyl)-6-heptyl-trans-decahydronaphthalene,
trans-2-(4-iodophenyl)-6-pentyl-trans-decahydronaphthalene,
trans-2-phenyl-6-pentyl-trans-decahydronaphthalene.

(16-b) Synthesis of trans-2-(4-iodophenyl)-6-pentyl-trans-decahydronaphthalene 227 g of trans-2-phenyl-6-pentyl-trans-decahydronaphthalene, which was obtained in (16-a), was dissolved in 80 ml of 1,2-dichloroethane and 670 ml of acetic acid. 125 g of iodine and 91 g of orthoperiodic acid were added, and then 180 ml of 10% sulfuric acid was added. After the mixture was heated for 1.5 hours under refluxing, the mixture was cooled to room temperature, and extraction was carried out using toluene. Then, the organic phase was rinsed with a saturated aqueous solution of sodium hydrogensulfite and a saturated saline solution, in sequence, and dried on anhydrous magnesium sulfate. After the solvent was evaporated, the residue was recrystallized from ethanol/toluene to obtain 254 g white crystals of trans-2-(4-iodophenyl)-6-pentyl-trans-decahydronaphthalene.

(16-c) Synthesis of trans-2-[4-(3,4,5-trifluorophenyl)phenyl]-6-pentyl-trans-decahydronaphthalene 25 g of trans-2-(4-iodophenyl)-6-pentyl-trans-decahydronaphthalene, which was obtained in (16-b), was dissolved in a mixed solution of 48 ml of toluene and 24 ml of ethanol. 0.8 g of tetrakis(triphenylphosphine)palladium (0) and 48 ml aqueous solution of 2 M sodium carbonate were added to the mixture, and 32 ml ethanol solution of 16 g of 3,4,5-trifluorophenylboric acid was further added dropwise over a period of 10 minutes. After heating the mixture for 24 hours at 70° C. while stirring, the mixture was cooled to room temperature, and water was added to the mixture. After extraction was carried out using toluene, the organic phase was rinsed with a saline solution and dried on anhydrous magnesium sulfate. After the solvent was evaporated, the residue was purified by silica gel column chromatography (hexane) and recrystallized from ethanol to obtain 18 g white crystals of trans-2-[4-(3,4,5-trifluorophenyl)phenyl]-6-pentyl-trans-decahydronaphthalene.

The following compounds were prepared in the same manner as mentioned above:
trans-2-[4-(3,4,5-trifluorophenyl)phenyl]-6-methyl-trans-decahydronaphthalene,
trans-2-[4-(3,4,5-trifluorophenyl)phenyl]-6-ethyl-trans-decahydronaphthalene,
trans-2-[4-(3,4,5-trifluorophenyl)phenyl]-6-propyl-trans-decahydronaphthalene,
trans-2-[4-(3,4,5-trifluorophenyl)phenyl]-6-butyl-trans-decahydronaphthalene,
trans-2-[4-(3,4,5-trifluorophenyl)phenyl]-6-hexyl-trans-decahydronaphthalene,
trans-2-[4-(3,4,5-trifluorophenyl)phenyl]-6-heptyl-trans-decahydronaphthalene,
trans-2-[4-(3,4-difluorophenyl)phenyl]-6-methyl-trans-decahydronaphthalene,
trans-2-[4-(3,4-difluorophenyl)phenyl]-6-ethyl-trans-decahydronaphthalene,
trans-2-[4-(3,4-difluorophenyl)phenyl]-6-propyl-trans-decahydronaphthalene,
trans-2-[4-(3,4-difluorophenyl)phenyl]-6-butyl-trans-decahydronaphthalene,
trans-2-[4-(3,4-difluorophenyl)phenyl]-6-pentyl-trans-decahydronaphthalene,
trans-2-[4-(3,4-difluorophenyl)phenyl]-6-hexyl-trans-decahydronaphthalene,
trans-2-[4-(3,4-difluorophenyl)phenyl]-6-heptyl-trans-decahydronaphthalene,
trans-2-[4-(4-fluorophenyl)phenyl]-6-methyl-trans-decahydronaphthalene,
trans-2-[4-(4-fluorophenyl)phenyl]-6-ethyl-trans-decahydronaphthalene, trans-2-[4-(4-fluorophenyl)phenyl]-6-propyl-trans-decahydronaphthalene,
trans-2-[4-(4-fluorophenyl)phenyl]-6-butyl-trans-decahydronaphthalene,
trans-2-[4-(4-fluorophenyl)phenyl]-6-pentyl-trans-decahydronaphthalene,
trans-2-[4-(4-fluorophenyl)phenyl]-6-hexyl-trans-decahydronaphthalene,
trans-2-[4-(4-fluorophenyl)phenyl]-6-heptyl-trans-decahydronaphthalene,
trans-2-[4-(3,5-difluorophenyl)phenyl]-6-methyl-trans-decahydronaphthalene,
trans-2-[4-(3,5-difluorophenyl)phenyl]-6-ethyl-trans-decahydronaphthalene,
trans-2-[4-(3,5-difluorophenyl)phenyl]-6-propyl-trans-decahydronaphthalene,
trans-2-[4-(3,5-difluorophenyl)phenyl]-6-butyl-trans-decahydronaphthalene,
trans-2-[4-(3,5-difluorophenyl)phenyl]-6-pentyl-trans-decahydronaphthalene,
trans-2-[4-(3,5-difluorophenyl)phenyl]-6-hexyl-trans-decahydronaphthalene,
trans-2-[4-(3,5-difluorophenyl)phenyl]-6-heptyl-trans-decahydronaphthalene,
trans-2-[4-(3-fluorophenyl)phenyl]-6-methyl-trans-decahydronaphthalene,
trans-2-[4-(3-fluorophenyl)phenyl]-6-ethyl-trans-decahydronaphthalene,
trans-2-[4-(3-fluorophenyl)phenyl]-6-propyl-trans-decahydronaphthalene,
trans-2-[4-(3-fluorophenyl)phenyl]-6-butyl-trans-decahydronaphthalene,
trans-2-[4-(3-fluorophenyl)phenyl]-6-pentyl-trans-decahydronaphthalene,
trans-2-[4-(3-fluorophenyl)phenyl]-6-hexyl-trans-decahydronaphthalene,
trans-2-[4-(3-fluorophenyl)phenyl]-6-heptyl-trans-decahydronaphthalene,
trans-2-[3-fluoro-4-(3,4,5-trifluorophenyl)phenyl]-6-methyl-trans-decahydronaphthalene,
trans-2-[3-fluoro-4-(3,4,5-trifluorophenyl)phenyl]-6-ethyl-trans-decahydronaphthalene,
trans-2-[3-fluoro-4-(3,4,5-trifluorophenyl)phenyl]-6-propyl-trans-decahydronaphthalene,
trans-2-[3-fluoro-4-(3,4,5-trifluorophenyl)phenyl]-6-butyl-trans-decahydronaphthalene,
trans-2-[3-fluoro-4-(3,4,5-trifluorophenyl)phenyl]-6-pentyl-trans-decahydronaphthalene,
trans-2-[3-fluoro-4-(3,4,5-trifluorophenyl)phenyl]-6-hexyl-trans-decahydronaphthalene,
trans-2-[3-fluoro-4-(3,4,5-trifluorophenyl)phenyl]-6-heptyl-trans-decahydronaphthalene,
trans-2-[3-fluoro-4-(3,4-difluorophenyl)phenyl]-6-methyl-trans-decahydronaphthalene,
trans-2-[3-fluoro-4-(3,4-difluorophenyl)phenyl]-6-ethyl-trans-decahydronaphthalene,
trans-2-[3-fluoro-4-(3,4-difluorophenyl)phenyl]-6-propyl-trans-decahydronaphthalene,
trans-2-[3-fluoro-4-(3,4-difluorophenyl)phenyl]-6-butyl-trans-decahydronaphthalene,
trans-2-[3-fluoro-4-(3,4-difluorophenyl)phenyl]-6-pentyl-trans-decahydronaphthalene,
trans-2-[3-fluoro-4-(3,4-difluorophenyl)phenyl]-6-hexyl-trans-decahydronaphthalene,
trans-2-[3-fluoro-4-(3,4-difluorophenyl)phenyl]-6-heptyl-trans-decahydronaphthalene,
trans-2-[3-fluoro-4-(3,5-difluorophenyl)phenyl]-6-methyl-trans-decahydronaphthalene,
trans-2-[3-fluoro-4-(3,5-difluorophenyl)phenyl]-6-ethyl-trans-decahydronaphthalene,
trans-2-[3-fluoro-4-(3,5-difluorophenyl)phenyl]-6-propyl-trans-decahydronaphthalene,
trans-2-[3-fluoro-4-(3,5-difluorophenyl)phenyl]-6-butyl-trans-decahydronaphthalene,
trans-2-[3-fluoro-4-(3,5-difluorophenyl)phenyl]-6-pentyl-trans-decahydronaphthalene,
trans-2-[3-fluoro-4-(3,5-difluorophenyl)phenyl]-6-hexyl-trans-decahydronaphthalene,
trans-2-[3-fluoro-4-(3,5-difluorophenyl)phenyl]-6-heptyl-trans-decahydronaphthalene,
trans-2-[3-fluoro-4-(4-fluorophenyl)phenyl]-6-methyl-trans-decahydronaphthalene,
trans-2-[3-fluoro-4-(4-fluorophenyl)phenyl]-6-ethyl-trans-decahydronaphthalene,
trans-2-[3-fluoro-4-(4-fluorophenyl)phenyl]-6-propyl-trans-decahydronaphthalene,
trans-2-[3-fluoro-4-(4-fluorophenyl)phenyl]-6-butyl-trans-decahydronaphthalene,
trans-2-[3-fluoro-4-(4-fluorophenyl)phenyl]-6-pentyl-trans-decahydronaphthalene,
trans-2-[3-fluoro-4-(4-fluorophenyl)phenyl]-6-hexyl-trans-decahydronaphthalene,
trans-2-[3-fluoro-4-(4-fluorophenyl)phenyl]-6-heptyl-trans-decahydronaphthalene,
trans-2-[3-fluoro-4-(3-fluorophenyl)phenyl]-6-methyl-trans-decahydronaphthalene,
trans-2-[3-fluoro-4-(3-fluorophenyl)phenyl]-6-ethyl-trans-decahydronaphthalene,
trans-2-[3-fluoro-4-(3-fluorophenyl)phenyl]-6-propyl-trans-decahydronaphthalene,
trans-2-[3-fluoro-4-(3-fluorophenyl)phenyl]-6-butyl-trans-decahydronaphthalene,
trans-2-[3-fluoro-4-(3-fluorophenyl)phenyl]-6-pentyl-trans-decahydronaphthalene,
trans-2-[3-fluoro-4-(3-fluorophenyl)phenyl]-6-hexyl-trans-decahydronaphthalene,
trans-2-[3-fluoro-4-(3-fluorophenyl)phenyl]-6-heptyl-trans-decahydronaphthalene,
trans-2-[4-(4-trifluoromethoxyphenyl)phenyl]-6-methyl-trans-decahydronaphthalene,
trans-2-[4-(4-trifluoromethoxyphenyl)phenyl]-6-ethyl-trans-decahydronaphthalene,
trans-2-[4-(4-trifluoromethoxyphenyl)phenyl]-6-propyl-trans-decahydronaphthalene,
trans-2-[4-(4-trifluoromethoxyphenyl)phenyl]-6-butyl-trans-decahydronaphthalene,
trans-2-[4-(4-trifluoromethoxyphenyl)phenyl]-6-pentyl-trans-decahydronaphthalene,
trans-2-[4-(4-trifluoromethoxyphenyl)phenyl]-6-hexyl-trans-decahydronaphthalene,
trans-2-[4-(4-trifluoromethoxyphenyl)phenyl]-6-heptyl-trans-decahydronaphthalene,
trans-2-[3-fluoro-4-(4-trifluoromethoxyphenyl)phenyl]-6-methyl-trans-decahydronaphthalene,
trans-2-[3-fluoro-4-(4-trifluoromethoxyphenyl)phenyl]-6-ethyl-trans-decahydronaphthalene,
trans-2-[3-fluoro-4-(4-trifluoromethoxyphenyl)phenyl]-6-propyl-trans-decahydronaphthalene,
trans-2-[3-fluoro-4-(4-trifluoromethoxyphenyl)phenyl]-6-butyl-trans-decahydronaphthalene,
trans-2-[3-fluoro-4-(4-trifluoromethoxyphenyl)phenyl]-6-pentyl-trans-decahydronaphthalene,
trans-2-[3-fluoro-4-(4-trifluoromethoxyphenyl)phenyl]-6-hexyl-trans-decahydronaphthalene,
trans-2-[3-fluoro-4-(4-trifluoromethoxyphenyl)phenyl]-6-heptyl-trans-decahydronaphthalene, trans-2-[4-(3-fluoro-4-trifluoromethoxyphenyl)phenyl]-6-methyl-trans-decahydronaphthalene,
trans-2-[4-(3-fluoro-4-trifluoromethoxyphenyl)phenyl]-6-ethyl-trans-decahydronaphthalene,
trans-2-[4-(3-fluoro-4-trifluoromethoxyphenyl)phenyl]-6-propyl-trans-decahydronaphthalene,
trans-2-[4-(3-fluoro-4-trifluoromethoxyphenyl)phenyl]-6-butyl-trans-decahydronaphthalene,
trans-2-[4-(3-fluoro-4-trifluoromethoxyphenyl)phenyl]-6-pentyl-trans-decahydronaphthalene,
trans-2-[4-(3-fluoro-4-trifluoromethoxyphenyl)phenyl]-6-hexyl-trans-decahydronaphthalene,
trans-2-[4-(3-fluoro-4-trifluoromethoxyphenyl)phenyl]-6-heptyl-trans-decahydronaphthalene,
trans-2-[4-(3,5-difluoro-4-trifluoromethoxyphenyl)phenyl]-6-methyl-trans-decahydronaphthalene,
trans-2-[4-(3,5-difluoro-4-trifluoromethoxyphenyl)phenyl]-6-ethyl-trans-decahydronaphthalene,
trans-2-[4-(3,5-difluoro-4-trifluoromethoxyphenyl)phenyl]-6-propyl-trans-decahydronaphthalene,
trans-2-[4-(3,5-difluoro-4-trifluoromethoxyphenyl)phenyl]-6-butyl-trans-decahydronaphthalene,
trans-2-[4-(3,5-difluoro-4-trifluoromethoxyphenyl)phenyl]-6-pentyl-trans-decahydronaphthalene,
trans-2-[4-(3,5-difluoro-4-trifluoromethoxyphenyl)phenyl]-6-hexyl-trans-decahydronaphthalene,
trans-2-[4-(3,5-difluoro-4-trifluoromethoxyphenyl)phenyl]-6-heptyl-trans-decahydronaphthalene,
trans-2-[3-fluoro-4-(3-fluoro-4-trifluoromethoxyphenyl)phenyl]-6-methyl-trans-decahydronaphthalene,
trans-2-[3-fluoro-4-(3-fluoro-4-trifluoromethoxyphenyl)phenyl]-6-ethyl-trans-decahydronaphthalene,
trans-2-[3-fluoro-4-(3-fluoro-4-trifluoromethoxyphenyl)phenyl]-6-propyl-trans-decahydronaphthalene,
trans-2-[3-fluoro-4-(3-fluoro-4-trifluoromethoxyphenyl)phenyl]-6-butyl-trans-decahydronaphthalene,
trans-2-[3-fluoro-4-(3-fluoro-4-trifluoromethoxyphenyl)phenyl]-6-pentyl-trans-decahydronaphthalene,
trans-2-[3-fluoro-4-(3-fluoro-4-trifluoromethoxyphenyl)phenyl]-6-hexyl-trans-decahydronaphthalene,
trans-2-[3-fluoro-4-(3-fluoro-4-trifluoromethoxyphenyl)phenyl]-6-heptyl-trans-decahydronaphthalene,
trans-2-[3-fluoro-4-(3,5-difluoro-4-trifluoromethoxyphenyl)phenyl]-6-methyl-trans-decahydronaphthalene,
trans-2-[3-fluoro-4-(3,5-difluoro-4-trifluoromethoxyphenyl)phenyl]-6-ethyl-trans-decahydronaphthalene,
trans-2-[3-fluoro-4-(3,5-difluoro-4-trifluoromethoxyphenyl)phenyl]-6-propyl-trans-decahydronaphthalene,
trans-2-[3-fluoro-4-(3,5-difluoro-4-trifluoromethoxyphenyl)phenyl]-6-butyl-trans-decahydronaphthalene,
trans-2-[3-fluoro-4-(3,5-difluoro-4-trifluoromethoxyphenyl)phenyl]-6-pentyl-trans-decahydronaphthalene,
trans-2-[3-fluoro-4-(3,5-difluoro-4-trifluoromethoxyphenyl)phenyl]-6-hexyl-trans-decahydronaphthalene,
trans-2-[3-fluoro-4-(3,5-difluoro-4-trifluoromethoxyphenyl)phenyl]-6-heptyl-trans-decahydronaphthalene,
trans-2-[4-(4-difluoromethoxyphenyl)phenyl]-6-methyl-trans-decahydronaphthalene,
trans-2-[4-(4-difluoromethoxyphenyl)phenyl]-6-ethyl-trans-decahydronaphthalene,
trans-2-[4-(4-difluoromethoxyphenyl)phenyl]-6-propyl-trans-decahydronaphthalene,
trans-2-[4-(4-difluoromethoxyphenyl)phenyl]-6-butyl-trans-decahydronaphthalene,
trans-2-[4-(4-difluoromethoxyphenyl)phenyl]-6-pentyl-trans-decahydronaphthalene,
trans-2-[4-(4-difluoromethoxyphenyl)phenyl]-6-hexyl-trans-decahydronaphthalene,
trans-2-[4-(4-difluoromethoxyphenyl)phenyl]-6-heptyl-trans-decahydronaphthalene,
trans-2-[3-fluoro-4-(4-difluoromethoxyphenyl)phenyl]-6-methyl-trans-decahydronaphthalene,
trans-2-[3-fluoro-4-(4-difluoromethoxyphenyl)phenyl]-6-ethyl-trans-decahydronaphthalene,
trans-2-[3-fluoro-4-(4-difluoromethoxyphenyl)phenyl]-6-propyl-trans-decahydronaphthalene,
trans-2-[3-fluoro-4-(4-difluoromethoxyphenyl)phenyl]-6-butyl-trans-decahydronaphthalene,
trans-2-[3-fluoro-4-(4-difluoromethoxyphenyl)phenyl]-6-pentyl-trans-decahydronaphthalene,
trans-2-[3-fluoro-4-(4-difluoromethoxyphenyl)phenyl]-6-hexyl-trans-decahydronaphthalene,
trans-2-[3-fluoro-4-(4-difluoromethoxyphenyl)phenyl]-6-heptyl-trans-decahydronaphthalene,
trans-2-[4-(3-fluoro-4-difluoromethoxyphenyl)phenyl]-6-methyl-trans-decahydronaphthalene,
trans-2-[4-(3-fluoro-4-difluoromethoxyphenyl)phenyl]-6-ethyl-trans-decahydronaphthalene,
trans-2-[4-(3-fluoro-4-difluoromethoxyphenyl)phenyl]-6-propyl-trans-decahydronaphthalene,
trans-2-[4-(3-fluoro-4-difluoromethoxyphenyl)phenyl]-6-butyl-trans-decahydronaphthalene,
trans-2-[4-(3-fluoro-4-difluoromethoxyphenyl)phenyl]-6-pentyl-trans-decahydronaphthalene,
trans-2-[4-(3-fluoro-4-difluoromethoxyphenyl)phenyl]-6-hexyl-trans-decahydronaphthalene,
trans-2-[4-(3-fluoro-4-difluoromethoxyphenyl)phenyl-6-heptyl-trans-decahydronaphthalene,
trans-2-[4-(3,5-difluoro-4-difluoromethoxyphenyl)phenyl]-6-methyl-trans-decahydronaphthalene,
trans-2-[4-(3,5-difluoro-4-difluoromethoxyphenyl)phenyl]-6-ethyl-trans-decahydronaphthalene,
trans-2-[4-(3,5-difluoro-4-difluoromethoxyphenyl)phenyl]-6-propyl-trans-decahydronaphthalene,
trans-2-[4-(3,5-difluoro-4-difluoromethoxyphenyl)phenyl]-6-butyl-trans-decahydronaphthalene,
trans-2-[4-(3,5-difluoro-4-difluoromethoxyphenyl)phenyl]-6-pentyl-trans-decahydronaphthalene,
trans-2-[4-(3,5-difluoro-4-difluoromethoxyphenyl)phenyl]-6-hexyl-trans-decahydronaphthalene,
trans-2-[4-(3,5-difluoro-4-difluoromethoxyphenyl)phenyl]-6-heptyl-trans-decahydronaphthalene,
trans-2-[3-fluoro-4-(3-fluoro-4-difluoromethoxyphenyl)phenyl]-6-methyl-trans-decahydronaphthalene,
trans-2-[3-fluoro-4-(3-fluoro-4-difluoromethoxyphenyl)phenyl]-6-ethyl-trans-decahydronaphthalene,
trans-2-[3-fluoro-4-(3-fluoro-4-difluoromethoxyphenyl)phenyl]-6-propyl-trans-decahydronaphthalene,
trans-2-[3-fluoro-4-(3-fluoro-4-difluoromethoxyphenyl)phenyl]-6-butyl-trans-decahydronaphthalene,
trans-2-[3-fluoro-4-(3-fluoro-4-difluoromethoxyphenyl)phenyl]-6-pentyl-trans-decahydronaphthalene,
trans-2-[3-fluoro-4-(3-fluoro-4-difluoromethoxyphenyl)phenyl]-6-hexyl-trans-decahydronaphthalene,
trans-2-[3-fluoro-4-(3-fluoro-4-difluoromethoxyphenyl)phenyl]-6-heptyl-trans-decahydronaphthalene,
trans-2-[3-fluoro-4-(3,5-difluoro-4-difluoromethoxyphenyl)phenyl]-6-methyl-trans-decahydronaphthalene, trans-2-[3-fluoro-4-(3,5-difluoro-4-difluoromethoxyphenyl)phenyl]-6-ethyl-trans-decahydronaphthalene,
trans-2-[3-fluoro-4-(3,5-difluoro-4-difluoromethoxyphenyl)phenyl]-6-propyl-trans-decahydronaphthalene,
trans-2-[3-fluoro-4-(3,5-difluoro-4-difluoromethoxyphenyl)phenyl]-6-butyl-trans-decahydronaphthalene,
trans-2-[3-fluoro-4-(3,5-difluoro-4-difluoromethoxyphenyl)phenyl]-6-pentyl-trans-decahydronaphthalene,
trans-2-[3-fluoro-4-(3,5-difluoro-4-difluoromethoxyphenyl)phenyl]-6-hexyl-trans-decahydronaphthalene,
trans-2-[3-fluoro-4-(3,5-difluoro-4-difluoromethoxyphenyl)phenyl]-6-heptyl-trans-decahydronaphthalene,
trans-2-[4-(4-chlorophenyl)phenyl]-6-methyl-trans-decahydronaphthalene,
trans-2-[4-(4-chlorophenyl)phenyl]-6-ethyl-trans-decahydronaphthalene,
trans-2-[4-(4-chlorophenyl)phenyl]-6-propyl-trans-decahydronaphthalene,
trans-2-[4-(4-chlorophenyl)phenyl]-6-butyl-trans-decahydronaphthalene,
trans-2-[4-(4-chlorophenyl)phenyl]-6-pentyl-trans-decahydronaphthalene,
trans-2-[4-(4-chlorophenyl)phenyl]-6-hexyl-trans-decahydronaphthalene,
trans-2-[4-(4-chlorophenyl)phenyl]-6-heptyl-trans-decahydronaphthalene,
trans-2-[4-(3-fluoro-4-chlorophenyl)phenyl]-6-methyl-trans-decahydronaphthalene,
trans-2-[4-(3-fluoro-4-chlorophenyl)phenyl]-6-ethyl-trans-decahydronaphthalene,
trans-2-[4-(3-fluoro-4-chlorophenyl)phenyl]-6-propyl-trans-decahydronaphthalene,
trans-2-[4-(3-fluoro-4-chlorophenyl)phenyl]-6-butyl-trans-decahydronaphthalene,
trans-2-[4-(3-fluoro-4-chlorophenyl)phenyl]-6-pentyl-trans-decahydronaphthalene,
trans-2-[4-(3-fluoro-4-chlorophenyl)phenyl]-6-hexyl-trans-decahydronaphthalene,
trans-2-[4-(3-fluoro-4-chlorophenyl)phenyl]-6-heptyl-trans-decahydronaphthalene,
trans-2-[4-(3,5-difluoro-4-chlorophenyl)phenyl]-6-methyl-trans-decahydronaphthalene,
trans-2-[4-(3,5-difluoro-4-chlorophenyl)phenyl]-6-ethyl-trans-decahydronaphthalene,
trans-2-[4-(3,5-difluoro-4-chlorophenyl)phenyl]-6-propyl-trans-decahydronaphthalene,
trans-2-[4-(3,5-difluoro-4-chlorophenyl)phenyl]-6-butyl-trans-decahydronaphthalene,
trans-2-[4-(3,5-difluoro-4-chlorophenyl)phenyl]-6-pentyl-trans-decahydronaphthalene,
trans-2-[4-(3,5-difluoro-4-chlorophenyl)phenyl]-6-hexyl-trans-decahydronaphthalene,
trans-2-[4-(3,5-difluoro-4-chlorophenyl)phenyl]-6-heptyl-trans-decahydronaphthalene,
trans-2-[3-fluoro-4-(4-chlorophenyl)phenyl]-6-methyl-trans-decahydronaphthalene,
trans-2-[3-fluoro-4-(4-chlorophenyl)phenyl]-6-ethyl-trans-decahydronaphthalene,
trans-2-[3-fluoro-4-(4-chlorophenyl)phenyl]-6-propyl-trans-decahydronaphthalene,
trans-2-[3-fluoro-4-(4-chlorophenyl)phenyl]-6-butyl-trans-decahydronaphthalene,
trans-2-[3-fluoro-4-(4-chlorophenyl)phenyl]-6-pentyl-trans-decahydronaphthalene,
trans-2-[3-fluoro-4-(4-chlorophenyl)phenyl]-6-hexyl-trans-decahydronaphthalene,
trans-2-[3-fluoro-4-(4-chlorophenyl)phenyl]-6-heptyl-trans-decahydronaphthalene,
trans-2-[3-fluoro-4-(3-fluoro-4-chlorophenyl)phenyl]-6-methyl-trans-decahydronaphthalene,
trans-2-[3-fluoro-4-(3-fluoro-4-chlorophenyl)phenyl]-6-ethyl-trans-decahydronaphthalene,
trans-2-[3-fluoro-4-(3-fluoro-4-chlorophenyl)phenyl]-6-propyl-trans-decahydronaphthalene,
trans-2-[3-fluoro-4-(3-fluoro-4-chlorophenyl)phenyl]-6-butyl-trans-decahydronaphthalene,
trans-2-[3-fluoro-4-(3-fluoro-4-chlorophenyl)phenyl]-6-pentyl-trans-decahydronaphthalene,
trans-2-[3-fluoro-4-(3-fluoro-4-chlorophenyl)phenyl]-6-hexyl-trans-decahydronaphthalene,
trans-2-[3-fluoro-4-(3-fluoro-4-chlorophenyl)phenyl]-6-heptyl-trans-decahydronaphthalene,
trans-2-[3-fluoro-4-(3,5-difluoro-4-chlorophenyl)phenyl]-6-methyl-trans-decahydronaphthalene,
trans-2-[3-fluoro-4-(3,5-difluoro-4-chlorophenyl)phenyl]-6-ethyl-trans-decahydronaphthalene,
trans-2-[3-fluoro-4-(3,5-difluoro-4-chlorophenyl)phenyl]-6-propyl-trans-decahydronaphthalene,
trans-2-[3-fluoro-4-(3,5-difluoro-4-chlorophenyl)phenyl]-6-butyl-trans-decahydronaphthalene,
trans-2-[3-fluoro-4-(3,5-difluoro-4-chlorophenyl)phenyl]-6-pentyl-trans-decahydronaphthalene,
trans-2-[3-fluoro-4-(3,5-difluoro-4-chlorophenyl)phenyl]-6-hexyl-trans-decahydronaphthalene,
trans-2-[3-fluoro-4-(3,5-difluoro-4-chlorophenyl)phenyl]-6-heptyl-trans-decahydronaphthalene,
trans-2-[4-(4-trifluoromethylphenyl)phenyl]-6-methyl-trans-decahydronaphthalene,
trans-2-[4-(4-trifluoromethylphenyl)phenyl]-6-ethyl-trans-decahydronaphthalene,
trans-2-[4-(4-trifluoromethylphenyl)phenyl]-6-propyl-trans-decahydronaphthalene,
trans-2-[4-(4-trifluoromethylphenyl)phenyl]-6-butyl-trans-decahydronaphthalene,
trans-2-[4-(4-trifluoromethylphenyl)phenyl]-6-pentyl-trans-decahydronaphthalene,
trans-2-[4-(4-trifluoromethylphenyl)phenyl]-6-hexyl-trans-decahydronaphthalene,
trans-2-[4-(4-trifluoromethylphenyl)phenyl]-6-heptyl-trans-decahydronaphthalene,
trans-2-[4-[4-(2,2,2-trifluoroethoxy)phenyl]phenyl]-6-methyl-trans-decahydronaphthalene,
trans-2-[4-[4-(2,2,2-trifluoroethoxy)phenyl]phenyl]-6-ethyl-trans-decahydronaphthalene,
trans-2-[4-[4-(2,2,2-trifluoroethoxy)phenyl]phenyl]-6-propyl-trans-decahydronaphthalene,
trans-2-[4-[4-(2,2,2-trifluoroethoxy)phenyl]phenyl]-6-butyl-trans-decahydronaphthalene,
trans-2-[4-[4-(2,2,2-trifluoroethoxy)phenyl]phenyl]-6-pentyl-trans-decahydronaphthalene,
trans-2-[4-[4-(2,2,2-trifluoroethoxy)phenyl]phenyl]-6-hexyl-trans-decahydronaphthalene,
trans-2-[4-[4-(2,2,2-trifluoroethoxy)phenyl]phenyl]-6-heptyl-trans-decahydronaphthalene,
trans-2-[4-[4-(1,1,2,2-tetrafluoroethoxy)phenyl]phenyl]-6-methyl-trans-decahydronaphthalene,
trans-2-[4-[4-(1,1,2,2-tetrafluoroethoxy)phenyl]phenyl]-6-ethyl-trans-decahydronaphthalene,
trans-2-[4-[4-(1,1,2,2-tetrafluoroethoxy)phenyl]phenyl]-6-propyl-trans-decahydronaphthalene,
trans-2-[4-[4-(1,1,2,2-tetrafluoroethoxy)phenyl]phenyl]-6-butyl-trans-decahydronaphthalene,
trans-2-[4-[4-(1,1,2,2-tetrafluoroethoxy)phenyl]phenyl]-6-pentyl-trans-decahydronaphthalene,
trans-2-[4-[4-(1,1,2,2-tetrafluoroethoxy)phenyl]phenyl]-6-hexyl-trans-decahydronaphthalene, trans-2-[4-[4-(1,1,2,2-tetrafluoroethoxy)phenyl]phenyl]-6-heptyl-trans-decahydronaphthalene,
trans-2-[4-(3-fluoro-4-trifluoromethylphenyl)phenyl]-6-methyl-trans-decahydronaphthalene,
trans-2-[4-(3-fluoro-4-trifluoromethylphenyl)phenyl]-6-ethyl-trans-decahydronaphthalene,
trans-2-[4-(3-fluoro-4-trifluoromethylphenyl)phenyl]-6-propyl-trans-decahydronaphthalene,
trans-2-[4-(3-fluoro-4-trifluoromethylphenyl)phenyl]-6-butyl-trans-decahydronaphthalene,
trans-2-[4-(3-fluoro-4-trifluoromethylphenyl)phenyl]-6-pentyl-trans-decahydronaphthalene,
trans-2-[4-(3-fluoro-4-trifluoromethylphenyl)phenyl]-6-hexyl-trans-decahydronaphthalene,
trans-2-[4-(3-fluoro-4-trifluoromethylphenyl)phenyl]-6-heptyl-trans-decahydronaphthalene,
trans-2-[4-[3-fluoro-4-(2,2,2-trifluoroethoxy)phenyl]phenyl]-6-methyl-trans-decahydronaphthalene,
trans-2-[4-[3-fluoro-4-(2,2,2-trifluoroethoxy)phenyl]phenyl]-6-ethyl-trans-decahydronaphthalene,
trans-2-[4-[3-fluoro-4-(2,2,2-trifluoroethoxy)phenyl]phenyl]-6-propyl-trans-decahydronaphthalene,
trans-2-[4-[3-fluoro-4-(2,2,2-trifluoroethoxy)phenyl]phenyl]-6-butyl-trans-decahydronaphthalene,
trans-2-[4-[3-fluoro-4-(2,2,2-trifluoroethoxy)phenyl]phenyl]-6-pentyl-trans-decahydronaphthalene,
trans-2-[4-[3-fluoro-4-(2,2,2-trifluoroethoxy)phenyl]phenyl]-6-hexyl-trans-decahydronaphthalene,
trans-2-[4-(3-fluoro-4-(2,2,2-trifluoroethoxy)phenyl]phenyl]-6-heptyl-trans-decahydronaphthalene,
trans-2-[4-[3-fluoro-4-(1,1,2,2-tetrafluoroethoxy)phenyl]phenyl]-6-methyl-trans-decahydronaphthalene,
trans-2-[4-[3-fluoro-4-(1,1,2,2-tetrafluoroethoxy)phenyl]phenyl]-6-ethyl-trans-decahydronaphthalene,
trans-2-[4-[3-fluoro-4-(1,1,2,2-tetrafluoroethoxy)phenyl]phenyl]-6-propyl-trans-decahydronaphthalene,
trans-2-[4-[3-fluoro-4-(1,1,2,2-tetrafluoroethoxy)phenyl]phenyl]-6-butyl-trans-decahydronaphthalene,
trans-2-[4-[3-fluoro-4-(1,1,2,2-tetrafluoroethoxy)phenyl]phenyl]-6-pentyl-trans-decahydronaphthalene,
trans-2-[4-[3-fluoro-4-(1,1,2,2-tetrafluoroethoxy)phenyl]phenyl]-6-hexyl-trans-decahydronaphthalene,
trans-2-[4-[3-fluoro-4-(1,1,2,2-tetrafluoroethoxy)phenyl]phenyl]-6-heptyl-trans-decahydronaphthalene,
trans-2-[4-(3,5-difluoro-4-trifluoromethylphenyl)phenyl]-6-methyl-trans-decahydronaphthalene,
trans-2-[4-(3,5-difluoro-4-trifluoromethylphenyl)phenyl]-6-ethyl-trans-decahydronaphthalene,
trans-2-[4-(3,5-difluoro-4-trifluoromethylphenyl)phenyl]-6-propyl-trans-decahydronaphthalene,
trans-2-[4-(3,5-difluoro-4-trifluoromethylphenyl)phenyl]-6-butyl-trans-decahydronaphthalene,
trans-2-[4-(3,5-difluoro-4-trifluoromethylphenyl)phenyl]-6-pentyl-trans-decahydronaphthalene,
trans-2-[4-(3,5-difluoro-4-trifluoromethylphenyl)phenyl]-6-hexyl-trans-decahydronaphthalene,
trans-2-[4-(3,5-difluoro-4-trifluoromethylphenyl)phenyl]-6-heptyl-trans-decahydronaphthalene,
trans-2-[4-[3,5-difluoro-4-(2,2,2-trifluoroethoxy)phenyl]phenyl]-6-methyl-trans-decahydronaphthalene,
trans-2-[4-[3,5-difluoro-4-(2,2,2-trifluoroethoxy)phenyl]phenyl]-6-ethyl-trans-decahydronaphthalene,
trans-2-[4-[3,5-difluoro-4-(2,2,2-trifluoroethoxy)phenyl]phenyl]-6-propyl-trans-decahydronaphthalene,
trans-2-[4-[3,5-difluoro-4-(2,2,2-trifluoroethoxy)phenyl]phenyl]-6-butyl-trans-decahydronaphthalene,
trans-2-[4-[3,5-difluoro-4-(2,2,2-trifluoroethoxy)phenyl]phenyl]-6-pentyl-trans-decahydronaphthalene,
trans-2-[4-[3,5-difluoro-4-(2,2,2-trifluoroethoxy)phenyl]phenyl]-6-hexyl-trans-decahydronaphthalene,
trans-2-[4-[3,5-difluoro-4-(2,2,2-trifluoroethoxy)phenyl]phenyl]-6-heptyl-trans-decahydronaphthalene,
trans-2-[4-[3,5-difluoro-4-(1,1,2,2-tetrafluoroethoxy)phenyl]phenyl]-6-methyl-trans-decahydronaphthalene,
trans-2-[4-[3,5-difluoro-4-(1,1,2,2-tetrafluoroethoxy)phenyl]phenyl]-6-ethyl-trans-decahydronaphthalene,
trans-2-[4-[3,5-difluoro-4-(1,1,2,2-tetrafluoroethoxy)phenyl]phenyl]-6-propyl-trans-decahydronaphthalene,
trans-2-[4-[3,5-difluoro-4-(1,1,2,2-tetrafluoroethoxy)phenyl]phenyl]-6-butyl-trans-decahydronaphthalene,
trans-2-[4-[3,5-difluoro-4-(1,1,2,2-tetrafluoroethoxy)phenyl]phenyl]-6-pentyl-trans-decahydronaphthalene,
trans-2-[4-[3,5-difluoro-4-(1,1,2,2-tetrafluoroethoxy)phenyl]phenyl]-6-hexyl-trans-decahydronaphthalene,
trans-2-[4-[3,5-difluoro-4-(1,1,2,2-tetrafluoroethoxy)phenyl]phenyl]-6-heptyl-trans-decahydronaphthalene,
trans-2-[3-fluoro-4-(4-trifluoromethylphenyl)phenyl]-6-methyl-trans-decahydronaphthalene,
trans-2-[3-fluoro-4-(4-trifluoromethylphenyl)phenyl]-6-ethyl-trans-decahydronaphthalene,
trans-2-[3-fluoro-4-(4-trifluoromethylphenyl)phenyl]-6-propyl-trans-decahydronaphthalene,
trans-2-[3-fluoro-4-(4-trifluoromethylphenyl)phenyl]-6-butyl-trans-decahydronaphthalene,
trans-2-[3-fluoro-4-(4-trifluoromethylphenyl)phenyl]-6-pentyl-trans-decahydronaphthalene,
trans-2-[3-fluoro-4-(4-trifluoromethylphenyl)phenyl]-6-hexyl-trans-decahydronaphthalene,
trans-2-[3-fluoro-4-(4-trifluoromethylphenyl)phenyl]-6-heptyl-trans-decahydronaphthalene,
trans-2-[3-fluoro-4-[4-(2,2,2-trifluoroethoxy)phenyl]phenyl]-6-methyl-trans-decahydronaphthalene,
trans-2-[3-fluoro-4-[4-(2,2,2-trifluoroethoxy)phenyl]phenyl]-6-ethyl-trans-decahydronaphthalene,
trans-2-[3-fluoro-4-[4-(2,2,2-trifluoroethoxy)phenyl]phenyl]-6-propyl-trans-decahydronaphthalene,
trans-2-[3-fluoro-4-[4-(2,2,2-trifluoroethoxy)phenyl]phenyl]-6-butyl-trans-decahydronaphthalene,
trans-2-[3-fluoro-4-[4-(2,2,2-trifluoroethoxy)phenyl]phenyl]-6-pentyl-trans-decahydronaphthalene,
trans-2-[3-fluoro-4-[4-(2,2,2-trifluoroethoxy)phenyl]phenyl]-6-hexyl-trans-decahydronaphthalene,
trans-2-[3-fluoro-4-[4-(2,2,2-trifluoroethoxy)phenyl]phenyl]-6-heptyl-trans-decahydronaphthalene,
trans-2-[3-fluoro-4-[4-(1,1,2,2-tetrafluoroethoxy)phenyl]phenyl]-6-methyl-trans-decahydronaphthalene,
trans-2-[3-fluoro-4-[4-(1,1,2,2-tetrafluoroethoxy)phenyl]phenyl]-6-ethyl-trans-decahydronaphthalene,
trans-2-[3-fluoro-4-[4-(1,1,2,2-tetrafluoroethoxy)phenyl]phenyl]-6-propyl-trans-decahydronaphthalene,
trans-2-[3-fluoro-4-[4-(1,1,2,2-tetrafluoroethoxy)phenyl]phenyl]-6-butyl-trans-decahydronaphthalene,
trans-2-[3-fluoro-4-[4-(1,1,2,2-tetrafluoroethoxy)phenyl]phenyl]-6-pentyl-trans-decahydronaphthalene,
trans-2-[3-fluoro-4-[4-(1,1,2,2-tetrafluoroethoxy)phenyl]phenyl]-6-hexyl-trans-decahydronaphthalene,
trans-2-[3-fluoro-4-[4-(1,1,2,2-tetrafluoroethoxy)phenyl]phenyl]-6-heptyl-trans-decahydronaphthalene,
trans-2-[3-fluoro-4-(3-fluoro-4-trifluoromethylphenyl)phenyl]-6-methyl-trans-decahydronaphthalene,
trans-2-[3-fluoro-4-(3-fluoro-4-trifluoromethylphenyl)phenyl]-6-ethyl-trans-decahydronaphthalene,
trans-2-[3-fluoro-4-(3-fluoro-4-trifluoromethylphenyl)phenyl]-6-propyl-trans-decahydronaphthalene,
trans-2-[3-fluoro-4-(3-fluoro-4-trifluoromethylphenyl)phenyl]-6-butyl-trans-decahydronaphthalene, trans-2-[3-fluoro-4-(3-fluoro-4-trifluoromethylphenyl)
phenyl]-6-pentyl-trans-decahydronaphthalene,
trans-2-[3-fluoro-4-(3-fluoro-4-trifluoromethylphenyl)
phenyl]-6-hexyl-trans-decahydronaphthalene,
trans-2-[3-fluoro-4-(3-fluoro-4-trifluoromethylphenyl)
phenyl]-6-heptyl-trans-decahydronaphthalene,
trans-2-[3-fluoro-4-[3-fluoro-4-(2,2,2-trifluoroethoxy)
phenyl]phenyl]-6-methyl-trans-decahydronaphthalene,
trans-2-[3-fluoro-4-[3-fluoro-4-(2,2,2-trifluoroethoxy)
phenyl]phenyl]-6-ethyl-trans-decahydronaphthalene,
trans-2-[3-fluoro-4-[3-fluoro-4-(2,2,2-trifluoroethoxy)
phenyl]phenyl]-6-propyl-trans-decahydronaphthalene,
trans-2-[3-fluoro-4-[3-fluoro-4-(2,2,2-trifluoroethoxy)
phenyl]phenyl]-6-butyl-trans-decahydronaphthalene,
trans-2-[3-fluoro-4-[3-fluoro-4-(2,2,2-trifluoroethoxy)
phenyl]phenyl]-6-pentyl-trans-decahydronaphthalene,
trans-2-[3-fluoro-4-[3-fluoro-4-(2,2,2-trifluoroethoxy)
phenyl]phenyl]-6-hexyl-trans-decahydronaphthalene,
trans-2-[3-fluoro-4-[3-fluoro-4-(2,2,2-trifluoroethoxy)
phenyl]phenyl]-6-heptyl-trans-decahydronaphthalene,
trans-2-[3-fluoro-4-[3-fluoro-4-(1,1,2,2-tetrafluoroethoxy)
phenyl]phenyl]-6-methyl-trans-decahydronaphthalene,
trans-2-[3-fluoro-4-[3-fluoro-4-(1,1,2,2-tetrafluoroethoxy)
phenyl]phenyl]-6-ethyl-trans-decahydronaphthalene,
trans-2-[3-fluoro-4-[3-fluoro-4-(1,1,2,2-tetrafluoroethoxy)
phenyl]phenyl]-6-propyl-trans-decahydronaphthalene,
trans-2-[3-fluoro-4-[3-fluoro-4-(1,1,2,2-tetrafluoroethoxy)
phenyl]phenyl]-6-butyl-trans-decahydronaphthalene,
trans-2-[3-fluoro-4-[3-fluoro-4-(1,1,2,2-tetrafluoroethoxy)
phenyl]phenyl]-6-pentyl-trans-decahydronaphthalene,
trans-2-[3-fluoro-4-[3-fluoro-4-(1,1,2,2-tetrafluoroethoxy)
phenyl]phenyl]-6-hexyl-trans-decahydronaphthalene,
trans-2-[3-fluoro-4-[3-fluoro-4-(1,1,2,2-tetrafluoroethoxy)
phenyl]phenyl]-6-heptyl-trans-decahydronaphthalene,
trans-2-[4-(4-methoxyphenyl)phenyl]-6-methyl-trans-
decahydronaphthalene,
trans-2-[4-(4-methoxyphenyl)phenyl]-6-ethyl-trans-
decahydronaphthalene,
trans-2-[4-(4-methoxyphenyl)phenyl]-6-propyl-trans-
decahydronaphthalene,
trans-2-[4-(4-methoxyphenyl)phenyl]-6-butyl-trans-
decahydronaphthalene,
trans-2-[4-(4-methoxyphenyl)phenyl]-6-pentyl-trans-
decahydronaphthalene,
trans-2-[4-(4-methoxyphenyl)phenyl]-6-hexyl-trans-
decahydronaphthalene,
trans-2-[4-(4-methoxyphenyl)phenyl]-6-heptyl-trans-
decahydronaphthalene,
trans-2-[4-(3-fluoro-4-methoxyphenyl)phenyl]-6-methyl-
trans-decahydronaphthalene,
trans-2-[4-(3-fluoro-4-methoxyphenyl)phenyl]-6-ethyl-
trans-decahydronaphthalene,
trans-2-[4-(3-fluoro-4-methoxyphenyl)phenyl]-6-propyl-
trans-decahydronaphthalene,
trans-2-[4-(3-fluoro-4-methoxyphenyl)phenyl]-6-butyl-
trans-decahydronaphthalene,
trans-2-[4-(3-fluoro-4-methoxyphenyl)phenyl]-6-pentyl-
trans-decahydronaphthalene,
trans-2-[4-(3-fluoro-4-methoxyphenyl)phenyl]-6-hexyl-
trans-decahydronaphthalene,
trans-2-[4-(3-fluoro-4-methoxyphenyl)phenyl]-6-heptyl-
trans-decahydronaphthalene,
trans-2-[4-(3,5-difluoro-4-methoxyphenyl)phenyl]-6-
methyl-trans-decahydronaphthalene,
trans-2-[4-(3,5-difluoro-4-methoxyphenyl)phenyl]-6-ethyl-
trans-decahydronaphthalene,
trans-2-[4-(3,5-difluoro-4-methoxyphenyl)phenyl]-6-
propyl-trans-decahydronaphthalene,
trans-2-[4-(3,5-difluoro-4-methoxyphenyl)phenyl]-6-butyl-
trans-decahydronaphthalene,
trans-2-[4-(3,5-difluoro-4-methoxyphenyl)phenyl]-6-
pentyl-trans-decahydronaphthalene,
trans-2-[4-(3,5-difluoro-4-methoxyphenyl)phenyl]-6-hexyl-
trans-decahydronaphthalene,
trans-2-[4-(3,5-difluoro-4-methoxyphenyl)phenyl]-6-
heptyl-trans-decahydronaphthalene,
trans-2-[3-fluoro-4-(4-methoxyphenyl)phenyl]-6-methyl-
trans-decahydronaphthalene,
trans-2-[3-fluoro-4-(4-methoxyphenyl)phenyl]-6-ethyl-
trans-decahydronaphthalene,
trans-2-[3-fluoro-4-(4-methoxyphenyl)phenyl]-6-propyl-
trans-decahydronaphthalene,
trans-2-[3-fluoro-4-(4-methoxyphenyl)phenyl]-6-butyl-
trans-decahydronaphthalene,
trans-2-[3-fluoro-4-(4-methoxyphenyl)phenyl]-6-pentyl-
trans-decahydronaphthalene,
trans-2-[3-fluoro-4-(4-methoxyphenyl)phenyl]-6-hexyl-
trans-decahydronaphthalene,
trans-2-[3-fluoro-4-(4-methoxyphenyl)phenyl]-6-heptyl-
trans-decahydronaphthalene,
trans-2-[3-fluoro-4-(3-fluoro-4-methoxyphenyl)phenyl]-6-
methyl-trans-decahydronaphthalene,
trans-2-[3-fluoro-4-(3-fluoro-4-methoxyphenyl)phenyl]-6-
ethyl-trans-decahydronaphthalene,
trans-2-[3-fluoro-4-(3-fluoro-4-methoxyphenyl)phenyl]-6-
propyl-trans-decahydronaphthalene,
trans-2-[3-fluoro-4-(3-fluoro-4-methoxyphenyl)phenyl]-6-
butyl-trans-decahydronaphthalene,
trans-2-[3-fluoro-4-(3-fluoro-4-methoxyphenyl)phenyl]-6-
pentyl-trans-decahydronaphthalene,
trans-2-[3-fluoro-4-(3-fluoro-4-methoxyphenyl)phenyl]-6-
hexyl-trans-decahydronaphthalene,
trans-2-[3-fluoro-4-(3-fluoro-4-methoxyphenyl)phenyl]-6-
heptyl-trans-decahydronaphthalene,
trans-2-[3-fluoro-4-(3,5-difluoro-4-methoxyphenyl)
phenyl]-6-methyl-trans-decahydronaphthalene,
trans-2-[3-fluoro-4-(3,5-difluoro-4-methoxyphenyl)
phenyl]-6-ethyl-trans-decahydronaphthalene,
trans-2-[3-fluoro-4-(3,5-difluoro-4-methoxyphenyl)
phenyl]-6-propyl-trans-decahydronaphthalene,
trans-2-[3-fluoro-4-(3,5-difluoro-4-methoxyphenyl)
phenyl]-6-butyl-trans-decahydronaphthalene,
trans-2-[3-fluoro-4-(3,5-difluoro-4-methoxyphenyl)
phenyl]-6-pentyl-trans-decahydronaphthalene,
trans-2-[3-fluoro-4-(3,5-difluoro-4-methoxyphenyl)
phenyl]-6-hexyl-trans-decahydronaphthalene,
trans-2-[3-fluoro-4-(3,5-difluoro-4-methoxyphenyl)
phenyl]-6-heptyl-trans-decahydronaphthalene,
trans-2-[4-(4-benzyloxyphenyl)phenyl]-6-methyl-trans-
decahydronaphthalene,
trans-2-[4-(4-benzyloxyphenyl)phenyl]-6-ethyl-trans-
decahydronaphthalene,
trans-2-[4-(4-benzyloxyphenyl)phenyl]-6-propyl-trans-
decahydronaphthalene,
trans-2-[4-(4-benzyloxyphenyl)phenyl]-6-butyl-trans-
decahydronaphthalene,
trans-2-[4-(4-benzyloxyphenyl)phenyl]-6-pentyl-trans-
decahydronaphthalene,
trans-2-[4-(4-benzyloxyphenyl)phenyl]-6-hexyl-trans-
decahydronaphthalene,
trans-2-[4-(4-benzyloxyphenyl)phenyl]-6-heptyl-trans-
decahydronaphthalene,
trans-2-[4-(3-fluoro-4-benzyloxyphenyl)phenyl]-6-methyl-
trans-decahydronaphthalene,
trans-2-[4-(3-fluoro-4-benzyloxyphenyl)phenyl]-6-ethyl-
trans-decahydronaphthalene, trans-2-[4-(3-fluoro-4-benzyloxyphenyl)phenyl]-6-propyl-trans-decahydronaphthalene,
trans-2-[4-(3-fluoro-4-benzyloxyphenyl)phenyl]-6-butyl-trans-decahydronaphthalene,
trans-2-[4-(3-fluoro-4-benzyloxyphenyl)phenyl]-6-pentyl-trans-decahydronaphthalene,
trans-2-[4-(3-fluoro-4-benzyloxyphenyl)phenyl]-6-hexyl-trans-decahydronaphthalene,
trans-2-[4-(3-fluoro-4-benzyloxyphenyl)phenyl]-6-heptyl-trans-decahydronaphthalene,
trans-2-[4-(3,5-difluoro-4-benzyloxyphenyl)phenyl]-6-methyl-trans-decahydronaphthalene,
trans-2-[4-(3,5-difluoro-4-benzyloxyphenyl)phenyl]-6-ethyl-trans-decahydronaphthalene,
trans-2-[4-(3,5-difluoro-4-benzyloxyphenyl)phenyl]-6-propyl-trans-decahydronaphthalene,
trans-2-[4-(3,5-difluoro-4-benzyloxyphenyl)phenyl]-6-butyl-trans-decahydronaphthalene,
trans-2-[4-(3,5-difluoro-4-benzyloxyphenyl)phenyl]-6-pentyl-trans-decahydronaphthalene,
trans-2-[4-(3,5-difluoro-4-benzyloxyphenyl)phenyl]-6-hexyl-trans-decahydronaphthalene,
trans-2-[4-(3,5-difluoro-4-benzyloxyphenyl)phenyl]-6-heptyl-trans-decahydronaphthalene,
trans-2-[3-fluoro-4-(4-benzyloxyphenyl)phenyl]-6-methyl-trans-decahydronaphthalene,
trans-2-[3-fluoro-4-(4-benzyloxyphenyl)phenyl]-6-ethyl-trans-decahydronaphthalene,
trans-2-[3-fluoro-4-(4-benzyloxyphenyl)phenyl]-6-propyl-trans-decahydronaphthalene,
trans-2-[3-fluoro-4-(4-benzyloxyphenyl)phenyl]-6-butyl-trans-decahydronaphthalene,
trans-2-[3-fluoro-4-(4-benzyloxyphenyl)phenyl]-6-pentyl-trans-decahydronaphthalene,
trans-2-[3-fluoro-4-(4-benzyloxyphenyl)phenyl]-6-hexyl-trans-decahydronaphthalene,
trans-2-[3-fluoro-4-(4-benzyloxyphenyl)phenyl]-6-heptyl-trans-decahydronaphthalene,
trans-2-[3-fluoro-4-(3-fluoro-4-benzyloxyphenyl)phenyl]-6-methyl-trans-decahydronaphthalene,
trans-2-[3-fluoro-4-(3-fluoro-4-benzyloxyphenyl)phenyl]-6-ethyl-trans-decahydronaphthalene,
trans-2-[3-fluoro-4-(3-fluoro-4-benzyloxyphenyl)phenyl]-6-propyl-trans-decahydronaphthalene,
trans-2-[3-fluoro-4-(3-fluoro-4-benzyloxyphenyl)phenyl]-6-butyl-trans-decahydronaphthalene,
trans-2-[3-fluoro-4-(3-fluoro-4-benzyloxyphenyl)phenyl]-6-pentyl-trans-decahydronaphthalene,
trans-2-[3-fluoro-4-(3-fluoro-4-benzyloxyphenyl)phenyl]-6-hexyl-trans-decahydronaphthalene,
trans-2-[3-fluoro-4-(3-fluoro-4-benzyloxyphenyl)phenyl]-6-heptyl-trans-decahydronaphthalene,
trans-2-[3-fluoro-4-(3,5-difluoro-4-benzyloxyphenyl)phenyl]-6-methyl-trans-decahydronaphthalene,
trans-2-[3-fluoro-4-(3,5-difluoro-4-benzyloxyphenyl)phenyl]-6-ethyl-trans-decahydronaphthalene,
trans-2-[3-fluoro-4-(3,5-difluoro-4-benzyloxyphenyl)phenyl]-6-propyl-trans-decahydronaphthalene,
trans-2-[3-fluoro-4-(3,5-difluoro-4-benzyloxyphenyl)phenyl]-6-butyl-trans-decahydronaphthalene,
trans-2-[3-fluoro-4-(3,5-difluoro-4-benzyloxyphenyl)phenyl]-6-pentyl-trans-decahydronaphthalene,
trans-2-[3-fluoro-4-(3,5-difluoro-4-benzyloxyphenyl)phenyl]-6-hexyl-trans-decahydronaphthalene,
trans-2-[3-fluoro-4-(3,5-difluoro-4-benzyloxyphenyl)phenyl]-6-heptyl-trans-decahydronaphthalene,
trans-2-[4-(4-ethoxyphenyl)phenyl]-6-methyl-trans-decahydronaphthalene,
trans-2-[4-(4-ethoxyphenyl)phenyl]-6-ethyl-trans-decahydronaphthalene,
trans-2-[4-(4-ethoxyphenyl)phenyl]-6-propyl-trans-decahydronaphthalene,
trans-2-[4-(4-ethoxyphenyl)phenyl]-6-butyl-trans-decahydronaphthalene,
trans-2-[4-(4-ethoxyphenyl)phenyl]-6-pentyl-trans-decahydronaphthalene,
trans-2-[4-(4-ethoxyphenyl)phenyl]-6-hexyl-trans-decahydronaphthalene,
trans-2-[4-(4-ethoxyphenyl)phenyl]-6-heptyl-trans-decahydronaphthalene,
trans-2-[4 (2,3-difluoro-4-ethoxyphenyl)phenyl]-6-methyl-trans-decahydronaphthalene,
trans-2-[4-(2,3-difluoro-4-ethoxyphenyl)phenyl]-6-ethyl-trans-decahydronaphthalene,
trans-2-[4-(2,3-difluoro-4-ethoxyphenyl)phenyl]-6-propyl-trans-decahydronaphthalene,
trans-2-[4-(2,3-difluoro-4-ethoxyphenyl)phenyl]-6-butyl-trans-decahydronaphthalene,
trans-2-[4-(2,3-difluoro-4-ethoxyphenyl)phenyl]-6-pentyl-trans-decahydronaphthalene,
trans-2-[4-(2,3-difluoro-4-ethoxyphenyl)phenyl]-6-hexyl-trans-decahydronaphthalene,
trans-2-[4-(2,3-difluoro-4-ethoxyphenyl)phenyl]-6-heptyl-trans-decahydronaphthalene,
trans-2-[4-(4-allyloxyphenyl)phenyl]-6-methyl-trans-decahydronaphthalene,
trans-2-[4-(4-allyloxyphenyl)phenyl]-6-ethyl-trans-decahydronaphthalene,
trans-2-[4-(4-allyloxyphenyl)phenyl]-6-propyl-trans-decahydronaphthalene,
trans-2-[4-(4-allyloxyphenyl)phenyl]-6-butyl-trans-decahydronaphthalene,
trans-2-[4-(4-allyloxyphenyl)phenyl]-6-pentyl-trans-decahydronaphthalene,
trans-2-[4-(4-allyloxyphenyl)phenyl]-6-hexyl-trans-decahydronaphthalene,
trans-2-[4-(4-allyloxyphenyl)phenyl]-6-heptyl-trans-decahydronaphthalene,
trans-2-[4-(4-methylphenyl)phenyl]-6-methyl-trans-decahydronaphthalene,
trans-2-[4-(4-methylphenyl)phenyl]-6-ethyl-trans-decahydronaphthalene,
trans-2-[4-(4-methylphenyl)phenyl]-6-propyl-trans-decahydronaphthalene,
trans-2-[4-(4-methylphenyl)phenyl]-6-butyl-trans-decahydronaphthalene,
trans-2-[4-(4-methylphenyl)phenyl]-6-pentyl-trans-decahydronaphthalene,
trans-2-[4-(4-methylphenyl)phenyl]-6-hexyl-trans-decahydronaphthalene,
trans-2-[4-(4-methylphenyl)phenyl]-6-heptyl-trans-decahydronaphthalene,
trans-2-[4-(4-ethylphenyl)phenyl]-6-methyl-trans-decahydronaphthalene,
trans-2-[4-(4-ethylphenyl)phenyl]-6-ethyl-trans-decahydronaphthalene,
trans-2-[4-(4-ethylphenyl)phenyl]-6-propyl-trans-decahydronaphthalene,
trans-2-[4-(4-ethylphenyl)phenyl]-6-butyl-trans-decahydronaphthalene,
trans-2-[4-(4-ethylphenyl)phenyl]-6-pentyl-trans-decahydronaphthalene,
trans-2-[4-(4-ethylphenyl)phenyl]-6-hexyl-trans-decahydronaphthalene,
trans-2-[4-(4-ethylphenyl)phenyl]-6-heptyl-trans-decahydronaphthalene, trans-2-[4-(4-propylphenyl)phenyl]-6-methyl-trans-decahydronaphthalene,
trans-2-[4-(4-propylphenyl)phenyl]-6-ethyl-trans-decahydronaphthalene,
trans-2-[4-(4-propylphenyl)phenyl]-6-propyl-trans-decahydronaphthalene,
trans-2-[4-(4-propylphenyl)phenyl]-6-butyl-trans-decahydronaphthalene,
trans-2-[4-(4-propylphenyl)phenyl]-6-pentyl-trans-decahydronaphthalene,
trans-2-[4-(4-propylphenyl)phenyl]-6-hexyl-trans-decahydronaphthalene,
trans-2-[4-(4-propylphenyl)phenyl]-6-heptyl-trans-decahydronaphthalene,
trans-2-[4-[4-(3-butenyl)phenyl]phenyl]-6-methyl-trans-decahydronaphthalene,
trans-2-[4-[4-(3-butenyl)phenyl]phenyl]-6-ethyl-trans-decahydronaphthalene,
trans-2-[4-[4-(3-butenyl)phenyl]phenyl]-6-butyl-trans-decahydronaphthalene,
trans-2-[4-[4-(3-butenyl)phenyl]phenyl]-6-pentyl-trans-decahydronaphthalene,
trans-2-[4-[4-(3-butenyl)phenyl]phenyl]-6-hexyl-trans-decahydronaphthalene,
trans-2-[4-[4-(3-butenyl)phenyl]phenyl]-6-heptyl-trans-decahydronaphthalene,
trans-2-[4-[4-(trans-3-pentenyl)phenyl]phenyl]-6-methyl-trans-decahydronaphthalene,
trans-2-[4-[4-(trans-3-pentenyl)phenyl]phenyl]-6-ethyl-trans-decahydronaphthalene,
trans-2-[4-[4-(trans-3-pentenyl)phenyl]phenyl]-6-propyl-trans-decahydronaphthalene,
trans-2-[4-[4-(trans-3-pentenyl)phenyl]phenyl]-6-butyl-trans-decahydronaphthalene,
trans-2-[4-[4-(trans-3-pentenyl)phenyl]phenyl]-6-pentyl-trans-decahydronaphthalene,
trans-2-[4-[4-(trans-3-pentenyl)phenyl]phenyl]-6-hexyl-trans-decahydronaphthalene,
trans-2-[4-[4-(trans-3-pentenyl)phenyl]phenyl]-6-heptyl-trans-decahydronaphthalene,
trans-2-[4-[4-(4,4-dimethyl-1,3-oxazolin-2-yl)phenyl]phenyl]-6-methyl-trans-decahydronaphthalene,
trans-2-[4-[4-(4,4-dimethyl-1,3-oxazolin-2-yl)phenyl]phenyl]-6-ethyl-trans-decahydronaphthalene,
trans-2-[4-[4-(4,4-dimethyl-1,3-oxazolin-2-yl)phenyl]phenyl]-6-propyl-trans-decahydronaphthalene,
trans-2-[4-[4-(4,4-dimethyl-1,3-oxazolin-2-yl)phenyl]phenyl]-6-butyl-trans-decahydronaphthalene,
trans-2-[4-[4-(4,4-dimethyl-1,3-oxazolin-2-yl)phenyl]phenyl]-6-pentyl-trans-decahydronaphthalene,
trans-2-[4-[4-(4,4-dimethyl-1,3-oxazolin-2-yl)phenyl]phenyl]-6-hexyl-trans-decahydronaphthalene,
trans-2-[4-[4-(4,4-dimethyl-1,3-oxazolin-2-yl)phenyl]phenyl]-6-heptyl-trans-decahydronaphthalene,
trans-2-[4-[3-fluoro-4-(4,4-dimethyl-1,3-oxazolin-2-yl)phenyl]phenyl]-6-methyl-trans-decahydronaphthalene,
trans-2-[4-[3-fluoro-4-(4,4-dimethyl-1,3-oxazolin-2-yl)phenyl]phenyl]-6-ethyl-trans-decahydronaphthalene,
trans-2-[4-[3-fluoro-4-(4,4-dimethyl-1,3-oxazolin-2-yl)phenyl]phenyl]-6-propyl-trans-decahydronaphthalene,
trans-2-[4-[3-fluoro-4-(4,4-dimethyl-1,3-oxazolin-2-yl)phenyl]phenyl]-6-butyl-trans-decahydronaphthalene,
trans-2-[4-[3-fluoro-4-(4,4-dimethyl-1,3-oxazolin-2-yl)phenyl]phenyl]-6-pentyl-trans-decahydronaphthalene,
trans-2-[4-[3-fluoro-4-(4,4-dimethyl-1,3-oxazolin-2-yl)phenyl]phenyl]-6-hexyl-trans-decahydronaphthalene,
trans-2-[4-[3-fluoro-4-(4,4-dimethyl-1,3-oxazolin-2-yl)phenyl]phenyl]-6-heptyl-trans-decahydronaphthalene,
trans-2-[4-[3,5-difluoro-4-(4,4-dimethyl-1,3-oxazolin-2-yl)phenyl]phenyl]-6-methyl-trans-decahydronaphthalene,
trans-2-[4-[3,5-difluoro-4-(4,4-dimethyl-1,3-oxazolin-2-yl)phenyl]phenyl]-6-ethyl-trans-decahydronaphthalene,
trans-2-[4-[3,5-difluoro-4-(4,4-dimethyl-1,3-oxazolin-2-yl)phenyl]phenyl]-6-propyl-trans-decahydronaphthalene,
trans-2-[4-[3,5-difluoro-4-(4,4-dimethyl-1,3-oxazolin-2-yl)phenyl]phenyl]-6-butyl-trans-decahydronaphthalene,
trans-2-[4-[3,5-difluoro-4-(4,4-dimethyl-1,3-oxazolin-2-yl)phenyl]phenyl]-6-pentyl-trans-decahydronaphthalene,
trans-2-[4-[3,5-difluoro-4-(4,4-dimethyl-1,3-oxazolin-2-yl)phenyl]phenyl]-6-hexyl-trans-decahydronaphthalene,
trans-2-[4-[3,5-difluoro-4-(4,4-dimethyl-1,3-oxazolin-2-yl)phenyl]phenyl]-6-heptyl-trans-decahydronaphthalene,
trans-2-[3-fluoro-4-[4-(4,4-dimethyl-1,3-oxazolin-2-yl)phenyl]phenyl]-6-methyl-trans-decahydronaphthalene,
trans-2-[3-fluoro-4-[4-(4,4-dimethyl-1,3-oxazolin-2-yl)phenyl]phenyl]-6-ethyl-trans-decahydronaphthalene,
trans-2-[3-fluoro-4-[4-(4,4-dimethyl-1,3-oxazolin-2-yl)phenyl]phenyl]-6-propyl-trans-decahydronaphthalene,
trans-2-[3-fluoro-4-[4-(4,4-dimethyl-1,3-oxazolin-2-yl)phenyl]phenyl]-6-butyl-trans-decahydronaphthalene,
trans-2-[3-fluoro-4-[4-(4,4-dimethyl-1,3-oxazolin-2-yl)phenyl]phenyl]-6-pentyl-trans-decahydronaphthalene,
trans-2-[3-fluoro-4-[4-(4,4-dimethyl-1,3-oxazolin-2-yl)phenyl]phenyl]-6-hexyl-trans-decahydronaphthalene,
trans-2-[3-fluoro-4-[4-(4,4-dimethyl-1,3-oxazolin-2-yl)phenyl]phenyl]-6-heptyl-trans-decahydronaphthalene,
trans-2-[3-fluoro-4-[3-fluoro-4-(4,4-dimethyl-1,3-oxazolin-2-yl)phenyl]phenyl]-6-methyl-trans-decahydronaphthalene,
trans-2-[3-fluoro-4-[3-fluoro-4-(4,4-dimethyl-1,3-oxazolin-2-yl)phenyl]phenyl]-6-ethyl-trans-decahydronaphthalene,
trans-2-[3-fluoro-4-[3-fluoro-4-(4,4-dimethyl-1,3-oxazolin-2-yl)phenyl]phenyl]-6-propyl-trans-decahydronaphthalene,
trans-2-[3-fluoro-4-[3-fluoro-4-(4,4-dimethyl-1,3-oxazolin-2-yl)phenyl]phenyl]-6-butyl-trans-decahydronaphthalene,
trans-2-[3-fluoro-4-[3-fluoro-4-(4,4-dimethyl-1,3-oxazolin-2-yl)phenyl]phenyl]-6-pentyl-trans-decahydronaphthalene,
trans-2-[3-fluoro-4-[3-fluoro-4-(4,4-dimethyl-1,3-oxazolin-2-yl)phenyl]phenyl]-6-hexyl-trans-decahydronaphthalene,
trans-2-[3-fluoro-4-[3-fluoro-4-(4,4-dimethyl-1,3-oxazolin-2-yl)phenyl]phenyl]-6-heptyl-trans-decahydronaphthalene,
trans-2-[3-fluoro-4-[3,5-difluoro-4-(4,4-dimethyl-1,3-oxazolin-2-yl)phenyl]phenyl]-6-methyl-trans-decahydronaphthalene,
trans-2-[3-fluoro-4-[3,5-difluoro-4-(4,4-dimethyl-1,3-oxazolin-2-yl)phenyl]phenyl]-6-ethyl-trans-decahydronaphthalene,
trans-2-[3-fluoro-4-[3,5-difluoro-4-(4,4-dimethyl-1,3-oxazolin-2-yl)phenyl]phenyl]-6-propyl-trans-decahydronaphthalene,
trans-2-[3-fluoro-4-[3,5-difluoro-4-(4,4-dimethyl-1,3-oxazolin-2-yl)phenyl]phenyl]-6-butyl-trans-decahydronaphthalene,
trans-2-[3-fluoro-4-[3,5-difluoro-4-(4,4-dimethyl-1,3-oxazolin-2-yl)phenyl]phenyl]-6-pentyl-trans-decahydronaphthalene,
trans-2-[3-fluoro-4-[3,5-difluoro-4-(4,4-dimethyl-1,3-oxazolin-2-yl)phenyl]phenyl]-6-hexyl-trans-decahydronaphthalene, trans-2-[3-fluoro-4-[3,5-difluoro-4-(4,4-dimethyl-1,3-oxazolin-2-yl)phenyl]phenyl]-6-heptyl-trans-decahydronaphthalene.

Example 17

Synthesis of trans-2-[3,5-difluoro-4-(3,4-difluorophenyl)phenyl]-6-propyl-trans-decahydronaphthalene (I-21)

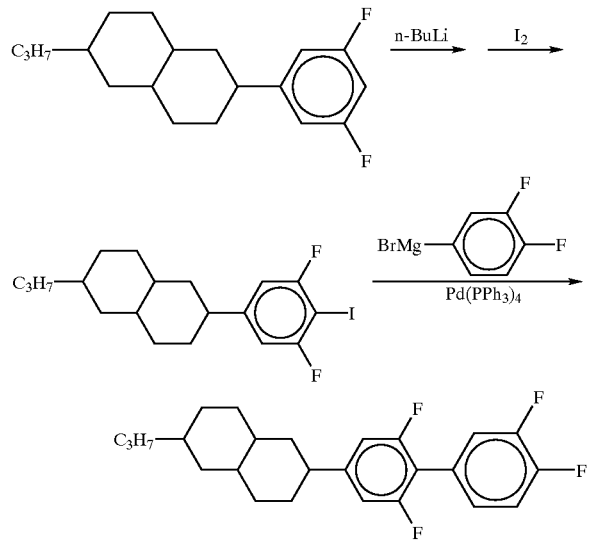

(17-a) Synthesis of trans-2-(3,5-difluoro-4-iodophenyl)-6-propyl-trans-decahydronaphthalene 50 ml of 1.5 M hexane solution of n-butyl lithium was added dropwise to a 100 ml THF solution of 17 g of trans-2-(3,5-difluorophenyl)-6-propyl-trans-decahydronaphthalene, which was cooled to −45° C., over a period of 10 minutes. After stirring the mixture for 30 minutes, the temperature was increased to room temperature, and water was added. A 10% aqueous solution of sodium hydrogen sulfite was added until the color of iodine was not observed. The organic phase was extracted using hexane, rinsed with a saturated saline solution, and dried on anhydrous magnesium sulfate. Then, the solvent was evaporated to obtain 23 g of white solid trans-2-(3,5-difluoro-4-iodophenyl)-6-propyl-trans-decahydronaphthalene.

(17-b) Synthesis of trans-2-[3,5-difluoro-4-(3,4-difluorophenyl)phenyl]-6-propyl-trans-decahydronaphthalene 23 g of trans-2-(3,5-difluoro-4-iodophenyl)-6-propyl-trans-decahydronaphthalene, which was obtained in (17-a), was dissolved in a mixed solution of 38 ml of toluene and 20 ml of ethanol. 1.2 g of tetrakis(triphenylphosphine)palladium(0) and 37 ml aqueous solution of 2 M sodium carbonate were added to the mixture, and 10 ml ethanol solution of 11 g of 3,4-difluorophenylboric acid was further added dropwise over a period of 10 minutes. After heating the mixture for 18 hours at 70° C. while stirring, the mixture was cooled to room temperature, and water was added to the mixture. After extraction was carried out using toluene, the organic phase was rinsed with a saline solution and dried on anhydrous magnesium sulfate. After the solvent was evaporated, the residue was purified by silica gel column chromatography and recrystallized three times from ethanol to obtain 11 g white crystals of trans-2-[3,5-difluoro-4-(3,4-difluorophenyl)phenyl]-6-propyl-trans-decahydronaphthalene.

The following compounds were prepared in the same manner as mentioned above:

trans-2-[3,5-difluoro-4-(3,4-difluorophenyl)phenyl]-6-methyl-trans-decahydronaphthalene,
trans-2-[3,5-difluoro-4-(3,4-difluorophenyl)phenyl]-6-ethyl-trans-decahydronaphthalene,
trans-2-[3,5-difluoro-4-(3,4-difluorophenyl)phenyl]-6-butyl-trans-decahydronaphthalene,
trans-2-[3,5-difluoro-4-(3,4-difluorophenyl)phenyl]-6-pentyl-trans-decahydronaphthalene,
trans-2-[3,5-difluoro-4-(3,4-difluorophenyl)phenyl]-6-hexyl-trans-decahydronaphthalene,
trans-2-[3,5-difluoro-4-(3,4-difluorophenyl)phenyl]-6-heptyl-trans-decahydronaphthalene,
trans-2-[3,5-difluoro-4-(3,4,5-trifluorophenyl)phenyl]-6-methyl-trans-decahydronaphthalene,
trans-2-[3,5-difluoro-4-(3,4,5-trifluorophenyl)phenyl]-6-ethyl-trans-decahydronaphthalene,
trans-2-[3,5-difluoro-4-(3,4,5-trifluorophenyl)phenyl]-6-propyl-trans-decahydronaphthalene,
trans-2-[3,5-difluoro-4-(3,4,5-trifluorophenyl)phenyl]-6-butyl-trans-decahydronaphthalene,
trans-2-[3,5-difluoro-4-(3,4,5-trifluorophenyl)phenyl]-6-pentyl-trans-decahydronaphthalene,
trans-2-[3,5-difluoro-4-(3,4,5-trifluorophenyl)phenyl]-6-hexyl-trans-decahydronaphthalene,
trans-2-[3,5-difluoro-4-(3,4,5-trifluorophenyl)phenyl]-6-heptyl-trans-decahydronaphthalene,
trans-2-[3,5-difluoro-4-(4-fluorophenyl)phenyl]-6-methyl-trans-decahydronaphthalene,
trans-2-[3,5-difluoro-4-(4-fluorophenyl)phenyl]-6-ethyl-trans-decahydronaphthalene,
trans-2-[3,5-difluoro-4-(4-fluorophenyl)phenyl]-6-propyl-trans-decahydronaphthalene,
trans-2-[3,5-difluoro-4-(4-fluorophenyl)phenyl]-6-butyl-trans-decahydronaphthalene,
trans-2-[3,5-difluoro-4-(4-fluorophenyl)phenyl]-6-pentyl-trans-decahydronaphthalene,
trans-2-[3,5-difluoro-4-(4-fluorophenyl)phenyl]-6-hexyl-trans-decahydronaphthalene,
trans-2-[3,5-difluoro-4-(4-fluorophenyl)phenyl]-6-heptyl-trans-decahydronaphthalene,
trans-2-[3,5-difluoro-4-(3,5-difluorophenyl)phenyl]-6-methyl-trans-decahydronaphthalene,
trans-2-[3,5-difluoro-4-(3,5-difluorophenyl)phenyl]-6-ethyl-trans-decahydronaphthalene,
trans-2-[3,5-difluoro-4-(3,5-difluorophenyl)phenyl]-6-propyl-trans-decahydronaphthalene,
trans-2-[3,5-difluoro-4-(3,5-difluorophenyl)phenyl]-6-butyl-trans-decahydronaphthalene,
trans-2-[3,5-difluoro-4-(3,5-difluorophenyl)phenyl]-6-pentyl-trans-decahydronaphthalene,
trans-2-[3,5-difluoro-4-(3,5-difluorophenyl)phenyl]-6-hexyl-trans-decahydronaphthalene,
trans-2-[3,5-difluoro-4-(3,5-difluorophenyl)phenyl]-6-heptyl-trans-decahydronaphthalene,
trans-2-[3,5-difluoro-4-(3-fluorophenyl)phenyl]-6-methyl-trans-decahydronaphthalene,
trans-2-[3,5-difluoro-4-(3-fluorophenyl)phenyl]-6-ethyl-trans-decahydronaphthalene,
trans-2-[3,5-difluoro-4-(3-fluorophenyl)phenyl]-6-propyl-trans-decahydronaphthalene,
trans-2-[3,5-difluoro-4-(3-fluorophenyl)phenyl]-6-butyl-trans-decahydronaphthalene,
trans-2-[3,5-difluoro-4-(3-fluorophenyl)phenyl]-6-pentyl-trans-decahydronaphthalene,
trans-2-[3,5-difluoro-4-(3-fluorophenyl)phenyl]-6-hexyl-trans-decahydronaphthalene, trans-2-[3,5-difluoro-4-(3-fluorophenyl)phenyl]-6-heptyl-trans-decahydronaphthalene,
trans-2-[3,5-difluoro-4-(4-trifluoromethoxyphenyl)phenyl]-6-methyl-trans-decahydronaphthalene,
trans-2-[3,5-difluoro-4-(4-trifluoromethoxyphenyl)phenyl]-6-ethyl-trans-decahydronaphthalene,
trans-2-[3,5-difluoro-4-(4-trifluoromethoxyphenyl)phenyl]-6-propyl-trans-decahydronaphthalene,
trans-2-[3,5-difluoro-4-(4-trifluoromethoxyphenyl)phenyl]-6-butyl-trans-decahydronaphthalene,
trans-2-[3,5-difluoro-4-(4-trifluoromethoxyphenyl)phenyl]-6-pentyl-trans-decahydronaphthalene,
trans-2-[3,5-difluoro-4-(4-trifluoromethoxyphenyl)phenyl]-6-hexyl-trans-decahydronaphthalene,
trans-2-[3,5-difluoro-4-(4-trifluoromethoxyphenyl)phenyl]-6-heptyl-trans-decahydronaphthalene,
trans-2-[3,5-difluoro-4-(3-fluoro-4-trifluoromethoxyphenyl)phenyl]-6-methyl-trans-decahydronaphthalene,
trans-2-[3,5-difluoro-4-(3-fluoro-4-trifluoromethoxyphenyl)phenyl]-6-ethyl-trans-decahydronaphthalene,
trans-2-[3,5-difluoro-4-(3-fluoro-4-trifluoromethoxyphenyl)phenyl]-6-propyl-trans-decahydronaphthalene,
trans-2-[3,5-difluoro-4-(3-fluoro-4-trifluoromethoxyphenyl)phenyl]-6-butyl-trans-decahydronaphthalene,
trans-2-[3,5-difluoro-4-(3-fluoro-4-trifluoromethoxyphenyl)phenyl]-6-pentyl-trans-decahydronaphthalene,
trans-2-[3,5-difluoro-4-(3-fluoro-4-trifluoromethoxyphenyl)phenyl]-6-hexyl-trans-decahydronaphthalene,
trans-2-[3,5-difluoro-4-(3-fluoro-4-trifluoromethoxyphenyl)phenyl]-6-heptyl-trans-decahydronaphthalene,
trans-2-[3,5-difluoro-4-(4-difluoromethoxyphenyl)phenyl]-6-methyl-trans-decahydronaphthalene,
trans-2-[3,5-difluoro-4-(4-difluoromethoxyphenyl)phenyl]-6-ethyl-trans-decahydronaphthalene,
trans-2-[3,5-difluoro-4-(4-difluoromethoxyphenyl)phenyl]-6-propyl-trans-decahydronaphthalene,
trans-2-[3,5-difluoro-4-(4-difluoromethoxyphenyl)phenyl]-6-butyl-trans-decahydronaphthalene,
trans-2-[3,5-difluoro-4-(4-difluoromethoxyphenyl)phenyl]-6-pentyl-trans-decahydronaphthalene,
trans-2-[3,5-difluoro-4-(4-difluoromethoxyphenyl)phenyl]-6-hexyl-trans-decahydronaphthalene,
trans-2-[3,5-difluoro-4-(4-difluoromethoxyphenyl)phenyl]-6-heptyl-trans-decahydronaphthalene,
trans-2-[3,5-difluoro-4-(3-fluoro-4-difluoromethoxyphenyl)phenyl]-6-methyl-trans-decahydronaphthalene,
trans-2-[3,5-difluoro-4-(3-fluoro-4-difluoromethoxyphenyl)phenyl]-6-ethyl-trans-decahydronaphthalene,
trans-2-[3,5-difluoro-4-(3-fluoro-4-difluoromethoxyphenyl)phenyl]-6-propyl-trans-decahydronaphthalene,
trans-2-[3,5-difluoro-4-(3-fluoro-4-difluoromethoxyphenyl)phenyl]-6-butyl-trans-decahydronaphthalene,
trans-2-[3,5-difluoro-4-(3-fluoro-4-difluoromethoxyphenyl)phenyl]-6-pentyl-trans-decahydronaphthalene,
trans-2-[3,5-difluoro-4-(3-fluoro-4-difluoromethoxyphenyl)phenyl]-6-hexyl-trans-decahydronaphthalene,
trans-2-[3,5-difluoro-4-(3-fluoro-4-difluoromethoxyphenyl)phenyl]-6-heptyl-trans-decahydronaphthalene,
trans-2-[3,5-difluoro-4-(4-trifluoromethylphenyl)phenyl]-6-methyl-trans-decahydronaphthalene,
trans-2-[3,5-difluoro-4-(4-trifluoromethylphenyl)phenyl]-6-ethyl-trans-decahydronaphthalene,
trans-2-[3,5-difluoro-4-(4-trifluoromethylphenyl)phenyl]-6—propyl-trans-decahydronaphthalene,
trans-2-[3,5-difluoro-4-(4-trifluoromethylphenyl)phenyl]-6-butyl-trans-decahydronaphthalene,
trans-2-[3,5-difluoro-4-(4-trifluoromethylphenyl)phenyl]-6-pentyl-trans-decahydronaphthalene,
trans-2-[3,5-difluoro-4-(4-trifluoromethylphenyl)phenyl]-6-hexyl-trans-decahydronaphthalene,
trans-2-[3,5-difluoro-4-(4-trifluoromethylphenyl)phenyl]-6-heptyl-trans-decahydronaphthalene,
trans-2-[3,5-difluoro-4-(4-methylphenyl)phenyl]-6-methyl-trans-decahydronaphthalene,
trans-2-[3,5-difluoro-4-(4-methylphenyl)phenyl]-6-ethyl-trans-decahydronaphthalene,
trans-2-[3,5-difluoro-4-(4-methylphenyl)phenyl]-6-propyl-trans-decahydronaphthalene,
trans-2-[3,5-difluoro-4-(4-methylphenyl)phenyl]-6-butyl-trans-decahydronaphthalene,
trans-2-[3,5-difluoro-4-(4-methylphenyl)phenyl]-6-pentyl-trans-decahydronaphthalene,
trans-2-[3,5-difluoro-4-(4-methylphenyl)phenyl]-6-hexyl-trans-decahydronaphthalene,
trans-2-[3,5-difluoro-4-(4-methylphenyl)phenyl]-6-heptyl-trans-decahydronaphthalene,
trans-2-[3,5-difluoro-4-(4-ethylphenyl)phenyl]-6-methyl-trans-decahydronaphthalene,
trans-2-[3,5-difluoro-4-(4-ethylphenyl)phenyl]-6-ethyl-trans-decahydronaphthalene,
trans-2-[3,5-difluoro-4-(4-ethylphenyl)phenyl]-6-propyl-trans-decahydronaphthalene,
trans-2-[3,5-difluoro-4-(4-ethylphenyl)phenyl]-6-butyl-trans-decahydronaphthalene,
trans-2-[3,5-difluoro-4-(4-ethylphenyl)phenyl]-6-pentyl-trans-decahydronaphthalene,
trans-2-[3,5-difluoro-4-(4-ethylphenyl)phenyl]-6-hexyl-trans-decahydronaphthalene,
trans-2-[3,5-difluoro-4-(4-ethylphenyl)phenyl]-6-heptyl-trans-decahydronaphthalene,
trans-2-[3,5-difluoro-4-(4-propylphenyl)phenyl]-6-methyl-trans-decahydronaphthalene,
trans-2-[3,5-difluoro-4-(4-propylphenyl)phenyl]-6-ethyl-trans-decahydronaphthalene,
trans-2-[3,5-difluoro-4-(4-propylphenyl)phenyl]-6-propyl-trans-decahydronaphthalene,
trans-2-[3,5-difluoro-4-(4-propylphenyl)phenyl]-6-butyl-trans-decahydronaphthalene,
trans-2-[3,5-difluoro-4-(4-propylphenyl)phenyl]-6-pentyl-trans-decahydronaphthalene,
trans-2-[3,5-difluoro-4-(4-propylphenyl)phenyl]-6-hexyl-trans-decahydronaphthalene,
trans-2-[3,5-difluoro-4-(4-propylphenyl)phenyl]-6-heptyl-trans-decahydronaphthalene,
trans-2-[3,5-difluoro-4-(4-methoxyphenyl)phenyl]-6-methyl-trans-decahydronaphthalene,
trans-2-[3,5-difluoro-4-(4-methoxyphenyl)phenyl]-6-ethyl-trans-decahydronaphthalene,
trans-2-[3,5-difluoro-4-(4-methoxyphenyl)phenyl]-6-propyl-trans-decahydronaphthalene,
trans-2-[3,5-difluoro-4-(4-methoxyphenyl)phenyl]-6-butyl-trans-decahydronaphthalene,
trans-2-[3,5-difluoro-4-(4-methoxyphenyl)phenyl]-6-pentyl-trans-decahydronaphthalene,
trans-2-[3,5-difluoro-4-(4-methoxyphenyl)phenyl]-6-hexyl-trans-decahydronaphthalene,
trans-2-[3,5-difluoro-4-(4-methoxyphenyl)phenyl]-6-heptyl-trans-decahydronaphthalene, trans-2-[3,5-difluoro-4-(3-fluoro-4-methoxyphenyl)phenyl]-6-methyl-trans-decahydronaphthalene,
trans-2-[3,5-difluoro-4-(3-fluoro-4-methoxyphenyl)phenyl]-6-ethyl-trans-decahydronaphthalene,
trans-2-[3,5-difluoro-4-(3-fluoro-4-methoxyphenyl)phenyl]-6-propyl-trans-decahydronaphthalene,
trans-2-[3,5-difluoro-4-(3-fluoro-4-methoxyphenyl)phenyl]-6-butyl-trans-decahydronaphthalene,
trans-2-[3,5-difluoro-4-(3-fluoro-4-methoxyphenyl)phenyl]-6-pentyl-trans-decahydronaphthalene,
trans-2-[3,5-difluoro-4-(3-fluoro-4-methoxyphenyl)phenyl]-6-hexyl-trans-decahydronaphthalene,
trans-2-[3,5-difluoro-4-(3-fluoro-4-methoxyphenyl)phenyl]-6-heptyl-trans-decahydronaphthalene,
trans-2-[3,5-difluoro-4-(3,5-difluoro-4-methoxyphenyl)phenyl]-6-methyl-trans-decahydronaphthalene,
trans-2-[3,5-difluoro-4-(3,5-difluoro-4-methoxyphenyl)phenyl]-6-ethyl-trans-decahydronaphthalene,
trans-2-[3,5-difluoro-4-(3,5-difluoro-4-methoxyphenyl)phenyl]-6-propyl-trans-decahydronaphthalene,
trans-2-[3,5-difluoro-4-(3,5-difluoro-4-methoxyphenyl)phenyl]-6-butyl-trans-decahydronaphthalene,
trans-2-[3,5-difluoro-4-(3,5-difluoro-4-methoxyphenyl)phenyl]-6-pentyl-trans-decahydronaphthalene,
trans-2-[3,5-difluoro-4-(3,5-difluoro-4-methoxyphenyl)phenyl]-6-hexyl-trans-decahydronaphthalene,
trans-2-[3,5-difluoro-4-(3,5-difluoro-4-methoxyphenyl)phenyl]-6-heptyl-trans-decahydronaphthalene,
trans-2-[3,5-difluoro-4-(4-benzyloxyphenyl)phenyl]-6-methyl-trans-decahydronaphthalene,
trans-2-[3,5-difluoro-4-(4-benzyloxyphenyl)phenyl]-6-ethyl-trans-decahydronaphthalene,
trans-2-[3,5-difluoro-4-(4-benzyloxyphenyl)phenyl]-6-propyl-trans-decahydronaphthalene,
trans-2-[3,5-difluoro-4-(4-benzyloxyphenyl)phenyl]-6-butyl-trans-decahydronaphthalene,
trans-2-[3,5-difluoro-4-(4-benzyloxyphenyl)phenyl]-6-pentyl-trans-decahydronaphthalene,
trans-2-[3,5-difluoro-4-(4-benzyloxyphenyl)phenyl]-6-hexyl-trans-decahydronaphthalene,
trans-2-[3,5-difluoro-4-(4-benzyloxyphenyl)phenyl]-6-heptyl-trans-decahydronaphthalene,
trans-2-[3,5-difluoro-4-(3-fluoro-4-benzyloxyphenyl)phenyl]-6-methyl-trans-decahydronaphthalene,
trans-2-[3,5-difluoro-4-(3-fluoro-4-benzyloxyphenyl)phenyl]-6-ethyl-trans-decahydronaphthalene,
trans-2-[3,5-difluoro-4-(3-fluoro-4-benzyloxyphenyl)phenyl]-6-propyl-trans-decahydronaphthalene,
trans-2-[3,5-difluoro-4-(3-fluoro-4-benzyloxyphenyl)phenyl]-6-butyl-trans-decahydronaphthalene,
trans-2-[3,5-difluoro-4-(3-fluoro-4-benzyloxyphenyl)phenyl]-6-pentyl-trans-decahydronaphthalene,
trans-2-[3,5-difluoro-4-(3-fluoro-4-benzyloxyphenyl)phenyl]-6-hexyl-trans-decahydronaphthalene,
trans-2-[3,5-difluoro-4-(3-fluoro-4-benzyloxyphenyl)phenyl]-6-heptyl-trans-decahydronaphthalene,
trans-2-[3,5-difluoro-4-(3,5-difluoro-4-benzyloxyphenyl)phenyl]-6-methyl-trans-decahydronaphthalene,
trans-2-[3,5-difluoro-4-(3,5-difluoro-4-benzyloxyphenyl)phenyl]-6-ethyl-trans-decahydronaphthalene,
trans-2-[3,5-difluoro-4-(3,5-difluoro-4-benzyloxyphenyl)phenyl]-6-propyl-trans-decahydronaphthalene,
trans-2-[3,5-difluoro-4-(3,5-difluoro-4-benzyloxyphenyl)phenyl]-6-butyl-trans-decahydronaphthalene,
trans-2-[3,5-difluoro-4-(3,5-difluoro-4-benzyloxyphenyl)phenyl]-6-pentyl-trans-decahydronaphthalene,
trans-2-[3,5-difluoro-4-(3,5-difluoro-4-benzyloxyphenyl)phenyl]-6-hexyl-trans-decahydronaphthalene,
trans-2-[3,5-difluoro-4-(3,5-difluoro-4-benzyloxyphenyl)phenyl]-6-heptyl-trans-decahydronaphthalene,
trans-2-[3,5-difluoro-4-[4-(3-butenyl)phenyl]phenyl]-6-methyl-trans-decahydronaphthalene,
trans-2-[3,5-difluoro-4-[4-(3-butenyl)phenyl]phenyl]-6-ethyl-trans-decahydronaphthalene,
trans-2-[3,5-difluoro-4-[4-(3-butenyl)phenyl]phenyl]-6-propyl-trans-decahydronaphthalene,
trans-2-[3,5-difluoro-4-[4-(3-butenyl)phenyl]phenyl]-6-butyl-trans-decahydronaphthalene,
trans-2-[3,5-difluoro-4-[4-(3-butenyl)phenyl]phenyl]-6-pentyl-trans-decahydronaphthalene,
trans-2-[3,5-difluoro-4-[4-(3-butenyl)phenyl]phenyl]-6-hexyl-trans-decahydronaphthalene,
trans-2-[3,5-difluoro-4-[4-(3-butenyl)phenyl]phenyl]-6-heptyl-trans-decahydronaphthalene,
trans-2-[3,5-difluoro-4-[4-(trans-3-pentenyl)phenyl]phenyl]-6-methyl-trans-decahydronaphthalene,
trans-2-[3,5-difluoro-4-[4-(trans-3-pentenyl)phenyl]phenyl]-6-ethyl-trans-decahydronaphthalene,
trans-2-[3,5-difluoro-4-[4-(trans-3-pentenyl)phenyl]phenyl]-6-propyl-trans-decahydronaphthalene,
trans-2-[3,5-difluoro-4-[4-(trans-3-pentenyl)phenyl]phenyl]-6-butyl-trans-decahydronaphthalene,
trans-2-[3,5-difluoro-4-[4-(trans-3-pentenyl)phenyl]phenyl]-6-pentyl-trans-decahydronaphthalene,
trans-2-[3,5-difluoro-4-[4-(trans-3-pentenyl)phenyl]phenyl]-6-hexyl-trans-decahydronaphthalene,
trans-2-[3,5-difluoro-4-[4-(trans-3-pentenyl)phenyl]phenyl]-6-heptyl-trans-decahydronaphthalene,
trans-2-[3,5-difluoro-4-[4-(4,4-dimethyl-1,3-oxazolin-2-yl)phenyl]phenyl]-6-methyl-trans-decahydronaphthalene,
trans-2-[3,5-difluoro-4-[4-(4,4-dimethyl-1,3-oxazolin-2-yl)phenyl]phenyl]-6-ethyl-trans-decahydronaphthalene,
trans-2-[3,5-difluoro-4-[4-(4,4-dimethyl-1,3-oxazolin-2-yl)phenyl]phenyl]-6-propyl-trans-decahydronaphthalene,
trans-2-[3,5-difluoro-4-[4-(4,4-dimethyl-1,3-oxazolin-2-yl)phenyl]phenyl]-6-butyl-trans-decahydronaphthalene,
trans-2-[3,5-difluoro-4-[4-(4,4-dimethyl-1,3-oxazolin-2-yl)phenyl]phenyl]-6-pentyl-trans-decahydronaphthalene,
trans-2-[3,5-difluoro-4-[4-(4,4-dimethyl-1,3-oxazolin-2-yl)phenyl]phenyl]-6-hexyl-trans-decahydronaphthalene,
trans-2-[3,5-difluoro-4-[4-(4,4-dimethyl-1,3-oxazolin-2-yl)phenyl]phenyl]-6-heptyl-trans-decahydronaphthalene,
trans-2-[3,5-difluoro-4-[3-fluoro-4-(4,4-dimethyl-1,3-oxazolin-2-yl)phenyl]phenyl]-6-methyl-trans-decahydronaphthalene,
trans-2-[3,5-difluoro-4-[3-fluoro-4-(4,4-dimethyl-1,3-oxazolin-2-yl)phenyl]phenyl]-6-ethyl-trans-decahydronaphthalene,
trans-2-[3,5-difluoro-4-[3-fluoro-4-(4,4-dimethyl-1,3-oxazolin-2-yl)phenyl]phenyl]-6-propyl-trans-decahydronaphthalene,
trans-2-[3,5-difluoro-4-[3-fluoro-4-(4,4-dimethyl-1,3-oxazolin-2-yl)phenyl]phenyl]-6-butyl-trans-decahydronaphthalene,
trans-2-[3,5-difluoro-4-[3-fluoro-4-(4,4-dimethyl-1,3-oxazolin-2-yl)phenyl]phenyl]-6-pentyl-trans-decahydronaphthalene,
trans-2-[3,5-difluoro-4-[3-fluoro-4-(4,4-dimethyl-1,3-oxazolin-2-yl)phenyl]phenyl]-6-hexyl-trans-decahydronaphthalene,
trans-2-[3,5-difluoro-4-[3-fluoro-4-(4,4-dimethyl-1,3-oxazolin-2-yl)phenyl]phenyl]-6-heptyl-trans-decahydronaphthalene,
trans-2-[3,5-difluoro-4-[3,5-difluoro-4-(4,4-dimethyl-1,3-oxazolin-2-yl)phenyl]phenyl]-6-methyl-trans-decahydronaphthalene, trans-2-[3,5-difluoro-4-[3,5-difluoro-4-(4,4-dimethyl-1,3-oxazolin-2-yl)phenyl]phenyl]-6-ethyl-trans-decahydronaphthalene,
trans-2-[3,5-difluoro-4-[3,5-difluoro-4-(4,4-dimethyl-1,3-oxazolin-2-yl)phenyl]phenyl]-6-propyl-trans-decahydronaphthalene,
trans-2-[3,5-difluoro-4-[3,5-difluoro-4-(4,4-dimethyl-1,3-oxazolin-2-yl)phenyl]phenyl]-6-butyl-trans-decahydronaphthalene,
trans-2-[3,5-difluoro-4-[3,5-difluoro-4-(4,4-dimethyl-1,3-oxazolin-2-yl)phenyl]phenyl]-6-pentyl-trans-decahydronaphthalene,
trans-2-[3,5-difluoro-4-[3,5-difluoro-4-(4,4-dimethyl-1,3-oxazolin-2-yl)phenyl]phenyl]-6-hexyl-trans-decahydronaphthalene,
trans-2-[3,5-difluoro-4-[3,5-difluoro-4-(4,4-dimethyl-1,3-oxazolin-2-yl)phenyl]phenyl]-6-heptyl-trans-decahydronaphthalene.

Example 18

Synthesis of 4-(trans-6-propyl-trans-decahydronaphthalen-2-yl)benzoic acid

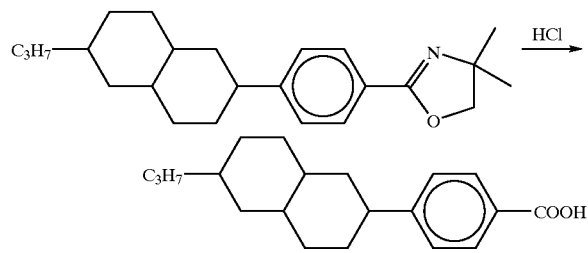

28 g of trans-2-[4-(4,4-dimethyl-1,3-oxazolidin-2-yl)phenyl]-6-trans-propyldecahydronaphthalene was dissolved in 140 ml of THF. The solution was heated for 4 hours under refluxing, and then the temperature was reduced to room temperature. The organic phase was separated, rinsed with a saturated saline solution and dried on anhydrous magnesium sulfate. Then, the solvent was evaporated to obtain 23 g of 4-(trans-6-propyl-trans-decahydronaphthalen-2-yl)benzoic acid The following compounds were prepared in the same manner as mentioned above:
4-(trans-6-methyl-trans-decahydronaphthalen-2-yl)benzoic acid,
4-(trans-6-ethyl-trans-decahydronaphthalen-2-yl)benzoic acid,
4-(trans-6-butyl-trans-decahydronaphthalen-2-yl)benzoic acid,
4-(trans-6-pentyl-trans-decahydronaphthalen-2-yl)benzoic acid,
4-(trans-6-hexyl-trans-decahydronaphthalen-2-yl)benzoic acid,
4-(trans-6-heptyl-trans-decahydronaphthalen-2-yl)benzoic acid,
3-fluoro-4-(trans-6-methyl-trans-decahydronaphthalen-2-yl)benzoic acid,
3-fluoro-4-(trans-6-ethyl-trans-decahydronaphthalen-2-yl)benzoic acid,
3-fluoro-4-(trans-6-propyl-trans-decahydronaphthalen-2-yl)benzoic acid,
3-fluoro-4-(trans-6-butyl-trans-decahydronaphthalen-2-yl)benzoic acid,
3-fluoro-4-(trans-6-pentyl-trans-decahydronaphthalen-2-yl)benzoic acid,
3-fluoro-4-(trans-6-hexyl-trans-decahydronaphthalen-2-yl)benzoic acid,
3-fluoro-4-(trans-6-heptyl-trans-decahydronaphthalen-2-yl)benzoic acid.

Example 19

Synthesis of 3-fluoro-4-cyanophenyl 4-(trans-6-propyl-trans-decahydronaphthalen-2-yl)benzoate

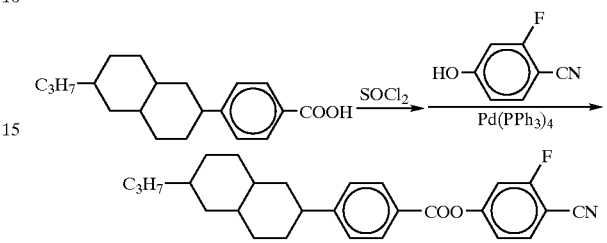

22 g of 4-(trans-6-propyl-trans-decahydronaphthalen-2-yl)benzoic acid, which was obtained in Example 18, was dissolved in 110 ml of dichloromethane. 17 g of thionyl chloride, 0.1 ml of pyridine, and 10 ml of DMF were added to the solution, and the mixture was heated for 1 hour under refluxing. After excessive thionyl chloride was evaporated, 110 ml of dichloromethane was added, then 10 g of 3-fluoro-4-cyanophenol and 10 g of pyridine were added, and the mixture was stirred for 8 hours at room temperature. 10% hydrochloric acid was added, and the organic phase was separated and rinsed with a saturated aqueous solution of sodium hydrogencarbonate and a saturated saline solution, in sequence, and dried on anhydrous sodium sulfate. After the solvent was evaporated, the residue was purified by silica gel chromatography (hexane/ethyl acetate), and recrystallized from ethanol to obtain 23 g white crystals of 3-fluoro-4-cyanophenyl 4-(trans-6-propyl-trans-decahydronaphthalen-2-yl)benzoate.

The following compounds were prepared in the same manner as mentioned above:
3-fluoro-4-cyanophenyl 4-(trans-6-methyl-trans-decahydronaphthalen-2-yl)benzoate,
3-fluoro-4-cyanophenyl 4-(trans-6-ethyl-trans-decahydronaphthalen-2-yl)benzoate,
3-fluoro-4-cyanophenyl 4-(trans-6-butyl-trans-decahydronaphthalen-2-yl)benzoate,
3-fluoro-4-cyanophenyl 4-(trans-6-pentyl-trans-decahydronaphthalen-2-yl)benzoate,
3-fluoro-4-cyanophenyl 4-(trans-6-hexyl-trans-decahydronaphthalen-2-yl)benzoate,
3-fluoro-4-cyanophenyl 4-(trans-6-heptyl-trans-decahydronaphthalen-2-yl)benzoate,
4-cyanophenyl 4-(trans-6-methyl-trans-decahydronaphthalen-2-yl)benzoate,
4-cyanophenyl 4-(trans-6-ethyl-trans-decahydronaphthalen-2-yl)benzoate,
4-cyanophenyl 4-(trans-6-propyl-trans-decahydronaphthalen-2-yl)benzoate,
4-cyanophenyl 4-(trans-6-butyl-trans-decahydronaphthalen-2-yl)benzoate,
4-cyanophenyl 4-(trans-6-pentyl-trans-decahydronaphthalen-2-yl)benzoate,
4-cyanophenyl 4-(trans-6-hexyl-trans-decahydronaphthalen-2-yl)benzoate,
4-cyanophenyl 4-(trans-6-heptyl-trans-decahydronaphthalen-2-yl)benzoate, 3,5-difluoro-4-cyanophenyl 4-(trans-6-methyl-trans-decahydronaphthalen-2-yl)benzoate,
3,5-difluoro-4-cyanophenyl 4-(trans-6-ethyl-trans-decahydronaphthalen-2-yl)benzoate,
3,5-difluoro-4-cyanophenyl 4-(trans-6-propyl-trans-decahydronaphthalen-2-yl)benzoate,
3,5-difluoro-4-cyanophenyl 4-(trans-6-butyl-trans-decahydronaphthalen-2-yl)benzoate,
3,5-difluoro-4-cyanophenyl 4-(trans-6-pentyl-trans-decahydronaphthalen-2-yl)benzoate,
3,5-difluoro-4-cyanophenyl 4-(trans-6-hexyl-trans-decahydronaphthalen-2-yl)benzoate,
3,5-difluoro-4-cyanophenyl 4-(trans-6-heptyl-trans-decahydronaphthalen-2-yl)benzoate,
3-fluoro-4-cyanophenyl 3-fluoro-4-(trans-6-methyl-trans-decahydronaphthalen-2-yl)benzoate,
3-fluoro-4-cyanophenyl 3-fluoro-4-(trans-6-ethyl-trans-decahydronaphthalen-2-yl)benzoate,
3-fluoro-4-cyanophenyl 3-fluoro-4-(trans-6-propyl-trans-decahydronaphthalen-2-yl)benzoate,
3-fluoro-4-cyanophenyl 3-fluoro-4-(trans-6-butyl-trans-decahydronaphthalen-2-yl)benzoate,
3-fluoro-4-cyanophenyl 3-fluoro-4-(trans-6-pentyl-trans-decahydronaphthalen-2-yl)benzoate,
3-fluoro-4-cyanophenyl 3-fluoro-4-(trans-6-hexyl-trans-decahydronaphthalen-2-yl)benzoate,
3-fluoro-4-cyanophenyl 3-fluoro-4-(trans-6-heptyl-trans-decahydronaphthalen-2-yl)benzoate,
4-cyanophenyl 3-fluoro-4-(trans-6-methyl-trans-decahydronaphthalen-2-yl)benzoate,
4-cyanophenyl 3-fluoro-4-(trans-6-ethyl-trans-decahydronaphthalen-2-yl)benzoate,
4-cyanophenyl 3-fluoro-4-(trans-6-propyl-trans-decahydronaphthalen-2-yl)benzoate,
4-cyanophenyl 3-fluoro-4-(trans-6-butyl-trans-decahydronaphthalen-2-yl)benzoate,
4-cyanophenyl 3-fluoro-4-(trans-6-pentyl-trans-decahydronaphthalen-2-yl)benzoate,
4-cyanophenyl 3-fluoro-4-(trans-6-hexyl-trans-decahydronaphthalen-2-yl)benzoate,
4-cyanophenyl 3-fluoro-4-(trans-6-heptyl-trans-decahydronaphthalen-2-yl)benzoate,
3,5-difluoro-4-cyanophenyl 3-fluoro-4-(trans-6-methyl-trans-decahydronaphthalen-2-yl)benzoate,
3,5-difluoro-4-cyanophenyl 3-fluoro-4-(trans-6-ethyl-trans-decahydronaphthalen-2-yl)benzoate,
3,5-difluoro-4-cyanophenyl 3-fluoro-4-(trans-6-propyl-trans-decahydronaphthalen-2-yl)benzoate,
3,5-difluoro-4-cyanophenyl 3-fluoro-4-(trans-6-butyl-trans-decahydronaphthalen-2-yl)benzoate,
3,5-difluoro-4-cyanophenyl 3-fluoro-4-(trans-6-pentyl-trans-decahydronaphthalen-2-yl)benzoate,
3,5-difluoro-4-cyanophenyl 3-fluoro-4-(trans-6-hexyl-trans-decahydronaphthalen-2-yl)benzoate,
3,5-difluoro-4-cyanophenyl 3-fluoro-4-(trans-6-heptyl-trans-decahydronaphthalen-2-yl)benzoate,
3-fluoro-4-cyanophenyl 3,5-difluoro-4-(trans-6-methyl-trans-decahydronaphthalen-2-yl)benzoate,
3-fluoro-4-cyanophenyl 3,5-difluoro-4-(trans-6-ethyl-trans-decahydronaphthalen-2-yl)benzoate,
3-fluoro-4-cyanophenyl 3,5-difluoro-4-(trans-6-propyl-trans-decahydronaphthalen-2-yl)benzoate,
3-fluoro-4-cyanophenyl 3,5-difluoro-4-(trans-6-butyl-trans-decahydronaphthalen-2-yl)benzoate,
3-fluoro-4-cyanophenyl 3,5-difluoro-4-(trans-6-pentyl-trans-decahydronaphthalen-2-yl)benzoate,
3-fluoro-4-cyanophenyl 3,5-difluoro-4-(trans-6-hexyl-trans-decahydronaphthalen-2-yl)benzoate,
3-fluoro-4-cyanophenyl 3,5-difluoro-4-(trans-6-heptyl-trans-decahydronaphthalen-2-yl)benzoate,
4-cyanophenyl 3,5-difluoro-4-(trans-6-methyl-trans-decahydronaphthalen-2-yl)benzoate,
4-cyanophenyl 3,5-difluoro-4-(trans-6-ethyl-trans-decahydronaphthalen-2-yl)benzoate,
4-cyanophenyl 3,5-difluoro-4-(trans-6-propyl-trans-decahydronaphthalen-2-yl)benzoate,
4-cyanophenyl 3,5-difluoro-4-(trans-6-butyl-trans-decahydronaphthalen-2-yl)benzoate,
4-cyanophenyl 3,5-difluoro-4-(trans-6-pentyl-trans-decahydronaphthalen-2-yl)benzoate,
4-cyanophenyl 3,5-difluoro-4-(trans-6-hexyl-trans-decahydronaphthalen-2-yl)benzoate,
4-cyanophenyl 3,5-difluoro-4-(trans-6-heptyl-trans-decahydronaphthalen-2-yl)benzoate,
3,5-difluoro-4-cyanophenyl 3,5-difluoro-4-(trans-6-methyl-trans-decahydronaphthalen-2-yl)benzoate,
3,5-difluoro-4-cyanophenyl 3,5-difluoro-4-(trans-6-ethyl-trans-decahydronaphthalen-2-yl)benzoate,
3,5-difluoro-4-cyanophenyl 3,5-difluoro-4-(trans-6-propyl-trans-decahydronaphthalen-2-yl)benzoate,
3,5-difluoro-4-cyanophenyl 3,5-difluoro-4-(trans-6-butyl-trans-decahydronaphthalen-2-yl)benzoate,
3,5-difluoro-4-cyanophenyl 3,5-difluoro-4-(trans-6-pentyl-trans-decahydronaphthalen-2-yl)benzoate,
3,5-difluoro-4-cyanophenyl 3,5-difluoro-4-(trans-6-hexyl-trans-decahydronaphthalen-2-yl)benzoate,
3,5-difluoro-4-cyanophenyl 3,5-difluoro-4-(trans-6-heptyl-trans-decahydronaphthalen-2-yl)benzoate,
4-fluorophenyl 3-fluoro-4-(trans-6-methyl-trans-decahydronaphthalen-2-yl)benzoate,
4-fluorophenyl 3-fluoro-4-(trans-6-ethyl-trans-decahydronaphthalen-2-yl)benzoate,
4-fluorophenyl 3-fluoro-4-(trans-6-propyl-trans-decahydronaphthalen-2-yl)benzoate,
4-fluorophenyl 3-fluoro-4-(trans-6-butyl-trans-decahydronaphthalen-2-yl)benzoate,
4-fluorophenyl 3-fluoro-4-(trans-6-pentyl-trans-decahydronaphthalen-2-yl)benzoate,
4-fluorophenyl 3-fluoro-4-(trans-6-hexyl-trans-decahydronaphthalen-2-yl)benzoate,
4-fluorophenyl 3-fluoro-4-(trans-6-heptyl-trans-decahydronaphthalen-2-yl)benzoate,
4-trifluoromethoxyphenyl 3-fluoro-4-(trans-6-methyl-trans-decahydronaphthalen-2-yl)benzoate,
4-trifluoromethoxyphenyl 3-fluoro-4-(trans-6-ethyl-trans-decahydronaphthalen-2-yl)benzoate,
4-trifluoromethoxyphenyl 3-fluoro-4-(trans-6-propyl-trans-decahydronaphthalen-2-yl)benzoate,
4-trifluoromethoxyphenyl 3-fluoro-4-(trans-6-butyl-trans-decahydronaphthalen-2-yl)benzoate,
4-trifluoromethoxyphenyl 3-fluoro-4-(trans-6-pentyl-trans-decahydronaphthalen-2-yl)benzoate,
4-trifluoromethoxyphenyl 3-fluoro-4-(trans-6-hexyl-trans-decahydronaphthalen-2-yl)benzoate,
4-trifluoromethoxyphenyl 3-fluoro-4-(trans-6-heptyl-trans-decahydronaphthalen-2-yl)benzoate,
4-trifluoromethylphenyl 3-fluoro-4-(trans-6-methyl-trans-decahydronaphthalen-2-yl)benzoate,
4-trifluoromethylphenyl 3-fluoro-4-(trans-6-ethyl-trans-decahydronaphthalen-2-yl)benzoate,
4-trifluoromethylphenyl 3-fluoro-4-(trans-6-propyl-trans-decahydronaphthalen-2-yl)benzoate,
4-trifluoromethylphenyl 3-fluoro-4-(trans-6-butyl-trans-decahydronaphthalen-2-yl)benzoate,
4-trifluoromethylphenyl 3-fluoro-4-(trans-6-pentyl-trans-decahydronaphthalen-2-yl)benzoate, 4-trifluoromethylphenyl 3-fluoro-4-(trans-6-hexyl-trans-decahydronaphthalen-2-yl)benzoate,
4-trifluoromethylphenyl 3-fluoro-4-(trans-6-heptyl-trans-decahydronaphthalen-2-yl)benzoate,
3,4-difluorophenyl 3-fluoro-4-(trans-6-methyl-trans-decahydronaphthalen-2-yl)benzoate,
3,4-difluorophenyl 3-fluoro-4-(trans-6-ethyl-trans-decahydronaphthalen-2-yl)benzoate,
3,4-difluorophenyl 3-fluoro-4-(trans-6-propyl-trans-decahydronaphthalen-2-yl)benzoate,
3,4-difluorophenyl 3-fluoro-4-(trans-6-butyl-trans-decahydronaphthalen-2-yl)benzoate,
3,4-difluorophenyl 3-fluoro-4-(trans-6-pentyl-trans-decahydronaphthalen-2-yl)benzoate,
3,4-difluorophenyl 3-fluoro-4-(trans-6-hexyl-trans-decahydronaphthalen-2-yl)benzoate,
3,4-difluorophenyl 3-fluoro-4-(trans-6-heptyl-trans-decahydronaphthalen-2-yl)benzoate,
3,4,5-trifluorophenyl 3-fluoro-4-(trans-6-methyl-trans-decahydronaphthalen-2-yl)benzoate,
3,4,5-trifluorophenyl 3-fluoro-4-(trans-6-ethyl-trans-decahydronaphthalen-2-yl)benzoate,
3,4,5-trifluorophenyl 3-fluoro-4-(trans-6-propyl-trans-decahydronaphthalen-2-yl)benzoate,
3,4,5-trifluorophenyl 3-fluoro-4-(trans-6-butyl-trans-decahydronaphthalen-2-yl)benzoate,
3,4,5-trifluorophenyl 3-fluoro-4-(trans-6-pentyl-trans-decahydronaphthalen-2-yl)benzoate,
3,4,5-trifluorophenyl 3-fluoro-4-(trans-6-hexyl-trans-decahydronaphthalen-2-yl)benzoate,
3,4,5-trifluorophenyl 3-fluoro-4-(trans-6-heptyl-trans-decahydronaphthalen-2-yl)benzoate,
4-methylphenyl 3-fluoro-4-(trans-6-methyl-trans-decahydronaphthalen-2-yl)benzoate,
4-methylphenyl 3-fluoro-4-(trans-6-ethyl-trans-decahydronaphthalen-2-yl)benzoate,
3-4-methylphenyl fluoro-4-(trans-6-propyl-trans-decahydronaphthalen-2-yl)benzoate,
4-methylphenyl 3-fluoro-4-(trans-6-butyl-trans-decahydronaphthalen-2-yl)benzoate,
4-methylphenyl 3-fluoro-4-(trans-6-pentyl-trans-decahydronaphthalen-2-yl)benzoate,
4-methylphenyl 3-fluoro-4-(trans-6-hexyl-trans-decahydronaphthalen-2-yl)benzoate,
4-methylphenyl 3-fluoro-4-(trans-6-heptyl-trans-decahydronaphthalen-2-yl)benzoate,
4-ethylphenyl 3-fluoro-4-(trans-6-methyl-trans-decahydronaphthalen-2-yl)benzoate,
4-ethylphenyl 3-fluoro-4-(trans-6-ethyl-trans-decahydronaphthalen-2-yl)benzoate,
4-ethylphenyl 3-fluoro-4-(trans-6-propyl-trans-decahydronaphthalen-2-yl)benzoate,
4-ethylphenyl 3-fluoro-4-(trans-6-butyl-trans-decahydronaphthalen-2-yl)benzoate,
4-ethylphenyl 3-fluoro-4-(trans-6-pentyl-trans-decahydronaphthalen-2-yl)benzoate,
4-ethylphenyl 3-fluoro-4-(trans-6-hexyl-trans-decahydronaphthalen-2-yl)benzoate,
4-ethylphenyl 3-fluoro-4-(trans-6-heptyl-trans-decahydronaphthalen-2-yl)benzoate,
4-methoxyphenyl 3-fluoro-4-(trans-6-methyl-trans-decahydronaphthalen-2-yl)benzoate,
4-methoxyphenyl 3-fluoro-4-(trans-6-ethyl-trans-decahydronaphthalen-2-yl)benzoate,
4-methoxyphenyl 3-fluoro-4-(trans-6-propyl-trans-decahydronaphthalen-2-yl)benzoate,
4-methoxyphenyl 3-fluoro-4-(trans-6-butyl-trans-decahydronaphthalen-2-yl)benzoate,
4-methoxyphenyl 3-fluoro-4-(trans-6-pentyl-trans-decahydronaphthalen-2-yl)benzoate,
4-methoxyphenyl 3-fluoro-4-(trans-6-hexyl-trans-decahydronaphthalen-2-yl)benzoate,
4-methoxyphenyl 3-fluoro-4-(trans-6-heptyl-trans-decahydronaphthalen-2-yl)benzoate,
4-(3-butenyl)phenyl 3-fluoro-4-(trans-6-methyl-trans-decahydronaphthalen-2-yl)benzoate.,
4-(3-butenyl)phenyl 3-fluoro-4-(trans-6-ethyl-trans-decahydronaphthalen-2-yl)benzoate,
4-(3-butenyl)phenyl 3-fluoro-4-(trans-6-propyl-trans-decahydronaphthalen-2-yl)benzoate,
4-(3-butenyl)phenyl 3-fluoro-4-(trans-6-butyl-trans-decahydronaphthalen-2-yl)benzoate,
4-(3-butenyl)phenyl 3-fluoro-4-(trans-6-pentyl-trans-decahydronaphthalen-2-yl)benzoate,
4-(3-butenyl)phenyl 3-fluoro-4-(trans-6-hexyl-trans-decahydronaphthalen-2-yl)benzoate,
4-(3-butenyl)phenyl 3-fluoro-4-(trans-6-heptyl-trans-decahydronaphthalen-2-yl)benzoate,
4-phenyl 3-fluoro-4-(trans-6-methyl-trans-decahydronaphthalen-2-yl)benzoate,
4-phenyl 3-fluoro-4-(trans-6-ethyl-trans-decahydronaphthalen-2-yl)benzoate,
4-phenyl 3-fluoro-4-(trans-6-propyl-trans-decahydronaphthalen-2-yl)benzoate,
4-phenyl 3-fluoro-4-(trans-6-butyl-trans-decahydronaphthalen-2-yl)benzoate,
4-phenyl 3-fluoro-4-(trans-6-pentyl-trans-decahydronaphthalen-2-yl)benzoate,
4-phenyl 3-fluoro-4-(trans-6-hexyl-trans-decahydronaphthalen-2-yl)benzoate,
4-phenyl 3-fluoro-4-(trans-6-heptyl-trans-decahydronaphthalen-2-yl)benzoate,
4-chlorophenyl 3-fluoro-4-(trans-6-methyl-trans-decahydronaphthalen-2-yl)benzoate,
4-chlorophenyl 3-fluoro-4-(trans-6-ethyl-trans-decahydronaphthalen-2-yl)benzoate,
4-chlorophenyl 3-fluoro-4-(trans-6-propyl-trans-decahydronaphthalen-2-yl)benzoate,
4-chlorophenyl 3-fluoro-4-(trans-6-butyl-trans-decahydronaphthalen-2-yl)benzoate,
4-chlorophenyl 3-fluoro-4-(trans-6-pentyl-trans-decahydronaphthalen-2-yl)benzoate,
4-chlorophenyl 3-fluoro-4-(trans-6-hexyl-trans-decahydronaphthalen-2-yl)benzoate,
4-chlorophenyl 3-fluoro-4-(trans-6-heptyl-trans-decahydronaphthalen-2-yl)benzoate,
4-allyloxyphenyl 3-fluoro-4-(trans-6-methyl-trans-decahydronaphthalen-2-yl)benzoate,
4-allyloxyphenyl 3-fluoro-4-(trans-6-ethyl-trans-decahydronaphthalen-2-yl)benzoate,
4-allyloxyphenyl 3-fluoro-4-(trans-6-propyl-trans-decahydronaphthalen-2-yl)benzoate,
4-allyloxyphenyl 3-fluoro-4-(trans-6-butyl-trans-decahydronaphthalen-2-yl)benzoate,
4-allyloxyphenyl 3-fluoro-4-(trans-6-pentyl-trans-decahydronaphthalen-2-yl)benzoate,
4-allyloxyphenyl 3-fluoro-4-(trans-6-hexyl-trans-decahydronaphthalen-2-yl)benzoate,
4-allyloxyphenyl 3-fluoro-4-(trans-6-heptyl-trans-decahydronaphthalen-2-yl)benzoate.

Example 20

Synthesis of 6-(1,2-difluoronaphthalen-6-yl)-2-propyl-trans-decahydronaphthalene (I-27)

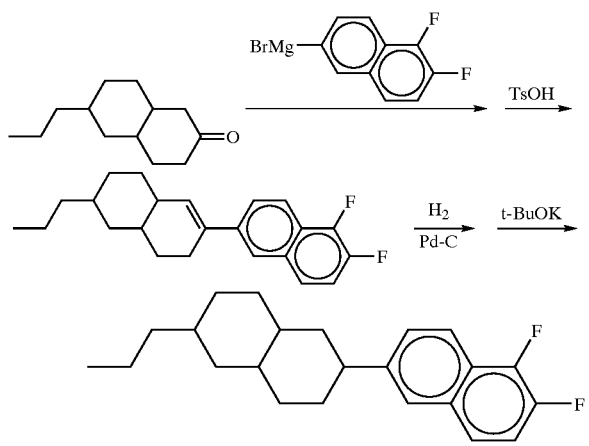

(20-a) Synthesis of 6-(1,2-difluoronaphthalen-6-yl)-2-propyl-trans-1,2,3,4,7,8,9,10-octahydronaphthalene Reaction of 12 g of 6-propyldecahydro-2-naphthalenone with a Grignard reagent prepared from 1,2-difluoro-6-bromonaphthalene and dehydration were carried out to obtain 15 g of pale yellow liquid 6-(1,2-difluoronaphthalen-6-yl)-2-propyl-trans-1,2,3,4,7,8,9,10-octahydronaphthalene.

(20-b) Synthesis of 6-(1,2-difluoronaphthalen-6-yl)-2-propyl-trans-decahydronaphthalene Catalytic hydrogenation reduction and isomerization of 15 g of 6-(1,2-difluoronaphthalen-6-yl)-2-propyl-trans-1,2,3,4,7,8,9,10-octahydronaphthalene, which was obtained in (20-a), were carried out to obtain 3 g of white solid 6-(1,2-difluoronaphthalen-6-yl)-2-propyl-trans-decahydronaphthalene.

The following compounds were prepared in the same manner as mentioned above:

6-(2-fluoronaphthalen-6-yl)-2-methyl-trans-decahydronaphthalene,
6-(2-fluoronaphthalen-6-yl)-2-ethyl-trans-decahydronaphthalene,
6-(2-fluoronaphthalen-6-yl)-2-propyl-trans-decahydronaphthalene,
6-(2-fluoronaphthalen-6-yl)-2-butyl-trans-decahydronaphthalene,
6-(2-fluoronaphthalen-6-yl)-2-pentyl-trans-decahydronaphthalene,
6-(2-fluoronaphthalen-6-yl)-2-hexyl-trans-decahydronaphthalene,
6-(2-fluoronaphthalen-6-yl)-2-heptyl-trans-decahydronaphthalene,
6-(1,2-difluoronaphthalen-6-yl)-2-methyl-trans-decahydronaphthalene,
6-(1,2-difluoronaphthalen-6-yl)-2-ethyl-trans-decahydronaphthalene,
6-(1,2-difluoronaphthalen-6-yl)-2-butyl-trans-decahydronaphthalene,
6-(1,2-difluoronaphthalen-6-yl)-2-pentyl-trans-decahydronaphthalene,
6-(1,2-difluoronaphthalen-6-yl)-2-hexyl-trans-decahydronaphthalene,
6-(1,2-difluoronaphthalen-6-yl)-2-heptyl-trans-decahydronaphthalene,
6-(2,3-difluoronaphthalen-6-yl)-2-methyl-trans-decahydronaphthalene,
6-(2,3-difluoronaphthalen-6-yl)-2-ethyl-trans-decahydronaphthalene,
6-(2,3-difluoronaphthalen-6-yl)-2-propyl-trans-decahydronaphthalene,
6-(2,3-difluoronaphthalen-6-yl)-2-butyl-trans-decahydronaphthalene,
6-(2,3-difluoronaphthalen-6-yl)-2-pentyl-trans-decahydronaphthalene,
6-(2,3-difluoronaphthalen-6-yl)-2-hexyl-trans-decahydronaphthalene,
6-(2,3-difluoronaphthalen-6-yl)-2-heptyl-trans-decahydronaphthalene,
6-(1,2,3-trifluoronaphthalen-6-yl)-2-methyl-trans-decahydronaphthalene,
6-(1,2,3-trifluoronaphthalen-6-yl)-2-ethyl-trans-decahydronaphthalene,
6-(1,2,3-trifluoronaphthalen-6-yl)-2-propyl-trans-decahydronaphthalene,
6-(1,2,3-trifluoronaphthalen-6-yl)-2-butyl-trans-decahydronaphthalene,
6-(1,2,3-trifluoronaphthalen-6-yl)-2-pentyl-trans-decahydronaphthalene,
6-(1,2,3-trifluoronaphthalen-6-yl)-2-hexyl-trans-decahydronaphthalene,
6-(1,2,3-trifluoronaphthalen-6-yl)-2-heptyl-trans-decahydronaphthalene,
6-(1,7-difluoronaphthalen-3-yl)-2-methyl-trans-decahydronaphthalene,
6-(1,7-difluoronaphthalen-3-yl)-2-ethyl-trans-decahydronaphthalene,
6-(1,7-difluoronaphthalen-3-yl)-2-propyl-trans-decahydronaphthalene,
6-(1,7-difluoronaphthalen-3-yl)-2-butyl-trans-decahydronaphthalene,
6-(1,7-difluoronaphthalen-3-yl)-2-pentyl-trans-decahydronaphthalene,
6-(1,7-difluoronaphthalen-3-yl)-2-hexyl-trans-decahydronaphthalene,
6-(1,7-difluoronaphthalen-3-yl)-2-heptyl-trans-decahydronaphthalene,
6-(1,2,8-trifluoronaphthalen-6-yl)-2-methyl-trans-decahydronaphthalene,
6-(1,2,8-trifluoronaphthalen-6-yl)-2-ethyl-trans-decahydronaphthalene,
6-(1,2,8-trifluoronaphthalen-6-yl)-2-propyl-trans-decahydronaphthalene,
6-(1,2,8-trifluoronaphthalen-6-yl)-2-butyl-trans-decahydronaphthalene,
6-(1,2,8-trifluoronaphthalen-6-yl)-2-pentyl-trans-decahydronaphthalene,
6-(1,2,8-trifluoronaphthalen-6-yl)-2-hexyl-trans-decahydronaphthalene,
6-(1,2,8-trifluoronaphthalen-6-yl)-2-heptyl-trans-decahydronaphthalene,
6-(1,6,7-trifluoronaphthalen-6-yl)-2-methyl-trans-decahydronaphthalene,
6-(1,6,7-trifluoronaphthalen-6-yl)-2-ethyl-trans-decahydronaphthalene,
6-(1,6,7-trifluoronaphthalen-6-yl)-2-propyl-trans-decahydronaphthalene,
6-(1,6,7-trifluoronaphthalen-6-yl)-2-butyl-trans-decahydronaphthalene,
6-(1,6,7-trifluoronaphthalen-6-yl)-2-pentyl-trans-decahydronaphthalene,
6-(1,6,7-trifluoronaphthalen-6-yl)-2-hexyl-trans-decahydronaphthalene,
6-(1,6,7-trifluoronaphthalen-6-yl)-2-heptyl-trans-decahydronaphthalene, 6-(1,2,3,8-tetrafluoronaphthalen-6-yl)-2-methyl-trans-decahydronaphthalene,
6-(1,2,3,8-tetrafluoronaphthalen-6-yl)-2-ethyl-trans-decahydronaphthalene,
6-(1,2,3,8-tetrafluoronaphthalen-6-yl)-2-propyl-trans-decahydronaphthalene,
6-(1,2,3,8-tetrafluoronaphthalen-6-yl)-2-butyl-trans-decahydronaphthalene,
6-(1,2,3,8-tetrafluoronaphthalen-6-yl)-2-pentyl-trans-decahydronaphthalene,
6-(1,2,3,8-tetrafluoronaphthalen-6-yl)-2-hexyl-trans-decahydronaphthalene,
6-(1,2,3,8-tetrafluoronaphthalen-6-yl)-2-heptyl-trans-decahydronaphthalene,
6-(2-trifluoromethoxynaphthalen-6-yl)-2-methyl-trans-decahydronaphthalene,
6-(2-trifluoromethoxynaphthalen-6-yl)-2-ethyl-trans-decahydronaphthalene,
6-(2-trifluoromethoxynaphthalen-6-yl)-2-propyl-trans-decahydronaphthalene,
6-(2-trifluoromethoxynaphthalen-6-yl)-2-butyl-trans-decahydronaphthalene,
6-(2-trifluoromethoxynaphthalen-6-yl)-2-pentyl-trans-decahydronaphthalene,
6-(2-trifluoromethoxynaphthalen-6-yl)-2-hexyl-trans-decahydronaphthalene,
6-(2-trifluoromethoxynaphthalen-6-yl)-2-heptyl-trans-decahydronaphthalene,
6-(1-fluoro-2-trifluoromethoxynaphthalen-6-yl)-2-methyl-trans-decahydronaphthalene,
6-(1-fluoro-2-trifluoromethoxynaphthalen-6-yl)-2-ethyl-trans-decahydronaphthalene,
6-(1-fluoro-2-trifluoromethoxynaphthalen-6-yl)-2-propyl-trans-decahydronaphthalene,
6-(1-fluoro-2-trifluoromethoxynaphthalen-6-yl)-2-butyl-trans-decahydronaphthalene,
6-(1-fluoro-2-trifluoromethoxynaphthalen-6-yl)-2-pentyl-trans-decahydronaphthalene,
6-(1-fluoro-2-trifluoromethoxynaphthalen-6-yl)-2-hexyl-trans-decahydronaphthalene,
6-(1-fluoro-2-trifluoromethoxynaphthalen-6-yl)-2-heptyl-trans-decahydronaphthalene,
6-(2-trifluoromethoxy-3-fluoronaphthalen-6-yl)-2-methyl-trans-decahydronaphthalene,
6-(2-trifluoromethoxy-3-fluoronaphthalen-6-yl)-2-ethyl-trans-decahydronaphthalene,
6-(2-trifluoromethoxy-3-fluoronaphthalen-6-yl)-2-propyl-trans-decahydronaphthalene,
6-(2-trifluoromethoxy-3-fluoronaphthalen-6-yl)-2-butyl-trans-decahydronaphthalene,
6-(2-trifluoromethoxy-3-fluoronaphthalen-6-yl)-2-pentyl-trans-decahydronaphthalene,
6-(2-trifluoromethoxy-3-fluoronaphthalen-6-yl)-2-hexyl-trans-decahydronaphthalene,
6-(2-trifluoromethoxy-3-fluoronaphthalen-6-yl)-2-heptyl-trans-decahydronaphthalene,
6-(1,3-difluoro-2-trifluoromethoxynaphthalen-6-yl)-2-methyl-trans-decahydronaphthalene,
6-(1,3-difluoro-2-trifluoromethoxynaphthalen-6-yl)-2-ethyl-trans-decahydronaphthalene,
6-(1,3-difluoro-2-trifluoromethoxynaphthalen-6-yl)-2-propyl-trans-decahydronaphthalene,
6-(1,3-difluoro-2-trifluoromethoxynaphthalen-6-yl)-2-butyl-trans-decahydronaphthalene,
6-(1,3-difluoro-2-trifluoromethoxynaphthalen-6-yl)-2-pentyl-trans-decahydronaphthalene,
6-(1,3-difluoro-2-trifluoromethoxynaphthalen-6-yl)-2-hexyl-trans-decahydronaphthalene,
6-(1,3-difluoro-2-trifluoromethoxynaphthalen-6-yl)-2-heptyl-trans-decahydronaphthalene,
6-(1-fluoro-7-trifluoromethoxynaphthalen-3-yl)-2-methyl-trans-decahydronaphthalene,
6-(1-fluoro-7-trifluoromethoxynaphthalen-3-yl)-2-ethyl-trans-decahydronaphthalene,
6-(1-fluoro-7-trifluoromethoxynaphthalen-3-yl)-2-propyl-trans-decahydronaphthalene,
6-(1-fluoro-7-trifluoromethoxynaphthalen-3-yl)-2-butyl-trans-decahydronaphthalene,
6-(1-fluoro-7-trifluoromethoxynaphthalen-3-yl)-2-pentyl-trans-decahydronaphthalene,
6-(1-fluoro-7-trifluoromethoxynaphthalen-3-yl)-2-hexyl-trans-decahydronaphthalene,
6-(1-fluoro-7-trifluoromethoxynaphthalen-3-yl)-2-heptyl-trans-decahydronaphthalene,
6-(1,8-difluoro-2-trifluoromethoxynaphthalen-6-yl)-2-methyl-trans-decahydronaphthalene,
6-(1,8-difluoro-2-trifluoromethoxynaphthalen-6-yl)-2-ethyl-trans-decahydronaphthalene,
6-(1,8-difluoro-2-trifluoromethoxynaphthalen-6-yl)-2-propyl-trans-decahydronaphthalene,
6-(1,8-difluoro-2-trifluoromethoxynaphthalen-6-yl)-2-butyl-trans-decahydronaphthalene,
6-(1,8-difluoro-2-trifluoromethoxynaphthalen-6-yl)-2-pentyl-trans-decahydronaphthalene,
6-(1,8-difluoro-2-trifluoromethoxynaphthalen-6-yl)-2-hexyl-trans-decahydronaphthalene,
6-(1,8-difluoro-2-trifluoromethoxynaphthalen-6-yl)-2-heptyl-trans-decahydronaphthalene,
6-(1,6-difluoro-7-trifluoromethoxynaphthalen-3-yl)-2-methyl-trans-decahydronaphthalene,
6-(1,6-difluoro-7-trifluoromethoxynaphthalen-3-yl)-2-ethyl-trans-decahydronaphthalene,
6-(1,6-difluoro-7-trifluoromethoxynaphthalen-3-yl)-2-propyl-trans-decahydronaphthalene,
6-(1,6-difluoro-7-trifluoromethoxynaphthalen-3-yl)-2-butyl-trans-decahydronaphthalene,
6-(1,6-difluoro-7-trifluoromethoxynaphthalen-3-yl)-2-pentyl-trans-decahydronaphthalene,
6-(1,6-difluoro-7-trifluoromethoxynaphthalen-3-yl)-2-hexyl-trans-decahydronaphthalene,
6-(1,6-difluoro-7-trifluoromethoxynaphthalen-3-yl)-2-heptyl-trans-decahydronaphthalene,
6-(1,3,8-trifluoro-2-trifluoromethoxynaphthalen-6-yl)-2-methyl-trans-decahydronaphthalene,
6-(1,3,8-trifluoro-2-trifluoromethoxynaphthalen-6-yl)-2-ethyl-trans-decahydronaphthalene,
6-(1,3,8-trifluoro-2-trifluoromethoxynaphthalen-6-yl)-2-propyl-trans-decahydronaphthalene,
6-(1,3,8-trifluoro-2-trifluoromethoxynaphthalen-6-yl)-2-butyl-trans-decahydronaphthalene,
6-(1,3,8-trifluoro-2-trifluoromethoxynaphthalen-6-yl)-2-pentyl-trans-decahydronaphthalene,
6-(1,3,8-trifluoro-2-trifluoromethoxynaphthalen-6-yl)-2-hexyl-trans-decahydronaphthalene,
6-(1,3,8-trifluoro-2-trifluoromethoxynaphthalen-6-yl)-2-heptyl-trans-decahydronaphthalene,
6-(2-difluoromethoxynaphthalen-6-yl)-2-methyl-trans-decahydronaphthalene,
6-(2-difluoromethoxynaphthalen-6-yl)-2-ethyl-trans-decahydronaphthalene,
6-(2-difluoromethoxynaphthalen-6-yl)-2-propyl-trans-decahydronaphthalene,
6-(2-difluoromethoxynaphthalen-6-yl)-2-butyl-trans-decahydronaphthalene,
6-(2-difluoromethoxynaphthalen-6-yl)-2-pentyl-trans-decahydronaphthalene, 6-(2-difluoromethoxynaphthalen-6-yl)-2-hexyl-trans-decahydronaphthalene,
6-(2-difluoromethoxynaphthalen-6-yl)-2-heptyl-trans-decahydronaphthalene,
6-(1-fluoro-2-difluoromethoxynaphthalen-6-yl)-2-methyl-trans-decahydronaphthalene,
6-(1-fluoro-2-difluoromethoxynaphthalen-6-yl)-2-ethyl-trans-decahydronaphthalene,
6-(1-fluoro-2-difluoromethoxynaphthalen-6-yl)-2-propyl-trans-decahydronaphthalene,
6-(1-fluoro-2-difluoromethoxynaphthalen-6-yl)-2-butyl-trans-decahydronaphthalene,
6-(1-fluoro-2-difluoromethoxynaphthalen-6-yl)-2-pentyl-trans-decahydronaphthalene,
6-(1-fluoro-2-difluoromethoxynaphthalen-6-yl)-2-hexyl-trans-decahydronaphthalene,
6-(1-fluoro-2-difluoromethoxynaphthalen-6-yl)-2-heptyl-trans-decahydronaphthalene,
6-(2-difluoromethoxy-3-fluoronaphthalen-6-yl)-2-methyl-trans-decahydronaphthalene,
6-(2-difluoromethoxy-3-fluoronaphthalen-6-yl)-2-ethyl-trans-decahydronaphthalene,
6-(2-difluoromethoxy-3-fluoronaphthalen-6-yl)-2-propyl-trans-decahydronaphthalene,
6-(2-difluoromethoxy-3-fluoronaphthalen-6-yl)-2-butyl-trans-decahydronaphthalene,
6-(2-difluoromethoxy-3-fluoronaphthalen-6-yl)-2-pentyl-trans-decahydronaphthalene,
6-(2-difluoromethoxy-3-fluoronaphthalen-6-yl)-2-hexyl-trans-decahydronaphthalene,
6-(2-difluoromethoxy-3-fluoronaphthalen-6-yl)-2-heptyl-trans-decahydronaphthalene,
6-(1,3-difluoro-2-difluoromethoxynaphthalen-6-yl)-2-methyl-trans-decahydronaphthalene,
6-(1,3-difluoro-2-difluoromethoxynaphthalen-6-yl)-2-ethyl-trans-decahydronaphthalene,
6-(1,3-difluoro-2-difluoromethoxynaphthalen-6-yl)-2-propyl-trans-decahydronaphthalene,
6-(1,3-difluoro-2-difluoromethoxynaphthalen-6-yl)-2-butyl-trans-decahydronaphthalene,
6-(1,3-difluoro-2-difluoromethoxynaphthalen-6-yl)-2-pentyl-trans-decahydronaphthalene,
6-(1,3-difluoro-2-difluoromethoxynaphthalen-6-yl)-2-hexyl-trans-decahydronaphthalene,
6-(1,3-difluoro-2-difluoromethoxynaphthalen-6-yl)-2-heptyl-trans-decahydronaphthalene,
6-(1-fluoro-7-difluoromethoxynaphthalen-3-yl)-2-methyl-trans-decahydronaphthalene,
6-(1-fluoro-7-difluoromethoxynaphthalen-3-yl)-2-ethyl-trans-decahydronaphthalene,
6-(1-fluoro-7-difluoromethoxynaphthalen-3-yl)-2-propyl-trans-decahydronaphthalene,
6-(1-fluoro-7-difluoromethoxynaphthalen-3-yl)-2-butyl-trans-decahydronaphthalene,
6-(1-fluoro-7-difluoromethoxynaphthalen-3-yl)-2-pentyl-trans-decahydronaphthalene,
6-(1-fluoro-7-difluoromethoxynaphthalen-3-yl)-2-hexyl-trans-decahydronaphthalene,
6-(1-fluoro-7-difluoromethoxynaphthalen-3-yl)-2-heptyl-trans-decahydronaphthalene,
6-(1,8-difluoro-2-difluoromethoxynaphthalen-6-yl)-2-methyl-trans-decahydronaphthalene,
6-(1,8-difluoro-2-difluoromethoxynaphthalen-6-yl)-2-ethyl-trans-decahydronaphthalene,
6-(1,8-difluoro-2-difluoromethoxynaphthalen-6-yl)-2-propyl-trans-decahydronaphthalene,
6-(1,8-difluoro-2-difluoromethoxynaphthalen-6-yl)-2-butyl-trans-decahydronaphthalene,
6-(1,8-difluoro-2-difluoromethoxynaphthalen-6-yl)-2-pentyl-trans-decahydronaphthalene,
6-(1,8-difluoro-2-difluoromethoxynaphthalen-6-yl)-2-hexyl-trans-decahydronaphthalene,
6-(1,8-difluoro-2-difluoromethoxynaphthalen-6-yl)-2-heptyl-trans-decahydronaphthalene,
6-(1,6-difluoro-7-difluoromethoxynaphthalen-3-yl)-2-methyl-trans-decahydronaphthalene,
6-(1,6-difluoro-7-difluoromethoxynaphthalen-3-yl)-2-ethyl-trans-decahydronaphthalene,
6-(1,6-difluoro-7-difluoromethoxynaphthalen-3-yl)-2-propyl-trans-decahydronaphthalene,
6-(1,6-difluoro-7-difluoromethoxynaphthalen-3-yl)-2-butyl-trans-decahydronaphthalene,
6-(1,6-difluoro-7-difluoromethoxynaphthalen-3-yl)-2-pentyl-trans-decahydronaphthalene,
6-(1,6-difluoro-7-difluoromethoxynaphthalen-3-yl)-2-hexyl-trans-decahydronaphthalene,
6-(1,6-difluoro-7-difluoromethoxynaphthalen-3-yl)-2-heptyl-trans-decahydronaphthalene,
6-(1,3,8-trifluoro-2-difluoromethoxynaphthalen-6-yl)-2-methyl-trans-decahydronaphthalene,
6-(1,3,8-trifluoro-2-difluoromethoxynaphthalen-6-yl)-2-ethyl-trans-decahydronaphthalene,
6-(1,3,8-trifluoro-2-difluoromethoxynaphthalen-6-yl)-2-propyl-trans-decahydronaphthalene,
6-(1,3,8-trifluoro-2-difluoromethoxynaphthalen-6-yl)-2-butyl-trans-decahydronaphthalene,
6-(1,3,8-trifluoro-2-difluoromethoxynaphthalen-6-yl)-2-pentyl-trans-decahydronaphthalene,
6-(1,3,8-trifluoro-2-difluoromethoxynaphthalen-6-yl)-2-hexyl-trans-decahydronaphthalene,
6-(1,3,8-trifluoro-2-difluoromethoxynaphthalen-6-yl)-2-heptyl-trans-decahydronaphthalene,
6-(2-chloronaphthalen-6-yl)-2-methyl-trans-decahydronaphthalene,
6-(2-chloronaphthalen-6-yl)-2-ethyl-trans-decahydronaphthalene,
6-(2-chloronaphthalen-6-yl)-2-propyl-trans-decahydronaphthalene,
6-(2-chloronaphthalen-6-yl)-2-butyl-trans-decahydronaphthalene,
6-(2-chloronaphthalen-6-yl)-2-pentyl-trans-decahydronaphthalene,
6-(2-chloronaphthalen-6-yl)-2-hexyl-trans-decahydronaphthalene,
6-(2-chloronaphthalen-6-yl)-2-heptyl-trans-decahydronaphthalene,
6-(1-fluoro-2-chloronaphthalen-6-yl)-2-methyl-trans-decahydronaphthalene,
6-(1-fluoro-2-chloronaphthalen-6-yl)-2-ethyl-trans-decahydronaphthalene,
6-(1-fluoro-2-chloronaphthalen-6-yl)-2-propyl-trans-decahydronaphthalene,
6-(1-fluoro-2-chloronaphthalen-6-yl)-2-butyl-trans-decahydronaphthalene,
6-(1-fluoro-2-chloronaphthalen-6-yl)-2-pentyl-trans-decahydronaphthalene,
6-(1-fluoro-2-chloronaphthalen-6-yl)-2-hexyl-trans-decahydronaphthalene,
6-(1-fluoro-2-chloronaphthalen-6-yl)-2-heptyl-trans-decahydronaphthalene,
6-(2-chloro-3-fluoronaphthalen-6-yl)-2-methyl-trans-decahydronaphthalene,
6-(2-chloro-3-fluoronaphthalen-6-yl)-2-ethyl-trans-decahydronaphthalene,
6-(2-chloro-3-fluoronaphthalen-6-yl)-2-propyl-trans-decahydronaphthalene, 6-(2-chloro-3-fluoronaphthalen-6-yl)-2-butyl-trans-decahydronaphthalene,
6-(2-chloro-3-fluoronaphthalen-6-yl)-2-pentyl-trans-decahydronaphthalene,
6-(2-chloro-3-fluoronaphthalen-6-yl)-2-hexyl-trans-decahydronaphthalene,
6-(2-chloro-3-fluoronaphthalen-6-yl)-2-heptyl-trans-decahydronaphthalene,
6-(2-chloro-1,3-difluoronaphthalen-6-yl)-2-methyl-trans-decahydronaphthalene,
6-(2-chloro-1,3-difluoronaphthalen-6-yl)-2-ethyl-trans-decahydronaphthalene,
6-(2-chloro-1,3-difluoronaphthalen-6-yl)-2-propyl-trans-decahydronaphthalene,
6-(2-chloro-1,3-difluoronaphthalen-6-yl)-2-butyl-trans-decahydronaphthalene,
6-(2-chloro-1,3-difluoronaphthalen-6-yl)-2-pentyl-trans-decahydronaphthalene,
6-(2-chloro-1,3-difluoronaphthalen-6-yl)-2-hexyl-trans-decahydronaphthalene,
6-(2-chloro-1,3-difluoronaphthalen-6-yl)-2-heptyl-trans-decahydronaphthalene,
6-(1-fluoro-7-chloronaphthalen-3-yl)-2-methyl-trans-decahydronaphthalene,
6-(1-fluoro-7-chloronaphthalen-3-yl)-2-ethyl-trans-decahydronaphthalene,
6-(1-fluoro-7-chloronaphthalen-3-yl)-2-propyl-trans-decahydronaphthalene,
6-(1-fluoro-7-chloronaphthalen-3-yl)-2-butyl-trans-decahydronaphthalene,
6-(1-fluoro-7-chloronaphthalen-3-yl)-2-pentyl-trans-decahydronaphthalene,
6-(1-fluoro-7-chloronaphthalen-3-yl)-2-hexyl-trans-decahydronaphthalene,
6-(1-fluoro-7-chloronaphthalen-3-yl)-2-heptyl-trans-decahydronaphthalene,
6-(1,8-difluoro-7-chloronaphthalen-6-yl)-2-methyl-trans-decahydronaphthalene,
6-(1,8-difluoro-7-chloronaphthalen-6-yl)-2-ethyl-trans-decahydronaphthalene,
6-(1,8-difluoro-7-chloronaphthalen-6-yl)-2-propyl-trans-decahydronaphthalene,
6-(1,8-difluoro-7-chloronaphthalen-6-yl)-2-butyl-trans-decahydronaphthalene,
6-(11,8-difluoro-7-chloronaphthalen-6-yl)-2-pentyl-trans-decahydronaphthalene,
6-(1,8-difluoro-7-chloronaphthalen-6-yl)-2-hexyl-trans-decahydronaphthalene,
6-(1,8-difluoro-7-chloronaphthalen-6-yl)-2-heptyl-trans-decahydronaphthalene,
6-(1,6-difluoro-7-chloronaphthalen-3-yl)-2-methyl-trans-decahydronaphthalene,
6-(1,6-difluoro-7-chloronaphthalen-3-yl)-2-ethyl-trans-decahydronaphthalene,
6-(1,6-difluoro-7-chloronaphthalen-3-yl)-2-propyl-trans-decahydronaphthalene,
6-(1,6-difluoro-7-chloronaphthalen-3-yl)-2-butyl-trans-decahydronaphthalene,
6-(1,6-difluoro-7-chloronaphthalen-3-yl)-2-pentyl-trans-decahydronaphthalene,
6-(1,6-difluoro-7-chloronaphthalen-3-yl)-2-hexyl-trans-decahydronaphthalene,
6-(1,6-difluoro-7-chloronaphthalen-3-yl)-2-heptyl-trans-decahydronaphthalene,
6-(1,3,8-trifluoro-7-chloronaphthalen-6-yl)-2-methyl-trans-decahydronaphthalene,
6-(1,3,8-trifluoro-7-chloronaphthalen-6-yl)-2-ethyl-trans-decahydronaphthalene,
6-(1,3,8-trifluoro-7-chloronaphthalen-6-yl)-2-propyl-trans-decahydronaphthalene,
6-(1,3,8-trifluoro-7-chloronaphthalen-6-yl)-2-butyl-trans-decahydronaphthalene,
6-(1,3,8-trifluoro-7-chloronaphthalen-6-yl)-2-pentyl-trans-decahydronaphthalene,
6-(1,3,8-trifluoro-7-chloronaphthalen-6-yl)-2-hexyl-trans-decahydronaphthalene,
6-(1,3,8-trifluoro-7-chloronaphthalen-6-yl)-2-heptyl-trans-decahydronaphthalene,
6-(2-cyanonaphthalen-6-yl)-2-methyl-trans-decahydronaphthalene,
6-(2-cyanonaphthalen-6-yl)-2-ethyl-trans-decahydronaphthalene,
6-(2-cyanonaphthalen-6-yl)-2-propyl-trans-decahydronaphthalene,
6-(2-cyanonaphthalen-6-yl)-2-butyl-trans-decahydronaphthalene,
6-(2-cyanonaphthalen-6-yl)-2-pentyl-trans-decahydronaphthalene,
6-(2-cyanonaphthalen-6-yl)-2-hexyl-trans-decahydronaphthalene,
6-(2-cyanonaphthalen-6-yl)-2-heptyl-trans-decahydronaphthalene,
6-(2-cyano-1-fluoronaphthalen-6-yl)-2-methyl-trans-decahydronaphthalene,
6-(2-cyano-1-fluoronaphthalen-6-yl)-2-ethyl-trans-decahydronaphthalene,
6-(2-cyano-1-fluoronaphthalen-6-yl)-2-propyl-trans-decahydronaphthalene,
6-(2-cyano-1-fluoronaphthalen-6-yl)-2-butyl-trans-decahydronaphthalene,
6-(2-cyano-1-fluoronaphthalen-6-yl)-2-pentyl-trans-decahydronaphthalene,
6-(2-cyano-1-fluoronaphthalen-6-yl)-2-hexyl-trans-decahydronaphthalene,
6-(2-cyano-1-fluoronaphthalen-6-yl)-2-heptyl-trans-decahydronaphthalene,
6-(2-cyano-3-fluoronaphthalen-6-yl)-2-methyl-trans-decahydronaphthalene,
6-(2-cyano-3-fluoronaphthalen-6-yl)-2-ethyl-trans-decahydronaphthalene,
6-(2-cyano-3-fluoronaphthalen-6-yl)-2-propyl-trans-decahydronaphthalene,
6-(2-cyano-3-fluoronaphthalen-6-yl)-2-butyl-trans-decahydronaphthalene,
6-(2-cyano-3-fluoronaphthalen-6-yl)-2-pentyl-trans-decahydronaphthalene,
6-(2-cyano-3-fluoronaphthalen-6-yl)-2-hexyl-trans-decahydronaphthalene,
6-(2-cyano-3-fluoronaphthalen-6-yl)-2-heptyl-trans-decahydronaphthalene,
6-(2-cyano-1,3-difluoronaphthalen-6-yl)-2-methyl-trans-decahydronaphthalene,
6-(2-cyano-1,3-difluoronaphthalen-6-yl)-2-ethyl-trans-decahydronaphthalene,
6-(2-cyano-1,3-difluoronaphthalen-6-yl)-2-propyl-trans-decahydronaphthalene,
6-(2-cyano-1,3-difluoronaphthalen-6-yl)-2-butyl-trans-decahydronaphthalene,
6-(2-cyano-1,3-difluoronaphthalen-6-yl)-2-pentyl-trans-decahydronaphthalene,
6-(2-cyano-1,3-difluoronaphthalen-6-yl)-2-hexyl-trans-decahydronaphthalene,
6-(2-cyano-1,3-difluoronaphthalen-6-yl)-2-heptyl-trans-decahydronaphthalene,
6-(1-fluoro-7-cyanonaphthalen-3-yl)-2-methyl-trans-decahydronaphthalene, 6-(1-fluoro-7-cyanonaphthalen-3-yl)-2-ethyl-trans-decahydronaphthalene,
6-(1-fluoro-7-cyanonaphthalen-3-yl)-2-propyl-trans-decahydronaphthalene,
6-(1-fluoro-7-cyanonaphthalen-3-yl)-2-butyl-trans-decahydronaphthalene,
6-(1-fluoro-7-cyanonaphthalen-3-yl)-2-pentyl-trans-decahydronaphthalene,
6-(1-fluoro-7-cyanonaphthalen-3-yl)-2-hexyl-trans-decahydronaphthalene,
6-(1-fluoro-7-cyanonaphthalen-3-yl)-2-heptyl-trans-decahydronaphthalene,
6-(1,8-difluoro-7-cyanonaphthalen-6-yl)-2-methyl-trans-decahydronaphthalene,
6-(1,8-difluoro-7-cyanonaphthalen-6-yl)-2-ethyl-trans-decahydronaphthalene,
6-(1,8-difluoro-7-cyanonaphthalen-6-yl)-2-propyl-trans-decahydronaphthalene,
6-(1,8-difluoro-7-cyanonaphthalen-6-yl)-2-butyl-trans-decahydronaphthalene,
6-(1,8-difluoro-7-cyanonaphthalen-6-yl)-2-pentyl-trans-decahydronaphthalene,
6-(1,8-difluoro-7-cyanonaphthalen-6-yl)-2-hexyl-trans-decahydronaphthalene,
6-(1,8-difluoro-7-cyanonaphthalen-6-yl)-2-heptyl-trans-decahydronaphthalene,
6-(1,6-difluoro-7-cyanonaphthalen-3-yl)-2-methyl-trans-decahydronaphthalene,
6-(1,6-difluoro-7-cyanonaphthalen-3-yl)-2-ethyl-trans-decahydronaphthalene,
6-(1,6-difluoro-7-cyanonaphthalen-3-yl)-2-propyl-trans-decahydronaphthalene,
6-(1,6-difluoro-7-cyanonaphthalen-3-yl)-2-butyl-trans-decahydronaphthalene,
6-(1,6-difluoro-7-cyanonaphthalen-3-yl)-2-pentyl-trans-decahydronaphthalene,
6-(1,6-difluoro-7-cyanonaphthalen-3-yl)-2-hexyl-trans-decahydronaphthalene,
6-(1,6-difluoro-7-cyanonaphthalen-3-yl)-2-heptyl-trans-decahydronaphthalene,
6-(1,3,8-trifluoro-7-cyanonaphthalen-6-yl)-2-methyl-trans-decahydronaphthalene,
6-(1,3,8-trifluoro-7-cyanonaphthalen-6-yl)-2-ethyl-trans-decahydronaphthalene,
6-(1,3,8-trifluoro-7-cyanonaphthalen-6-yl)-2-propyl-trans-decahydronaphthalene,
6-(1,3,8-trifluoro-7-cyanonaphthalen-6-yl)-2-butyl-trans-decahydronaphthalene,
6-(1,3,8-trifluoro-7-cyanonaphthalen-6-yl)-2-pentyl-trans-decahydronaphthalene,
6-(1,3,8-trifluoro-7-cyanonaphthalen-6-yl)-2-hexyl-trans-decahydronaphthalene,
6-(1,3,8-trifluoro-7-cyanonaphthalen-6-yl)-2-heptyl-trans-decahydronaphthalene,
6-[2-(trifluoromethyl)naphthalen-6-yl]-2-methyl-trans-decahydronaphthalene,
6-[2-(trifluoromethyl)naphthalen-6-yl]-2-ethyl-trans-decahydronaphthalene,
6-[2-(trifluoromethyl)naphthalen-6-yl]-2-propyl-trans-decahydronaphthalene,
6-[2-(trifluoromethyl)naphthalen-6-yl]-2-butyl-trans-decahydronaphthalene,
6-[2-(trifluoromethyl)naphthalen-6-yl]-2-pentyl-trans-decahydronaphthalene,
6-[2-(trifluoromethyl)naphthalen-6-yl]-2-hexyl-trans-decahydronaphthalene,
6-[2-(trifluoromethyl)naphthalen-6-yl]-2-heptyl-trans-decahydronaphthalene,
6-[1-fluoro-2-(trifluoromethyl)naphthalen-6-yl]-2-methyl-trans-decahydronaphthalene,
6-[1-fluoro-2-(trifluoromethyl)naphthalen-6-yl]-2-ethyl-trans-decahydronaphthalene,
6-[1-fluoro-2-(trifluoromethyl)naphthalen-6-yl]-2-propyl-trans-decahydronaphthalene,
6-[1-fluoro-2-(trifluoromethyl)naphthalen-6-yl]-2-butyl-trans-decahydronaphthalene,
6-[1-fluoro-2-(trifluoromethyl)naphthalen-6-yl]-2-pentyl-trans-decahydronaphthalene,
6-[1-fluoro-2-(trifluoromethyl)naphthalen-6-yl]-2-hexyl-trans-decahydronaphthalene,
6-[1-fluoro-2-(trifluoromethyl)naphthalen-6-yl]-2-heptyl-trans-decahydronaphthalene,
6-[3-fluoro-2-(trifluoromethyl)naphthalen-6-yl]-2-methyl-trans-decahydronaphthalene,
6-[3-fluoro-2-(trifluoromethyl)naphthalen-6-yl]-2-ethyl-trans-decahydronaphthalene,
0.6-[3-fluoro-2-(trifluoromethyl)naphthalen-6-yl]-2-propyl-trans-decahydronaphthalene,
6-[3-fluoro-2-(trifluoromethyl)naphthalen-6-yl]-2-butyl-trans-decahydronaphthalene,
6-[3-fluoro-2-(trifluoromethyl)naphthalen-6-yl]-2-pentyl-trans-decahydronaphthalene,
6-[3-fluoro-2-(trifluoromethyl)naphthalen-6-yl)-2-hexyl-trans-decahydronaphthalene,
6-[3-fluoro-2-(trifluoromethyl)naphthalen-6-yl]-2-heptyl-trans-decahydronaphthalene,
6-[1,3-difluoro-2-(trifluoromethyl)naphthalen-6-yl]-2-methyl-trans-decahydronaphthalene,
6-[1,3-difluoro-2-(trifluoromethyl)naphthalen-6-yl]-2-ethyl-trans-decahydronaphthalene,
6-(1,3-difluoro-2-(trifluoromethyl)naphthalen-6-yl]-2-propyl-trans-decahydronaphthalene,
6-[1,3-difluoro-2-(trifluoromethyl)naphthalen-6-yl]-2-butyl-trans-decahydronaphthalene,
6-[1,3-difluoro-2-(trifluoromethyl)naphthalen-6-yl]-2-pentyl-trans-decahydronaphthalene,
6-[1,3-difluoro-2-(trifluoromethyl)naphthalen-6-yl]-2-hexyl-trans-decahydronaphthalene,
6-[1,3-difluoro-2-(trifluoromethyl)naphthalen-6-yl]-2-heptyl-trans-decahydronaphthalene,
6-[1-fluoro-7-(trifluoromethyl)naphthalen-3-yl]-2-methyl-trans-decahydronaphthalene,
6-[1-fluoro-7-(trifluoromethyl)naphthalen-3-yl]-2-ethyl-trans-decahydronaphthalene,
6-[1-fluoro-7-(trifluoromethyl)naphthalen-3-yl]-2-propyl-trans-decahydronaphthalene,
6-[1-fluoro-7-(trifluoromethyl)naphthalen-3-yl]-2-butyl-trans-decahydronaphthalene,
6-[1-fluoro-7-(trifluoromethyl)naphthalen-3-yl]-2-pentyl-trans-decahydronaphthalene,
6-[1-fluoro-7-(trifluoromethyl)naphthalen-3-yl]-2-hexyl-trans-decahydronaphthalene,
6-[1-fluoro-7-(trifluoromethyl)naphthalen-3-yl]-2-heptyl-trans-decahydronaphthalene,
6-[1,8-difluoro-7-(trifluoromethyl)naphthalen-6-yl]-2-methyl-trans-decahydronaphthalene,
6-[1,8-difluoro-7-(trifluoromethyl)naphthalen-6-yl]-2-ethyl-trans-decahydronaphthalene,
6-(1,8-difluoro-7-(trifluoromethyl)naphthalen-6-yl]-2-propyl-trans-decahydronaphthalene,
6-[1,8-difluoro-7-(trifluoromethyl)naphthalen-6-yl]-2-butyl-trans-decahydronaphthalene,
6-[1,8-difluoro-7-(trifluoromethyl)naphthalen-6-yl)-2-pentyl-trans-decahydronaphthalene,
6-[1,8-difluoro-7-(trifluoromethyl)naphthalen-6-yl]-2-hexyl-trans-decahydronaphthalene, 6-[1,8-difluoro-7-(trifluoromethyl)naphthalen-6-yl]-2-heptyl-trans-decahydronaphthalene,
6-[1,6-difluoro-7-(trifluoromethyl)naphthalen-3-yl]-2-methyl-trans-decahydronaphthalene,
6-[1,6-difluoro-7-(trifluoromethyl)naphthalen-3-yl]-2-ethyl-trans-decahydronaphthalene,
6-[1,6-difluoro-7-(trifluoromethyl)naphthalen-3-yl]-2-propyl-trans-decahydronaphthalene,
6-(1,6-difluoro-7-(trifluoromethyl)naphthalen-3-yl]-2-butyl-trans-decahydronaphthalene,
6-[1,6-difluoro-7-(trifluoromethyl)naphthalen-3-yl]-2-pentyl-trans-decahydronaphthalene,
6-[1,6-difluoro-7-(trifluoromethyl)naphthalen-3-yl]-2-hexyl-trans-decahydronaphthalene,
6-[1,6-difluoro-7-(trifluoromethyl)naphthalen-3-yl]-2-heptyl-trans-decahydronaphthalene,
6-[1,3,8-trifluoro-7-(trifluoromethyl)naphthalen-6-yl]-2-methyl-trans-decahydronaphthalene,
6-[1,3,8-trifluoro-7-(trifluoromethyl)naphthalen-6-yl]-2-ethyl-trans-decahydronaphthalene,
6-[1,3,8-trifluoro-7-(trifluoromethyl)naphthalen-6-yl]-2-propyl-trans-decahydronaphthalene,
6-[1,3,8-trifluoro-7-(trifluoromethyl)naphthalen-6-yl]-2-butyl-trans-decahydronaphthalene,
6-[1,3,8-trifluoro-7-(trifluoromethyl)naphthalen-6-yl]-2-pentyl-trans-decahydronaphthalene,
6-[1,3,8-trifluoro-7-(trifluoromethyl)naphthalen-6-yl]-2-hexyl-trans-decahydronaphthalene,
6-[1,3,8-trifluoro-7-(trifluoromethyl)naphthalen-6-yl]-2-heptyl-trans-decahydronaphthalene,
methyl-6-(6-methyl-trans-decahydronaphthalen-2-yl)naphthalene-2-carboxylate,
methyl-6-(6-ethyl-trans-decahydronaphthalen-2-yl)naphthalene-2-carboxylate,
methyl-6-(6-propyl-trans-decahydronaphthalen-2-yl)naphthalene-2-carboxylate,
methyl-6-(6-butyl-trans-decahydronaphthalen-2-yl)naphthalene-2-carboxylate,
methyl-6-(6-pentyl-trans-decahydronaphthalen-2-yl)naphthalene-2-carboxylate,
methyl-6-(6-hexyl-trans-decahydronaphthalen-2-yl)naphthalene-2-carboxylate,
methyl-6-(6-heptyl-trans-decahydronaphthalen-2-yl)naphthalene-2-carboxylate,
methyl 1-fluoro-6-(6-methyl-trans-decahydronaphthalen-2-yl)naphthalene-2-carboxylate,
methyl 1-fluoro-6-(6-ethyl-trans-decahydronaphthalen-2-yl)naphthalene-2-carboxylate,
methyl 1-fluoro-6-(6-propyl-trans-decahydronaphthalen-2-yl)naphthalene-2-carboxylate,
methyl 1-fluoro-6-(6-butyl-trans-decahydronaphthalen-2-yl)naphthalene-2-carboxylate,
methyl 1-fluoro-6-(6-pentyl-trans-decahydronaphthalen-2-yl)naphthalene-2-carboxylate,
methyl 1-fluoro-6-(6-hexyl-trans-decahydronaphthalen-2-yl)naphthalene-2-carboxylate,
methyl l-fluoro-6-(6-heptyl-trans-decahydronaphthalen-2-yl)naphthalene-2-carboxylate,
methyl 3-fluoro-6-(6-methyl-trans-decahydronaphthalen-2-yl)naphthalene-2-carboxylate,
methyl 3-fluoro-6-(6-ethyl-trans-decahydronaphthalen-2-yl)naphthalene-2-carboxylate,
methyl 3-fluoro-6-(6-propyl-trans-decahydronaphthalen-2-yl)naphthalene-2-carboxylate,
methyl 3-fluoro-6-(6-butyl-trans-decahydronaphthalen-2-yl)naphthalene-2-carboxylate,
methyl 3-fluoro-6-(6-pentyl-trans-decahydronaphthalen-2-yl)naphthalene-2-carboxylate,
methyl 3-fluoro-6-(6-hexyl-trans-decahydronaphthalen-2-yl)naphthalene-2-carboxylate,
methyl 3-fluoro-6-(6-heptyl-trans-decahydronaphthalen-2-yl)naphthalene-2-carboxylate,
methyl 1,3-difluoro-6-(6-methyl-trans-decahydronaphthalen-2-yl)naphthalene-2-carboxylate,
methyl 1,3-difluoro-6-(6-ethyl-trans-decahydronaphthalen-2-yl)naphthalene-2-carboxylate,
methyl 1,3-difluoro-6-(6-propyl-trans-decahydronaphthalen-2-yl)naphthalene-2-carboxylate,
methyl 1,3-difluoro-6-(6-butyl-trans-decahydronaphthalen-2-yl)naphthalene-2-carboxylate,
methyl 1,3-difluoro-6-(6-pentyl-trans-decahydronaphthalen-2-yl)naphthalene-2-carboxylate,
methyl 1,3-difluoro-6-(6-hexyl-trans-decahydronaphthalen-2-yl)naphthalene-2-carboxylate,
methyl 1,3-difluoro-6-(6-heptyl-trans-decahydronaphthalen-2-yl)naphthalene-2-carboxylate,
methyl l-fluoro-7-(6-methyl-trans-decahydronaphthalen-2-yl)naphthalene-3-carboxylate,
methyl 1-fluoro-7-(6-ethyl-trans-decahydronaphthalen-2-yl)naphthalene-3-carboxylate,
methyl 1-fluoro-7-(6-propyl-trans-decahydronaphthalen-2-yl)naphthalene-3-carboxylate,
methyl l-fluoro-7-(6-butyl-trans-decahydronaphthalen-2-yl)naphthalene-3-carboxylate,
methyl 1-fluoro-7-(6-pentyl-trans-decahydronaphthalen-2-yl)naphthalene-3-carboxylate,
methyl 1-fluoro-7-(6-hexyl-trans-decahydronaphthalen-2-yl)naphthalene-3-carboxylate,
methyl 1-fluoro-7-(6-heptyl-trans-decahydronaphthalen-2-yl)naphthalene-3-carboxylate,
methyl 1,2-difluoro-7-(6-methyl-trans-decahydronaphthalen-2-yl)naphthalene-3-carboxylate,
methyl 1,2-difluoro-7-(6-ethyl-trans-decahydronaphthalen-2-yl)naphthalene-3-carboxylate,
methyl 1,2-difluoro-7-(6-propyl-trans-decahydronaphthalen-2-yl)naphthalene-3-carboxylate,
methyl 1,2-difluoro-7-(6-butyl-trans-decahydronaphthalen-2-yl)naphthalene-3-carboxylate,
methyl 1,2-difluoro-7-(6-pentyl-trans-decahydronaphthalen-2-yl)naphthalene-3-carboxylate,
methyl 1,2-difluoro-7-(6-hexyl-trans-decahydronaphthalen-2-yl)naphthalene-3-carboxylate,
methyl 1,2-difluoro-7-(6-heptyl-trans-decahydronaphthalen-2-yl)naphthalene-3-carboxylate,
methyl 1-fluoro-3-(6-methyl-trans-decahydronaphthalen-2-yl)naphthalene-7-carboxylate,
methyl l-fluoro-3-(6-ethyl-trans-decahydronaphthalen-2-yl)naphthalene-7-carboxylate,
methyl 1-fluoro-3-(6-propyl-trans-decahydronaphthalen-2-yl)naphthalene-7-carboxylate,
ethyl 1-fluoro-3-(6-butyl-trans-decahydronaphthalen-2-yl)naphthalene-7-carboxylate,
methyl l-fluoro-3-(6-pentyl-trans-decahydronaphthalen-2-yl)naphthalene-7-carboxylate,
methyl 1-fluoro-3-(6-hexyl-trans-decahydronaphthalen-2-yl)naphthalene-7-carboxylate,
methyl l-fluoro-3-(6-heptyl-trans-decahydronaphthalen-2-yl)naphthalene-7-carboxylate,
methyl 1,8-difluoro-6-(6-methyl-trans-decahydronaphthalen-2-yl)naphthalene-2-carboxylate,
methyl 1,8-difluoro-6-(6-ethyl-trans-decahydronaphthalen-2-yl)naphthalene-2-carboxylate,
methyl 1,8-difluoro-6-(6-propyl-trans-decahydronaphthalen-2-yl)naphthalene-2-carboxylate,
methyl 1,8-difluoro-6-(6-butyl-trans-decahydronaphthalen-2-yl)naphthalene-2-carboxylate, methyl 1,8-difluoro-6-(6-pentyl-trans-decahydronaphthalen-2-yl)naphthalene-2-carboxylate,
methyl 1,8-difluoro-6-(6-hexyl-trans-decahydronaphthalen-2-yl)naphthalene-2-carboxylate,
methyl 1,8-difluoro-6-(6-heptyl-trans-decahydronaphthalen-2-yl)naphthalene-2-carboxylate,
methyl 1,6-difluoro-3-(6-methyl-trans-decahydronaphthalen-2-yl)naphthalene-7-carboxylate,
methyl 1,6-difluoro-3-(6-ethyl-trans-decahydronaphthalen-2-yl)naphthalene-7-carboxylate,
ethyl 1,6-difluoro-3-(6-propyl-trans-decahydronaphthalen-2-l)naphthalene-7-carboxylate,
methyl 1,6-difluoro-3-(6-butyl-trans-decahydronaphthalen-2-yl)naphthalene-7-carboxylate,
methyl 1,6-difluoro-3-(6-pentyl-trans-decahydronaphthalen-2-yl)naphthalene-7-carboxylate,
methyl 1,6-difluoro-3-(6-hexyl-trans-decahydronaphthalen-2-yl)naphthalene-7-carboxylate,
methyl 1,6-difluoro-3-(6-heptyl-trans-decahydronaphthalen-2-yl)naphthalene-7-carboxylate,
methyl 1,3,8-trifluoro-6-(6-methyl-trans-decahydronaphthalen-2-yl)naphthalene-2-carboxylate,
methyl 1,3,8-trifluoro-6-(6-ethyl-trans-decahydronaphthalen-2-yl)naphthalene-2-carboxylate,
methyl 1,3,8-trifluoro-6-(6-propyl-trans-decahydronaphthalen-2-yl)naphthalene-2-carboxylate,
methyl 1,3,8-trifluoro-6-(6-butyl-trans-decahydronaphthalen-2-yl)naphthalene-2-carboxylate,
methyl 1,3,8-trifluoro-6-(6-pentyl-trans-decahydronaphthalen-2-yl)naphthalene-2-carboxylate,
methyl 1,3,8-trifluoro-6-(6-hexyl-trans-decahydronaphthalen-2-yl)naphthalene-2-carboxylate,
methyl 1,3,8-trifluoro-6-(6-heptyl-trans-decahydronaphthalen-2-yl)naphthalene-2-carboxylate,
methyl 3-fluoro-2-(6-methyl-trans-decahydronaphthalen-2-yl)naphthalene-6-carboxylate,
methyl 3-fluoro-2-(6-ethyl-trans-decahydronaphthalen-2-yl)naphthalene-6-carboxylate,
methyl 3-fluoro-2-(6-propyl-trans-decahydronaphthalen-2-yl)naphthalene-6-carboxylate,
methyl 3-fluoro-2-(6-butyl-trans-decahydronaphthalen-2-yl)naphthalene-6-carboxylate,
methyl 3-fluoro-2-(6-pentyl-trans-decahydronaphthalen-2-yl)naphthalene-6-carboxylate,
methyl 3-fluoro-2-(6-hexyl-trans-decahydronaphthalen-2-yl)naphthalene-6-carboxylate,
methyl 3-fluoro-2-(6-heptyl-trans-decahydronaphthalen-2-yl)naphthalene-6-carboxylate,
methyl 1,7-difluoro-6-(6-methyl-trans-decahydronaphthalen-2-yl)naphthalene-2-carboxylate,
methyl 1,7-difluoro-6-(6-ethyl-trans-decahydronaphthalen-2-yl)naphthalene-2-carboxylate,
methyl 1,7-difluoro-6-(6-propyl-trans-decahydronaphthalen-2-yl)naphthalene-2-carboxylate,
methyl 1,7-difluoro-6-(6-butyl-trans-decahydronaphthalen-2-yl)naphthalene-2-carboxylate,
methyl 1,7-difluoro-6-(6-pentyl-trans-decahydronaphthalen-2-yl)naphthalene-2-carboxylate,
methyl 1,7-difluoro-6-(6-hexyl-trans-decahydronaphthalen-2-yl)naphthalene-2-carboxylate,
methyl 1,7-difluoro-6-(6-heptyl-trans-decahydronaphthalen-2-yl)naphthalene-2-carboxylate,
methyl 1,2-difluoro-3-(6-methyl-trans-decahydronaphthalen-2-yl)naphthalene-7-carboxylate,
methyl 1,2-difluoro-3-(6-ethyl-trans-decahydronaphthalen-2-yl)naphthalene-7-carboxylate,
methyl 1,2-difluoro-3-(6-propyl-trans-decahydronaphthalen-2-yl)naphthalene-7-carboxylate,
methyl 1,2-difluoro-3-(6-butyl-trans-decahydronaphthalen-2-yl)naphthalene-7-carboxylate,
methyl 1,2-difluoro-3-(6-pentyl-trans-decahydronaphthalen-2-yl)naphthalene-7-carboxylate,
methyl 1,2-difluoro-3-(6-hexyl-trans-decahydronaphthalen-2-yl)naphthalene-7-carboxylate,
methyl 1,2-difluoro-3-(6-heptyl-trans-decahydronaphthalen-2-yl)naphthalene-7-carboxylate,
methyl 1,2,8-trifluoro-3-(6-methyl-trans-decahydronaphthalen-2-yl)naphthalene-7-carboxylate,
methyl 1,2,8-trifluoro-3-(6-ethyl-trans-decahydronaphthalen-2-yl)naphthalene-7-carboxylate,
methyl 1,2,8-trifluoro-3-(6-propyl-trans-decahydronaphthalen-2-yl)naphthalene-7-carboxylate,
methyl 1,2,8-trifluoro-3-(6-butyl-trans-decahydronaphthalen-2-yl)naphthalene-7-carboxylate,
methyl 1,2,8-trifluoro-3-(6-pentyl-trans-decahydronaphthalen-2-yl)naphthalene-7-carboxylate,
methyl 1,2,8-trifluoro-3-(6-hexyl-trans-decahydronaphthalen-2-yl)naphthalene-7-carboxylate,
methyl 1,2,8-trifluoro-3-(6-heptyl-trans-decahydronaphthalen-2-yl)naphthalene-7-carboxylate,
methyl 1-fluoro-2-(6-methyl-trans-decahydronaphthalen-2-yl)naphthalene-6-carboxylate,
methyl 1-fluoro-2-(6-ethyl-trans-decahydronaphthalen-2-yl)naphthalene-6-carboxylate,
methyl 1-fluoro-2-(6-propyl-trans-decahydronaphthalen-2-yl)naphthalene-6-carboxylate,
methyl 1-fluoro-2-(6-butyl-trans-decahydronaphthalen-2-yl)naphthalene-6-carboxylate,
methyl 1-fluoro-2-(6-pentyl-trans-decahydronaphthalen-2-yl)naphthalene-6-carboxylate,
methyl 1-fluoro-2-(6-hexyl-trans-decahydronaphthalen-2-yl)naphthalene-6-carboxylate,
methyl 1-fluoro-2-(6-heptyl-trans-decahydronaphthalen-2-yl)naphthalene-6-carboxylate,
methyl 1,7-difluoro-2-(6-methyl-trans-decahydronaphthalen-2-yl)naphthalene-6-carboxylate,
methyl 1,7-difluoro-2-(6-ethyl-trans-decahydronaphthalen-2-yl)naphthalene-6-carboxylate,
methyl 1,7-difluoro-2-(6-propyl-trans-decahydronaphthalen-2-yl)naphthalene-6-carboxylate,
methyl 1,7-difluoro-2-(6-butyl-trans-decahydronaphthalen-2-yl)naphthalene-6-carboxylate,
methyl 1,7-difluoro-2-(6-pentyl-trans-decahydronaphthalen-2-yl)naphthalene-6-carboxylate,
methyl 1,7-difluoro-2-(6-hexyl-trans-decahydronaphthalen-2-yl)naphthalene-6-carboxylate,
methyl 1,7-difluoro-2-(6-heptyl-trans-decahydronaphthalen-2-yl)naphthalene-6-carboxylate,
methyl 1,8-difluoro-2-(6-methyl-trans-decahydronaphthalen-2-yl)naphthalene-6-carboxylate,
methyl 1,8-difluoro-2-(6-ethyl-trans-decahydronaphthalen-2-yl)naphthalene-6-carboxylate,
methyl 1,8-difluoro-2-(6-propyl-trans-decahydronaphthalen-2-yl)naphthalene-6-carboxylate,
methyl 1,8-difluoro-2-(6-butyl-trans-decahydronaphthalen-2-yl)naphthalene-6-carboxylate,
methyl 1,8-difluoro-2-(6-pentyl-trans-decahydronaphthalen-2-yl)naphthalene-6-carboxylate,
methyl 1,8-difluoro-2-(6-hexyl-trans-decahydronaphthalen-2-yl)naphthalene-6-carboxylate,
methyl 1,8-difluoro-2-(6-heptyl-trans-decahydronaphthalen-2-yl)naphthalene-6-carboxylate,
methyl 1,2,8-trifluoro-7-(6-methyl-trans-decahydronaphthalen-2-yl)naphthalene-3-carboxylate,
methyl 1,2,8-trifluoro-7-(6-ethyl-trans-decahydronaphthalen-2-yl)naphthalene-3-carboxylate, methyl 1,2,8-trifluoro-7-(6-propyl-trans-decahydronaphthalen-2-yl)naphthalene-3-carboxylate,
methyl 1,2,8-trifluoro-7-(6-butyl-trans-decahydronaphthalen-2-yl)naphthalene-3-carboxylate,
methyl 1,2,8-trifluoro-7-(6-pentyl-trans-decahydronaphthalen-2-yl)naphthalene-3-carboxylate,
methyl 1,2,8-trifluoro-7-(6-hexyl-trans-decahydronaphthalen-2-yl)naphthalene-3-carboxylate,
methyl 1,2,8-trifluoro-7-(6-heptyl-trans-decahydronaphthalen-2-yl)naphthalene-3-carboxylate.

Example 21

Synthesis of 2,6-bis(3-butenyl)-trans-decahydronaphthalene (I-22)

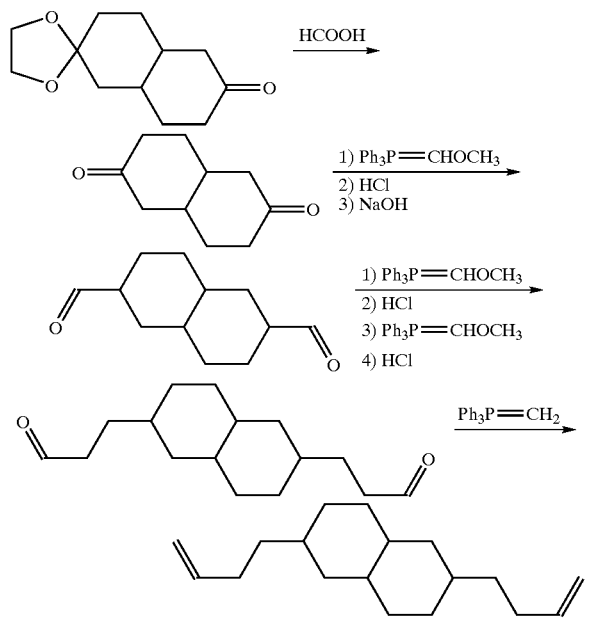

(21-a) Synthesis of trans-decahydronaphthalen-2,6-dione 21 g of trans-decahydronaphthalen-2,6-dione monoethyleneacetal was dissolved in 110 ml of toluene. 50 ml of formic acid was added to the solution, and the mixture was stirred for 1 hour at room temperature. Water was added to the mixture, and the organic phase was separated, rinsed with water, a saturated aqueous solution of sodium hydrogencarbonate, and a saturated saline solution, in sequence, and dried on anhydrous sodium sulfate. Then, the solvent was evaporated to obtain 16 g of pale yellow solid trans-decahydronaphthalen-2,6-dione.

(21-b) Synthesis of trans-decahydronaphthalene-2,6-dicarbaldehyde

An 80 ml THF solution of 16 g of trans-decahydronaphthalen-2,6-dione, which was obtained in (21-a), was added dropwise to a Wittig reagent prepared from 72 g of methoxymethyltriphenylphosphonium chloride and 26 g of potassium t-butoxide in 290 ml of THF, while the mixture was cooled to 10° C. or lower. The temperature was reduced to room temperature. After the mixture was stirred for 4 hours, water and hexane were added. The organic phase was separated and rinsed with water, and the solvent was evaporated. The pale yellow oily substance obtained was dissolved in 90 ml of THF. 90 ml of 10% hydrochloric acid was added to the solution, and the mixture was heated for 3 hours under refluxing. The temperature was reduced to room temperature, and the organic phase was separated. The aqueous phase was extracted with ethyl acetate. Organic phases were combined, and rinsed with a saturated aqueous solution of sodium hydrogencarbonate, water, and a saturated saline solution, in sequence. Then, the solvent was evaporated. The pale yellow solid substance obtained was dissolved in 85 ml of methanol. 10 ml of 10% aqueous solution of sodium hydroxide was added to the solution while the mixture was cooled to 10° C. or lower. After the mixture was stirred for 2.5 hours at room temperature, the temperature was reduced to room temperature. Then, the solvent was evaporated, and the pale yellow solid substance obtained was rinsed with water and recrystallized from a hexane solution to obtain 16 g of white solid trans-decahydronaphthalene-2,6-dicarbaldehyde.

(21-c) Synthesis of 2,6-bis(3-oxopropyl)-trans-decahydronaphthalene

Reaction of 16 g of trans-decahydronaphthalene-2,6-dicarbaldehyde, which was obtained in (21-a), with a Wittig reagent which is similar to that used in (1-b) was repeated twice to obtain 15 g of pale yellow solid 2,6-bis(3-oxopropyl)-trans-decahydronaphthalene.

(21-d) Synthesis of 2,6-bis(3-butenyl)-trans-decahydronaphthalene

An 85 ml THF solution of 15 g of 2,6-bis(3-oxopropyl)-trans-decahydronaphthalene, which was obtained in (21-c), was added dropwise to a Wittig reagent prepared from 60 g of methyltriphenylphosphonium iodide and 18 g of potassium t-butoxide in 300 ml of THF, while the mixture was cooled to 10° C. or lower. The temperature was reduced to room temperature. After the mixture was stirred for 4 hours, water and hexane were added. The organic phase was separated and rinsed with water, and the solvent was evaporated. The residue was purified by silica gel column chromatography (hexane) to obtain 6 g of 2,6-bis(3-butenyl)-trans-decahydronaphthalene (I-22) a colorless oily substance.

The following compounds were prepared in the same manner as mentioned above:
2,6-bis(3-pentenyl)-trans-decahydronaphthalene,
2,6-bis(1-pentenyl)-trans-decahydronaphthalene,
2,6-bis(1-propenyl)-trans-decahydronaphthalene,
2,6-divinyl-trans-decahydronaphthalene.

Example 22

Synthesis of 2-(trans-4-propylcyclohexyl)-6-vinyl-trans-decahydronaphthalene (I-23)

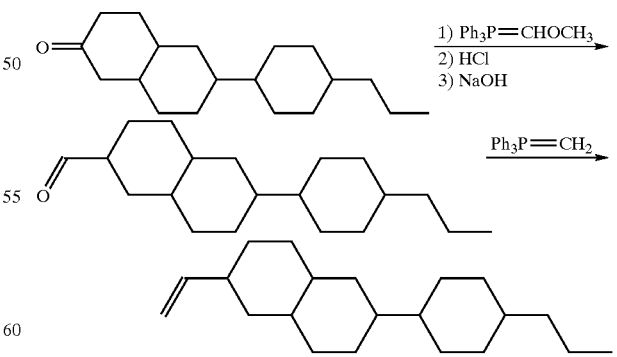

(22-a) Synthesis of 6-(trans-4-propylcyclohexyl)-trans-decahydronaphthalene-2-carbaldehyde Reaction of 28 g of 6-(trans-4-propylcyclohexyl)-trans-decahydro-2-naphthalenone with the Wittig reagent described above was carried out to obtain 28 g of white solid 6-(trans-4-propylcyclohexyl)-trans-decahydronaphthalene-2-carbaldehyde.

(22-b) Synthesis of 2-(trans-4-propylcyclohexyl)-6-vinyl-trans-decahydronaphthalene Reaction of 28 g of 6-(trans-4-propylcyclohexyl)-trans-decahydronaphthalene-2-carbaldehyde, which was obtained in (22-a), with a Wittig reagent which is similar to that used in (1-d) was carried out to obtain 10 g of white solid 2-(trans-4-propylcyclohexyl)-6-vinyl-trans-decahydronaphthalene (I-4).

The following compound was prepared in the same manner as mentioned above:
2-(trans-4-propylcyclohexyl)-6-(3-butenyl)-trans-decahydronaphthalene.

Example 23

Synthesis of 2-(trans-4-propylcyclohexyl)-6-(trans-1-propenyl)-trans-decahydronaphthalene (I-24)

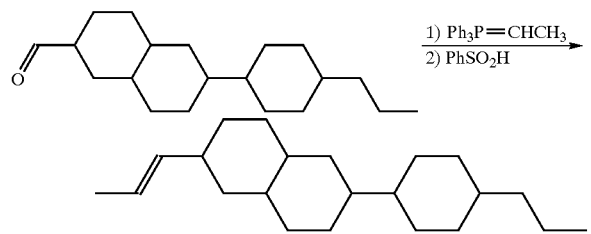

Reaction of 12 g of 6-(trans-4-propylcyclohexyl)-trans-decahydronaphthalene-2-carbaldehyde, which was obtained in (22-a), with the Wittig reagent described above, and treatment with benzenesulfinic acid were carried out to obtain 4 g of white solid 2-(trans-4-propylcyclohexyl)-6-(trans-1-propenyl)-trans-decahydronaphthalene (I-24).

The following compounds were prepared in the same manner as mentioned above:
2-(trans-4-propylcyclohexyl)-6-(trans-1-pentenyl)-trans-decahydronaphthalene,
2-(trans-4-propylcyclohexyl)-6-(trans-3-pentenyl)-trans-decahydronaphthalene.

Example 24

Synthesis of 2-(trans-4-propylcyclohexyl)-6-(2,2-difluoroethenyl)-trans-decahydronaphthalene (I-25)

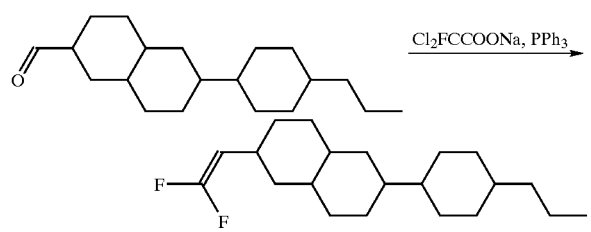

To a solution of 8.7 g of 6-(trans-4-propylcyclohexyl) decahydronaphthalene-2-carbaldehyde, which was obtained in (22-a), and 8.7 g of triphenylphosphine in 10 ml of diethyleneglycol dimethylether (Diglyme), the solution being heated at 160° C. while stirring, a 20 ml Diglyme solution of 7.1 g of sodium chlorodifluoroacetate was added dropwise over a period of 30 minutes. After the heating was continued under the same conditions for 2 hours, the mixture was left to cool to room temperature. Water and hexane were added to the mixture, and the organic phase was separated, rinsed with 10% hydrochloric acid, a saturated aqueous solution of sodium carbonate, and a saturated saline solution, in sequence, and dried on anhydrous sodium sulfate. Then, the solvent was evaporated. The residue was purified by silica gel column chromatography (hexane) and recrystallized from ethanol at 10° C. or lower to obtain 0.6 g of 2-(trans-4-propylcyclohexyl)-6-(2,2-difluoroethenyl)-trans-decahydronaphthalene (I-25).

Example 25

Synthesis of trans-6-propyl-2-[4-(4-methylphenyl)ethynylphenyl]-trans-decahydronaphthalene

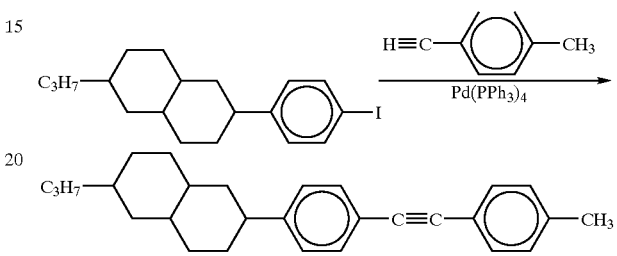

23 g of trans-6-propyl-2-(4-iodophenyl)-trans-decahydronaphthalene was dissolved in 45 ml of DMF. 1.3 g of tetrakis(triphenylphosphine)palladium(0), 0.4 g of copper iodide (I), and 6.0 g of (4-methyl)phenylacetylene were added to the mixture. After heating the mixture for 2 hours at 50° C. while stirring, the mixture was cooled to room temperature, and 10% hydrochloric acid was added to the mixture. After extraction was carried out using toluene, the organic phase was rinsed with a saline solution and dried on anhydrous magnesium sulfate. After the solvent was evaporated, the residue was purified by silica gel column chromatography (hexane) and recrystallized once from ethanol to obtain 10 g white crystals of trans-6-propyl-2-[4-(4-methylphenyl)ethynylphenyl]-trans-decahydronaphthalene.

The following compounds were prepared in the same manner as mentioned above:
trans-6-methyl-2-[4-(4-methylphenyl)ethynylphenyl]-trans-decahydronaphthalene,
trans-6-ethyl-2-[4-(4-methylphenyl)ethynylphenyl]-trans-decahydronaphthalene,
trans-6-butyl-2-[4-(4-methylphenyl)ethynylphenyl]-trans-decahydronaphthalene,
trans-6-pentyl-2-[4-(4-methylphenyl)ethynylphenyl]-trans-decahydronaphthalene,
trans-6-hexyl-2-[4-(4-methylphenyl)ethynylphenyl]-trans-decahydronaphthalene,
trans-6-heptyl-2-[4-(4-methylphenyl)ethynylphenyl]-trans-decahydronaphthalene,
trans-6-methyl-2-[3-fluoro-4-(4-methylphenyl)ethynylphenyl]-trans-decahydronaphthalene,
trans-6-ethyl-2-[3-fluoro-4-(4-methylphenyl)ethynylphenyl]-trans-decahydronaphthalene,
trans-6-propyl-2-[3-fluoro-4-(4-methylphenyl)ethynylphenyl]-trans-decahydronaphthalene,
trans-6-butyl-2-[3-fluoro-4-(4-methylphenyl)ethynylphenyl]-trans-decahydronaphthalene,
trans-6-pentyl-2-[3-fluoro-4-(4-methylphenyl)ethynylphenyl]-trans-decahydronaphthalene,
trans-6-hexyl-2-[3-fluoro-4-(4-methylphenyl)ethynylphenyl]-trans-decahydronaphthalene,
trans-6-heptyl-2-[3-fluoro-4-(4-methylphenyl)ethynylphenyl]-trans-decahydronaphthalene, trans-6-methyl-2-[3,5-difluoro-4-(4-methylphenyl)ethynylphenyl]-trans-decahydronaphthalene,
trans-6-ethyl-2-[3,5-difluoro-4-(4-methylphenyl)ethynylphenyl]-trans-decahydronaphthalene,
trans-6-propyl-2-[3,5-difluoro-4-(4-methylphenyl)ethynylphenyl]-trans-decahydronaphthalene,
trans-6-butyl-2-[3,5-difluoro-4-(4-methylphenyl)ethynylphenyl]-trans-decahydronaphthalene,
trans-6-pentyl-2-[3,5-difluoro-4-(4-methylphenyl)ethynylphenyl]-trans-decahydronaphthalene,
trans-6-hexyl-2-[3,5-difluoro-4-(4-methylphenyl)ethynylphenyl]-trans-decahydronaphthalene,
trans-6-heptyl-2-[3,5-difluoro-4-(4-methylphenyl)ethynylphenyl]-trans-decahydronaphthalene,
trans-6-methyl-2-[4-(4-ethylphenyl)ethynylphenyl]-trans-decahydronaphthalene,
trans-6-ethyl-2-[4-(4-ethylphenyl)ethynylphenyl]-trans-decahydronaphthalene,
trans-6-propyl-2-[4-(4-ethylphenyl)ethynylphenyl]-trans-decahydronaphthalene,
trans-6-butyl-2-[4-(4-ethylphenyl)ethynylphenyl]-trans-decahydronaphthalene,
trans-6-pentyl-2-[4-(4-ethylphenyl)ethynylphenyl]-trans-decahydronaphthalene,
trans-6-hexyl-2-[4-(4-ethylphenyl)ethynylphenyl]-trans-decahydronaphthalene,
trans-6-heptyl-2-[4-(4-ethylphenyl)ethynylphenyl]-trans-decahydronaphthalene,
trans-6-methyl-2-[4-(4-propylphenyl)ethynylphenyl]-trans-decahydronaphthalene,
trans-6-ethyl-2-[4-(4-propylphenyl)ethynylphenyl]-trans-decahydronaphthalene,
trans-6-propyl-2-[4-(4-propylphenyl)ethynylphenyl]-trans-decahydronaphthalene,
trans-6-butyl-2-[4-(4-propylphenyl)ethynylphenyl]-trans-decahydronaphthalene,
trans-6-pentyl-2-[4-(4-propylphenyl)ethynylphenyl]-trans-decahydronaphthalene,
trans-6-hexyl-2-[4-(4-propylphenyl)ethynylphenyl]-trans-decahydronaphthalene,
trans-6-heptyl-2-[4-(4-propylphenyl)ethynylphenyl]-trans-decahydronaphthalene,
trans-6-methyl-2-[4-(4-methoxyphenyl)ethynylphenyl]-trans-decahydronaphthalene,
trans-6-ethyl-2-[4-(4-methoxyphenyl)ethynylphenyl]-trans-decahydronaphthalene,
trans-6-propyl-2-[4-(4-methoxyphenyl)ethynylphenyl]-trans-decahydronaphthalene,
trans-6-butyl-2-[4-(4-methoxyphenyl)ethynylphenyl]-trans-decahydronaphthalene,
trans-6-pentyl-2-[4-(4-methoxyphenyl)ethynylphenyl]-trans-decahydronaphthalene,
trans-6-hexyl-2-[4-(4-methoxyphenyl)ethynylphenyl]-trans-decahydronaphthalene,
trans-6-heptyl-2-[4-(4-methoxyphenyl)ethynylphenyl]-trans-decahydronaphthalene,
trans-6-methyl-2-[4-(4-allyloxyphenyl)ethynylphenyl]-trans-decahydronaphthalene,
trans-6-ethyl-2-[4-(4-allyloxyphenyl)ethynylphenyl]-trans-decahydronaphthalene,
trans-6-propyl-2-[4-(4-allyloxyphenyl)ethynylphenyl]-trans-decahydronaphthalene,
trans-6-butyl-2-[4-(4-allyloxyphenyl)ethynylphenyl]-trans-decahydronaphthalene,
trans-6-pentyl-2-[4-(4-allyloxyphenyl)ethynylphenyl]-trans-decahydronaphthalene,
trans-6-hexyl-2-[4-(4-allyloxyphenyl)ethynylphenyl]-trans-decahydronaphthalene,
trans-6-heptyl-2-[4-(4-allyloxyphenyl)ethynylphenyl]-trans-decahydronaphthalene,
trans-6-methyl-2-[4-[4-(3-butenyl)phenyl]ethynylphenyl]-trans-decahydronaphthalene,
trans-6-ethyl-2-[4-[4-(3-butenyl)phenyl]ethynylphenyl]-trans-decahydronaphthalene,
trans-6-propyl-2-[4-[4-(3-butenyl)phenyl]ethynylphenyl]-trans-decahydronaphthalene,
trans-6-butyl-2-[4-[4-(3-butenyl)phenyl]ethynylphenyl]-trans-decahydronaphthalene,
trans-6-pentyl-2-[4-[4-(3-butenyl)phenyl]ethynylphenyl]-trans-decahydronaphthalene,
trans-6-hexyl-2-[4-[4-(3-butenyl)phenyl]ethynylphenyl]-trans-decahydronaphthalene,
trans-6-heptyl-2-[4-[4-(3-butenyl)phenyl]ethynylphenyl]-trans-decahydronaphthalene,
trans-6-methyl-2-[4-(4-fluorophenyl)ethynylphenyl]-trans-decahydronaphthalene,
trans-6-ethyl-2-[4-(4-fluorophenyl)ethynylphenyl]-trans-decahydronaphthalene,
trans-6-propyl-2-[4-(4-fluorophenyl)ethynylphenyl]-trans-decahydronaphthalene,
trans-6-butyl-2-[4-(4-fluorophenyl)ethynylphenyl]-trans-decahydronaphthalene,
trans-6-pentyl-2-[4-(4-fluorophenyl)ethynylphenyl]-trans-decahydronaphthalene,
trans-6-hexyl-2-[4-(4-fluorophenyl)ethynylphenyl]-trans-decahydronaphthalene,
trans-6-heptyl-2-[4-(4-fluorophenyl)ethynylphenyl]-trans-decahydronaphthalene,
trans-6-methyl-2-[4-(3,4-difluorophenyl)ethynylphenyl]-trans-decahydronaphthalene,
trans-6-ethyl-2-[4-(3,4-difluorophenyl)ethynylphenyl]-trans-decahydronaphthalene,
trans-6-propyl-2-[4-(3,4-difluorophenyl)ethynylphenyl]-trans-decahydronaphthalene,
trans-6-butyl-2-[4-(3,4-difluorophenyl)ethynylphenyl]-trans-decahydronaphthalene,
trans-6-pentyl-2-[4-(3,4-difluorophenyl)ethynylphenyl]-trans-decahydronaphthalene,
trans-6-hexyl-2-[4-(3,4-difluorophenyl)ethynylphenyl]-trans-decahydronaphthalene,
trans-6-heptyl-2-[4-(3,4-difluorophenyl)ethynylphenyl]-trans-decahydronaphthalene,
trans-6-methyl-2-[4-(3,4,5-trifluorophenyl)ethynylphenyl]-trans-decahydronaphthalene,
trans-6-ethyl-2-[4-(3,4,5-trifluorophenyl)ethynylphenyl]-trans-decahydronaphthalene,
trans-6-propyl-2-[4-(3,4,5-trifluorophenyl)ethynylphenyl]-trans-decahydronaphthalene,
trans-6-butyl-2-[4-(3,4,5-trifluorophenyl)ethynylphenyl]-trans-decahydronaphthalene,
trans-6-pentyl-2-[4-(3,4,5-trifluorophenyl)ethynylphenyl]-trans-decahydronaphthalene,
trans-6-hexyl-2-[4-(3,4,5-trifluorophenyl)ethynylphenyl]-trans-decahydronaphthalene,
trans-6-heptyl-2-[4-(3,4,5-trifluorophenyl)ethynylphenyl]-trans-decahydronaphthalene,
trans-6-methyl-2-[4-(4-trifluoromethoxyphenyl)ethynylphenyl]-trans-decahydronaphthalene,
trans-6-ethyl-2-[4-(4-trifluoromethoxyphenyl)ethynylphenyl]-trans-decahydronaphthalene,
trans-6-propyl-2-[4-(4-trifluoromethoxyphenyl)ethynylphenyl]-trans-decahydronaphthalene,
trans-6-butyl-2-[4-(4-trifluoromethoxyphenyl)ethynylphenyl]-trans-decahydronaphthalene,
trans-6-pentyl-2-[4-(4-trifluoromethoxyphenyl)ethynylphenyl]-trans-decahydronaphthalene, trans-6-hexyl-2-[4-(4-trifluoromethoxyphenyl)ethynylphenyl]-trans-decahydronaphthalene,
trans-6-heptyl-2-[4-(4-trifluoromethoxyphenyl)ethynylphenyl]-trans-decahydronaphthalene,
trans-6-methyl-2-[4-(4-trifluoromethylphenyl)ethynylphenyl]-trans-decahydronaphthalene,
trans-6-ethyl-2-[4-(4-trifluoromethylphenyl)ethynylphenyl]-trans-decahydronaphthalene,
trans-6-propyl-2-[4-(4-trifluoromethylphenyl)ethynylphenyl]-trans-decahydronaphthalene,
trans-6-butyl-2-[4-(4-trifluoromethylphenyl)ethynylphenyl]-trans-decahydronaphthalene,
trans-6-pentyl-2-[4-(4-trifluoromethylphenyl)ethynylphenyl]-trans-decahydronaphthalene,
trans-6-hexyl-2-[4-(4-trifluoromethylphenyl)ethynylphenyl]-trans-decahydronaphthalene,
trans-6-heptyl-2-[4-(4-trifluoromethylphenyl)ethynylphenyl]-trans-decahydronaphthalene,
trans-6-methyl-2-[4-(4-chlorophenyl)ethynylphenyl]-trans-decahydronaphthalene,
trans-6-ethyl-2-[4-(4-chlorophenyl)ethynylphenyl]-trans-decahydronaphthalene,
trans-6-propyl-2-[4-(4-chlorophenyl)ethynylphenyl]-trans-decahydronaphthalene,
trans-6-butyl-2-[4-(4-chlorophenyl)ethynylphenyl]-trans-decahydronaphthalene,
trans-6-pentyl-2-[4-(4-chlorophenyl)ethynylphenyl]-trans-decahydronaphthalene,
trans-6-hexyl-2-[4-(4-chlorophenyl)ethynylphenyl]-trans-decahydronaphthalene,
trans-6-heptyl-2-[4-(4-chlorophenyl)ethynylphenyl]-trans-decahydronaphthalene.

Example 26

Synthesis of trans-6-propyl-2-[2-[4-(4-cyano-3,5-difluorophenyl)phenyl]ethyl]-trans-decahydronaphthalene

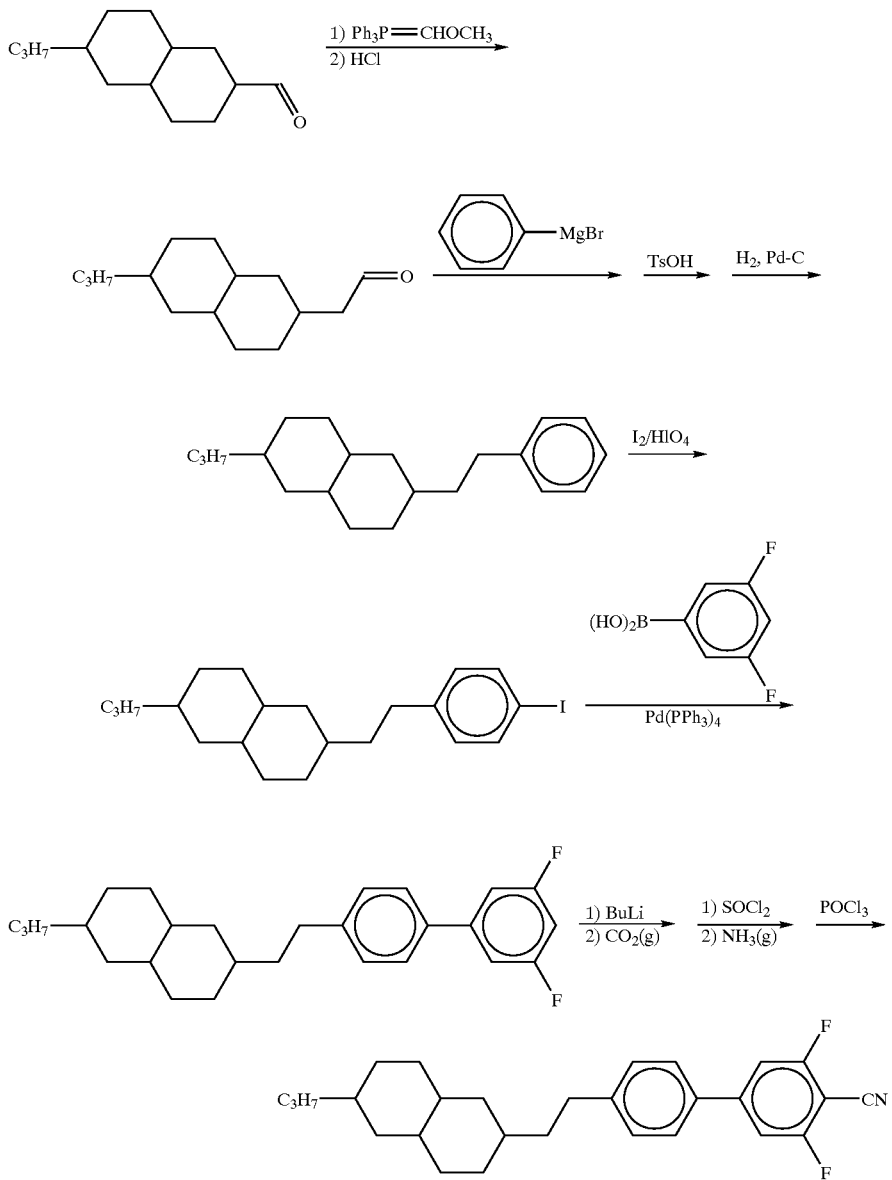

(26-a) Synthesis of trans-6-propyl-2-(2-oxoethyl)-trans-decahydronaphthalene

Reaction of 10 g of trans-6-propyl-trans-decahydronaphthalene-2-carbaldehyde, which was obtained in (12-a), with a Wittig reagent which is similar to that used in (12-a) was carried out to obtain 9 g of white solid trans-6-propyl-2-(2-oxoethyl)-trans-decahydronaphthalene.

(26-b) Synthesis of trans-6-propyl-2-(2-phenylethyl)-trans-decahydronaphthalene

Reaction of 9 g of trans-6-propyl-2-(2-oxoethyl)-trans-decahydronaphthalene, which was obtained in (26-a), with a Grignard reagent similar to that used in Example 2 was carried out to obtain 11 g of white solid trans-6-propyl-2-(2-phenylethyl)-trans-decahydronaphthalene.

(26-c) Synthesis of trans-6-propyl-2-[2-(4-iodophenyl)ethyl]-trans-decahydronaphthalene 11 g of trans-6-propyl-2-(2-phenylethyl)-trans-decahydronaphthalene, which was obtained in (26-b), was iodized in a manner similar to that in (1-a) to obtain 13 g of pale yellow solid trans-6-propyl-2-[2-(4-iodophenyl)ethyl]-trans-decahydronaphthalene.

(26-d) Synthesis of trans-6-propyl-2-[2-[4-(3,5-difluorophenyl)phenyl]ethyl]-trans-decahydronaphthalene Coupling reaction of 13 g of trans-6-propyl-2-[2-(4-iodophenyl)ethyl]-trans-decahydronaphthalene, which was obtained in (26-c), was carried out in a manner similar to that in (1-b) to obtain 7 g of white solid trans-6-propyl-2-[2-[4-(3,5-difluorophenyl)phenyl]ethyl]-trans-decahydronaphthalene.

(26-e) Synthesis of trans-6-propyl-2-[2-[4-(4-cyano-3,5-difluorophenyl)phenyl]ethyl]-trans-decahydronaphthalene 20 ml of a 1.5 M hexane solution of n-butyl lithium was added dropwise to a 35 ml THF solution of 7 g of trans-6-propyl-2-[2-[4-(3,5-difluorophenyl)phenyl]ethyl]-trans-decahydronaphthalene, which was obtained in (26-d), while cooling the solution to −78° C. After stirring for 10 minutes, carbon dioxide was injected into the mixture until saturation. After the mixture was left to stand until the temperature reached room temperature, 10% hydrochloric acid was added. The organic phase was extracted using ethyl acetate, rinsed with water, and dried on anhydrous magnesium sulfate. Then, the solvent was evaporated. The pale yellow solid substance obtained was suspended in 60 ml of 1,2-dichloroethane. 2 g of thionyl chloride, 0.1 ml of pyridine, and 1 ml of DMF were added to the suspension, and the mixture was stirred for 1 hour at room temperature. The solvent was evaporated, and the yellow oily substance obtained was dissolved in 150 ml of dichloromethane. Ammonia gas was injected into the solution while cooling the solution to 10° C. or lower until saturation. After stirring for 1 hour at room temperature, the solvent was evaporated. The yellowish brown solid substance obtained was suspended in 50 ml of DMF. 2 ml of phosphorus oxychloride was added to the suspension while cooling the suspension to 10° C. or lower, and the mixture was stirred for 3 hour at room temperature. Water was added to the mixture. The organic phase was extracted using toluene, rinsed with a saturated saline solution, and dried on anhydrous sodium sulfate. Then, the solvent was evaporated. The residue was purified by silica gel column chromatography (hexane), and recrystallized from ethanol to obtain 1 g of white solid trans-6-propyl-2-[2-[4-(4-cyano-3,5-difluorophenyl)phenyl]ethyl]-trans-decahydronaphthalene.

Example 27

Synthesis of trans-6-[4-(3-butenyl)phenyl]-trans-2-vinyldecahydronaphthalene

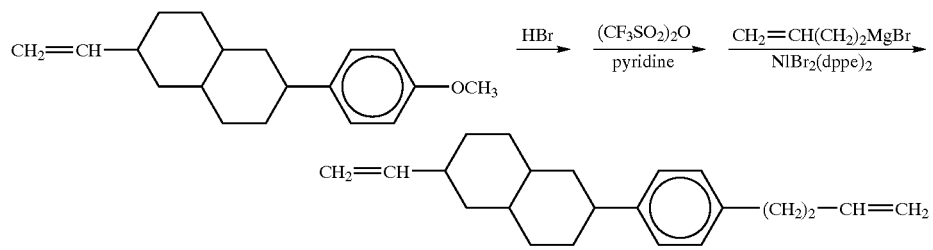

Trans-6-(4-methoxyphenyl)-trans-2-vinyldecahydronaphthalene obtained in a manner similar to that in Example 1 was dissolved in glacial acetic acid. A 47% aqueous solution of hydrobromic acid was added to the solution, and the mixture was heated for 20 hours under refluxing. The mixture was cooled to room temperature, and water was added to the mixture. Extraction was carried out using toluene, and the organic phase was rinsed with water and then dried on anhydrous sodium sulfate. Then, the solvent was evaporated. The oily substance obtained, which was trans-6-(4-hydroxyphenyl)-trans-2-vinyldecahydronaphthalene, was dissolved in methylene chloride. Trifluoromethanesulfonic anhydride was added dropwise to the solution while cooling the mixture at 10° C. or lower. Subsequently, pyridine was added dropwise, and the mixture was stirred for 1 hour. Water was added, and the mixture was left to stand until the temperature reached room temperature. Then, extraction was carried out using ethyl acetate, and the organic phase was rinsed with water and then dried on anhydrous sodium sulfate. Then, the solvent was evaporated. The oily substance obtained, which was trifluoromethanesulfonate, was dissolved in THF. Dibromobis(diphenylphosphinoethane)nickel(II) and triphenylphosphine were added to the solution. A Grignard reagent prepared from 3-butenyl bromide (1-bromo-3-butene) was added dropwise to the mixture, and the mixture was heated for 16 hours under refluxing. The mixture was left to stand until the temperature reached room temperature. Then, 10% hydrochloric acid was added to the mixture, and the organic phase was extracted using ethyl acetate, rinsed with water, and dried on anhydrous sodium sulfate. After the solvent was evaporated, the residue was purified by silica gel column chromatography (hexane) and recrystallized (ethanol) to obtain white solid trans-6-[4-(3-butenyl)phenyl]-trans-2-vinyldecahydronaphthalene.

The following compounds were prepared in the same manner as mentioned above:
trans-6-[4-(3-butenyl)phenyl]-trans-2-vinyldecahydronaphthalene,
trans-6-(4-methylphenyl)-trans-2-vinyldecahydronaphthalene,
trans-6-(4-ethylphenyl)-trans-2-vinyldecahydronaphthalene,
trans-6-(4-propylphenyl)-trans-2-vinyldecahydronaphthalene,
trans-6-(3-fluoro-4-methylphenyl)-trans-2-vinyldecahydronaphthalene,
trans-6-(4-ethyl-3-fluorophenyl)-trans-2-vinyldecahydronaphthalene,
trans-6-(3-fluoro-4-propylphenyl)-trans-2-vinyldecahydronaphthalene,
trans-6-[4-(3-butenyl)-3-fluorophenyl]-trans-2-vinyldecahydronaphthalene,
trans-6-(3,5-difluoro-4-methylphenyl)-trans-2-vinyldecahydronaphthalene,
trans-6-(3,5-difluoro-4-ethylphenyl)-trans-2-vinyldecahydronaphthalene,
trans-6-(3,5-difluoro-4-propylphenyl)-trans-2-vinyldecahydronaphthalene,
trans-6-[3,5-difluoro-4-(3-butenyl)phenyl]-trans-2-vinyldecahydronaphthalene,
trans-6-(4-methylphenyl)-trans-2-(1-propenyl)decahydronaphthalene,
trans-6-(4-ethylphenyl)-trans-2-(1-propenyl)decahydronaphthalene,
trans-6-(4-propylphenyl)-trans-2-(1-propenyl)decahydronaphthalene,
trans-6-[4-(3-butenyl)phenyl]-trans-2-(1-propenyl)decahydronaphthalene,
trans-6-(3-fluoro-4-methylphenyl)-trans-2-(1-propenyl)decahydronaphthalene,
trans-6-(4-ethyl-3-fluorophenyl)-trans-2-(1-propenyl)decahydronaphthalene,
trans-6-(3-fluoro-4-propylphenyl)-trans-2-(1-propenyl)decahydronaphthalene,
trans-6-[4-(3-butenyl)-3-fluorophenyl]-trans-2-(1-propenyl)decahydronaphthalene,
trans-6-(3,5-difluoro-4-methylphenyl)-trans-2-(1-propenyl)decahydronaphthalene,
trans-6-(3,5-difluoro-4-ethylphenyl)-trans-2-(1-propenyl)decahydronaphthalene,
trans-6-(3,5-difluoro-4-propylphenyl)-trans-2-(1-propenyl)decahydronaphthalene,
trans-6-[3,5-difluoro-4-(3-butenyl)phenyl]-trans-2-(1-propenyl)decahydronaphthalene,
trans-6-(4-methylphenyl)-trans-2-(3-butenyl)decahydronaphthalene,
trans-6-(4-ethylphenyl)-trans-2-(3-butenyl)decahydronaphthalene,
trans-6-(4-propylphenyl)-trans-2-(3-butenyl)decahydronaphthalene,
trans-6-[4-(3-butenyl)phenyl]-trans-2-(3-butenyl)decahydronaphthalene,
trans-6-(3-fluoro-4-methylphenyl)-trans-2-(3-butenyl)decahydronaphthalene,
trans-6-(4-ethyl-3-fluorophenyl)-trans-2-(3-butenyl)decahydronaphthalene,
trans-6-(3-fluoro-4-propylphenyl)-trans-2-(3-butenyl)decahydronaphthalene,
trans-6-[4-(3-butenyl)-3-fluorophenyl]-trans-2-(3-butenyl)decahydronaphthalene,
trans-6-(3,5-difluoro-4-methylphenyl)-trans-2-(3-butenyl)decahydronaphthalene,
trans-6-(3,5-difluoro-4-ethylphenyl)-trans-2-(3-butenyl)decahydronaphthalene,
trans-6-(3,5-difluoro-4-propylphenyl)-trans-2-(3-butenyl)decahydronaphthalene,
trans-6-[3,5-difluoro-4-(3-butenyl)phenyl]-trans-2-(3-butenyl)decahydronaphthalene,
trans-6-(4-cyanophenyl)-trans-2-vinyldecahydronaphthalene,
trans-6-(4-cyanophenyl)-trans-2-(1-propenyl)decahydronaphthalene,
trans-6-(4-cyanophenyl)-trans-2-(3-butenyl)decahydronaphthalene.

Example 28

Synthesis of trans-6-[4-(2-propenyloxy)phenyl]-trans-2-vinyldecahydronaphthalene

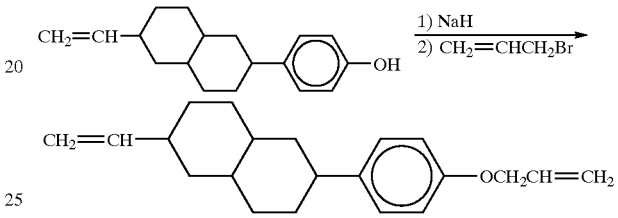

A THF solution of trans-6-(4-hydroxyphenyl)-trans-2-vinyldecahydronaphthalene obtained by the method disclosed in Example 7 was added dropwise to a suspension of sodium hydroxide in THF, the suspension being cooled to 10° C. or lower. After stirring for 30 minutes at room temperature, a THF solution of 2-propenyl bromide (1-bromo-2-propene) was added dropwise, and the mixture was heated for 1 hour under refluxing. The mixture was left to stand until the temperature reached room temperature, and extraction was carried out using toluene. The organic phase was rinsed with a saturated saline solution and then dried on anhydrous sodium sulfate. After the solvent was evaporated, the residue was purified by silica gel column chromatography (hexane) and recrystallized (ethanol) to obtain white solid trans-6-[4-(2-propenyloxy)phenyl]-trans-2-vinyldecahydronaphthalene.

The following compounds were prepared in the same manner as mentioned above:
trans-6-[4-(trans-2-butenyloxy)phenyl]-trans-2-vinyldecahydronaphthalene,
trans-6-[3-fluoro-4-(2-propenyloxy)phenyl]-trans-2-vinyldecahydronaphthalene,
trans-6-[4-(trans-2-butenyloxy)-3-fluorophenyl]-trans-2-vinyldecahydronaphthalene,
trans-6-[3,5-difluoro-4-(2-propenyloxy)phenyl]-trans-2-vinyldecahydronaphthalene.,
trans-6-[3,5-difluoro-4-(trans-2-butenyloxy)phenyl]-trans-2-vinyldecahydronaphthalene,
trans-6-[4-(2-propenyloxy)phenyl]-trans-2-(1-propenyl)decahydronaphthalene,
trans-6-[4-(trans-2-butenyloxy)phenyl]-trans-2-(1-propenyl)decahydronaphthalene,
trans-6-[3-fluoro-4-(2-propenyloxy)phenyl]-trans-2-(1-propenyl)decahydronaphthalene,
trans-6-[4-(trans-2-butenyloxy)-3-fluorophenyl]-trans-2-(1-propenyl)decahydronaphthalene,
trans-6-[3,5-difluoro-4-(2-propenyloxy)phenyl]-trans-2-(1-propenyl)decahydronaphthalene,
trans-6-[3,5-difluoro-4-(trans-2-butenyloxy)phenyl]-trans-2-(1-propenyl)decahydronaphthalene, trans-6-[4-(2-propenyloxy)phenyl]-trans-2-(1-butenyl)
  decahydronaphthalene,
trans-6-[4-(trans-2-butenyloxy)phenyl]-trans-2-(1-butenyl)
  decahydronaphthalene,
trans-6-[3-fluoro-4-(2-propenyloxy)phenyl]-trans-2-(1-
  butenyl)decahydronaphthalene,
trans-6-[4-(trans-2-butenyloxy)-3-fluorophenyl]-trans-2-(1-
  butenyl)decahydronaphthalene,
trans-6-[3,5-difluoro-4-(2-propenyloxy)phenyl]-trans-2-(1-
  butenyl)decahydronaphthalene,
trans-6-[3,5-difluoro-4-(trans-2-butenyloxy)phenyl]-trans-
  2-(1-butenyl)decahydronaphthalene.

Example 29

Synthesis of trans-2-[3-fluoro-4-(2-
propenyloxycarbonyl)phenyl]-trans-6-
vinyldecahydronaphthalene

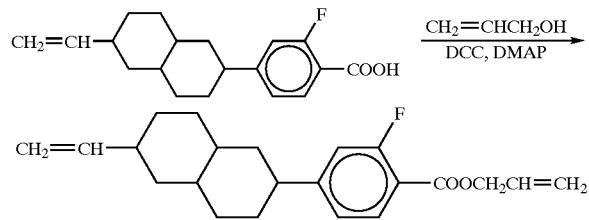

Trans-2-(4-carboxy-3-fluorophenyl)-trans-6-vinyldecahydronaphthalene obtained in a manner similar to that in Example 6, dicyclohexylcarbodiimide, and N,N-dimethyl-4-aminopyridine were dissolved in methylene chloride. To this solution, a methylene chloride solution of 2-propenol was added dropwise. After the mixture was stirred for 20 hours at room temperature, the mixture was filtered, and solvent was evaporated. Thereafter, the residue was purified by silica gel column chromatography (hexane) and recrystallized (ethanol) to obtain white solid trans-2-[3-fluoro-4-(2-propenyloxycarbonyl)phenyl]-trans-6-vinyldecahydronaphthalene Example 30

Synthesis of 2-[6-(3-butenyl)naphthalen-2-yl]-6-
propyl-trans-decahydronaphthalene (I-26)

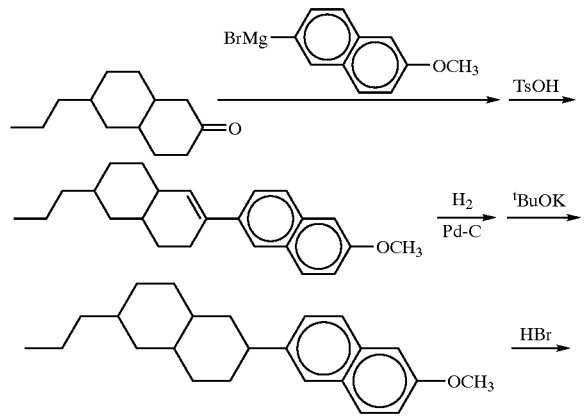

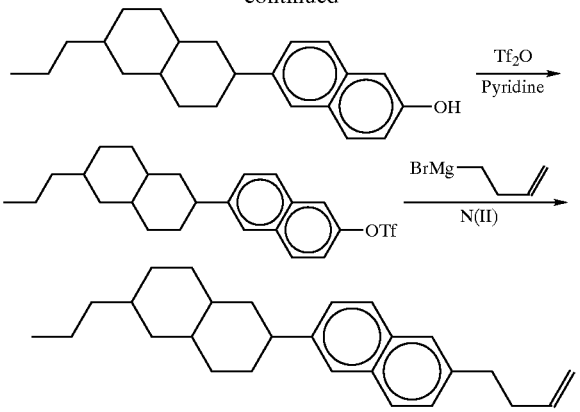

(30-a) Synthesis of 2-(6-methoxynaphthalen-2-yl)-trans-6-propyl-trans-3,4,4a,5,6,7,8,8a-octahydronaphthalene In a manner similar to that in (1-a), reaction of 24 g of 6-propyldecahydro-2-naphthalenone with a Grignard reagent prepared from 6-methoxy-2-bromonaphthalene and dehydration were carried out to obtain 32 g of pale yellow liquid 2-(6-methoxynaphthalen-2-yl)-trans-6-propyl-trans-3,4,4a,5,6,7,8,8a-octahydronaphthalene.

(30-b) Synthesis of 2-(6-methoxynaphthalen-2-yl)-trans-6-propyl-trans-decahydronaphthalene In a manner similar to that in (1-e), catalytic hydrogenation reduction and isomerization of 32 g of 2-(6-methoxynaphthalen-2-yl)-trans-6-propyl-trans-3,4,4a,5,6,7,8,8a-octahydronaphthalene, which was obtained in (30-a), were carried out to obtain 30 g of 2-(6-methoxynaphthalen-2-yl)-trans-6-propyl-trans-decahydronaphthalene as a pale yellow oily substance.

(30-c) Synthesis of 6-(trans-6-propyl-trans-3,4,4a,5,6,7,8,8a-octahydronaphthalen-2-yl)-2-naphthol 30 g of trans-2-propyl-trans-6-(3-fluoro-4-methoxyphenyl)-trans-decahydronaphthalene, which was obtained in (30-b), was dissolved in a mixture of 150 ml of glacial acetic acid and 150 ml of 48% hydrobromic acid, and the solution was heated for 8 hours under refluxing. The solution was cooled to room temperature. Water and ethyl acetate were added to the solution. After the organic phase was separated, the organic phase was rinsed with water, a saturated aqueous solution of sodium hydrogencarbonate, water, and a saturated saline solution, in sequence, and dried on anhydrous sodium sulfate. The solvent was evaporated to obtain 24 g yellow crystals of 6-(trans-6-propyl-trans-3,4,4a,5,6,7,8,8a-octahydronaphthalen-2-yl)-2-naphthol.

(30-d) Synthesis of 2-(6-trifluoromethanesulfonyloxynaphthalen-2-yl)-trans-6-propyl-trans-decahydronaphthalene A 120 ml dichloromethane solution of 25 g of trifluoromethanesulfonic anhydride was added dropwise to a 100 ml dichloromethane solution of 24 g yellow crystals of 6-(trans-6-propyl-trans-3,4,4a,5,6,7,8,8a-octahydronaphthalen-2-yl)-2-naphthol, which were obtained in (30-c), while the solution was cooled at 0°. Subsequently, a 70 ml dichloromethane solution of 14 g of pyridine was added dropwise. After the mixture was stirred for 1 hour at room temperature, 10% hydrochloric acid was added, and the organic phase was separated and rinsed with water, a saturated aqueous solution of sodium hydrogencarbonate, water, and a saturated saline solution, in sequence, and dried on anhydrous sodium sulfate. The solvent was evaporated, and the residue was purified by silica gel column chromatography (hexane) to obtain 25 g of white solid 2-(6-trifluoromethanesulfonyloxynaphthalen-2-yl)-trans-6-propyl-trans-decahydronaphthalene.

(30-e) Synthesis of 2-[6-(3-butenyl)naphthalen-2-yl]-6-propyl-trans-decahydronaphthalene A Grignard reagent prepared from 1.5 g of metal magnesium and 9 g of 4-bromo-1-butene was added dropwise to a 130 ml THF solution of 25 g of 2-(6-trifluoromethanesulfonyloxynaphthalen-2-yl)-trans-6-propyl-trans-decahydronaphthalene, which was obtained in (30-d), and 0.8 g of dichlorobis(diphenylphosphinoethane) nickel(II), the solution being cooled to 10° C. or lower. The temperature was reduced to room temperature, and the mixture was stirred for 6 hours. After 10% hydrochloric acid was added, the organic phase was separated, rinsed with water and a saturated saline solution, in sequence, and dried on anhydrous magnesium sulfate. The solvent was evaporated, and the residue was purified by silica gel column chromatography (hexane) and recrystallized from ethanol to obtain 3 g white crystals of 2-[6-(3-butenyl)naphthalen-2-yl]-6-propyl-trans-decahydronaphthalene The following compounds were prepared in the same manner as mentioned above:

2-[6-(3-butenyl)naphthalen-2-yl)-6-methyl-trans-decahydronaphthalene,
2-[6-(3-butenyl)naphthalen-2-yl]-6-ethyl-trans-decahydronaphthalene,
2-[6-(3-butenyl)naphthalen-2-yl]-6-butyl-trans-decahydronaphthalene,
2-[6-(3-butenyl)naphthalen-2-yl]-6-pentyl-trans-decahydronaphthalene,
2-[6-(3-butenyl)naphthalen-2-yl]-6-hexyl-trans-decahydronaphthalene,
2-[6-(3-butenyl)naphthalen-2-yl]-6-heptyl-trans-decahydronaphthalene,
2-[6-(trans-3-pentenyl)naphthalen-2-yl)-6-methyl-trans-decahydronaphthalene,
2-[6-(trans-3-pentenyl)naphthalen-2-yl]-6-ethyl-trans-decahydronaphthalene,
2-[6-(trans-3-pentenyl)naphthalen-2-yl]-6-propyl-trans-decahydronaphthalene,
2-[6-(trans-3-pentenyl)naphthalen-2-yl]-6-butyl-trans-decahydronaphthalene,
2-[6-(trans-3-pentenyl)naphthalen-2-yl]-6-pentyl-trans-decahydronaphthalene,
2-[6-(trans-3-pentenyl)naphthalen-2-yl]-6-hexyl-trans-decahydronaphthalene,
2-[6-(trans-3-pentenyl)naphthalen-2-yl]-6-heptyl-trans-decahydronaphthalene,
2-(6-methoxynaphthalen-2-yl)-6-methyl-trans-decahydronaphthalene,
2-(6-methoxynaphthalen-2-yl)-6-ethyl-trans-decahydronaphthalene,
2-(6-methoxynaphthalen-2-yl)-6-propyl-trans-decahydronaphthalene,
2-(6-methoxynaphthalen-2-yl)-6-butyl-trans-decahydronaphthalene,
2-(6-methoxynaphthalen-2-yl)-6-pentyl-trans-decahydronaphthalene,
2-(6-methoxynaphthalen-2-yl)-6-hexyl-trans-decahydronaphthalene,
2-(6-methoxynaphthalen-2-yl)-6-heptyl-trans-decahydronaphthalene,
2-[6-(2-propenyloxy)naphthalen-2-yl]-6-methyl-trans-decahydronaphthalene,
2-[6-(2-propenyloxy)naphthalen-2-yl]-6-ethyl-trans-decahydronaphthalene,
2-[6-(2-propenyloxy)naphthalen-2-yl]-6-propyl-trans-decahydronaphthalene,
2-[6-(2-propenyloxy)naphthalen-2-yl]-6-butyl-trans-decahydronaphthalene,
2-[6-(2-propenyloxy)naphthalen-2-yl]-6-pentyl-trans-decahydronaphthalene,
2-[6-(2-propenyloxy)naphthalen-2-yl]-6-hexyl-trans-decahydronaphthalene,
2-[6-(2-propenyloxy)naphthalen-2-yl]-6-heptyl-trans-decahydronaphthalene,
2-[6-(trans-2-butenyloxy)naphthalen-2-yl]-6-methyl-trans-decahydronaphthalene,
2-[6-(trans-2-butenyloxy)naphthalen-2-yl]-6-ethyl-trans-decahydronaphthalene,
2-[6-(trans-2-butenyloxy)naphthalen-2-yl]-6-propyl-trans-decahydronaphthalene,
2-[6-(trans-2-butenyloxy)naphthalen-2-yl]-6-butyl-trans-decahydronaphthalene,
2-[6-(trans-2-butenyloxy)naphthalen-2-yl]-6-pentyl-trans-decahydronaphthalene,
2-[6-(trans-2-butenyloxy)naphthalen-2-yl]-6-hexyl-trans-decahydronaphthalene,
2-[6-(trans-2-butenyloxy)naphthalen-2-yl]-6-heptyl-trans-decahydronaphthalene,
2-[1-fluoro-2-(3-butenyl)naphthalen-6-yl]-6-methyl-trans-decahydronaphthalene,
2-[1-fluoro-2-(3-butenyl)naphthalen-6-yl]-6-ethyl-trans-decahydronaphthalene,
2-[1-fluoro-2-(3-butenyl)naphthalen-6-yl]-6-propyl-trans-decahydronaphthalene,
2-[1-fluoro-2-(3-butenyl)naphthalen-6-yl]-6-butyl-trans-decahydronaphthalene,
2-[1-fluoro-2-(3-butenyl)naphthalen-6-yl]-6-pentyl-trans-decahydronaphthalene,
2-[1-fluoro-2-(3-butenyl)naphthalen-6-yl]-6-hexyl-trans-decahydronaphthalene,
2-[1-fluoro-2-(3-butenyl)naphthalen-6-yl]-6-heptyl-trans-decahydronaphthalene,
2-[1-fluoro-2-(trans-3-pentenyl)naphthalen-6-yl]-6-methyl-trans-decahydronaphthalene,
2-[1-fluoro-2-(trans-3-pentenyl)naphthalen-6-yl]-6-ethyl-trans-decahydronaphthalene,
2-[1-fluoro-2-(trans-3-pentenyl)naphthalen-6-yl]-6-propyl-trans-decahydronaphthalene,
2-[1-fluoro-2-(trans-3-pentenyl)naphthalen-6-yl]-6-butyl-trans-decahydronaphthalene,
2-[1-fluoro-2-(trans-3-pentenyl)naphthalen-6-yl]-6-pentyl-trans-decahydronaphthalene,
2-[1-fluoro-2-(trans-3-pentenyl)naphthalen-6-yl]-6-hexyl-trans-decahydronaphthalene,
2-[1-fluoro-2-(trans-3-pentenyl)naphthalen-6-yl]-6-heptyl-trans-decahydronaphthalene,
2-(1-fluoro-2-methoxynaphthalen-6-yl)-6-methyl-trans-decahydronaphthalene,
2-(1-fluoro-2-methoxynaphthalen-6-yl)-6-ethyl-trans-decahydronaphthalene,
2-(1-fluoro-2-methoxynaphthalen-6-yl)-6-propyl-trans-decahydronaphthalene,
2-(1-fluoro-2-methoxynaphthalen-6-yl)-6-butyl-trans-decahydronaphthalene,
2-(1-fluoro-2-methoxynaphthalen-6-yl)-6-pentyl-trans-decahydronaphthalene,
2-(1-fluoro-2-methoxynaphthalen-6-yl)-6-hexyl-trans-decahydronaphthalene,
2-(1-fluoro-2-methoxynaphthalen-6-yl)-6-heptyl-trans-decahydronaphthalene,
2-[1-fluoro-2-(2-propenyloxy)naphthalen-6-yl]-6-methyl-trans-decahydronaphthalene,
2-[1-fluoro-2-(2-propenyloxy)naphthalen-6-yl]-6-ethyl-trans-decahydronaphthalene, 2-[1-fluoro-2-(2-propenyloxy)naphthalen-6-yl]-6-propyl-trans-decahydronaphthalene,
2-[1-fluoro-2-(2-propenyloxy)naphthalen-6-yl]-6-butyl-trans-decahydronaphthalene,
2-[1-fluoro-2-(2-propenyloxy)naphthalen-6-yl]-6-pentyl-trans-decahydronaphthalene,
2-[1-fluoro-2-(2-propenyloxy)naphthalen-6-yl]-6-hexyl-trans-decahydronaphthalene,
2-[1-fluoro-2-(2-propenyloxy)naphthalen-6-yl]-6-heptyl-trans-decahydronaphthalene,
2-[1-fluoro-2-(trans-2-butenyloxy)naphthalen-6-yl]-6-methyl-trans-decahydronaphthalene,
2-[1-fluoro-2-(trans-2-butenyloxy)naphthalen-6-yl]-6-ethyl-trans-decahydronaphthalene,
2-[1-fluoro-2-(trans-2-butenyloxy)naphthalen-6-yl]-6-propyl-trans-decahydronaphthalene,
2-[1-fluoro-2-(trans-2-butenyloxy)naphthalen-6-yl]-6-butyl-trans-decahydronaphthalene,
2-[1-fluoro-2-(trans-2-butenyloxy)naphthalen-6-yl]-6-pentyl-trans-decahydronaphthalene,
2-[1-fluoro-2-(trans-2-butenyloxy)naphthalen-6-yl]-6-hexyl-trans-decahydronaphthalene,
2-[1-fluoro-2-(trans-2-butenyloxy)naphthalen-6-yl]-6-heptyl-trans-decahydronaphthalene,
2-[3-fluoro-2-(3-butenyl)naphthalen-6-yl]-6-methyl-trans-decahydronaphthalene,
2-[3-fluoro-2-(3-butenyl)naphthalen-6-yl]-6-ethyl-trans-decahydronaphthalene,
2-[3-fluoro-2-(3-butenyl)naphthalen-6-yl]-6-propyl-trans-decahydronaphthalene,
2-[3-fluoro-2-(3-butenyl)naphthalen-6-yl]-6-butyl-trans-decahydronaphthalene,
2-[3-fluoro-2-(3-butenyl)naphthalen-6-yl]-6-pentyl-trans-decahydronaphthalene,
2-[3-fluoro-2-(3-butenyl)naphthalen-6-yl]-6-hexyl-trans-decahydronaphthalene,
2-[3-fluoro-2-(3-butenyl)naphthalen-6-yl]-6-heptyl-trans-decahydronaphthalene,
2-[3-fluoro-2-(trans-3-pentenyl)naphthalen-6-yl]-6-methyl-trans-decahydronaphthalene,
2-[3-fluoro-2-(trans-3-pentenyl)naphthalen-6-yl]-6-ethyl-trans-decahydronaphthalene,
2-[3-fluoro-2-(trans-3-pentenyl)naphthalen-6-yl]-6-propyl-trans-decahydronaphthalene,
2-[3-fluoro-2-(trans-3-pentenyl)naphthalen-6-yl]-6-butyl-trans-decahydronaphthalene,
2-[3-fluoro-2-(trans-3-pentenyl)naphthalen-6-yl]-6-pentyl-trans-decahydronaphthalene,
2-[3-fluoro-2-(trans-3-pentenyl)naphthalen-6-yl]-6-hexyl-trans-decahydronaphthalene,
2-[3-fluoro-2-(trans-3-pentenyl)naphthalen-6-yl]-6-heptyl-trans-decahydronaphthalene,
2-(3-fluoro-2-methoxynaphthalen-6-yl)-6-methyl-trans-decahydronaphthalene,
2-(3-fluoro-2-methoxynaphthalen-6-yl)-6-ethyl-trans-decahydronaphthalene,
2-(3-fluoro-2-methoxynaphthalen-6-yl)-6-propyl-trans-decahydronaphthalene,
2-(3-fluoro-2-methoxynaphthalen-6-yl)-6-butyl-trans-decahydronaphthalene,
2-(3-fluoro-2-methoxynaphthalen-6-yl)-6-pentyl-trans-decahydronaphthalene,
2-(3-fluoro-2-methoxynaphthalen-6-yl)-6-hexyl-trans-decahydronaphthalene,
2-(3-fluoro-2-methoxynaphthalen-6-yl)-6-heptyl-trans-decahydronaphthalene,
2-[3-fluoro-2-(2-propenyloxy)naphthalen-6-yl]-6-methyl-trans-decahydronaphthalene,
2-[3-fluoro-2-(2-propenyloxy)naphthalen-6-yl]-6-ethyl-trans-decahydronaphthalene,
2-[3-fluoro-2-(2-propenyloxy)naphthalen-6-yl]-6-propyl-trans-decahydronaphthalene,
2-[3-fluoro-2-(2-propenyloxy)naphthalen-6-yl]-6-butyl-trans-decahydronaphthalene,
2-[3-fluoro-2-(2-propenyloxy)naphthalen-6-yl]-6-pentyl-trans-decahydronaphthalene,
2-[3-fluoro-2-(2-propenyloxy)naphthalen-6-yl]-6-hexyl-trans-decahydronaphthalene,
2-[3-fluoro-2-(2-propenyloxy)naphthalen-6-yl]-6-heptyl-trans-decahydronaphthalene,
2-[3-fluoro-2-(trans-2-butenyloxy)naphthalen-6-yl]-6-methyl-trans-decahydronaphthalene,
2-[3-fluoro-2-(trans-2-butenyloxy)naphthalen-6-yl]-6-ethyl-trans-decahydronaphthalene,
2-(3-fluoro-2-(trans-2-butenyloxy)naphthalen-6-yl]-6-propyl-trans-decahydronaphthalene,
2-[3-fluoro-2-(trans-2-butenyloxy)naphthalen-6-yl]-6-butyl-trans-decahydronaphthalene,
2-(3-fluoro-2-(trans-2-butenyloxy)naphthalen-6-yl]-6-pentyl-trans-decahydronaphthalene,
2-[3-fluoro-2-(trans-2-butenyloxy)naphthalen-6-yl]-6-hexyl-trans-decahydronaphthalene,
2-[3-fluoro-2-(trans-2-butenyloxy)naphthalen-6-yl]-6-heptyl-trans-decahydronaphthalene,
2-[1,3-difluoro-2-(3-butenyl)naphthalen-6-yl]-6-methyl-trans-decahydronaphthalene,
2-[1,3-difluoro-2-(3-butenyl)naphthalen-6-yl]-6-ethyl-trans-decahydronaphthalene,
2-[1,3-difluoro-2-(3-butenyl)naphthalen-6-yl]-6-propyl-trans-decahydronaphthalene,
2-[1,3-difluoro-2-(3-butenyl)naphthalen-6-yl]-6-butyl-trans-decahydronaphthalene,
2-[1,3-difluoro-2-(3-butenyl)naphthalen-6-yl]-6-pentyl-trans-decahydronaphthalene,
2-[1,3-difluoro-2-(3-butenyl)naphthalen-6-yl]-6-hexyl-trans-decahydronaphthalene,
2-[1,3-difluoro-2-(3-butenyl)naphthalen-6-yl]-6-heptyl-trans-decahydronaphthalene,
2-[1,3-difluoro-2-(trans-3-pentenyl)naphthalen-6-yl]-6-methyl-trans-decahydronaphthalene,
2-[1,3-difluoro-2-(trans-3-pentenyl)naphthalen-6-yl]-6-ethyl-trans-decahydronaphthalene,
2-[1,3-difluoro-2-(trans-3-pentenyl)naphthalen-6-yl]-6-propyl-trans-decahydronaphthalene,
2-[1,3-difluoro-2-(trans-3-pentenyl)naphthalen-6-yl]-6-butyl-trans-decahydronaphthalene,
2-[1,3-difluoro-2-(trans-3-pentenyl)naphthalen-6-yl]-6-pentyl-trans-decahydronaphthalene,
2-[1,3-difluoro-2-(trans-3-pentenyl)naphthalen-6-yl]-6-hexyl-trans-decahydronaphthalene,
2-[1,3-difluoro-2-(trans-3-pentenyl)naphthalen-6-yl]-6-heptyl-trans-decahydronaphthalene,
2-(1,3-difluoro-2-methoxynaphthalen-6-yl)-6-methyl-trans-decahydronaphthalene,
2-(1,3-difluoro-2-methoxynaphthalen-6-yl)-6-ethyl-trans-decahydronaphthalene,
2-(1,3-difluoro-2-methoxynaphthalen-6-yl)-6-propyl-trans-decahydronaphthalene,
2-(1,3-difluoro-2-methoxynaphthalen-6-yl)-6-butyl-trans-decahydronaphthalene,
2-(1,3-difluoro-2-methoxynaphthalen-6-yl)-6-pentyl-trans-decahydronaphthalene,
2-(1,3-difluoro-2-methoxynaphthalen-6-yl)-6-hexyl-trans-decahydronaphthalene,
2-(1,3-difluoro-2-methoxynaphthalen-6-yl)-6-heptyl-trans-decahydronaphthalene, 2-[1,3-difluoro-2-(2-propenyloxy)naphthalen-6-yl]-6-methyl-trans-decahydronaphthalene,
2-[1,3-difluoro-2-(2-propenyloxy)naphthalen-6-yl]-6-ethyl-trans-decahydronaphthalene,
2-[1,3-difluoro-2-(2-propenyloxy)naphthalen-6-yl]-6-propyl-trans-decahydronaphthalene,
2-[1,3-difluoro-2-(2-propenyloxy)naphthalen-6-yl]-6-butyl-trans-decahydronaphthalene,
2-[1,3-difluoro-2-(2-propenyloxy)naphthalen-6-yl)-6-pentyl-trans-decahydronaphthalene,
2-[1,3-difluoro-2-(2-propenyloxy)naphthalen-6-yl]-6-hexyl-trans-decahydronaphthalene,
2-[1,3-difluoro-2-(2-propenyloxy)naphthalen-6-yl]-6-heptyl-trans-decahydronaphthalene,
2-[1,3-difluoro-2-(trans-2-butenyloxy)naphthalen-6-yl]-6-methyl-trans-decahydronaphthalene,
2-[1,3-difluoro-2-(trans-2-butenyloxy)naphthalen-6-yl)-6-ethyl-trans-decahydronaphthalene,
2-[1,3-difluoro-2-(trans-2-butenyloxy)naphthalen-6-yl]-6-propyl-trans-decahydronaphthalene,
2-[1,3-difluoro-2-(trans-2-butenyloxy)naphthalen-6-yl]-6-butyl-trans-decahydronaphthalene,
2-[1,3-difluoro-2-(trans-2-butenyloxy)naphthalen-6-yl]-6-pentyl-trans-decahydronaphthalene,
2-[1,3-difluoro-2-(trans-2-butenyloxy)naphthalen-6-yl]-6-hexyl-trans-decahydronaphthalene,
2-[1,3-difluoro-2-(trans-2-butenyloxy)naphthalen-6-yl]-6-heptyl-trans-decahydronaphthalene,
2-[1-fluoro-3-(3-butenyl)naphthalen-7-yl]-6-methyl-trans-decahydronaphthalene,
2-[1-fluoro-3-(3-butenyl)naphthalen-7-yl]-6-ethyl-trans-decahydronaphthalene,
2-[1-fluoro-3-(3-butenyl)naphthalen-7-yl]-6-propyl-trans-decahydronaphthalene,
2-[1-fluoro-3-(3-butenyl)naphthalen-7-yl]-6-butyl-trans-decahydronaphthalene,
2-[1-fluoro-3-(3-butenyl)naphthalen-7-yl]-6-pentyl-trans-decahydronaphthalene,
2-[1-fluoro-3-(3-butenyl)naphthalen-7-yl]-6-hexyl-trans-decahydronaphthalene,
2-[1-fluoro-3-(3-butenyl)naphthalen-7-yl]-6-heptyl-trans-decahydronaphthalene,
2-[1-fluoro-3-(trans-3-pentenyl)naphthalen-7-yl]-6-methyl-trans-decahydronaphthalene,
2-[1-fluoro-3-(trans-3-pentenyl)naphthalen-7-yl]-6-ethyl-trans-decahydronaphthalene,
2-[1-fluoro-3-(trans-3-pentenyl)naphthalen-7-yl]-6-propyl-trans-decahydronaphthalene,
2-[1-fluoro-3-(trans-3-pentenyl)naphthalen-7-yl]-6-butyl-trans-decahydronaphthalene,
2-[1-fluoro-3-(trans-3-pentenyl)naphthalen-7-yl)-6-pentyl-trans-decahydronaphthalene,
2-[1-fluoro-3-(trans-3-pentenyl)naphthalen-7-yl]-6-hexyl-trans-decahydronaphthalene,
2-[1-fluoro-3-(trans-3-pentenyl)naphthalen-7-yl]-6-heptyl-trans-decahydronaphthalene,
2-(1-fluoro-3-methoxynaphthalen-7-yl)-6-methyl-trans-decahydronaphthalene,
2-(1-fluoro-3-methoxynaphthalen-7-yl)-6-ethyl-trans-decahydronaphthalene,
2-(1-fluoro-3-methoxynaphthalen-7-yl)-6-propyl-trans-decahydronaphthalene,
2-(1-fluoro-3-methoxynaphthalen-7-yl)-6-butyl-trans-decahydronaphthalene,
2-(1-fluoro-3-methoxynaphthalen-7-yl)-6-pentyl-trans-decahydronaphthalene,
2-(1-fluoro-3-methoxynaphthalen-7-yl)-6-hexyl-trans-decahydronaphthalene,
2-(1-fluoro-3-methoxynaphthalen-7-yl)-6-heptyl-trans-decahydronaphthalene,
2-[1-fluoro-3-(2-propenyloxy)naphthalen-7-yl]-6-methyl-trans-decahydronaphthalene,
2-[1-fluoro-3-(2-propenyloxy)naphthalen-7-yl]-6-ethyl-trans-decahydronaphthalene,
2-[1-fluoro-3-(2-propenyloxy)naphthalen-7-yl]-6-propyl-trans-decahydronaphthalene,
2-[1-fluoro-3-(2-propenyloxy)naphthalen-7-yl]-6-butyl-trans-decahydronaphthalene,
2-[1-fluoro-3-(2-propenyloxy)naphthalen-7-yl]-6-pentyl-trans-decahydronaphthalene,
2-[1-fluoro-3-(2-propenyloxy)naphthalen-7-yl]-6-hexyl-trans-decahydronaphthalene,
2-[1-fluoro-3-(2-propenyloxy)naphthalen-7-yl]-6-heptyl-trans-decahydronaphthalene,
2-[1-fluoro-3-(trans-2-butenyloxy)naphthalen-7-yl]-6-methyl-trans-decahydronaphthalene,
2-[1-fluoro-3-(trans-2-butenyloxy)naphthalen-7-yl]-6-ethyl-trans-decahydronaphthalene,
2-[1-fluoro-3-(trans-2-butenyloxy)naphthalen-7-yl]-6-propyl-trans-decahydronaphthalene,
2-[1-fluoro-3-(trans-2-butenyloxy)naphthalen-7-yl]-6-butyl-trans-decahydronaphthalene,
2-[1-fluoro-3-(trans-2-butenyloxy)naphthalen-7-yl]-6-pentyl-trans-decahydronaphthalene,
2-[1-fluoro-3-(trans-2-butenyloxy)naphthalen-7-yl]-6-hexyl-trans-decahydronaphthalene,
2-[1-fluoro-3-(trans-2-butenyloxy)naphthalen-7-yl]-6-heptyl-trans-decahydronaphthalene,
2-[1,2-difluoro-3-(3-butenyl)naphthalen-7-yl]-6-methyl-trans-decahydronaphthalene,
2-[1,2-difluoro-3-(3-butenyl)naphthalen-7-yl]-6-ethyl-trans-decahydronaphthalene,
2-[1,2-difluoro-3-(3-butenyl)naphthalen-7-yl]-6-propyl-trans-decahydronaphthalene,
2-[1,2-difluoro-3-(3-butenyl)naphthalen-7-yl]-6-butyl-trans-decahydronaphthalene,
2-[1,2-difluoro-3-(3-butenyl)naphthalen-7-yl]-6-pentyl-trans-decahydronaphthalene,
2-[1,2-difluoro-3-(3-butenyl)naphthalen-7-yl]-6-hexyl-trans-decahydronaphthalene,
2-[1,2-difluoro-3-(3-butenyl)naphthalen-7-yl]-6-heptyl-trans-decahydronaphthalene,
2-[1,2-difluoro-3-(trans-3-pentenyl)naphthalen-7-yl]-6-methyl-trans-decahydronaphthalene,
2-[1,2-difluoro-3-(trans-3-pentenyl)naphthalen-7-yl]-6-ethyl-trans-decahydronaphthalene,
2-[1,2-difluoro-3-(trans-3-pentenyl)naphthalen-7-yl]-6-propyl-trans-decahydronaphthalene,
2-[1,2-difluoro-3-(trans-3-pentenyl)naphthalen-7-yl]-6-butyl-trans-decahydronaphthalene,
2-[1,2-difluoro-3-(trans-3-pentenyl)naphthalen-7-yl]-6-pentyl-trans-decahydronaphthalene,
2-[1,2-difluoro-3-(trans-3-pentenyl)naphthalen-7-yl]-6-hexyl-trans-decahydronaphthalene,
2-[1,2-difluoro-3-(trans-3-pentenyl)naphthalen-7-yl]-6-heptyl-trans-decahydronaphthalene,
2-(1,2-difluoro-3-methoxynaphthalen-7-yl)-6-methyl-trans-decahydronaphthalene,
2-(1,2-difluoro-3-methoxynaphthalen-7-yl)-6-ethyl-trans-decahydronaphthalene,
2-(1,2-difluoro-3-methoxynaphthalen-7-yl)-6-propyl-trans-decahydronaphthalene,
2-(1,2-difluoro-3-methoxynaphthalen-7-yl)-6-butyl-trans-decahydronaphthalene,
2-(1,2-difluoro-3-methoxynaphthalen-7-yl)-6-pentyl-trans-decahydronaphthalene, 2-(1,2-difluoro-3-methoxynaphthalen-7-yl)-6-hexyl-trans-decahydronaphthalene,
2-(1,2-difluoro-3-methoxynaphthalen-7-yl)-6-heptyl-trans-decahydronaphthalene,
2-[1,2-difluoro-3-(2-propenyloxy)naphthalen-7-yl]-6-methyl-trans-decahydronaphthalene,
2-[1,2-difluoro-3-(2-propenyloxy)naphthalen-7-yl]-6-ethyl-trans-decahydronaphthalene,
2-[1,2-difluoro-3-(2-propenyloxy)naphthalen-7-yl]-6-propyl-trans-decahydronaphthalene,
2-[1,2-difluoro-3-(2-propenyloxy)naphthalen-7-yl]-6-butyl-trans-decahydronaphthalene,
2-(1,2-difluoro-3-(2-propenyloxy)naphthalen-7-yl]-6-pentyl-trans-decahydronaphthalene,
2-[1,2-difluoro-3-(2-propenyloxy)naphthalen-7-yl]-6-hexyl-trans-decahydronaphthalene,
2-[1,2-difluoro-3-(2-propenyloxy)naphthalen-7-yl]-6-heptyl-trans-decahydronaphthalene,
2-[1,2-difluoro-3-(trans-2-butenyloxy)naphthalen-7-yl]-6-methyl-trans-decahydronaphthalene,
2-[1,2-difluoro-3-(trans-2-butenyloxy)naphthalen-7-yl]-6-ethyl-trans-decahydronaphthalene,
2-[1,2-difluoro-3-(trans-2-butenyloxy)naphthalen-7-yl]-6-propyl-trans-decahydronaphthalene,
2-[1,2-difluoro-3-(trans-2-butenyloxy)naphthalen-7-yl]-6-butyl-trans-decahydronaphthalene,
2-[1,2-difluoro-3-(trans-2-butenyloxy)naphthalen-7-yl]-6-pentyl-trans-decahydronaphthalene,
2-(1,2-difluoro-3-(trans-2-butenyloxy)naphthalen-7-yl]-6-hexyl-trans-decahydronaphthalene,
2-[1,2-difluoro-3-(trans-2-butenyloxy)naphthalen-7-yl]-6-heptyl-trans-decahydronaphthalene,
2-[1-fluoro-7-(3-butenyl)naphthalen-3-yl]-6-methyl-trans-decahydronaphthalene,
2-[1-fluoro-7-(3-butenyl)naphthalen-3-yl]-6-ethyl-trans-decahydronaphthalene,
2-[1-fluoro-7-(3-butenyl)naphthalen-3-yl]-6-propyl-trans-decahydronaphthalene,
2-[1-fluoro-7-(3-butenyl)naphthalen-3-yl]-6-butyl-trans-decahydronaphthalene,
2-[1-fluoro-7-(3-butenyl)naphthalen-3-yl]-6-pentyl-trans-decahydronaphthalene,
2-[1-fluoro-7-(3-butenyl)naphthalen-3-yl]-6-hexyl-trans-decahydronaphthalene,
2-[1-fluoro-7-(3-butenyl)naphthalen-3-yl]-6-heptyl-trans-decahydronaphthalene,
2-[1-fluoro-7-(trans-3-pentenyl)naphthalen-3-yl]-6-methyl-trans-decahydronaphthalene,
2-[1-fluoro-7-(trans-3-pentenyl)naphthalen-3-yl]-6-ethyl-trans-decahydronaphthalene,
2-[1-fluoro-7-(trans-3-pentenyl)naphthalen-3-yl]-6-propyl-trans-decahydronaphthalene,
2-[1-fluoro-7-(trans-3-pentenyl)naphthalen-3-yl]-6-butyl-trans-decahydronaphthalene,
2-[1-fluoro-7-(trans-3-pentenyl)naphthalen-3-yl]-6-pentyl-trans-decahydronaphthalene,
2-[1-fluoro-7-(trans-3-pentenyl)naphthalen-3-yl]-6-hexyl-trans-decahydronaphthalene,
2-[1-fluoro-7-(trans-3-pentenyl)naphthalen-3-yl]-6-heptyl-trans-decahydronaphthalene,
2-(1-fluoro-3-methoxynaphthalen-7-yl)-6-methyl-trans-decahydronaphthalene,
2-(1-fluoro-3-methoxynaphthalen-7-yl)-6-ethyl-trans-decahydronaphthalene,
2-(1-fluoro-3-methoxynaphthalen-7-yl)-6-propyl-trans-decahydronaphthalene,
2-(1-fluoro-3-methoxynaphthalen-7-yl)-6-butyl-trans-decahydronaphthalene,
2-(1-fluoro-3-methoxynaphthalen-7-yl)-6-pentyl-trans-decahydronaphthalene,
2-(1-fluoro-3-methoxynaphthalen-7-yl)-6-hexyl-trans-decahydronaphthalene,
2-(1-fluoro-3-methoxynaphthalen-7-yl)-6-heptyl-trans-decahydronaphthalene,
2-[1-fluoro-3-(2-propenyloxy)naphthalen-7-yl]-6-methyl-trans-decahydronaphthalene,
2-[1-fluoro-3-(2-propenyloxy)naphthalen-7-yl]-6-ethyl-trans-decahydronaphthalene,
2-[1-fluoro-3-(2-propenyloxy)naphthalen-7-yl]-6-propyl-trans-decahydronaphthalene,
2-[1-fluoro-3-(2-propenyloxy)naphthalen-7-yl]-6-butyl-trans-decahydronaphthalene,
2-[1-fluoro-3-(2-propenyloxy)naphthalen-7-yl]-6-pentyl-trans-decahydronaphthalene,
2-[1-fluoro-3-(2-propenyloxy)naphthalen-7-yl]-6-hexyl-trans-decahydronaphthalene,
2-[1-fluoro-3-(2-propenyloxy)naphthalen-7-yl]-6-heptyl-trans-decahydronaphthalene,
2-[1-fluoro-3-(trans-2-butenyloxy)naphthalen-7-yl]-6-methyl-trans-decahydronaphthalene,
2-[1-fluoro-3-(trans-2-butenyloxy)naphthalen-7-yl]-6-ethyl-trans-decahydronaphthalene,
2-[1-fluoro-3-(trans-2-butenyloxy)naphthalen-7-yl]-6-propyl-trans-decahydronaphthalene, 2-[1-fluoro-3-(trans-2-butenyloxy)naphthalen-7-yl]-6-butyl-trans-decahydronaphthalene,
2-[1-fluoro-3-(trans-2-butenyloxy)naphthalen-7-yl]-6-pentyl-trans-decahydronaphthalene,
2-[1-fluoro-3-(trans-2-butenyloxy)naphthalen-7-yl]-6-hexyl-trans-decahydronaphthalene,
2-[1-fluoro-3-(trans-2-butenyloxy)naphthalen-7-yl]-6-heptyl-trans-decahydronaphthalene,
2-[1,8-difluoro-6-(3-butenyl)naphthalen-2-yl]-6-methyl-trans-decahydronaphthalene,
2-[1,8-difluoro-6-(3-butenyl)naphthalen-2-yl]-6-ethyl-trans-decahydronaphthalene,
2-(1,8-difluoro-6-(3-butenyl)naphthalen-2-yl]-6-propyl-trans-decahydronaphthalene,
2-[1,8-difluoro-6-(3-butenyl)naphthalen-2-yl]-6-butyl-trans-decahydronaphthalene,
2-[1,8-difluoro-6-(3-butenyl)naphthalen-2-yl]-6-pentyl-trans-decahydronaphthalene,
2-[1,8-difluoro-6-(3-butenyl)naphthalen-2-yl]-6-hexyl-trans-decahydronaphthalene,
2-[1,8-difluoro-6-(3-butenyl)naphthalen-2-yl]-6-heptyl-trans-decahydronaphthalene,
2-[1,8-difluoro-6-(trans-3-pentenyl)naphthalen-2-yl)-6-methyl-trans-decahydronaphthalene,
2-[1,8-difluoro-6-(trans-3-pentenyl)naphthalen-2-yl]-6-ethyl-trans-decahydronaphthalene,
2-[1,8-difluoro-6-(trans-3-pentenyl)naphthalen-2-yl]-6-propyl-trans-decahydronaphthalene,
2-[1,8-difluoro-6-(trans-3-pentenyl)naphthalen-2-yl]-6-butyl-trans-decahydronaphthalene,
2-[1,8-difluoro-6-(trans-3-pentenyl)naphthalen-2-yl]-6-pentyl-trans-decahydronaphthalene,
2-[1,8-difluoro-6-(trans-3-pentenyl)naphthalen-2-yl]-6-hexyl-trans-decahydronaphthalene,
2-[1,8-difluoro-6-(trans-3-pentenyl)naphthalen-2-yl]-6-heptyl-trans-decahydronaphthalene,
2-(1,8-difluoro-6-methoxynaphthalen-2-yl)-6-methyl-trans-decahydronaphthalene,
2-(1,8-difluoro-6-methoxynaphthalen-2-yl)-6-ethyl-trans-decahydronaphthalene,
2-(1,8-difluoro-6-methoxynaphthalen-2-yl)-6-propyl-trans-decahydronaphthalene,
2-(1,8-difluoro-6-methoxynaphthalen-2-yl)-6-butyl-trans-decahydronaphthalene,
2-(1,8-difluoro-6-methoxynaphthalen-2-yl)-6-pentyl-trans-decahydronaphthalene,
2-(1,8-difluoro-6-methoxynaphthalen-2-yl)-6-hexyl-trans-decahydronaphthalene,
2-(1,8-difluoro-6-methoxynaphthalen-2-yl)-6-heptyl-trans-decahydronaphthalene,
2-(1,8-difluoro-6-(2-propenyloxy)naphthalen-2-yl]-6-methyl-trans-decahydronaphthalene,
2-[1,8-difluoro-6-(2-propenyloxy)naphthalen-2-yl]-6-ethyl-trans-decahydronaphthalene,
2-[1,8-difluoro-6-(2-propenyloxy)naphthalen-2-yl]-6-propyl-trans-decahydronaphthalene,
2-[1,8-difluoro-6-(2-propenyloxy)naphthalen-2-yl)-6-butyl-trans-decahydronaphthalene,
2-[1,8-difluoro-6-(2-propenyloxy)naphthalen-2-yl]-6-pentyl-trans-decahydronaphthalene,
2-(1,8-difluoro-6-(2-propenyloxy)naphthalen-2-yl]-6-hexyl-trans-decahydronaphthalene,
2-[1,8-difluoro-6-(2-propenyloxy)naphthalen-2-yl]-6-heptyl-trans-decahydronaphthalene,
2-[1,8-difluoro-6-(trans-2-butenyloxy)naphthalen-2-yl]-6-methyl-trans-decahydronaphthalene,
2-[1,8-difluoro-6-(trans-2-butenyloxy)naphthalen-2-yl]-6-ethyl-trans-decahydronaphthalene,
2-[1,8-difluoro-6-(trans-2-butenyloxy)naphthalen-2-yl]-6-propyl-trans-decahydronaphthalene,
2-[1,8-difluoro-6-(trans-2-butenyloxy)naphthalen-2-yl]-6-butyl-trans-decahydronaphthalene,
2-[1,8-difluoro-6-(trans-2-butenyloxy)naphthalen-2-yl]-6-pentyl-trans-decahydronaphthalene,
2-[1,8-difluoro-6-(trans-2-butenyloxy)naphthalen-2-yl]-6-hexyl-trans-decahydronaphthalene,
2-[1,8-difluoro-6-(trans-2-butenyloxy)naphthalen-2-yl]-6-heptyl-trans-decahydronaphthalene,
2-[1,6-difluoro-3-(3-butenyl)naphthalen-7-yl]-6-methyl-trans-decahydronaphthalene,
2-[1,6-difluoro-3-(3-butenyl)naphthalen-7-yl]-6-ethyl-trans-decahydronaphthalene,
2-[1,6-difluoro-3-(3-butenyl)naphthalen-7-yl]-6-propyl-trans-decahydronaphthalene,
2-[1,6-difluoro-3-(3-butenyl)naphthalen-7-yl]-6-butyl-trans-decahydronaphthalene,
2-[1,6-difluoro-3-(3-butenyl)naphthalen-7-yl]-6-pentyl-trans-decahydronaphthalene,
2-(1,6-difluoro-3-(3-butenyl)naphthalen-7-yl]-6-hexyl-trans-decahydronaphthalene,
2-[1,6-difluoro-3-(3-butenyl)naphthalen-7-yl]-6-heptyl-trans-decahydronaphthalene,
2-[1,6-difluoro-3-(trans-3-pentenyl)naphthalen-7-yl]-6-methyl-trans-decahydronaphthalene,
2-[1,6-difluoro-3-(trans-3-pentenyl)naphthalen-7-yl]-6-ethyl-trans-decahydronaphthalene,
2-[1,6-difluoro-3-(trans-3-pentenyl)naphthalen-7-yl]-6-propyl-trans-decahydronaphthalene,
2-[1,6-difluoro-3-(trans-3-pentenyl)naphthalen-7-yl]-6-butyl-trans-decahydronaphthalene,
2-[1,6-difluoro-3-(trans-3-pentenyl)naphthalen-7-yl]-6-pentyl-trans-decahydronaphthalene,
2-[1,6-difluoro-3-(trans-3-pentenyl)naphthalen-7-yl]-6-hexyl-trans-decahydronaphthalene,
2-[1,6-difluoro-3-(trans-3-pentenyl)naphthalen-7-yl]-6-heptyl-trans-decahydronaphthalene,
2-(1,6-difluoro-3-methoxynaphthalen-7-yl)-6-methyl-trans-decahydronaphthalene,
2-(1,6-difluoro-3-methoxynaphthalen-7-yl)-6-ethyl-trans-decahydronaphthalene,
2-(1,6-difluoro-3-methoxynaphthalen-7-yl)-6-propyl-trans-decahydronaphthalene,
2-(1,6-difluoro-3-methoxynaphthalen-7-yl)-6-butyl-trans-decahydronaphthalene,
2-(1,6-difluoro-3-methoxynaphthalen-7-yl)-6-pentyl-trans-decahydronaphthalene,
2-(1,6-difluoro-3-methoxynaphthalen-7-yl)-6-hexyl-trans-decahydronaphthalene,
2-(1,6-difluoro-3-methoxynaphthalen-7-yl)-6-heptyl-trans-decahydronaphthalene,
2-[1,6-difluoro-3-(2-propenyloxy)naphthalen-7-yl]-6-methyl-trans-decahydronaphthalene,
2-[1,6-difluoro-3-(2-propenyloxy)naphthalen-7-yl]-6-ethyl-trans-decahydronaphthalene,
2-[1,6-difluoro-3-(2-propenyloxy)naphthalen-7-yl]-6-propyl-trans-decahydronaphthalene,
2-[1,6-difluoro-3-(2-propenyloxy)naphthalen-7-yl]-6-butyl-trans-decahydronaphthalene,
2-[1,6-difluoro-3-(2-propenyloxy)naphthalen-7-yl]-6-pentyl-trans-decahydronaphthalene,
2-[1,6-difluoro-3-(2-propenyloxy)naphthalen-7-yl]-6-hexyl-trans-decahydronaphthalene,
2-[1,6-difluoro-3-(2-propenyloxy)naphthalen-7-yl]-6-heptyl-trans-decahydronaphthalene,
2-[1,6-difluoro-3-(trans-2-butenyloxy)naphthalen-7-yl]-6-methyl-trans-decahydronaphthalene, 2-[1,6-difluoro-3-(trans-2-butenyloxy)naphthalen-7-yl]-6-ethyl-trans-decahydronaphthalene,
2-[1,6-difluoro-3-(trans-2-butenyloxy)naphthalen-7-yl]-6-propyl-trans-decahydronaphthalene,
2-[1,6-difluoro-3-(trans-2-butenyloxy)naphthalen-7-yl]-6-butyl-trans-decahydronaphthalene,
2-[1,6-difluoro-3-(trans-2-butenyloxy)naphthalen-7-yl)-6-pentyl-trans-decahydronaphthalene,
2-[1,6-difluoro-3-(trans-2-butenyloxy)naphthalen-7-yl]-6-hexyl-trans-decahydronaphthalene,
2-(1,6-difluoro-3-(trans-2-butenyloxy)naphthalen-7-yl]-6-heptyl-trans-decahydronaphthalene,
2-[1,3,8-trifluoro-6-(3-butenyl)naphthalen-2-yl]-6-methyl-trans-decahydronaphthalene,
2-[1,3,8-trifluoro-6-(3-butenyl)naphthalen-2-yl]-6-ethyl-trans-decahydronaphthalene,
2-[1,3,8-trifluoro-6-(3-butenyl)naphthalen-2-yl]-6-propyl-trans-decahydronaphthalene,
2-[1,3,8-trifluoro-6-(3-butenyl)naphthalen-2-yl]-6-butyl-trans-decahydronaphthalene,
2-[1,3,8-trifluoro-6-(3-butenyl)naphthalen-2-yl]-6-pentyl-trans-decahydronaphthalene,
2-[1,3,8-trifluoro-6-(3-butenyl)naphthalen-2-yl]-6-hexyl-trans-decahydronaphthalene,
2-[1,3,8-trifluoro-6-(3-butenyl)naphthalen-2-yl]-6-heptyl-trans-decahydronaphthalene,
2-[1,3,8-trifluoro-6-(trans-3-pentenyl)naphthalen-2-yl]-6-methyl-trans-decahydronaphthalene,
2-[1,3,8-trifluoro-6-(trans-3-pentenyl)naphthalen-2-yl]-6-ethyl-trans-decahydronaphthalene,
2-[1,3,8-trifluoro-6-(trans-3-pentenyl)naphthalen-2-yl]-6-propyl-trans-decahydronaphthalene,
2-[1,3,8-trifluoro-6-(trans-3-pentenyl)naphthalen-2-yl]-6-butyl-trans-decahydronaphthalene,
2-[1,3,8-trifluoro-6-(trans-3-pentenyl)naphthalen-2-yl]-6-pentyl-trans-decahydronaphthalene,
2-[1,3,8-trifluoro-6-(trans-3-pentenyl)naphthalen-2-yl]-6-hexyl-trans-decahydronaphthalene,
2-[1,3,8-trifluoro-6-(trans-3-pentenyl)naphthalen-2-yl]-6-heptyl-trans-decahydronaphthalene,
2-(1,3,8-trifluoro-6-methoxynaphthalen-2-yl)-6-methyl-trans-decahydronaphthalene,
2-(1,3,8-trifluoro-6-methoxynaphthalen-2-yl)-6-ethyl-trans-decahydronaphthalene,
2-(1,3,8-trifluoro-6-methoxynaphthalen-2-yl)-6-propyl-trans-decahydronaphthalene,
2-(1,3,8-trifluoro-6-methoxynaphthalen-2-yl)-6-butyl-trans-decahydronaphthalene,
2-(1,3,8-trifluoro-6-methoxynaphthalen-2-yl)-6-pentyl-trans-decahydronaphthalene,
2-(1,3,8-trifluoro-6-methoxynaphthalen-2-yl)-6-hexyl-trans-decahydronaphthalene,
2-(1,3,8-trifluoro-6-methoxynaphthalen-2-yl)-6-heptyl-trans-decahydronaphthalene,
2-[1,3,8-trifluoro-6-(2-propenyloxy)naphthalen-2-yl]-6-methyl-trans-decahydronaphthalene,
2-[1,3,8-trifluoro-6-(2-propenyloxy)naphthalen-2-yl]-6-ethyl-trans-decahydronaphthalene,
2-[1,3,8-trifluoro-6-(2-propenyloxy)naphthalen-2-yl]-6-propyl-trans-decahydronaphthalene,
2-[1,3,8-trifluoro-6-(2-propenyloxy)naphthalen-2-yl]-6-butyl-trans-decahydronaphthalene,
2-[1,3,8-trifluoro-6-(2-propenyloxy)naphthalen-2-yl]-6-pentyl-trans-decahydronaphthalene,
2-[1,3,8-trifluoro-6-(2-propenyloxy)naphthalen-2-yl]-6-hexyl-trans-decahydronaphthalene,
2-[1,3,8-trifluoro-6-(2-propenyloxy)naphthalen-2-yl]-6-heptyl-trans-decahydronaphthalene,
2-[1,3,8-trifluoro-6-(trans-2-butenyloxy)naphthalen-2-yl]-6-methyl-trans-decahydronaphthalene,
2-[1,3,8-trifluoro-6-(trans-2-butenyloxy)naphthalen-2-yl]-6-ethyl-trans-decahydronaphthalene,
2-[1,3,8-trifluoro-6-(trans-2-butenyloxy)naphthalen-2-yl]-6-propyl-trans-decahydronaphthalene,
2-[1,3,8-trifluoro-6-(trans-2-butenyloxy)naphthalen-2-yl]-6-butyl-trans-decahydronaphthalene,
2-[1,3,8-trifluoro-6-(trans-2-butenyloxy)naphthalen-2-yl]-6-pentyl-trans-decahydronaphthalene,
2-[1,3,8-trifluoro-6-(trans-2-butenyloxy)naphthalen-2-yl]-6-hexyl-trans-decahydronaphthalene,
2-[1,3,8-trifluoro-6-(trans-2-butenyloxy)naphthalen-2-yl]-6-heptyl-trans-decahydronaphthalene,
2-[3-fluoro-2-(3-butenyl)naphthalen-6-yl]-6-methyl-trans-decahydronaphthalene,
2-[3-fluoro-2-(3-butenyl)naphthalen-6-yl]-6-ethyl-trans-decahydronaphthalene,
2-[3-fluoro-2-(3-butenyl)naphthalen-6-yl]-6-propyl-trans-decahydronaphthalene,
2-[3-fluoro-2-(3-butenyl)naphthalen-6-yl]-6-butyl-trans-decahydronaphthalene,
2-[3-fluoro-2-(3-butenyl)naphthalen-6-yl]-6-pentyl-trans-decahydronaphthalene,
2-[3-fluoro-2-(3-butenyl)naphthalen-6-yl]-6-hexyl-trans-decahydronaphthalene,
2-[3-fluoro-2-(3-butenyl)naphthalen-6-yl]-6-heptyl-trans-decahydronaphthalene,
2-[3-fluoro-2-(trans-3-pentenyl)naphthalen-6-yl]-6-methyl-trans-decahydronaphthalene,
2-[3-fluoro-2-(trans-3-pentenyl)naphthalen-6-yl]-6-ethyl-trans-decahydronaphthalene,
2-[3-fluoro-2-(trans-3-pentenyl)naphthalen-6-yl]-6-propyl-trans-decahydronaphthalene,
2-[3-fluoro-2-(trans-3-pentenyl)naphthalen-6-yl]-6-butyl-trans-decahydronaphthalene,
2-[3-fluoro-2-(trans-3-pentenyl)naphthalen-6-yl]-6-pentyl-trans-decahydronaphthalene,
2-[3-fluoro-2-(trans-3-pentenyl)naphthalen-6-yl]-6-hexyl-trans-decahydronaphthalene,
2-[3-fluoro-2-(trans-3-pentenyl)naphthalen-6-yl]-6-heptyl-trans-decahydronaphthalene,
2-(3-fluoro-2-methoxynaphthalen-6-yl)-6-methyl-trans-decahydronaphthalene,
2-(3-fluoro-2-methoxynaphthalen-6-yl)-6-ethyl-trans-decahydronaphthalene,
2-(3-fluoro-2-methoxynaphthalen-6-yl)-6-propyl-trans-decahydronaphthalene,
2-(3-fluoro-2-methoxynaphthalen-6-yl)-6-butyl-trans-decahydronaphthalene,
2-(3-fluoro-2-methoxynaphthalen-6-yl)-6-pentyl-trans-decahydronaphthalene,
2-(3-fluoro-2-methoxynaphthalen-6-yl)-6-hexyl-trans-decahydronaphthalene,
2-(3-fluoro-2-methoxynaphthalen-6-yl)-6-heptyl-trans-decahydronaphthalene,
2-[3-fluoro-2-(2-propenyloxy)naphthalen-6-yl]-6-methyl-trans-decahydronaphthalene,
2-[3-fluoro-2-(2-propenyloxy)naphthalen-6-yl]-6-ethyl-trans-decahydronaphthalene,
2-[3-fluoro-2-(2-propenyloxy)naphthalen-6-yl]-6-propyl-trans-decahydronaphthalene,
2-[3-fluoro-2-(2-propenyloxy)naphthalen-6-yl]-6-butyl-trans-decahydronaphthalene,
2-[3-fluoro-2-(2-propenyloxy)naphthalen-6-yl]-6-pentyl-trans-decahydronaphthalene,
2-[3-fluoro-2-(2-propenyloxy)naphthalen-6-yl]-6-hexyl-trans-decahydronaphthalene, 2-[3-fluoro-2-(2-propenyloxy)naphthalen-6-yl]-6-heptyl-trans-decahydronaphthalene,
2-[3-fluoro-2-(trans-2-butenyloxy)naphthalen-6-yl]-6-methyl-trans-decahydronaphthalene,
2-[3-fluoro-2-(trans-2-butenyloxy)naphthalen-6-yl]-6-ethyl-trans-decahydronaphthalene,
2-[3-fluoro-2-(trans-2-butenyloxy)naphthalen-6-yl]-6-propyl-trans-decahydronaphthalene,
2-[3-fluoro-2-(trans-2-butenyloxy)naphthalen-6-yl]-6-butyl-trans-decahydronaphthalene,
2-[3-fluoro-2-(trans-2-butenyloxy)naphthalen-6-yl]-6-pentyl-trans-decahydronaphthalene,
2-[3-fluoro-2-(trans-2-butenyloxy)naphthalen-6-yl]-6-hexyl-trans-decahydronaphthalene,
2-[3-fluoro-2-(trans-2-butenyloxy)naphthalen-6-yl]-6-heptyl-trans-decahydronaphthalene,
2-[1,7-difluoro-6-(3-butenyl)naphthalen-2-yl]-6-methyl-trans-decahydronaphthalene,
2-[1,7-difluoro-6-(3-butenyl)naphthalen-2-yl]-6-ethyl-trans-decahydronaphthalene,
2-[1,7-difluoro-6-(3-butenyl)naphthalen-2-yl]-6-propyl-trans-decahydronaphthalene,
2-[1,7-difluoro-6-(3-butenyl)naphthalen-2-yl]-6-butyl-trans-decahydronaphthalene,
2-[1,7-difluoro-6-(3-butenyl)naphthalen-2-yl]-6-pentyl-trans-decahydronaphthalene,
2-[1,7-difluoro-6-(3-butenyl)naphthalen-2-yl]-6-hexyl-trans-decahydronaphthalene,
2-[1,7-difluoro-6-(3-butenyl)naphthalen-2-yl]-6-heptyl-trans-decahydronaphthalene,
2-[1,7-difluoro-6-(trans-3-pentenyl)naphthalen-2-yl]-6-methyl-trans-decahydronaphthalene,
2-[1,7-difluoro-6-(trans-3-pentenyl)naphthalen-2-yl]-6-ethyl-trans-decahydronaphthalene,
2-[1,7-difluoro-6-(trans-3-pentenyl)naphthalen-2-yl]-6-propyl-trans-decahydronaphthalene,
2-[1,7-difluoro-6-(trans-3-pentenyl)naphthalen-2-yl]-6-butyl-trans-decahydronaphthalene,
2-[1,7-difluoro-6-(trans-3-pentenyl)naphthalen-2-yl]-6-pentyl-trans-decahydronaphthalene,
2-[1,7-difluoro-6-(trans-3-pentenyl)naphthalen-2-yl]-6-hexyl-trans-decahydronaphthalene,
2-[1,7-difluoro-6-(trans-3-pentenyl)naphthalen-2-yl]-6-heptyl-trans-decahydronaphthalene,
2-(1,7-difluoro-6-methoxynaphthalen-2-yl)-6-methyl-trans-decahydronaphthalene,
2-(1,7-difluoro-6-methoxynaphthalen-2-yl)-6-ethyl-trans-decahydronaphthalene,
2-(1,7-difluoro-6-methoxynaphthalen-2-yl)-6-propyl-trans-decahydronaphthalene,
2-(1,7-difluoro-6-methoxynaphthalen-2-yl)-6-butyl-trans-decahydronaphthalene,
2-(1,7-difluoro-6-methoxynaphthalen-2-yl)-6-pentyl-trans-decahydronaphthalene,
2-(1,7-difluoro-6-methoxynaphthalen-2-yl)-6-hexyl-trans-decahydronaphthalene,
2-(1,7-difluoro-6-methoxynaphthalen-2-yl)-6-heptyl-trans-decahydronaphthalene,
2-[1,7-difluoro-6-(2-propenyloxy)naphthalen-2-yl]-6-methyl-trans-decahydronaphthalene,
2-[1,7-difluoro-6-(2-propenyloxy)naphthalen-2-yl]-6-ethyl-trans-decahydronaphthalene,
2-[1,7-difluoro-6-(2-propenyloxy)naphthalen-2-yl]-6-propyl-trans-decahydronaphthalene,
2-[1,7-difluoro-6-(2-propenyloxy)naphthalen-2-yl]-6-butyl-trans-decahydronaphthalene,
2-[1,7-difluoro-6-(2-propenyloxy)naphthalen-2-yl]-6-pentyl-trans-decahydronaphthalene,
2-[1,7-difluoro-6-(2-propenyloxy)naphthalen-2-yl]-6-hexyl-trans-decahydronaphthalene,
2-[1,7-difluoro-6-(2-propenyloxy)naphthalen-2-yl]-6-heptyl-trans-decahydronaphthalene,
2-[1,7-difluoro-6-(trans-2-butenyloxy)naphthalen-2-yl]-6-methyl-trans-decahydronaphthalene,
2-[1,7-difluoro-6-(trans-2-butenyloxy)naphthalen-2-yl]-6-ethyl-trans-decahydronaphthalene,
2-[1,7-difluoro-6-(trans-2-butenyloxy)naphthalen-2-yl]-6-propyl-trans-decahydronaphthalene,
2-[1,7-difluoro-6-(trans-2-butenyloxy)naphthalen-2-yl]-6-butyl-trans-decahydronaphthalene,
2-[1,7-di fluoro-6-(trans-2-butenyloxy)naphthalen-2-yl]-6-pentyl-trans-decahydronaphthalene,
2-[1,7-difluoro-6-(trans-2-butenyloxy)naphthalen-2-yl]-6-hexyl-trans-decahydronaphthalene,
2-[1,7-difluoro-6-(trans-2-butenyloxy)naphthalen-2-yl]-6-heptyl-trans-decahydronaphthalene,
2-[1,2-difluoro-3-(3-butenyl)naphthalen-7-yl]-6-methyl-trans-decahydronaphthalene,
2-[1,2-difluoro-3-(3-butenyl)naphthalen-7-yl]-6-ethyl-trans-decahydronaphthalene,
2-[1,2-difluoro-3-(3-butenyl)naphthalen-7-yl]-6-propyl-trans-decahydronaphthalene,
2-[1,2-difluoro-3-(3-butenyl)naphthalen-7-yl]-6-butyl-trans-decahydronaphthalene,
2-[1,2-difluoro-3-(3-butenyl)naphthalen-7-yl]-6-pentyl-trans-decahydronaphthalene,
2-[1,2-difluoro-3-(3-butenyl)naphthalen-7-yl]-6-hexyl-trans-decahydronaphthalene,
2-[1,2-difluoro-3-(3-butenyl)naphthalen-7-yl]-6-heptyl-trans-decahydronaphthalene,
2-[1,2-difluoro-3-(trans-3-pentenyl)naphthalen-7-yl]-6-methyl-trans-decahydronaphthalene,
2-[1,2-difluoro-3-(trans-3-pentenyl)naphthalen-7-yl]-6-ethyl-trans-decahydronaphthalene,
2-[1,2-difluoro-3-(trans-3-pentenyl)naphthalen-7-yl]-6-propyl-trans-decahydronaphthalene,
2-[1,2-difluoro-3-(trans-3-pentenyl)naphthalen-7-yl]-6-butyl-trans-decahydronaphthalene,
2-[1,2-difluoro-3-(trans-3-pentenyl)naphthalen-7-yl]-6-pentyl-trans-decahydronaphthalene,
2-[1,2-difluoro-3-(trans-3-pentenyl)naphthalen-7-yl]-6-hexyl-trans-decahydronaphthalene,
2-[1,2-difluoro-3-(trans-3-pentenyl)naphthalen-7-yl]-6-heptyl-trans-decahydronaphthalene,
2-(1,2-difluoro-3-methoxynaphthalen-7-yl)-6-methyl-trans-decahydronaphthalene,
2-(1,2-difluoro-3-methoxynaphthalen-7-yl)-6-ethyl-trans-decahydronaphthalene,
2-(1,2-difluoro-3-methoxynaphthalen-7-yl)-6-propyl-trans-decahydronaphthalene,
2-(1,2-difluoro-3-methoxynaphthalen-7-yl)-6-butyl-trans-decahydronaphthalene,
2-(1,2-difluoro-3-methoxynaphthalen-7-yl)-6-pentyl-trans-decahydronaphthalene,
2-(1,2-difluoro-3-methoxynaphthalen-7-yl)-6-hexyl-trans-decahydronaphthalene,
2-(1,2-difluoro-3-methoxynaphthalen-7-yl)-6-heptyl-trans-decahydronaphthalene,
2-[1,2-difluoro-3-(2-propenyloxy)naphthalen-7-yl]-6-methyl-trans-decahydronaphthalene,
2-[1,2-difluoro-3-(2-propenyloxy)naphthalen-7-yl]-6-ethyl-trans-decahydronaphthalene,
2-[1,2-difluoro-3-(2-propenyloxy)naphthalen-7-yl]-6-propyl-trans-decahydronaphthalene,
2-[1,2-difluoro-3-(2-propenyloxy)naphthalen-7-yl]-6-butyl-trans-decahydronaphthalene, 2-[1,2-difluoro-3-(2-propenyloxy)naphthalen-7-yl]-6-pentyl-trans-decahydronaphthalene,
2-[1,2-difluoro-3-(2-propenyloxy)naphthalen-7-yl]-6-hexyl-trans-decahydronaphthalene,
2-[1,2-difluoro-3-(2-propenyloxy)naphthalen-7-yl]-6-heptyl-trans-decahydronaphthalene,
2-[1,2-difluoro-3-(trans-2-butenyloxy)naphthalen-7-yl]-6-methyl-trans-decahydronaphthalene,
2-[1,2-difluoro-3-(trans-2-butenyloxy)naphthalen-7-yl]-6-ethyl-trans-decahydronaphthalene,
2-[1,2-difluoro-3-(trans-2-butenyloxy)naphthalen-7-yl]-6-propyl-trans-decahydronaphthalene,
2-[1,2-difluoro-3-(trans-2-butenyloxy)naphthalen-7-yl]-6-butyl-trans-decahydronaphthalene,
2-[1,2-difluoro-3-(trans-2-butenyloxy)naphthalen-7-yl]-6-pentyl-trans-decahydronaphthalene,
2-[1,2-difluoro-3-(trans-2-butenyloxy)naphthalen-7-yl]-6-hexyl-trans-decahydronaphthalene,
2-[1,2-difluoro-3-(trans-2-butenyloxy)naphthalen-7-yl)-6-heptyl-trans-decahydronaphthalene,
2-[1,2,8-trifluoro-3-(3-butenyl)naphthalen-7-yl]-6-methyl-trans-decahydronaphthalene,
2-(1,2,8-trifluoro-3-(3-butenyl)naphthalen-7-yl]-6-ethyl-trans-decahydronaphthalene,
2-[1,2,8-trifluoro-3-(3-butenyl)naphthalen-7-yl]-6-propyl-trans-decahydronaphthalene,
2-[1,2,8-trifluoro-3-(3-butenyl)naphthalen-7-yl]-6-butyl-trans-decahydronaphthalene,
2-[1,2,8-trifluoro-3-(3-butenyl)naphthalen-7-yl]-6-pentyl-trans-decahydronaphthalene,
2-[1,2,8-trifluoro-3-(3-butenyl)naphthalen-7-yl]-6-hexyl-trans-decahydronaphthalene,
2-[1,2,8-trifluoro-3-(3-butenyl)naphthalen-7-yl]-6-heptyl-trans-decahydronaphthalene,
2-[1,2,8-trifluoro-3-(trans-3-pentenyl)naphthalen-7-yl]-6-methyl-trans-decahydronaphthalene,
2-[1,2,8-trifluoro-3-(trans-3-pentenyl)naphthalen-7-yl]-6-ethyl-trans-decahydronaphthalene,
2-[1,2,8-trifluoro-3-(trans-3-pentenyl)naphthalen-7-yl]-6-propyl-trans-decahydronaphthalene,
2-[1,2,8-trifluoro-3-(trans-3-pentenyl)naphthalen-7-yl]-6-butyl-trans-decahydronaphthalene,
2-[1,2,8-trifluoro-3-(trans-3-pentenyl)naphthalen-7-yl]-6-pentyl-trans-decahydronaphthalene,
2-[1,2,8-trifluoro-3-(trans-3-pentenyl)naphthalen-7-yl]-6-hexyl-trans-decahydronaphthalene,
2-[1,2,8-trifluoro-3-(trans-3-pentenyl)naphthalen-7-yl]-6-heptyl-trans-decahydronaphthalene,
2-(1,2,8-trifluoro-3-methoxynaphthalen-7-yl)-6-methyl-trans-decahydronaphthalene,
2-(1,2,8-trifluoro-3-methoxynaphthalen-7-yl)-6-ethyl-trans-decahydronaphthalene,
2-(1,2,8-trifluoro-3-methoxynaphthalen-7-yl)-6-propyl-trans-decahydronaphthalene,
2-(1,2,8-trifluoro-3-methoxynaphthalen-7-yl)-6-butyl-trans-decahydronaphthalene,
2-(1,2,8-trifluoro-3-methoxynaphthalen-7-yl)-6-pentyl-trans-decahydronaphthalene,
2-(1,2,8-trifluoro-3-methoxynaphthalen-7-yl)-6-hexyl-trans-decahydronaphthalene,
2-(1,2,8-trifluoro-3-methoxynaphthalen-7-yl)-6-heptyl-trans-decahydronaphthalene,
2-[1,2,8-trifluoro-3-(2-propenyloxy)naphthalen-7-yl]-6-methyl-trans-decahydronaphthalene,
2-[1,2,8-trifluoro-3-(2-propenyloxy)naphthalen-7-yl]-6-ethyl-trans-decahydronaphthalene,
2-[1,2,8-trifluoro-3-(2-propenyloxy)naphthalen-7-yl]-6-propyl-trans-decahydronaphthalene,
2-[1,2,8-trifluoro-3-(2-propenyloxy)naphthalen-7-yl]-6-butyl-trans-decahydronaphthalene,
2-[1,2,8-trifluoro-3-(2-propenyloxy)naphthalen-7-yl]-6-pentyl-trans-decahydronaphthalene,
2-[1,2,8-trifluoro-3-(2-propenyloxy)naphthalen-7-yl]-6-hexyl-trans-decahydronaphthalene,
2-[1,2,8-trifluoro-3-(2-propenyloxy)naphthalen-7-yl]-6-heptyl-trans-decahydronaphthalene,
2-[1,2,8-trifluoro-3-(trans-2-butenyloxy)naphthalen-6-yl]-6-methyl-trans-decahydronaphthalene,
2-[1,2,8-trifluoro-3-(trans-2-butenyloxy)naphthalen-6-yl]-6-ethyl-trans-decahydronaphthalene,
2-[1,2,8-trifluoro-3-(trans-2-butenyloxy)naphthalen-6-yl]-6-propyl-trans-decahydronaphthalene,
2-[1,2,8-trifluoro-3-(trans-2-butenyloxy)naphthalen-6-yl]-6-butyl-trans-decahydronaphthalene,
2-[1,2,8-trifluoro-3-(trans-2-butenyloxy)naphthalen-6-yl]-6-pentyl-trans-decahydronaphthalene,
2-[1,2,8-trifluoro-3-(trans-2-butenyloxy)naphthalen-6-yl]-6-hexyl-trans-decahydronaphthalene,
2-[1,2,8-trifluoro-3-(trans-2-butenyloxy)naphthalen-6-yl]-6-heptyl-trans-decahydronaphthalene,
2-[1-fluoro-2-(3-butenyl)naphthalen-6-yl]-6-methyl-trans-decahydronaphthalene,
2-[1-fluoro-2-(3-butenyl)naphthalen-6-yl]-6-ethyl-trans-decahydronaphthalene,
2-[1-fluoro-2-(3-butenyl)naphthalen-6-yl]-6-propyl-trans-decahydronaphthalene,
2-[1-fluoro-2-(3-butenyl)naphthalen-6-yl]-6-butyl-trans-decahydronaphthalene,
2-[1-fluoro-2-(3-butenyl)naphthalen-6-yl]-6-pentyl-trans-decahydronaphthalene,
2-[1-fluoro-2-(3-butenyl)naphthalen-6-yl]-6-hexyl-trans-decahydronaphthalene,
2-[1-fluoro-2-(3-butenyl)naphthalen-6-yl]-6-heptyl-trans-decahydronaphthalene,
2-[1-fluoro-2-(trans-3-pentenyl)naphthalen-6-yl]-6-methyl-trans-decahydronaphthalene,
2-[1-fluoro-2-(trans-3-pentenyl)naphthalen-6-yl]-6-ethyl-trans-decahydronaphthalene,
2-[1-fluoro-2-(trans-3-pentenyl)naphthalen-6-yl]-6-propyl-trans-decahydronaphthalene,
2-[1-fluoro-2-(trans-3-pentenyl)naphthalen-6-yl]-6-butyl-trans-decahydronaphthalene,
2-[1-fluoro-2-(trans-3-pentenyl)naphthalen-6-yl]-6-pentyl-trans-decahydronaphthalene,
2-[1-fluoro-2-(trans-3-pentenyl)naphthalen-6-yl]-6-hexyl-trans-decahydronaphthalene,
2-[1-fluoro-2-(trans-3-pentenyl)naphthalen-6-yl]-6-heptyl-trans-decahydronaphthalene,
2-(1-fluoro-2-methoxynaphthalen-6-yl)-6-methyl-trans-decahydronaphthalene,
2-(1-fluoro-2-methoxynaphthalen-6-yl)-6-ethyl-trans-decahydronaphthalene,
2-(1-fluoro-2-methoxynaphthalen-6-yl)-6-propyl-trans-decahydronaphthalene,
2-(1-fluoro-2-methoxynaphthalen-6-yl)-6-butyl-trans-decahydronaphthalene,
2-(1-fluoro-2-methoxynaphthalen-6-yl)-6-pentyl-trans-decahydronaphthalene,
2-(1-fluoro-2-methoxynaphthalen-6-yl)-6-hexyl-trans-decahydronaphthalene,
2-(1-fluoro-2-methoxynaphthalen-6-yl)-6-heptyl-trans-decahydronaphthalene,
2-[1-fluoro-2-(2-propenyloxy)naphthalen-6-yl]-6-methyl-trans-decahydronaphthalene,
2-[1-fluoro-2-(2-propenyloxy)naphthalen-6-yl]-6-ethyl-trans-decahydronaphthalene, 2-[1-fluoro-2-(2-propenyloxy)naphthalen-6-yl]-6-propyl-trans-decahydronaphthalene,
2-[1-fluoro-2-(2-propenyloxy)naphthalen-6-yl]-6-butyl-trans-decahydronaphthalene,
2-[1-fluoro-2-(2-propenyloxy)naphthalen-6-yl]-6-pentyl-trans-decahydronaphthalene,
2-[1-fluoro-2-(2-propenyloxy)naphthalen-6-yl]-6-hexyl-trans-decahydronaphthalene,
2-[1-fluoro-2-(2-propenyloxy)naphthalen-6-yl]-6-heptyl-trans-decahydronaphthalene,
2-[1-fluoro-2-(trans-2-butenyloxy)naphthalen-6-yl]-6-methyl-trans-decahydronaphthalene,
2-[1-fluoro-2-(trans-2-butenyloxy)naphthalen-6-yl]-6-ethyl-trans-decahydronaphthalene,
2-[1-fluoro-2-(trans-2-butenyloxy)naphthalen-6-yl]-6-propyl-trans-decahydronaphthalene,
2-[1-fluoro-2-(trans-2-butenyloxy)naphthalen-6-yl]-6-butyl-trans-decahydronaphthalene,
2-[1-fluoro-2-(trans-2-butenyloxy)naphthalen-6-yl]-6-pentyl-trans-decahydronaphthalene,
2-[1-fluoro-2-(trans-2-butenyloxy)naphthalen-6-yl]-6-hexyl-trans-decahydronaphthalene,
2-[1-fluoro-2-(trans-2-butenyloxy)naphthalen-6-yl]-6-heptyl-trans-decahydronaphthalene,
2-[1,7-difluoro-2-(3-butenyl)naphthalen-6-yl]-6-methyl-trans-decahydronaphthalene,
2-[1,7-difluoro-2-(3-butenyl)naphthalen-6-yl]-6-ethyl-trans-decahydronaphthalene,
2-[1,7-difluoro-2-(3-butenyl)naphthalen-6-yl]-6-propyl-trans-decahydronaphthalene,
2-[1,7-difluoro-2-(3-butenyl)naphthalen-6-yl]-6-butyl-trans-decahydronaphthalene,
2-[1,7-difluoro-2-(3-butenyl)naphthalen-6-yl]-6-pentyl-trans-decahydronaphthalene,
2-[1,7-difluoro-2-(3-butenyl)naphthalen-6-yl]-6-hexyl-trans-decahydronaphthalene,
2-[1,7-difluoro-2-(3-butenyl)naphthalen-6-yl]-6-heptyl-trans-decahydronaphthalene,
2-[1,7-difluoro-2-(trans-3-pentenyl)naphthalen-6-yl]-6-methyl-trans-decahydronaphthalene,
2-[1,7-difluoro-2-(trans-3-pentenyl)naphthalen-6-yl]-6-ethyl-trans-decahydronaphthalene,
2-[1,7-difluoro-2-(trans-3-pentenyl)naphthalen-6-yl]-6-propyl-trans-decahydronaphthalene,
2-[1,7-difluoro-2-(trans-3-pentenyl)naphthalen-6-yl]-6-butyl-trans-decahydronaphthalene,
2-[1,7-difluoro-2-(trans-3-pentenyl)naphthalen-6-yl]-6-pentyl-trans-decahydronaphthalene,
2-[1,7-difluoro-2-(trans-3-pentenyl)naphthalen-6-yl]-6-hexyl-trans-decahydronaphthalene,
2-[1,7-difluoro-2-(trans-3-pentenyl)naphthalen-6-yl]-6-heptyl-trans-decahydronaphthalene,
2-(1,7-difluoro-2-methoxynaphthalen-6-yl)-6-methyl-trans-decahydronaphthalene,
2-(1,7-difluoro-2-methoxynaphthalen-6-yl)-6-ethyl-trans-decahydronaphthalene,
2-(1,7-difluoro-2-methoxynaphthalen-6-yl)-6-propyl-trans-decahydronaphthalene,
2-(1,7-difluoro-2-methoxynaphthalen-6-yl)-6-butyl-trans-decahydronaphthalene,
2-(1,7-difluoro-2-methoxynaphthalen-6-yl)-6-pentyl-trans-decahydronaphthalene,
2-(1,7-difluoro-2-methoxynaphthalen-6-yl)-6-hexyl-trans-decahydronaphthalene,
2-(1,7-difluoro-2-methoxynaphthalen-6-yl)-6-heptyl-trans-decahydronaphthalene,
2-[1,7-difluoro-2-(2-propenyloxy)naphthalen-6-yl]-6-methyl-trans-decahydronaphthalene,
2-[1,7-difluoro-2-(2-propenyloxy)naphthalen-6-yl]-6-ethyl-trans-decahydronaphthalene,
2-[1,7-difluoro-2-(2-propenyloxy)naphthalen-6-yl]-6-propyl-trans-decahydronaphthalene,
2-[1,7-difluoro-2-(2-propenyloxy)naphthalen-6-yl]-6-butyl-trans-decahydronaphthalene,
2-[1,7-difluoro-2-(2-propenyloxy)naphthalen-6-yl]-6-pentyl-trans-decahydronaphthalene,
2-[1,7-difluoro-2-(2-propenyloxy)naphthalen-6-yl]-6-hexyl-trans-decahydronaphthalene,
2-[1,7-difluoro-2-(2-propenyloxy)naphthalen-6-yl]-6-heptyl-trans-decahydronaphthalene,
2-[1,7-difluoro-2-(trans-2-butenyloxy)naphthalen-6-yl]-6-methyl-trans-decahydronaphthalene,
2-[1,7-difluoro-2-(trans-2-butenyloxy)naphthalen-6-yl]-6-ethyl-trans-decahydronaphthalene,
2-[1,7-difluoro-2-(trans-2-butenyloxy)naphthalen-6-yl]-6-propyl-trans-decahydronaphthalene,
2-[1,7-difluoro-2-(trans-2-butenyloxy)naphthalen-6-yl]-6-butyl-trans-decahydronaphthalene,
2-[1,7-difluoro-2-(trans-2-butenyloxy)naphthalen-6-yl]-6-pentyl-trans-decahydronaphthalene,
2-[1,7-difluoro-2-(trans-2-butenyloxy)naphthalen-6-yl]-6-hexyl-trans-decahydronaphthalene,
2-[1,7-difluoro-2-(trans-2-butenyloxy)naphthalen-6-yl]-6-heptyl-trans-decahydronaphthalene,
2-[1,8-difluoro-2-(3-butenyl)naphthalen-6-yl]-6-methyl-trans-decahydronaphthalene,
2-[1,8-difluoro-2-(3-butenyl)naphthalen-6-yl]-6-ethyl-trans-decahydronaphthalene,
2-[1,8-difluoro-2-(3-butenyl)naphthalen-6-yl]-6-propyl-trans-decahydronaphthalene,
2-[1,8-difluoro-2-(3-butenyl)naphthalen-6-yl]-6-butyl-trans-decahydronaphthalene,
2-[1,8-difluoro-2-(3-butenyl)naphthalen-6-yl]-6-pentyl-trans-decahydronaphthalene,
2-[1,8-difluoro-2-(3-butenyl)naphthalen-6-yl]-6-hexyl-trans-decahydronaphthalene,
2-[1,8-difluoro-2-(3-butenyl)naphthalen-6-yl]-6-heptyl-trans-decahydronaphthalene,
2-[1,8-difluoro-2-(trans-3-pentenyl)naphthalen-6-yl]-6-methyl-trans-decahydronaphthalene,
2-[1,8-difluoro-2-(trans-3-pentenyl)naphthalen-6-yl]-6-ethyl-trans-decahydronaphthalene,
2-[1,8-difluoro-2-(trans-3-pentenyl)naphthalen-6-yl]-6-propyl-trans-decahydronaphthalene,
2-[1,8-difluoro-2-(trans-3-pentenyl)naphthalen-6-yl]-6-butyl-trans-decahydronaphthalene,
2-[1,8-difluoro-2-(trans-3-pentenyl)naphthalen-6-yl]-6-pentyl-trans-decahydronaphthalene,
2-[1,8-difluoro-2-(trans-3-pentenyl)naphthalen-6-yl]-6-hexyl-trans-decahydronaphthalene,
2-[1,8-difluoro-2-(trans-3-pentenyl)naphthalen-6-yl)-6-heptyl-trans-decahydronaphthalene,
2-(1,8-difluoro-2-methoxynaphthalen-6-yl)-6-methyl-trans-decahydronaphthalene,
2-(1,8-difluoro-2-methoxynaphthalen-6-yl)-6-ethyl-trans-decahydronaphthalene,
2-(1,8-difluoro-2-methoxynaphthalen-6-yl)-6-propyl-trans-decahydronaphthalene,
2-(1,8-difluoro-2-methoxynaphthalen-6-yl)-6-butyl-trans-decahydronaphthalene,
2-(1,8-difluoro-2-methoxynaphthalen-6-yl)-6-pentyl-trans-decahydronaphthalene,
2-(1,8-difluoro-2-methoxynaphthalen-6-yl)-6-hexyl-trans-decahydronaphthalene,
2-(1,8-difluoro-2-methoxynaphthalen-6-yl)-6-heptyl-trans-decahydronaphthalene, 2-(1,8-difluoro-2-(2-propenyloxy)naphthalen-6-yl]-6-methyl-trans-decahydronaphthalene,
2-[1,8-difluoro-2-(2-propenyloxy)naphthalen-6-yl]-6-ethyl-trans-decahydronaphthalene,
2-[1,8-difluoro-2-(2-propenyloxy)naphthalen-6-yl]-6-propyl-trans-decahydronaphthalene,
2-[1,8-difluoro-2-(2-propenyloxy)naphthalen-6-yl]-6-butyl-trans-decahydronaphthalene,
2-[1,8-difluoro-2-(2-propenyloxy)naphthalen-6-yl]-6-pentyl-trans-decahydronaphthalene,
2-[1,8-difluoro-2-(2-propenyloxy)naphthalen-6-yl]-6-hexyl-trans-decahydronaphthalene,
2-[1,8-difluoro-2-(2-propenyloxy)naphthalen-6-yl]-6-heptyl-trans-decahydronaphthalene,
2-[1,8-difluoro-2-(trans-2-butenyloxy)naphthalen-6-yl]-6-methyl-trans-decahydronaphthalene,
2-[1,8-difluoro-2-(trans-2-butenyloxy)naphthalen-6-yl]-6-ethyl-trans-decahydronaphthalene,
2-[1,8-difluoro-2-(trans-2-butenyloxy)naphthalen-6-yl]-6-propyl-trans-decahydronaphthalene,
2-[1,8-difluoro-2-(trans-2-butenyloxy)naphthalen-6-yl]-6-butyl-trans-decahydronaphthalene,
2-[1,8-difluoro-2-(trans-2-butenyloxy)naphthalen-6-yl]-6-pentyl-trans-decahydronaphthalene,
2-[1,8-difluoro-2-(trans-2-butenyloxy)naphthalen-6-yl]-6-hexyl-trans-decahydronaphthalene,
2-[1,8-difluoro-2-(trans-2-butenyloxy)naphthalen-6-yl]-6-heptyl-trans-decahydronaphthalene,
2-[1,2,8-trifluoro-7-(3-butenyl)naphthalen-3-yl]-6-methyl-trans-decahydronaphthalene,
2-[1,2,8-trifluoro-7-(3-butenyl)naphthalen-3-yl]-6-ethyl-trans-decahydronaphthalene,
2-[1,2,8-trifluoro-7-(3-butenyl)naphthalen-3-yl]-6-propyl-trans-decahydronaphthalene,
2-[1,2,8-trifluoro-7-(3-butenyl)naphthalen-3-yl]-6-butyl-trans-decahydronaphthalene,
2-[1,2,8-trifluoro-7-(3-butenyl)naphthalen-3-yl]-6-pentyl-trans-decahydronaphthalene,
2-[1,2,8-trifluoro-7-(3-butenyl)naphthalen-3-yl]-6-hexyl-trans-decahydronaphthalene,
2-[1,2,8-trifluoro-7-(3-butenyl)naphthalen-3-yl]-6-heptyl-trans-decahydronaphthalene,
2-[1,2,8-trifluoro-7-(trans-3-pentenyl)naphthalen-3-yl]-6-methyl-trans-decahydronaphthalene,
2-[1,2,8-trifluoro-7-(trans-3-pentenyl)naphthalen-3-yl)-6-ethyl-trans-decahydronaphthalene,
2-[1,2,8-trifluoro-7-(trans-3-pentenyl)naphthalen-3-yl]-6-propyl-trans-decahydronaphthalene,
2-[1,2,8-trifluoro-7-(trans-3-pentenyl)naphthalen-3-yl)-6-butyl-trans-decahydronaphthalene,
2-[1,2,8-trifluoro-7-(trans-3-pentenyl)naphthalen-3-yl]-6-pentyl-trans-decahydronaphthalene,
2-[1,2,8-trifluoro-7-(trans-3-pentenyl)naphthalen-3-yl]-6-hexyl-trans-decahydronaphthalene,
2-[1,2,8-trifluoro-7-(trans-3-pentenyl)naphthalen-3-yl]-6-heptyl-trans-decahydronaphthalene,
2-(1,2,8-trifluoro-7-methoxynaphthalen-3-yl)-6-methyl-trans-decahydronaphthalene,
2-(1,2,8-trifluoro-7-methoxynaphthalen-3-yl)-6-ethyl-trans-decahydronaphthalene,
2-(1,2,8-trifluoro-7-methoxynaphthalen-3-yl)-6-propyl-trans-decahydronaphthalene,
2-(1,2,8-trifluoro-7-methoxynaphthalen-3-yl)-6-butyl-trans-decahydronaphthalene,
2-(1,2,8-trifluoro-7-methoxynaphthalen-3-yl)-6-pentyl-trans-decahydronaphthalene,
2-(1,2,8-trifluoro-7-methoxynaphthalen-3-yl)-6-hexyl-trans-decahydronaphthalene,
2-(1,2,8-trifluoro-7-methoxynaphthalen-3-yl)-6-heptyl-trans-decahydronaphthalene,
2-[1,2,8-trifluoro-7-(2-propenyloxy)naphthalen-3-yl]-6-methyl-trans-decahydronaphthalene,
2-[1,2,8-trifluoro-7-(2-propenyloxy)naphthalen-3-yl]-6-ethyl-trans-decahydronaphthalene,
2-[1,2,8-trifluoro-7-(2-propenyloxy)naphthalen-3-yl]-6-propyl-trans-decahydronaphthalene,
2-[1,2,8-trifluoro-7-(2-propenyloxy)naphthalen-3-yl]-6-butyl-trans-decahydronaphthalene,
2-[1,2,8-trifluoro-7-(2-propenyloxy)naphthalen-3-yl]-6-pentyl-trans-decahydronaphthalene,
2-(1,2,8-trifluoro-7-(2-propenyloxy)naphthalen-3-yl]-6-hexyl-trans-decahydronaphthalene,
2-[1,2,8-trifluoro-7-(2-propenyloxy)naphthalen-3-yl]-6-heptyl-trans-decahydronaphthalene,
2-[1,2,8-trifluoro-7-(trans-2-butenyloxy)naphthalen-3-yl]-6-methyl-trans-decahydronaphthalene,
2-[1,2,8-trifluoro-7-(trans-2-butenyloxy)naphthalen-3-yl]-6-ethyl-trans-decahydronaphthalene,
2-(1,2,8-trifluoro-7-(trans-2-butenyloxy)naphthalen-3-yl]-6-propyl-trans-decahydronaphthalene,
2-[1,2,8-trifluoro-7-(trans-2-butenyloxy)naphthalen-3-yl]-6-butyl-trans-decahydronaphthalene,
2-[1,2,8-trifluoro-7-(trans-2-butenyloxy)naphthalen-3-yl]-6-pentyl-trans-decahydronaphthalene,
2-[1,2,8-trifluoro-7-(trans-2-butenyloxy)naphthalen-3-yl]-6-hexyl-trans-decahydronaphthalene,
2-[1,2,8-trifluoro-7-(trans-2-butenyloxy)naphthalen-3-yl]-6-heptyl-trans-decahydronaphthalene.

Example 31

Synthesis of 6-(6-propyltetrahydronaphthalen-2-yl)-2-vinyl-trans-decahydronaphthalene (I-28)

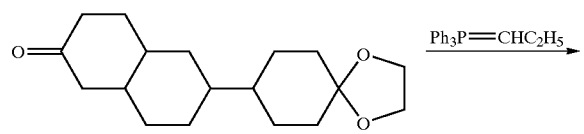

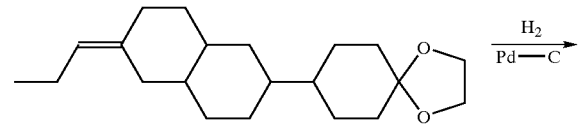

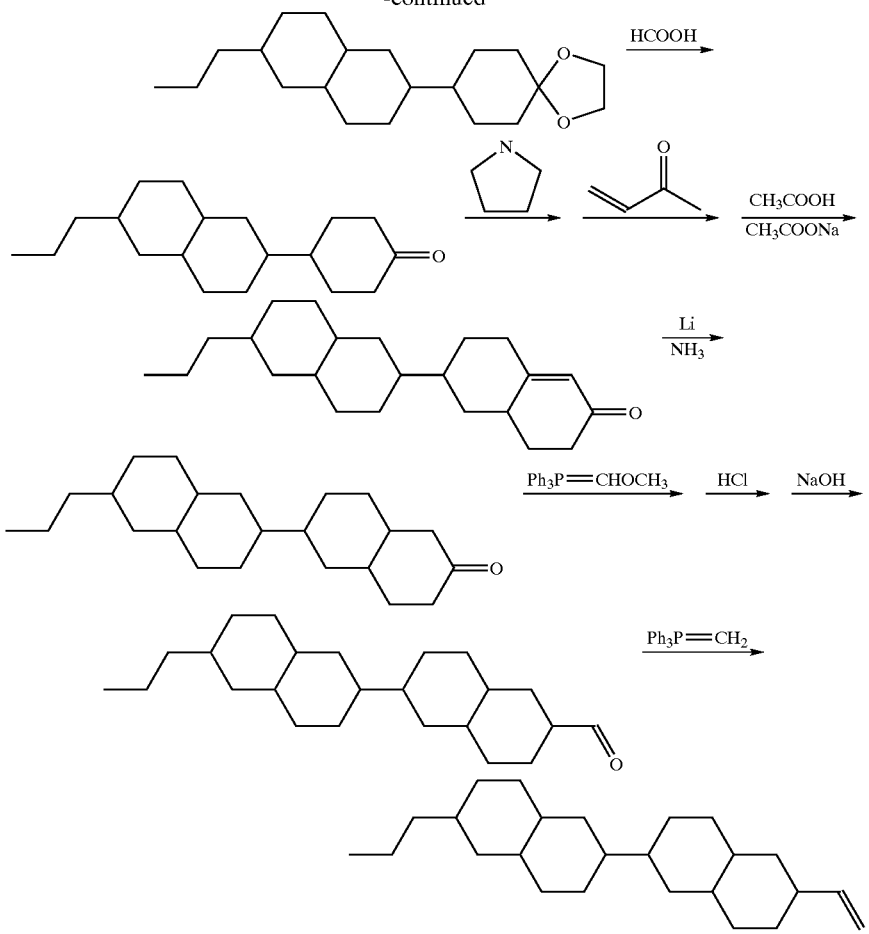

(31-a) Synthesis of 4-(3-propyridenebicyclo[4.4.0]decan-8-yl)cyclohexanone ethyleneacetal Reaction of 10 g of 4-(6-oxo-trans-decahydronaphthalen-2-yl)cyclohexanone ethyleneacetal with a Wittig reagent was carried out in a manner similar to that in (6-e) to obtain 9 g of white solid 4-(3-propyridenebicyclo[4.4.0]decan-8-yl)cyclohexanone ethyleneacetal.

(31-b) Synthesis of 4-(trans-6-propyl-trans-decahydronaphthalen-2-yl)cyclohexanone ethyleneacetal In a manner similar to that in (1-e), catalytic hydrogenation reduction of 9 g of 4-(3-propyridenebicyclo[4.4.0]decan-8-yl)cyclohexanone ethyleneacetal, which was obtained in (31-a), was carried out to obtain 8 g of pale yellow solid 4-(trans-6-propyl-trans-decahydronaphthalen-2-yl)cyclohexanone ethyleneacetal.

(31-c) Synthesis of 4-(trans-6-propyl-trans-decahydronaphthalen-2-yl)cyclohexanone In a manner similar to that in (1-c), deacetalization of 8 g of 4-(trans-6-propyl-trans-decahydronaphthalen-2-yl)cyclohexanone ethyleneacetal, which was obtained in (31-b), was carried out to obtain 6 g of pale yellow solid 4-(trans-6-propyl-trans-decahydronaphthalen-2-yl)cyclohexanone.

(31-d) Synthesis of 6-(trans-6-propyl-trans-decahydronaphthalen-2-yl)-4,4a,5,6,7,8-hexahydro-3H-2-naphthalenone 6 g of 4-(trans-6-propyl-trans-decahydronaphthalen-2-yl)cyclohexanone, which was obtained in (31-c), was dissolved in 30 ml of toluene, and 15 ml of pyrrolidine was added to the solution. The mixture was heated for 4 hours under refluxing using an apparatus equipped with a water separator until-evaporation of water stopped. Pyrrolidine and toluene were evaporated while the heating was maintained, then the temperature was reduced to room temperature, and 40 ml of toluene was added to the mixture. While cooling the mixture to 20° C. or lower, 8 ml of methyl vinyl ketone was added dropwise over a period of 5 minutes. After the dropwise addition, the mixture was heated for 2 hours under refluxing, and then the mixture was left to cool to room temperature. An aqueous solution in which 3 g of sodium acetate, 10 ml of glacial acetic acid, and 10 ml of water were mixed was added. After The mixture was heated for 2 hours under refluxing, the mixture was left to cool to room temperature. The organic phase was separated and rinsed with water, and the solvent was evaporated. 8 g of the oily substance obtained was dissolved in 40 ml of THF, and 30 ml of 3 M hydrochloric acid was added to the solution. After heating the mixture for 5 hours under refluxing, the temperature was reduced to room temperature, and the organic phase was separated, rinsed with a saturated saline solution, and dried on anhydrous magnesium sulfate. The solvent was evaporated to obtain 8 g of brown solid 6-(trans-6-propyl-trans-decahydronaphthalen-2-yl)-4,4a,5,6,7,8-hexahydro-3H-2-naphthalenone.

(31-e) Synthesis of 6-(trans-6-propyl-trans-decahydronaphthalen-2-yl)-trans-decahydro-2-naphthalenone A 40 ml THF solution of 8 g of 6-(trans-6-propyl-trans-decahydronaphthalen-2-yl)-4,4a,5,6,7,8-hexahydro-3H-2- naphthalenone, which was obtained in (31-d), and 20 ml of t-butanol was added dropwise to a solution of 2 g of metal lithium in 100 ml of liquid ammonia while maintaining the inner temperature between −30° C. and −40° C. After the dropwise addition, stirring was continued for 30 minutes. After solid ammonium chloride was added in small amounts to the mixture to oxidize lithium, the temperature was raised to room temperature, and ammonia was evaporated. Water was added, and extraction was carried out using toluene. The organic phase was rinsed with a saturated saline solution and dried on anhydrous magnesium sulfate, and the solvent was evaporated. The residue was purified by silica gel column chromatography (toluene) and recrystallized from a hexane solution to obtain 4 g of pale yellow liquid 6-(trans-6-propyl-trans-decahydronaphthalen-2-yl)-trans-decahydro-2-naphthalenone (31-f) Synthesis of 6-(6-propyl-trans-decahydronaphthalen-2-yl)-trans-decahydronaphthalene-2-carbaldehyde In a manner similar to that of (6-a), reaction of 6 g of 6-(6-propyl-trans-decahydronaphthalen-2-yl)-trans-decahydro-2-naphthalenone, which was obtained in (31-f), with a Wittig reagent was carried out to obtain 4 g of pale yellow solid 6-(6-propyl-trans-decahydronaphthalen-2-yl)-trans-decahydronaphthalene-2-carbaldehyde.

(31-g) Synthesis of 6-(6-propyl-trans-decahydronaphthalen-2-yl)-2-vinyl-trans-decahydronaphthalene In a manner similar to that of (6-e), reaction of 4 g of 6-(6-propyl-trans-decahydronaphthalen-2-yl)-trans-decahydronaphthalene-2-carbaldehyde, which was obtained in (31-f), with a Wittig reagent was carried out to obtain 2 g of white solid 6-(6-propyl-trans-decahydronaphthalen-2-yl)-2-vinyl-trans-decahydronaphthalene.

The following compounds were prepared in the same manner as mentioned above:

6-(6-methyltetrahydronaphthalen-2-yl)-2-methyl-trans-decahydronaphthalene,
6-(6-methyltetrahydronaphthalen-2-yl)-2-ethyl-trans-decahydronaphthalene,
6-(6-methyltetrahydronaphthalen-2-yl)-2-propyl-trans-decahydronaphthalene,
6-(6-methyltetrahydronaphthalen-2-yl)-2-butyl-trans-decahydronaphthalene,
6-(6-methyltetrahydronaphthalen-2-yl)-2-pentyl-trans-decahydronaphthalene,
6-(6-methyltetrahydronaphthalen-2-yl)-2-hexyl-trans-decahydronaphthalene,
6-(6-methyltetrahydronaphthalen-2-yl)-2-heptyl-trans-decahydronaphthalene,
6-(6-methyltetrahydronaphthalen-2-yl)-2-methoxy-trans-decahydronaphthalene,
6-(6-methyltetrahydronaphthalen-2-yl)-2-ethoxy-trans-decahydronaphthalene,
6-(6-methyltetrahydronaphthalen-2-yl)-2-propyloxy-trans-decahydronaphthalene,
6-(6-methyltetrahydronaphthalen-2-yl)-2-butyloxy-trans-decahydronaphthalene,
6-(6-methyltetrahydronaphthalen-2-yl)-2-pentyloxy-trans-decahydronaphthalene,
6-(6-methyltetrahydronaphthalen-2-yl)-2-hexyloxy-trans-decahydronaphthalene,
6-(6-methyltetrahydronaphthalen-2-yl)-2-vinyl-trans-decahydronaphthalene,
6-(6-methyltetrahydronaphthalen-2-yl)-2-(trans-1-propenyl)-trans-decahydronaphthalene,
6-[6-methyltetrahydronaphthalen-2-yl]-2-(3-butenyl)-trans-decahydronaphthalene,
6-(6-methyltetrahydronaphthalen-2-yl)-2-(trans-3-pentenyl)-trans-decahydronaphthalene,
6-(6-methyltetrahydronaphthalen-2-yl)-2-(2-propenyloxy)-trans-decahydronaphthalene,
6-(6-methyltetrahydronaphthalen-2-yl)-2-(trans-2-butenyloxy)-trans-decahydronaphthalene,
6-(6-methyltetrahydronaphthalen-2-yl)-2-(2-fluoroethenyl)-trans-decahydronaphthalene,
6-(6-methyltetrahydronaphthalen-2-yl)-2-(2,2-difluoroethenyl)-trans-decahydronaphthalene,
6-(6-ethyltetrahydronaphthalen-2-yl)-2-ethyl-trans-decahydronaphthalene,
6-(6-ethyltetrahydronaphthalen-2-yl)-2-propyl-trans-decahydronaphthalene,
6-(6-ethyltetrahydronaphthalen-2-yl)-2-butyl-trans-decahydronaphthalene,
6-(6-ethyltetrahydronaphthalen-2-yl)-2-pentyl-trans-decahydronaphthalene,
6-(6-ethyltetrahydronaphthalen-2-yl)-2-hexyl-trans-decahydronaphthalene,
6-(6-ethyltetrahydronaphthalen-2-yl)-2-heptyl-trans-decahydronaphthalene,
6-(6-ethyltetrahydronaphthalen-2-yl)-2-methoxy-trans-decahydronaphthalene,
6-(6-ethyltetrahydronaphthalen-2-yl)-2-ethoxy-trans-decahydronaphthalene,
6-(6-ethyltetrahydronaphthalen-2-yl)-2-propyloxy-trans-decahydronaphthalene,
6-(6-ethyltetrahydronaphthalen-2-yl)-2-butyloxy-trans-decahydronaphthalene,
6-(6-ethyltetrahydronaphthalen-2-yl)-2-pentyloxy-trans-decahydronaphthalene,
6-(6-ethyltetrahydronaphthalen-2-yl)-2-hexyloxy-trans-decahydronaphthalene,
6-(6-ethyltetrahydronaphthalen-2-yl)-2-vinyl-trans-decahydronaphthalene,
6-(6-ethyltetrahydronaphthalen-2-yl)-2-(trans-1-propenyl)-trans-decahydronaphthalene,
6-(6-ethyltetrahydronaphthalen-2-yl)-2-(3-butenyl)-trans-decahydronaphthalene,
6-(6-ethyltetrahydronaphthalen-2-yl)-2-(trans-3-pentenyl)-trans-decahydronaphthalene,
6-(6-ethyltetrahydronaphthalen-2-yl)-2-(2-propenyloxy)-trans-decahydronaphthalene,
6-(6-ethyltetrahydronaphthalen-2-yl)-2-(trans-2-butenyloxy)-trans-decahydronaphthalene,
6-(6-ethyltetrahydronaphthalen-2-yl)-2-(2-fluoroethenyl)-trans-decahydronaphthalene,
6-(6-ethyltetrahydronaphthalen-2-yl)-2-(2,2-difluoroethenyl)-trans-decahydronaphthalene,
6-(6-propyltetrahydronaphthalen-2-yl)-2-propyl-trans-decahydronaphthalene,
6-(6-propyltetrahydronaphthalen-2-yl)-2-butyl-trans-decahydronaphthalene,
6-(6-propyltetrahydronaphthalen-2-yl)-2-pentyl-trans-decahydronaphthalene,
6-(6-propyltetrahydronaphthalen-2-yl)-2-hexyl-trans-decahydronaphthalene,
6-(6-propyltetrahydronaphthalen-2-yl)-2-heptyl-trans-decahydronaphthalene,
6-(6-propyltetrahydronaphthalen-2-yl)-2-methoxy-trans-decahydronaphthalene,
6-(6-propyltetrahydronaphthalen-2-yl)-2-ethoxy-trans-decahydronaphthalene,
6-(6-propyltetrahydronaphthalen-2-yl)-2-propyloxy-trans-decahydronaphthalene,
6-(6-propyltetrahydronaphthalen-2-yl)-2-butyloxy-trans-decahydronaphthalene,
6-(6-propyltetrahydronaphthalen-2-yl)-2-pentyloxy-trans-decahydronaphthalene, 6-(6-propyltetrahydronaphthalen-2-yl)-2-hexyloxy-trans-decahydronaphthalene,
6-(6-propyltetrahydronaphthalen-2-yl)-2-(trans-1-propenyl)-trans-decahydronaphthalene,
6-(6-propyltetrahydronaphthalen-2-yl)-2-(3-butenyl)-trans-decahydronaphthalene,
6-(6-propyltetrahydronaphthalen-2-yl)-2-(trans-3-pentenyl)-trans-decahydronaphthalene,
6-(6-propyltetrahydronaphthalen-2-yl)-2-(2-propenyloxy)-trans-decahydronaphthalene,
6-(6-propyltetrahydronaphthalen-2-yl)-2-(trans-2-butenyloxy)-trans-decahydronaphthalene,
6-(6-propyltetrahydronaphthalen-2-yl)-2-(2-fluoroethenyl)-trans-decahydronaphthalene,
6-(6-propyltetrahydronaphthalen-2-yl)-2-(2,2-difluoroethenyl)-trans-decahydronaphthalene,
6-(6-butyltetrahydronaphthalen-2-yl)-2-butyl-trans-decahydronaphthalene,
6-(6-butyltetrahydronaphthalen-2-yl)-2-pentyl-trans-decahydronaphthalene,
6-(6-butyltetrahydronaphthalen-2-yl)-2-hexyl-trans-decahydronaphthalene,
6-(6-butyltetrahydronaphthalen-2-yl)-2-heptyl-trans-decahydronaphthalene,
6-(6-butyltetrahydronaphthalen-2-yl)-2-methoxy-trans-decahydronaphthalene,
6-(6-butyltetrahydronaphthalen-2-yl)-2-ethoxy-trans-decahydronaphthalene,
6-(6-butyltetrahydronaphthalen-2-yl)-2-propyloxy-trans-decahydronaphthalene,
6-(6-butyltetrahydronaphthalen-2-yl)-2-butyloxy-trans-decahydronaphthalene,
6-(6-butyltetrahydronaphthalen-2-yl)-2-pentyloxy-trans-decahydronaphthalene,
6-(6-butyltetrahydronaphthalen-2-yl)-2-hexyloxy-trans-decahydronaphthalene,
6-(6-butyltetrahydronaphthalen-2-yl)-2-vinyl-trans-decahydronaphthalene,
6-(6-butyltetrahydronaphthalen-2-yl)-2-(trans-1-propenyl)-trans-decahydronaphthalene,
6-(6-butyltetrahydronaphthalen-2-yl)-2-(3-butenyl)-trans-decahydronaphthalene,
6-(6-butyltetrahydronaphthalen-2-yl)-2-(trans-3-pentenyl)-trans-decahydronaphthalene,
6-(6-butyltetrahydronaphthalen-2-yl)-2-(2-propenyloxy)-trans-decahydronaphthalene,
6-(6-butyltetrahydronaphthalen-2-yl)-2-(trans-2-butenyloxy)-trans-decahydronaphthalene,
6-(6-butyltetrahydronaphthalen-2-yl)-2-(2-fluoroethenyl)-trans-decahydronaphthalene,
6-(6-butyltetrahydronaphthalen-2-yl)-2-(2,2-difluoroethenyl)-trans-decahydronaphthalene,
6-(6-pentyltetrahydronaphthalen-2-yl)-2-pentyl-trans-decahydronaphthalene,
6-(6-pentyltetrahydronaphthalen-2-yl)-2-hexyl-trans-decahydronaphthalene,
6-(6-pentyltetrahydronaphthalen-2-yl)-2-heptyl-trans-decahydronaphthalene,
6-(6-pentyltetrahydronaphthalen-2-yl)-2-methoxy-trans-decahydronaphthalene,
6-(6-pentyltetrahydronaphthalen-2-yl)-2-ethoxy-trans-decahydronaphthalene,
6-(6-pentyltetrahydronaphthalen-2-yl)-2-propyloxy-trans-decahydronaphthalene,
6-(6-pentyltetrahydronaphthalen-2-yl)-2-butyloxy-trans-decahydronaphthalene,
6-(6-pentyltetrahydronaphthalen-2-yl)-2-pentyloxy-trans-decahydronaphthalene,
6-(6-pentyltetrahydronaphthalen-2-yl)-2-hexyloxy-trans-decahydronaphthalene,
6-(6-pentyltetrahydronaphthalen-2-yl)-2-vinyl-trans-decahydronaphthalene,
6-(6-pentyltetrahydronaphthalen-2-yl)-2-(trans-1-propenyl)-trans-decahydronaphthalene,
6-(6-pentyltetrahydronaphthalen-2-yl)-2-(3-butenyl)-trans-decahydronaphthalene,
6-(6-pentyltetrahydronaphthalen-2-yl)-2-(trans-3-pentenyl)-trans-decahydronaphthalene,
6-(6-pentyltetrahydronaphthalen-2-yl)-2-(2-propenyloxy)-trans-decahydronaphthalene,
6-(6-pentyltetrahydronaphthalen-2-yl)-2-(trans-2-butenyloxy)-trans-decahydronaphthalene,
6-(6-pentyltetrahydronaphthalen-2-yl)-2-(2-fluoroethenyl)-trans-decahydronaphthalene,
6-(6-pentyltetrahydronaphthalen-2-yl)-2-(2,2-difluoroethenyl)-trans-decahydronaphthalene,
6-(6-hexyltetrahydronaphthalen-2-yl)-2-hexyl-trans-decahydronaphthalene,
6-(6-hexyltetrahydronaphthalen-2-yl)-2-heptyl-trans-decahydronaphthalene,
6-(6-hexyltetrahydronaphthalen-2-yl)-2-methoxy-trans-decahydronaphthalene,
6-(6-hexyltetrahydronaphthalen-2-yl)-2-ethoxy-trans-decahydronaphthalene,
6-(6-hexyltetrahydronaphthalen-2-yl)-2-propyloxy-trans-decahydronaphthalene,
6-(6-hexyltetrahydronaphthalen-2-yl)-2-butyloxy-trans-decahydronaphthalene,
6-(6-hexyltetrahydronaphthalen-2-yl)-2-pentyloxy-trans-decahydronaphthalene,
6-(6-hexyltetrahydronaphthalen-2-yl)-2-hexyloxy-trans-decahydronaphthalene,
6-(6-hexyltetrahydronaphthalen-2-yl)-2-vinyl-trans-decahydronaphthalene,
6-(6-hexyltetrahydronaphthalen-2-yl)-2-(trans-1-propenyl)-trans-decahydronaphthalene,
6-(6-hexyltetrahydronaphthalen-2-yl)-2-(3-butenyl)-trans-decahydronaphthalene,
6-(6-hexyltetrahydronaphthalen-2-yl)-2-(trans-3-pentenyl)-trans-decahydronaphthalene,
6-(6-hexyltetrahydronaphthalen-2-yl)-2-(2-propenyloxy)-trans-decahydronaphthalene,
6-(6-hexyltetrahydronaphthalen-2-yl)-2-(trans-2-butenyloxy)-trans-decahydronaphthalene,
6-(6-hexyltetrahydronaphthalen-2-yl)-2-(2-fluoroethenyl)-trans-decahydronaphthalene,
6-(6-hexyltetrahydronaphthalen-2-yl)-2-(2,2-difluoroethenyl)-trans-decahydronaphthalene,
6-(6-heptyltetrahydronaphthalen-2-yl)-2-heptyl-trans-decahydronaphthalene,
6-(6-heptyltetrahydronaphthalen-2-yl)-2-methoxy-trans-decahydronaphthalene,
6-(6-heptyltetrahydronaphthalen-2-yl)-2-ethoxy-trans-decahydronaphthalene,
6-(6-heptyltetrahydronaphthalen-2-yl)-2-propyloxy-trans-decahydronaphthalene,
6-(6-heptyltetrahydronaphthalen-2-yl)-2-butyloxy-trans-decahydronaphthalene,
6-(6-heptyltetrahydronaphthalen-2-yl)-2-pentyloxy-trans-decahydronaphthalene,
6-(6-heptyltetrahydronaphthalen-2-yl)-2-hexyloxy-trans-decahydronaphthalene,
6-(6-heptyltetrahydronaphthalen-2-yl)-2-vinyl-trans-decahydronaphthalene,
6-(6-heptyltetrahydronaphthalen-2-yl)-2-(trans-1-propenyl)-trans-decahydronaphthalene, 6-(6-heptyltetrahydronaphthalen-2-yl)-2-(3-butenyl)-trans-decahydronaphthalene,
6-(6-heptyltetrahydronaphthalen-2-yl)-2-(trans-3-pentenyl)-trans-decahydronaphthalene,
6-(6-heptyltetrahydronaphthalen-2-yl)-2-(2-propenyloxy)-trans-decahydronaphthalene,
6-(6-heptyltetrahydronaphthalen-2-yl)-2-(trans-2-butenyloxy)-trans-decahydronaphthalene,
6-(6-heptyltetrahydronaphthalen-2-yl)-2-(2-fluoroethenyl)-trans-decahydronaphthalene,
6-(6-heptyltetrahydronaphthalen-2-yl)-2-(2,2-difluoroethenyl)-trans-decahydronaphthalene,
6-(6-methoxytetrahydronaphthalen-2-yl)-2-methoxy-trans-decahydronaphthalene,
6-(6-methoxytetrahydronaphthalen-2-yl)-2-ethoxy-trans-decahydronaphthalene,
6-(6-methoxytetrahydronaphthalen-2-yl)-2-propyloxy-trans-decahydronaphthalene,
6-(6-methoxytetrahydronaphthalen-2-yl)-2-butyloxy-trans-decahydronaphthalene,
6-(6-methoxytetrahydronaphthalen-2-yl)-2-pentyloxy-trans-decahydronaphthalene,
6-(6-methoxytetrahydronaphthalen-2-yl)-2-hexyloxy-trans-decahydronaphthalene,
6-(6-methoxytetrahydronaphthalen-2-yl)-2-vinyl-trans-decahydronaphthalene,
6-(6-methoxytetrahydronaphthalen-2-yl)-2-(trans-1-propenyl)-trans-decahydronaphthalene,
6-(6-methoxytetrahydronaphthalen-2-yl)-2-(3-butenyl)-trans-decahydronaphthalene,
6-(6-methoxytetrahydronaphthalen-2-yl)-2-(trans-3-pentenyl)-trans-decahydronaphthalene,
6-(6-methoxytetrahydronaphthalen-2-yl)-2-(2-propenyloxy)-trans-decahydronaphthalene,
6-(6-methoxytetrahydronaphthalen-2-yl)-2-(trans-2-butenyloxy)-trans-decahydronaphthalene,
6-(6-methoxytetrahydronaphthalen-2-yl)-2-(2-fluoroethenyl)-trans-decahydronaphthalene,
6-(6-methoxytetrahydronaphthalen-2-yl)-2-(2,2-difluoroethenyl)-trans-decahydronaphthalene,
6-(6-ethoxytetrahydronaphthalen-2-yl)-2-ethoxy-trans-decahydronaphthalene,
6-(6-ethoxytetrahydronaphthalen-2-yl)-2-propyloxy-trans-decahydronaphthalene,
6-(6-ethoxytetrahydronaphthalen-2-yl)-2-butyloxy-trans-decahydronaphthalene,
6-(6-ethoxytetrahydronaphthalen-2-yl)-2-pentyloxy-trans-decahydronaphthalene,
6-(6-ethoxytetrahydronaphthalen-2-yl)-2-hexyloxy-trans-decahydronaphthalene,
6-(6-ethoxytetrahydronaphthalen-2-yl)-2-vinyl-trans-decahydronaphthalene,
6-(6-ethoxytetrahydronaphthalen-2-yl)-2-(trans-1-propenyl)-trans-decahydronaphthalene,
6-(6-ethoxytetrahydronaphthalen-2-yl)-2-(3-butenyl)-trans-decahydronaphthalene,
6-(6-ethoxytetrahydronaphthalen-2-yl)-2-(trans-3-pentenyl)-trans-decahydronaphthalene,
6-(6-ethoxytetrahydronaphthalen-2-yl)-2-(2-propenyloxy)-trans-decahydronaphthalene,
6-(6-ethoxytetrahydronaphthalen-2-yl)-2-(trans-2-butenyloxy)-trans-decahydronaphthalene,
6-(6-ethoxytetrahydronaphthalen-2-yl)-2-(2-fluoroethenyl)-trans-decahydronaphthalene,
6-(6-ethoxytetrahydronaphthalen-2-yl)-2-(2,2-difluoroethenyl)-trans-decahydronaphthalene,
6-(6-propyloxytetrahydronaphthalen-2-yl)-2-propyloxy-trans-decahydronaphthalene,
6-(6-propyloxytetrahydronaphthalen-2-yl)-2-butyloxy-trans-decahydronaphthalene,
6-(6-propyloxytetrahydronaphthalen-2-yl)-2-pentyloxy-trans-decahydronaphthalene,
6-(6-propyloxytetrahydronaphthalen-2-yl)-2-hexyloxy-trans-decahydronaphthalene,
6-(6-propyloxytetrahydronaphthalen-2-yl)-2-vinyl-trans-decahydronaphthalene,
6-(6-propyloxytetrahydronaphthalen-2-yl)-2-(trans-1-propenyl)-trans-decahydronaphthalene,
6-(6-propyloxytetrahydronaphthalen-2-yl)-2-(3-butenyl)-trans-decahydronaphthalene,
6-(6-propyloxytetrahydronaphthalen-2-yl)-2-(trans-3-pentenyl)-trans-decahydronaphthalene,
6-(6-propyloxytetrahydronaphthalen-2-yl)-2-(2-propenyloxy)-trans-decahydronaphthalene,
6-(6-propyloxytetrahydronaphthalen-2-yl)-2-(trans-2-butenyloxy)-trans-decahydronaphthalene,
6-(6-propyloxytetrahydronaphthalen-2-yl)-2-(2-fluoroethenyl)-trans-decahydronaphthalene,
6-(6-propyloxytetrahydronaphthalen-2-yl)-2-(2,2-difluoroethenyl)-trans-decahydronaphthalene,
6-(6-butyloxytetrahydronaphthalen-2-yl)-2-butyloxy-trans-decahydronaphthalene,
6-(6-butyloxytetrahydronaphthalen-2-yl)-2-pentyloxy-trans-decahydronaphthalene,
6-(6-butyloxytetrahydronaphthalen-2-yl)-2-hexyloxy-trans-decahydronaphthalene,
6-(6-butyloxytetrahydronaphthalen-2-yl)-2-vinyl-trans-decahydronaphthalene,
6-(6-butyloxytetrahydronaphthalen-2-yl)-2-(trans-1-propenyl)-trans-decahydronaphthalene,
6-(6-butyloxytetrahydronaphthalen-2-yl)-2-(3-butenyl)-trans-decahydronaphthalene,
6-(6-butyloxytetrahydronaphthalen-2-yl)-2-(trans-3-pentenyl)-trans-decahydronaphthalene,
6-(6-butyloxytetrahydronaphthalen-2-yl)-2-(2-propenyloxy)-trans-decahydronaphthalene,
6-(6-butyloxytetrahydronaphthalen-2-yl)-2-(trans-2-butenyloxy)-trans-decahydronaphthalene,
6-(6-butyloxytetrahydronaphthalen-2-yl)-2-(2-fluoroethenyl)-trans-decahydronaphthalene,
6-(6-butyloxytetrahydronaphthalen-2-yl)-2-(2,2-difluoroethenyl)-trans-decahydronaphthalene,
6-(6-pentyloxytetrahydronaphthalen-2-yl)-2-pentyloxy-trans-decahydronaphthalene,
6-(6-pentyloxytetrahydronaphthalen-2-yl)-2-hexyloxy-trans-decahydronaphthalene,
6-(6-pentyloxytetrahydronaphthalen-2-yl)-2-vinyl-trans-decahydronaphthalene,
6-(6-pentyloxytetrahydronaphthalen-2-yl)-2-(trans-1-propenyl)-trans-decahydronaphthalene,
6-(6-pentyloxytetrahydronaphthalen-2-yl)-2-(3-butenyl)-trans-decahydronaphthalene,
6-(6-pentyloxytetrahydronaphthalen-2-yl)-2-(trans-3-pentenyl)-trans-decahydronaphthalene,
6-(6-pentyloxytetrahydronaphthalen-2-yl)-2-(2-propenyloxy)-trans-decahydronaphthalene,
6-(6-pentyloxytetrahydronaphthalen-2-yl)-2-(trans-2-butenyloxy)-trans-decahydronaphthalene,
6-(6-pentyloxytetrahydronaphthalen-2-yl)-2-(2-fluoroethenyl)-trans-decahydronaphthalene,
6-(6-pentyloxytetrahydronaphthalen-2-yl)-2-(2,2-difluoroethenyl)-trans-decahydronaphthalene,
6-(6-hexyloxytetrahydronaphthalen-2-yl)-2-hexyloxy-trans-decahydronaphthalene,
6-(6-hexyloxytetrahydronaphthalen-2-yl)-2-vinyl-trans-decahydronaphthalene, 6-(6-hexyloxytetrahydronaphthalen-2-yl)-2-(trans-1-propenyl)-trans-decahydronaphthalene,
6-(6-hexyloxytetrahydronaphthalen-2-yl)-2-(3-butenyl)-trans-decahydronaphthalene,
6-(6-hexyloxytetrahydronaphthalen-2-yl)-2-(trans-3-pentenyl)-trans-decahydronaphthalene,
6-(6-hexyloxytetrahydronaphthalen-2-yl)-2-(2-propenyloxy)-trans-decahydronaphthalene,
6-(6-hexyloxytetrahydronaphthalen-2-yl)-2-(trans-2-butenyloxy)-trans-decahydronaphthalene,
6-(6-hexyloxytetrahydronaphthalen-2-yl)-2-(2-fluoroethenyl)-trans-decahydronaphthalene,
6-(6-hexyloxytetrahydronaphthalen-2-yl)-2-(2,2-difluoroethenyl)-trans-decahydronaphthalene,
6-(6-vinyltetrahydronaphthalen-2-yl)-2-vinyl-trans-decahydronaphthalene,
6-(6-vinyltetrahydronaphthalen-2-yl)-2-(trans-1-propenyl)-trans-decahydronaphthalene,
6-(6-vinyltetrahydronaphthalen-2-yl)-2-(3-butenyl)-trans-decahydronaphthalene,
6-(6-vinyltetrahydronaphthalen-2-yl)-2-(trans-3-pentenyl)-trans-decahydronaphthalene,
6-(6-vinyltetrahydronaphthalen-2-yl)-2-(2-propenyloxy)-trans-decahydronaphthalene,
6-(6-vinyltetrahydronaphthalen-2-yl)-2-(trans-2-butenyloxy)-trans-decahydronaphthalene,
6-(6-vinyltetrahydronaphthalen-2-yl)-2-(2-fluoroethenyl)-trans-decahydronaphthalene,
6-(6-vinyltetrahydronaphthalen-2-yl)-2-(2,2-difluoroethenyl)-trans-decahydronaphthalene,
6-[6-(trans-1-propenyl)-tetrahydronaphthalen-2-yl]-2-(trans-1-propenyl)-trans-decahydronaphthalene,
6-[6-(trans-1-propenyl)-tetrahydronaphthalen-2-yl]-2-(3-butenyl)-trans-decahydronaphthalene,
6-[6-(trans-1-propenyl)-tetrahydronaphthalen-2-yl]-2-(trans-3-pentenyl)-trans-decahydronaphthalene,
6-[6-(trans-1-propenyl)-tetrahydronaphthalen-2-yl]-2-(2-propenyloxy)-trans-decahydronaphthalene,
6-[6-(trans-1-propenyl)-tetrahydronaphthalen-2-yl]-2-(trans-2-butenyloxy)-trans-decahydronaphthalene,
6-[6-(trans-1-propenyl)-tetrahydronaphthalen-2-yl]-2-(2-fluoroethenyl)-trans-decahydronaphthalene,
6-[6-(trans-1-propenyl)-tetrahydronaphthalen-2-yl]-2-(2,2-difluoroethenyl)-trans-decahydronaphthalene,
6-[6-(3-butenyl)-tetrahydronaphthalen-2-yl]-2-(3-butenyl)-trans-decahydronaphthalene,
6-[6-(3-butenyl)-tetrahydronaphthalen-2-yl]-2-(trans-3-pentenyl)-trans-decahydronaphthalene,
6-[6-(3-butenyl)-tetrahydronaphthalen-2-yl]-2-(2-propenyloxy)-trans-decahydronaphthalene,
6-[6-(3-butenyl)-tetrahydronaphthalen-2-yl]-2-(trans-2-butenyloxy)-trans-decahydronaphthalene,
6-[6-(3-butenyl)-tetrahydronaphthalen-2-yl]-2-(2-fluoroethenyl)-trans-decahydronaphthalene,
6-[6-(3-butenyl)-tetrahydronaphthalen-2-yl]-2-(2,2-difluoroethenyl)-trans-decahydronaphthalene,
6-[6-(trans-3-pentenyl)-tetrahydronaphthalen-2-yl]-2-(trans-3-pentenyl)-trans-decahydronaphthalene,
6-[6-(trans-3-pentenyl)-tetrahydronaphthalen-2-yl]-2-(2-propenyloxy)-trans-decahydronaphthalene,
6-[6-(trans-3-pentenyl)-tetrahydronaphthalen-2-yl]-2-(trans-2-butenyloxy)-trans-decahydronaphthalene,
6-[6-(trans-3-pentenyl)-tetrahydronaphthalen-2-yl]-2-(2-fluoroethenyl)-trans-decahydronaphthalene,
6-[6-(trans-3-pentenyl)-tetrahydronaphthalen-2-yl]-2-(2,2-difluoroethenyl)-trans-decahydronaphthalene,
6-[6-(2-propenyloxy)-tetrahydronaphthalen-2-yl]-2-(2-propenyloxy)-trans-decahydronaphthalene,
6-[6-(2-propenyloxy)-tetrahydronaphthalen-2-yl]-2-(trans-2-butenyloxy)-trans-decahydronaphthalene,
6-[6-(2-propenyloxy)-tetrahydronaphthalen-2-yl]-2-(2-fluoroethenyl)-trans-decahydronaphthalene,
6-[6-(2-propenyloxy)-tetrahydronaphthalen-2-yl]-2-(2,2-difluoroethenyl)-trans-decahydronaphthalene,
6-[6-(trans-2-butenyloxy)-tetrahydronaphthalen-2-yl]-2-(trans-2-butenyloxy)-trans-decahydronaphthalene,
6-[6-(trans-2-butenyloxy)-tetrahydronaphthalen-2-yl]-2-(2-fluoroethenyl)-trans-decahydronaphthalene,
6-[6-(trans-2-butenyloxy)-tetrahydronaphthalen-2-yl]-2-(2,2-difluoroethenyl)-trans-decahydronaphthalene.

Example 32

Synthesis of 2-ethoxy-6-[3,5-difluoro-4-(3,4-difluorophenyl)phenyl]-trans-decahydronaphthalene

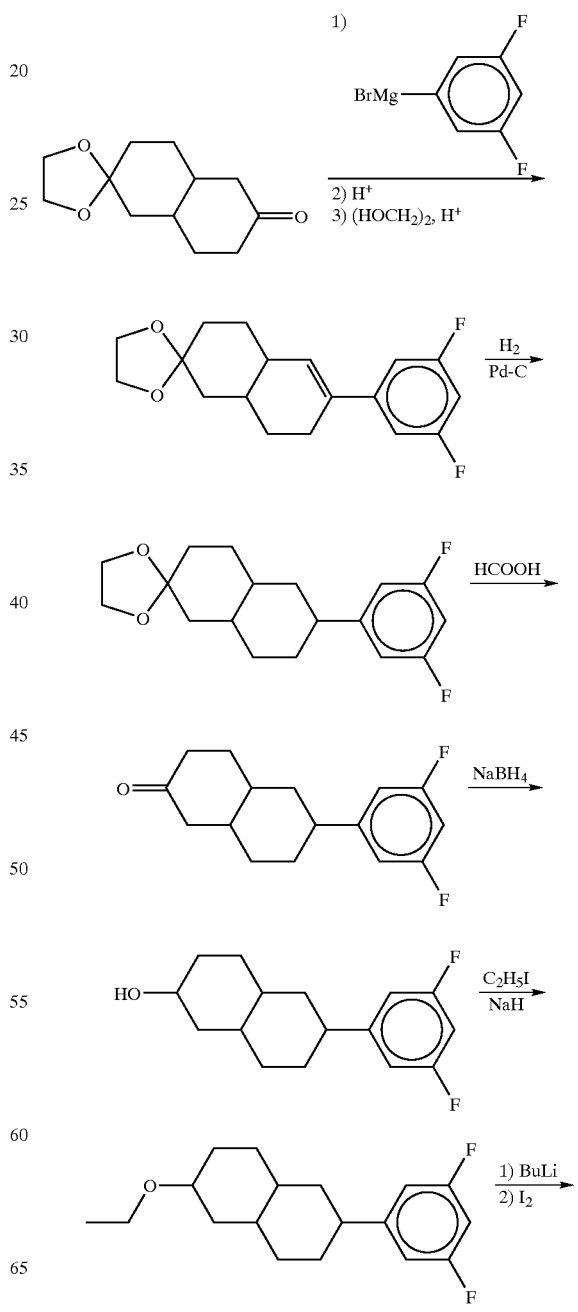

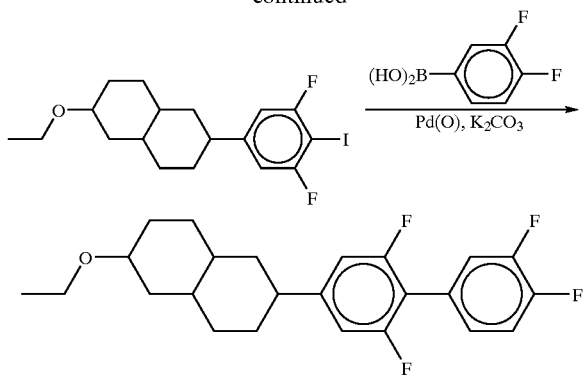

(32-a) Synthesis of 2-(3,5-difluorophenyl)-trans-3,4,4a,5,6,7,8,8a-octahydronaphthalene-6-one ethyleneacetal To a suspension of 3 g of metal magnesium in 15 ml of THF, a 95 ml THF solution of 23 g of 3,5-difluoro-1-bromobenzene was added dropwise to obtain a Grignard reagent. A 60 ml THF solution of 21 g of trans-decahydronaphthalen-2,6-dione monoethyleneacetal was added dropwise to the reagent while cooling the solution to 10° C. or lower. The temperature was reduced to room temperature, and the mixture was stirred for 1 hour. After a saturated aqueous solution of ammonium chloride was added, the organic phase was separated, rinsed with a saturated saline solution, and dried on anhydrous sodium sulfate, and the solvent was evaporated. The oily substance obtained was dissolved in 140 ml of toluene. 4 g of p-toluenesulfonic acid monohydrate was added to the solution, and the mixture was heated for 4 hours under refluxing using an apparatus equipped with a water separator until evaporation of water stopped. Then, 4 g of p-toluenesulfonic acid monohydrate and 12 g of ethylene glycol was further added, and the mixture was further heated for 4 hours under refluxing until evaporation of water stopped. The solution was cooled to room temperature. Water was added to the solution, and the organic phase was separated, rinsed with a saturated aqueous solution of sodium hydrogencarbonate, water, and a saturated saline solution, in sequence, and dried on anhydrous sodium sulfate. The solvent was evaporated to obtain 29 g of 2-(3,5-difluorophenyl)-trans-3,4,4a,5,6,7,8,8a-octahydronaphthalene-6-one ethyleneacetal as a pale yellow oily substance.

(32-b) Synthesis of 6-(3,5-difluorophenyl)-trans-decahydro-2-naphthalenone ethyleneacetal 29 g of 2-(3,5-difluorophenyl)-trans-3,4,4a,5,6,7,8,8a-octahydronaphthalene-6-one ethyleneacetal, which was obtained in (32-a), was dissolved in 150 ml of ethyl acetate. 6 g of carbon with 5% palladium was added to the solution, and hydrogenation was carried out for 6 hours at room temperature in hydrogen under a pressure of 490 KPa. The catalyst was separated by filtration through celite. The solvent was evaporated to obtain 22 g of 6-(3,5-difluorophenyl)-trans-decahydro-2-naphthalenone ethyleneacetal as a pale yellow oily substance.

(32-c) Synthesis of 6-(3,5-difluorophenyl)-trans-decahydro-2-naphthalenone 22 g of 6-(3,5-difluorophenyl)-trans-decahydro-2-naphthalenone ethyleneacetal, which was obtained in (32-b), was dissolved in 110 ml of toluene. 50 ml of formic acid was added to the solution, and the mixture was stirred for 1 hour at room temperature. Water was added to the mixture, and the organic phase was separated and rinsed with water, a saturated aqueous solution of sodium hydrogencarbonate, and a saturated saline solution, in sequence, and dried on anhydrous sodium sulfate. The solvent was evaporated to obtain 13 g of pale yellow solid 6-(3,5-difluorophenyl)-trans-decahydro-2-naphthalenone.

(32-d) Synthesis of 6-(3,5-difluorophenyl)-trans-decahydronaphthalen-2-ol 13 g of 6-(3,5-difluorophenyl)-trans-decahydro-2-naphthalenone, which was obtained in (32-c), was dissolved in 70 ml of methanol. While cooling the solution to 10° C. or lower, 2 g of sodium borohydride was added in small amounts to the solution. The mixture was stirred for 1 hour at room temperature. Water was added to the solution, and extraction was carried out using ethyl acetate. The extracts were rinsed with water and a saturated saline solution and dried on anhydrous sodium sulfate, and the solvent was evaporated to obtain 12 g of pale yellow solid 6-(3,5-difluorophenyl)-trans-decahydronaphthalen-2-ol.

(32-e) Synthesis of 2-(3,5-difluorophenyl)-6-ethoxy-trans-decahydronaphthalene

To a suspension of 4 g of 60% sodium hydride in 20 ml of DMF, a 60 ml N,N-dimethylformamide (DMF) solution of 12 g of 6-(3,5-difluorophenyl)-trans-decahydronaphthalen-2-ol, which was obtained in (32-d), was added dropwise while the mixture was cooled to 10° C. or lower. The temperature was reduced to room temperature, and the mixture was stirred for 30 minutes. Thereafter, a 20 ml DMF solution of 11 g of ethyl iodide was added dropwise to the mixture while it is cooled to 10° C. or lower. After heating the mixture at 60° C. for 8 hours while stirring, water and ethyl acetate were added to the mixture. The organic solution was separated, rinsed with water and a saturated saline solution, and dried on anhydrous sodium sulfate. Then, the solvent was evaporated, and the residue was purified by silica gel column chromatography (hexane) and recrystallized from ethanol to obtain 10 g of white solid 2-(3,5-difluorophenyl)-6-ethoxy-trans-decahydronaphthalene (32-f) Synthesis of 2-(3,5-difluoro-4-iodophenyl)-6-ethoxy-trans-decahydronaphthalene To a 50 ml THF solution of 10 g of 2-(3,5-difluorophenyl)-6-ethoxy-trans-decahydronaphthalene, which was obtained in (32-e), the solution being cooled to −70° C., 22 ml of 1.6 M hexane solution of butyl lithium was added dropwise over a period of 5 minutes while maintaining the inner temperature at −50° C. or lower. A 40 ml THF solution of 8 g of iodine was added dropwise to the mixture over a period of 10 minutes. After generation of heat stopped, the temperature was raised to room temperature, and water and ethyl acetate were added. The organic phase was separated, rinsed with an aqueous solution of sodium hydrogen sulfite, water, a saturated aqueous solution of sodium hydrogencarbonate, water, and a saturated saline solution, in sequence, and dried on anhydrous sodium sulfate. The solvent was evaporated to obtain 13 g of yellow solid 2-(3,5-difluoro-4-iodophenyl)-6-ethoxy-trans-decahydronaphthalene.

(32-g) Synthesis of 2-ethoxy-6-[3,5-difluoro-4-(3,4-difluorophenyl)phenyl]-trans-decahydronaphthalene 13 g of -(3,5-difluoro-4-iodophenyl)-6-ethoxy-trans-decahydronaphthalene, which was obtained in (32-f), was dissolved in 60 ml of toluene. 1.3 g of tetrakis (triphenylphosphine)palladium(0) and 30 ml of 2M aqueous solution of sodium carbonate were added, and a 30 ml ethanol solution of 8 g of 3,4-difluorophenylboronic acid was further added dropwise over a period of 10 minutes.

After heating the mixture for 24 hours at 70° C. while stirring, the mixture was cooled to room temperature, and water was added to the mixture. After extraction was carried out using toluene, the organic phase was rinsed with a saline solution and dried on anhydrous magnesium sulfate. After the solvent was evaporated, the residue was purified by silica gel column chromatography (hexane) and recrystallized from ethanol to obtain 4 g white crystals of 2-ethoxy-6-(3,5-difluoro-4-(3,4-difluorophenyl)phenyl]-trans-decahydronaphthalene.

The following compounds were prepared in the same manner as mentioned above:

2-vinyl-6-[4-(4-fluorophenyl)phenyl]-trans-decahydronaphthalene,
2-(trans-1-propenyl)-6-[4-(4-fluorophenyl)phenyl]-trans-decahydronaphthalene,
2-(3-butenyl)-6-[4-(4-fluorophenyl)phenyl]-trans-decahydronaphthalene,
2-(trans-3-pentenyl)-6-[4-(4-fluorophenyl)phenyl]-trans-decahydronaphthalene,
2-ethoxy-6-[4-(4-fluorophenyl)phenyl]-trans-decahydronaphthalene,
2-vinyl-6-[4-(4-trifluoromethoxyphenyl)phenyl]-trans-decahydronaphthalene.

Example 33

Synthesis of 3-fluoro-4-cyanophenyl 4-(6-vinyl-trans-decahydronaphthalen-2-yl)benzoate

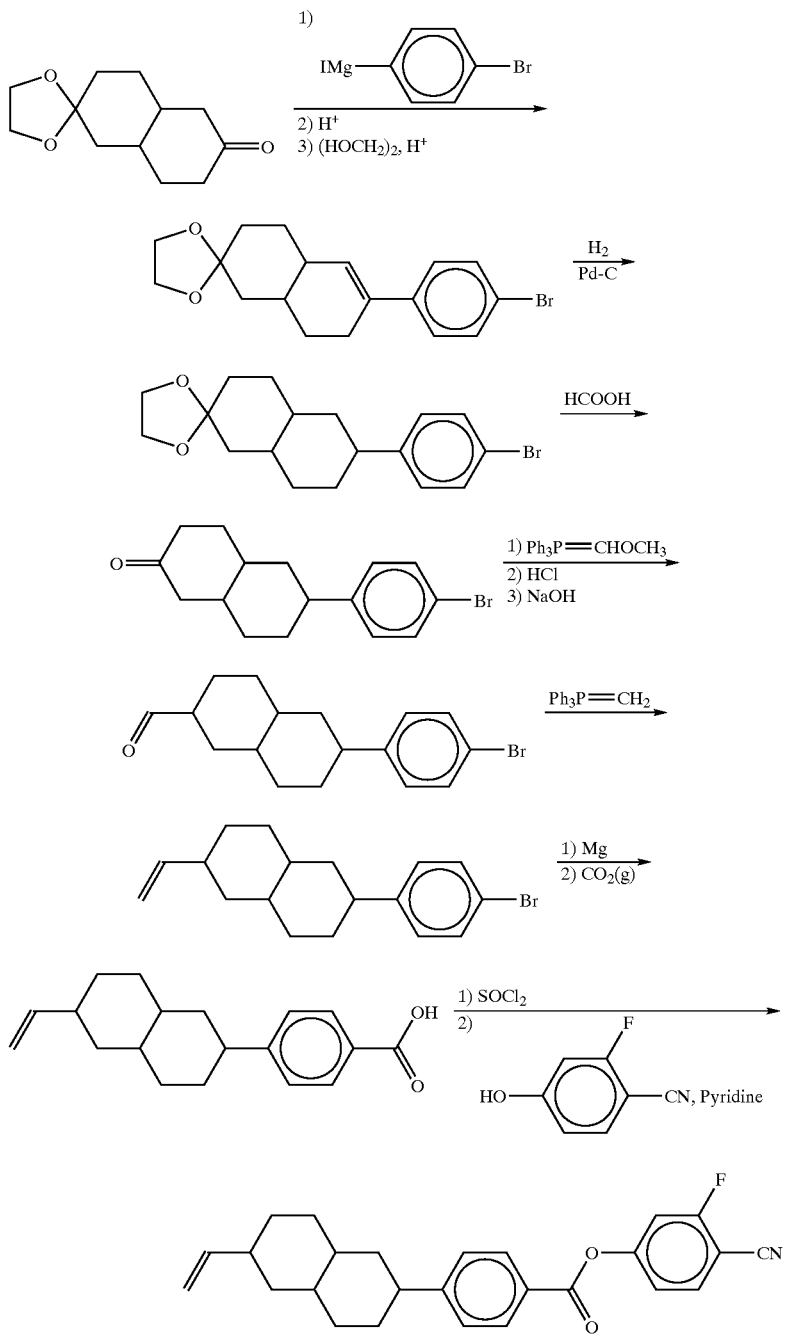

(33-a) Synthesis of 2-(4-bromophenyl)-trans-3,4,4a,5,6,7,8,8a-octahydronaphthalene-6-one ethyleneacetal In a manner similar to that in (1-a), reaction of 17 g of decahydronaphthalen-2,6-dione monoethyleneacetal with a Grignard reagent prepared from 4-bromo-1-iodobenzene, dehydration, and re-acetalization were carried out to obtain 24 g of pale yellow solid 2-(4-bromophenyl)-trans-3,4,4a,5,6,7,8,8a-octahydronaphthalene-6-one ethyleneacetal.

(33-b) Synthesis of 6-(4-bromophenyl)-trans-decahydro-2-naphthalenone ethyleneacetal In a manner similar to that in (1-b), catalytic hydrogenation reduction of 24 g of 6-(4-bromophenyl)-trans-1,2,3,4,7,8,9,10-octahydro-2-naphthalenone ethyleneacetal, which was obtained in (33-a), was carried out to obtain 21 g of pale yellow solid 6-(4-bromophenyl)-trans-decahydro-2-naphthalenone ethyleneacetal.

(33-c) Synthesis of 6-(4-bromophenyl)-trans-decahydro-2-naphthalenone

Deacetalization of 21 g of 2-(4-bromophenyl)-trans-3,4,4a,5,6,7,8,8a-octahydronaphthalene-6-one ethyleneacetal, which was obtained in (33-b), was carried out to obtain 14 g of pale yellow solid 6-(4-bromophenyl)-trans-decahydro-2-naphthalenone.

(33-d) Synthesis of 6-(4-bromophenyl)-trans-decahydronaphthalene-2-carbaldehyde

A 70 ml THF solution of 14 g of 6-(4-bromophenyl)-trans-decahydro-2-naphthalenone, which was obtained in (33-c), was added dropwise to a Wittig reagent prepared from 19 g of methoxymethyltriphenylphosphonium chloride and 7 g of potassium t-butoxide in 130 ml of THF, while the mixture was cooled to 10° C. or lower. The temperature was reduced to room temperature. After the mixture was stirred for 4 hours, water and hexane were added. The organic phase was separated and rinsed with water, and the solvent was evaporated. The pale yellow solid substance obtained was dissolved in 95 ml of THF. 80 ml of 10% hydrochloric acid was added, and the mixture was heated for 3 hours under refluxing. The temperature was reduced to room temperature, and the organic phase was separated. The aqueous phase was extracted with ethyl acetate. Organic phases were combined, rinsed with a saturated aqueous solution of sodium hydrogencarbonate, water, and a saturated saline solution, in sequence, and the solvent was evaporated. The pale yellow solid substance was dissolved in 90 ml of methanol. While the solution was cooled to 10° C. or lower, 10 ml of 10% aqueous solution of sodium hydroxide was added to the solution. After stirring for 2 hours, the temperature was reduced to room temperature, and the solvent was evaporated. The pale yellow solid substance obtained was rinsed with water and recrystallized from a hexane solution to obtain 11 g of pale yellow solid 6-(4-bromophenyl)-trans-decahydronaphthalene-2-carbaldehyde.

(33-e) Synthesis of 2-(4-bromophenyl)-6-vinyl-trans-decahydronaphthalene

A 60 ml THF solution of 11 g of 6-(4-bromophenyl)-trans-decahydronaphthalene-2-carbaldehyde, which was obtained in (33-d), was added dropwise to a Wittig reagent prepared from 14 g of methyltriphenylphosphonium bromide and 5 g of potassium t-butoxide in 90 ml of THF, while the mixture was cooled to 10° C. or lower. The temperature was reduced to room temperature. After the mixture was stirred for 3 hours, water and hexane were added. The organic phase was separated and rinsed with water, and the solvent was evaporated. The residue was purified by silica gel column chromatography (hexane) and recrystallized from ethanol to obtain 9 g of white solid 2-(4-bromophenyl)-6-vinyl-trans-decahydronaphthalene.

(33-f) Synthesis of 4-(6-vinyl-trans-decahydronaphthalen-2-yl)benzoic acid

To a suspension of 1 g of metal magnesium in 5 ml of THF, a 40 ml THF solution of 9 g of 2-(4-bromophenyl)-6-vinyl-trans-decahydronaphthalene was added dropwise to obtain a Grignard reagent. Carbon dioxide was injected into the reagent until saturation while cooling the solution to 10° C. or lower. After the mixture was stirred for 1 hour at room temperature, 10% hydrochloric acid was added. Then, the organic phase was separated, rinsed with a saturated saline solution, and dried on anhydrous magnesium sulfate. The solvent was evaporated to obtain 8 g of milky-white solid 4-(6-vinyl-trans-decahydronaphthalen-2-yl)benzoic acid.

(33-g) Synthesis of 3-fluoro-4-cyanophenyl 4-(6-vinyl-trans-decahydronaphthalen-2-yl)benzoate 8 g of 4-(6-vinyl-trans-decahydronaphthalen-2-yl)benzoic acid, which was obtained in (33-f), was dissolved in 40 ml of dichloromethane. 8 g of thionyl chloride, 0.1 ml of pyridine, and 2 ml of DMF were added to the solution, and the mixture was heated for 1 hour under refluxing. After excessive thionyl chloride and solvent were evaporated, 40 ml of dichloromethane was added, then 4 g of 3-fluoro-4-cyanophenol and 4 g of pyridine were added, and the mixture was stirred for 8 hours at room temperature. 10% hydrochloric acid was added, and the organic phase was separated and rinsed with a saturated aqueous solution of sodium hydrogencarbonate and a saturated saline solution, in sequence, and dried on anhydrous sodium sulfate. After the solvent was evaporated, the residue was purified by silica gel chromatography (hexane/ethyl acetate), and recrystallized from ethanol to obtain 5 g white crystals of 3-fluoro-4-cyanophenyl 4-(6-vinyl-trans-decahydronaphthalen-2-yl)benzoate.

The following compounds were prepared in the same manner as mentioned above:

4-fluorophenyl 4-(6-vinyl-trans-decahydronaphthalen-2-yl)benzoate, 4-fluorophenyl 4-[6-(trans-1-propenyl)-trans-decahydronaphthalen-2-yl]benzoate.

Example 34

Synthesis of 2-(3-butenyl)-6-[4-(4-methylphenylethynyl)phenyl]-trans-decahydronaphthalene

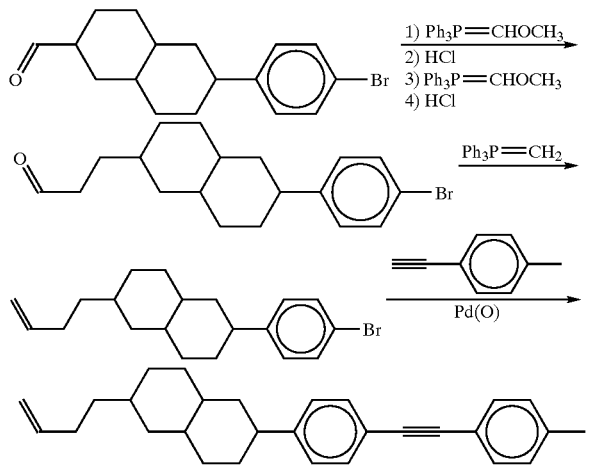

(34-a) Synthesis of 2-(4-bromophenyl)-6-(3-oxopropyl)-trans-decahydronaphthalene Reaction of 10 g of 6-(4-bromophenyl)-trans-decahydronaphthalene-2-carbaldehyde with a Wittig reagent and hydrolyzation with acid were carried out to obtain 7 g pale yellow crystals of 2-(4-bromophenyl)-6-(3-oxopropyl)-trans-decahydronaphthalene.

(34-b) Synthesis of 2-(4-bromophenyl)-6-(3-butenyl)-trans-decahydronaphthalene

In a manner similar to that in (2-e), reaction of 7 g of 2-(4-bromophenyl)-6-(3-oxopropyl)-trans-decahydronaphthalene was carried out to obtain 6 g white crystals of 2-(4-bromophenyl)-6-(3-butenyl)-trans-decahydronaphthalene.

(34-c) Synthesis of 2-(3-butenyl)-6-[4-(4-methylphenylethynyl)phenyl]-trans-decahydronaphthalene 6 g of 2-(4-bromophenyl)-6-(3-butenyl)-trans-decahydronaphthalene, which was obtained in (34-b), was dissolved in 30 ml of DMF. 0.8 g of tetrakis (triphenylphosphine)palladium(0), 0.6 g of copper iodide (I), and 2 g of (4-methyl)phenylacetylene were added to the mixture. After heating the mixture for 2 hours at 50° C. while stirring, the mixture was cooled to room temperature, and 10% hydrochloric acid was added to the mixture. After extraction was carried out using toluene, the organic phase was rinsed with a saline solution and dried on anhydrous magnesium sulfate. After the solvent was evaporated, the residue was purified by silica gel column chromatography (hexane) and recrystallized from ethanol to obtain 4 g white crystals of 2-(3-butenyl)-6-[4-(4-methylphenylethynyl) phenyl]-trans-decahydronaphthalene.

The following compounds were prepared in the same manner as mentioned above:

2-vinyl-6-[4-(4-fluorophenylethynyl)phenyl]-trans-decahydronaphthalene,
2-(trans-1-propenyl)-6-[4-(4-fluorophenylethynyl)phenyl]-trans-decahydronaphthalene,
2-(3-butenyl)-6-[4-(4-fluorophenylethynyl)phenyl]-trans-decahydronaphthalene,
2-(trans-3-pentenyl)-6-[4-(4-fluorophenylethynyl)phenyl]-trans-decahydronaphthalene,
2-ethoxy-6-[4-(4-fluorophenylethynyl)phenyl]-trans-decahydronaphthalene,
2-(trans-1-propenyl)-6-[2,3-difluoro-4-(2,3-difluoro-4-methoxyphenyl)phenyl]-trans-decahydronaphthalene,
2-ethoxy-6-[2,3-difluoro-4-[2,3-difluoro-4-(trans-2-butenyloxy)phenylethynyl]phenyl]-trans-decahydronaphthalene.

Example 35

Synthesis of 6-(4-ethoxy-trans-cyclohexyl)-2-(3,4,5-trifluorophenyl)-trans-decahydronaphthalene

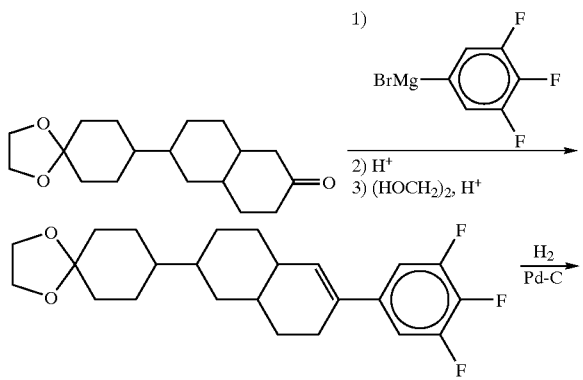

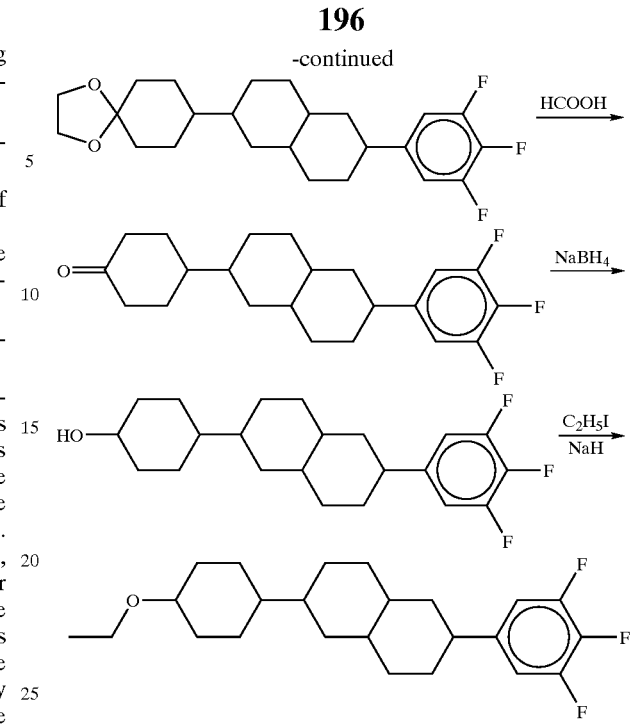

(35-a) Synthesis of 4-[2-(3,4,5-trifluorophenyl)-trans-3,4,4a,5,6,7,8,8a-octahydronaphthalen-6-yl]cyclohexanone ethyleneacetal In a manner similar to that in (1-a), reaction of 15 g of 4-(6-oxo-trans-octahydronaphthalen-2-yl)cyclohexanone monoethyleneacetal with a Grignard reagent prepared from 3,4,5-trifluoro-1-bromobenzene, dehydration, and re-acetalization were carried out to obtain 18 g of pale yellow solid 4-[2-(3,4,5-trifluorophenyl)-trans-3,4,4a,5,6,7,8,8a-octahydronaphthalen-6-yl]cyclohexanone ethyleneacetal.

(35-b) Synthesis of 4-[6-(3,4,5-trifluorophenyl)-trans-decahydronaphthalen-2-yl]cyclohexanone monoethyleneaceta In a manner similar to that in (1-b), catalytic hydrogenation reduction of 18 g of 4-[2-(3,4,5-trifluorophenyl)-trans-3,4,4a,5,6,7,8,8a-octahydronaphthalen-6-yl]cyclohexanone ethyleneacetal, which was obtained in (35-a), was carried out to obtain 16 g of pale yellow solid 4-[6-(3,4,5-trifluorophenyl)-trans-decahydronaphthalen-2-yl] cyclohexanone monoethyleneacetal.

(35-c) Synthesis of 4-[6-(3,4,5-trifluorophenyl)-trans-decahydronaphthalen-2-yl]cyclohexanone Deacetalization of 16 g of 4-[6-(3,4,5-trifluorophenyl)-trans-decahydronaphthalen-2-yl]cyclohexanone monoethyleneacetal, which was obtained in (35-b), was carried out to obtain 11 g of pale yellow solid 4-[6-(3,4,5-trifluorophenyl)-trans-decahydronaphthalen-2-yl] cyclohexanone.

(4-d) Synthesis of 2-(4-hydroxy-trans-cyclohexyl)-6-(3,4,5-trifluorophenyl)-trans-decahydronaphthalene Reduction of 11 g of 4-[6-(3,4,5-trifluorophenyl)-trans-decahydronaphthalen-2-yl]cyclohexanone, which was obtained in (35-c), was carried out to obtain 7 g of pale yellow solid 2-(4-hydroxy-trans-cyclohexyl)-6-(3,4,5-trifluorophenyl)-trans-decahydronaphthalene.

(35-e) Synthesis of 6-(4-ethoxy-trans-cyclohexyl)-2-(3,4,5-trifluorophenyl)-trans-decahydronaphthalene Etherification of 7 g of 2-(4-hydroxy-trans-cyclohexyl)-6-(3,4,5-trifluorophenyl)-trans-decahydronaphthalene, which was obtained in (35-d), was carried out to obtain 3 g of white solid 6-(4-ethoxy-trans-cyclohexyl)-2-(3,4,5-trifluorophenyl)-trans-decahydronaphthalene.

The following compounds were prepared in the same manner as mentioned above:
6-(4-ethoxy-trans-cyclohexyl)-2-(4-fluorophenyl)-trans-decahydronaphthalene,
6-(4-ethoxy-trans-cyclohexyl)-2-(4-trifluoromethoxyphenyl)-trans-decahydronaphthalene.

Example 36

Synthesis of 3,5-difluoro-4-cyanophenyl trans-4-(6-propyl-trans-decahydronaphthalen-2-yl)cyclohexanecarboxylate

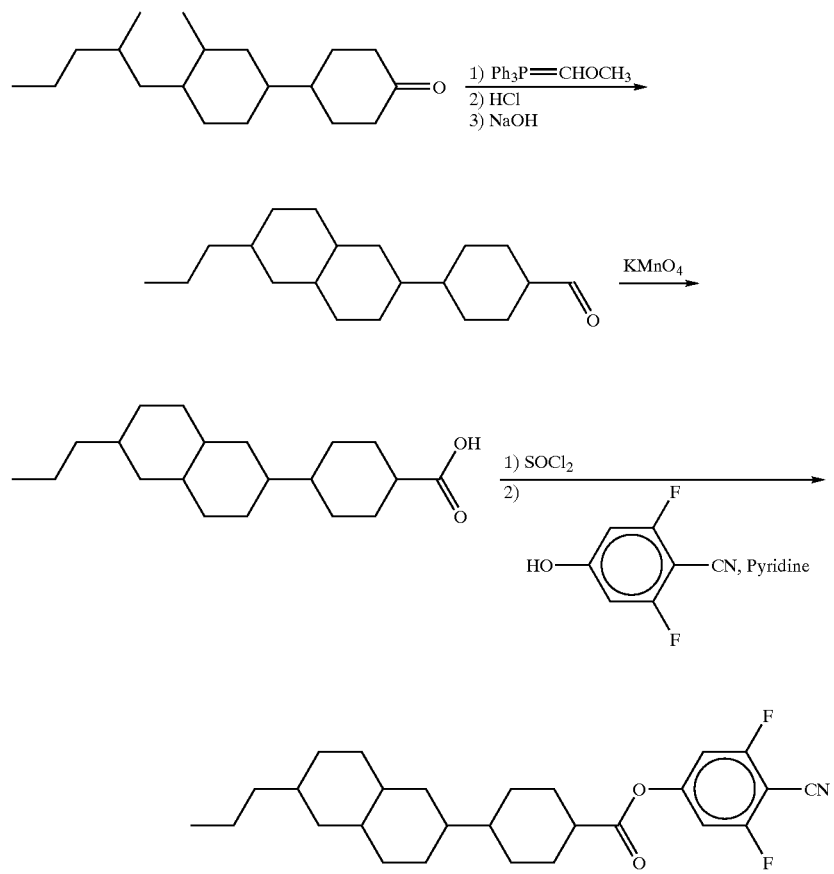

(36-a) Synthesis of trans-4-(6-propyl-trans-decahydronaphthalen-2-yl)cyclohexanecarbaldehyde Reaction of 10 g of 4-(6-propyl-trans-decahydronaphthalen-2-yl)cyclohexanone with a Wittig reagent was carried out to obtain 8 g pale yellow crystals of trans-4-(6-propyl-trans-decahydronaphthalen-2-yl)cyclohexanecarbaldehyde.

(36-b) Synthesis of trans-4-(6-propyl-trans-decahydronaphthalen-2-yl)cyclohexanecarboxylic acid flu 8 g of trans-4-(6-propyl-trans-decahydronaphthalen-2-yl)cyclohexanecarbaldehyde, which was obtained in (36-a), was added dropwise to a 30 ml aqueous solution of 8 g of concentrated sulfuric acid and 3 g of potassium permanganate while the mixture was cooled to 10° C. or lower. After stirring the mixture for 30 minutes at room temperature, water and ethyl acetate were added. The organic phase was separated and rinsed with water, a saturated aqueous solution of sodium hydrogencarbonate, water, and a saturated saline solution, in sequence. After the organic phase was dried on anhydrous sodium sulfate, the solvent was evaporated. The residue was recrystallized from a hexane solution to obtain 3 g white solid trans-4-(6-propyl-trans-decahydronaphthalen-2-yl)cyclohexanecarboxylic acid.

(36-c) Synthesis of 4-cyano-3,5-difluorophenyl trans-4-(6-propyl-trans-decahydronaphthalen-2-yl)cyclohexanecarboxylate Esterification reaction of 3 g of trans-4-(6-propyl-trans-decahydronaphthalen-2-yl)cyclohexanecarboxylic acid, which was obtained in (36-b), with 3,5-difluoro-4-cyanophenol was carried out to obtain 2 g white crystals of 4-cyano-3,5-difluorophenyl trans-4-[6-propyl-trans-decahydronaphthalen-2-yl]cyclohexanecarboxylate.

The following compounds were prepared in the same manner as mentioned above:

4-fluorophenyl 6-(trans-4-methylcyclohexyl)-trans-decahydronaphthalenecarboxylate, 4-fluorophenyl 6-(trans-4-ethylcyclohexyl)-trans-decahydronaphthalenecarboxylate, 3,5-difluoro-4-(trans-2-butenyloxy)phenyl trans-4-[6-(trans-3-pentenyl)-trans-decahydronaphthalen-2-yl]cyclohexanecarboxylate.

Example 37

Synthesis of 6-(trans-4-propylcyclohexyl)-2-(1,2-difluoronaphthalen-6-yl)-trans-decahydronaphthalene

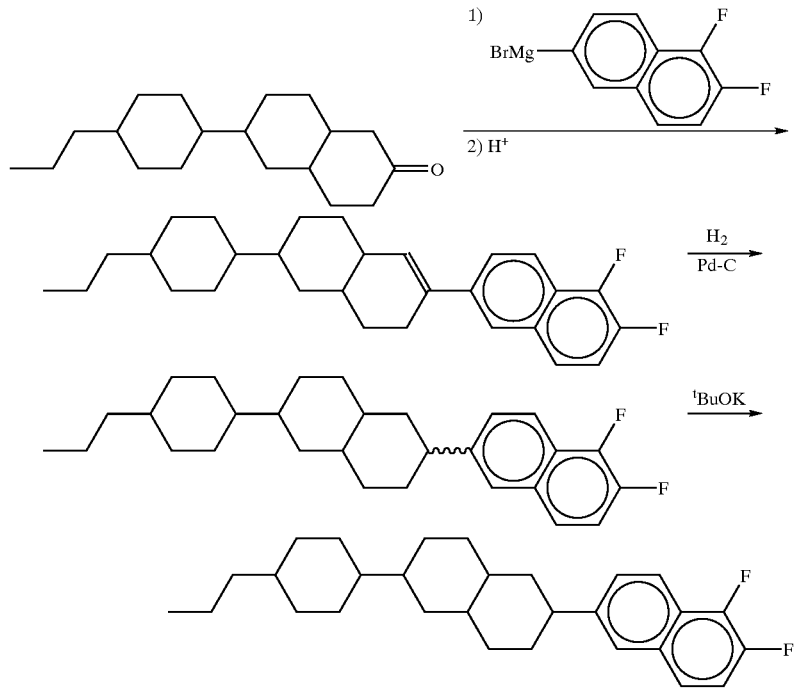

(37-a) Synthesis of 6-(1,2-difluoronaphthalen-6-yl)-2-(trans-4-propylcyclohexyl)-trans-3,4,4a,5,6,7,8,8a-octahydronaphthalene In a manner similar to that in (1-a), reaction of 7 g of 6-(trans-4-propylcyclohexyl)-trans-decahydronaphthalene with a Grignard reagent prepared from 1,2-difluoro-6-bromonaphthalene and dehydration were carried out to obtain 9 g of pale yellow solid 6-(1,2-difluoronaphthalen-6-yl)-2-(trans-4-propylcyclohexyl)-trans-3,4,4a,5,6,7,8,8a-octahydronaphthalene.

(37-b) Synthesis of 6-(trans-4-propylcyclohexyl)-2-(1,2-difluoronaphthalen-6-yl)-decahydronaphthalene In a manner similar to that in (1-b), catalytic hydrogenation reduction of 9 g of 6-(1,2-difluoronaphthalen-6-yl)-2-(trans-4-propylcyclohexyl)-trans-3,4,4a,5,6,7,8,8a-octahydronaphthalene, which was obtained in (37-a), was carried out to obtain a 7 g cis/trans mixture of pale yellow solid 6-(trans-4-propylcyclohexyl)-2-(1,2-difluoronaphthalen-6-yl)-decahydronaphthalene.

(37-c) Isomerization of 6-(trans-4-propylcyclohexyl)-2-(1,2-difluoronaphthalen-6-yl)-decahydronaphthalene 7 g cis/trans mixture of 6-(trans-4-propylcyclohexyl)-2-(1,2-difluoronaphthalen-6-yl)-decahydronaphthalene, which was obtained in (37-b), was dissolved in 40 ml of DMF. While the solution was cooled to 0° C., 2 g of potassium t-butoxide was added to the solution, and the mixture was stirred for 2 hours. After water and hexane were added to the mixture, the organic phase was separated and rinsed with water and a saturated saline solution, in sequence, and dried on anhydrous magnesium sulfate. Then, the solvent was evaporated. The residue was purified by silica gel column chromatography (hexane) and recrystallized from ethanol to obtain 3 g of white solid 6-(trans-4-propylcyclohexyl)-2-(1,2-difluoronaphthalen-6-yl)-decahydronaphthalene.

The following compounds were prepared in the same manner as mentioned above:

6-(trans-4-methylcyclohexyl)-2-(2-fluoronaphthalen-6-yl)-trans-decahydronaphthalene,
6-(trans-4-ethylcyclohexyl)-2-(2-fluoronaphthalen-6-yl)-trans-decahydronaphthalene,
6-(trans-4-propylcyclohexyl)-2-(2-fluoronaphthalen-6-yl)-trans-decahydronaphthalene.

Example 38

Preparation of Liquid Crystal Composition (1)

The versatile host liquid crystal (H-A):

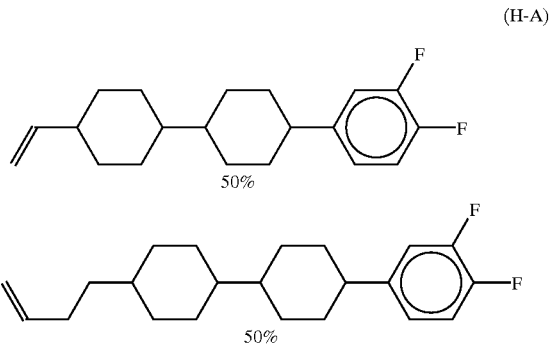

(H-A)

was prepared. This host liquid crystal (H-A) exhibits a nematic phase at 116.7° C. or less, and its melting point is 11° C. The physical property values at 20° C. of the threshold voltage (Vth) of a TN cell (cell thickness: 6 μm) prepared using this composition were as shown below.

Threshold voltage (Vth): 2.14 V
Dielectric anisotropy (Δε): 4.8
Birefringence (Δn): 0.090

Next, when a liquid crystal composition (H-1) was prepared comprised of 80% of this host liquid crystal (H-A) and 20% of compound (I-3):

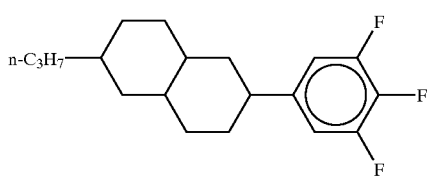

(I-3)

of the present invention obtained in Example 1, the upper limit temperature of the nematic phase was 88.7° C., which was slightly lower than that of the host liquid crystal (H-A). This composition was not observed to exhibit crystal precipitation or phase separation even when allowed to stand for 1 month or more at 0° C., indicating that compound (I-3) of the present invention has excellent co-solubility with versatile liquid crystal. Next, when its melting point was measured by cooling to −60° C. and crystallizing, it was determined to be +13° C., which is roughly equal to that of the host liquid crystal (H-A). Next, when a liquid crystal device was prepared in the same manner using this composition and its physical property values were measured, the following results were obtained.

$T_{N-I}$: 88.7° C.

$T_{C-N}$: 13° C.

Threshold voltage (Vth): 1.69 V

Dielectric anisotropy (Δε): 5.7

Response time (Στ=Σd) 31.0 msec

Birefringence (Δn): 0.080

Thus, by adding 20% of the compound of (I-3) of the present invention to host liquid crystal (H-A), its threshold voltage (Vth) was able to be lowered 0.45 V while suppressing the drop in nematic phase upper limit temperature $(T_{N-I})$ to 28° C. Moreover, the increase in its response time was able to be held to less than 6 msec. In addition, the melting point determined by cooling and crystallizing was 13° C., which was only slightly different from that of the host liquid crystal (H-A), indicating that (I-3) dissolves easily in the host liquid crystal. In addition, the nematic phase upper limit temperature of (I-3) alone as extrapolated from the nematic phase upper limit temperature $(T_{N-I})$ of (H-1) was −23° C.

Next, although the voltage holding rates of this element at room temperature and 80° C. were measured, both were extremely favorable, indicating that this element can be adequately used for active matrix driving.

Comparative Example 1

Comparative liquid crystal composition (HR-1) was prepared comprised of 20% of cyclohexylbenzene derivative (R-1):

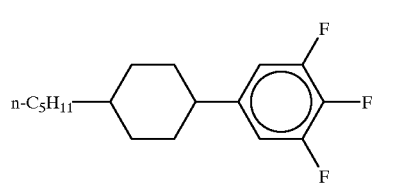

(R-1)

used in place of (I-3) in Example 1, and 80% of host liquid crystal (H-A). The nematic phase upper limit temperature $(T_{N-I})$ of this composition decreased considerably to 70° C. The nematic phase upper limit temperature of (R-1) alone as extrapolated from this was −100° C. or below. Thus, liquid crystallinity is considerably lower than (I-3).

The physical property values of this composition along with the photoelectric property values of an element prepared in the same manner are as shown below.

Threshold voltage (Vth): 1.58 V

Dielectric anisotropy (Δε): 5.6

Response time (τr=τd): 30.0 msec

Birefringence (Δn): 0.080

Thus, in comparison with (H-1), which is a composition containing the compound of (I-3) pertaining to the present invention, not only is the nematic phase upper limit temperature $(T_{N-I})$ nearly 20° C. lower, but the threshold voltage (Vth) is only decreased by about 0.1 V, and response time is essentially unchanged.

Example 39

Preparation of Liquid Crystal Composition (2)

Liquid crystal composition (H-2) was prepared comprised of 20 wt % of (I-18) in Table 3, which is a compound of the present invention:

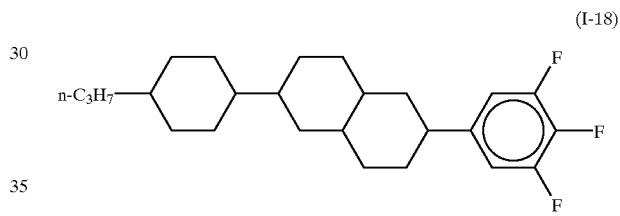

(I-18)

and 80 wt % of host liquid crystal (H-A). The physical property values of (H-2) and the photoelectric characteristic values of a liquid crystal device prepared in the same manner using (H-2) were as shown below.

$T_{N-I}$: 122.8° C.

$T_{C-N}$: 2° C.

Threshold voltage (Vth): 1.97 V

Dielectric anisotropy (Δε): 4.8

Response time (τr=τd): 41.3 msec

Birefringence (Δn): 0.088

Thus, by adding 20% of (I-18), the nematic phase upper limit temperature $(T_{N-I})$ was increased 6.1° C., melting point $(T_{C-N})$ was lowered 9° C., and nematic phase temperature range was increased 15.1° C. Moreover, threshold voltage (Vth) was also able to be decreased 0.17 V. In addition, although this (H-2) was allowed to stand for 2 hours at −20° C., crystal precipitation or phase separation was not observed.

Next, although the voltage holding rates of this element at room temperature and 80° C. were measured, both were extremely favorable, indicating that this element can be adequately used for active matrix driving.

Comparative Example 2

A comparative liquid crystal composition (HR-2) was prepared comprised of 20 wt % of phenylbicyclohexane derivative (R-2):

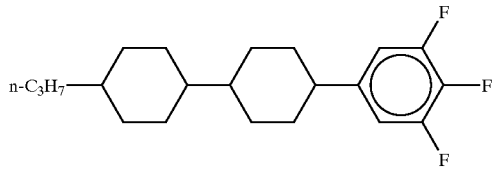

(R-2)

which, although having a similar structure to (I-18), the trans-decahydronaphthalene group is substituted with a cyclohexane-4,4'-diyl group, and 80 wt % of host liquid crystal (H-A). The physical property values of this composition along with the photoelectric characteristic values of an element prepared in the same manner are as shown below.

$T_{N-I}$: 111.0° C.

$T_{C-N}$: +25° C.

Threshold voltage (Vth): 2.00 V

Dielectric anisotropy ($\Delta\epsilon$): 5.9

Response time ($\tau r = \tau d$): 37.8 msec

Birefringence ($\Delta n$): 0.087

Thus, in comparison with the case of (H-2), the nematic phase upper limit temperature ($T_{N-I}$) dropped by nearly 11.8° C., and the threshold voltage (Vth) conversely became 0.03 V higher than (H-2) pertaining to the present invention.

Moreover, melting point also rose 13° C. higher than the host liquid crystal, indicating that the solubility of the compound of (R-2) relative to the host liquid crystal is not that good.

As has been described above, it was determined that the compound of (I-18) of the present invention has effects that are superior to those of compounds of the prior art in terms of preparing a liquid crystal composition that has a wide temperature range, low threshold voltage and allows high-speed response.

Example 40

Preparation of Liquid Crystal Composition (3)

Versatile n type host liquid crystal (H-B):

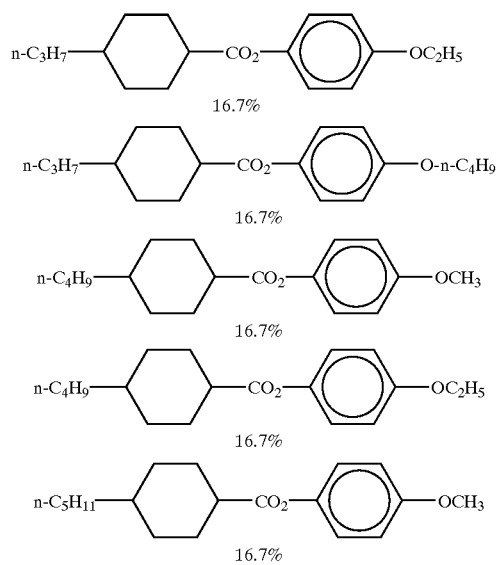

(H-B)

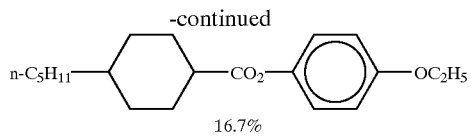

was prepared. This (H-B) exhibits a nematic phase at 72.5° C. or less, and its melting point is 17° C. The physical property values of this composition were as shown below.

Dielectric anisotropy ($\Delta\epsilon$): −1.3

Birefringence ($\Delta n$): 0.085

A liquid crystal composition (H-3) was prepared comprised of 80% of host liquid crystal (H-B) and 20% of compound (I-9):

(I-9)

obtained in Example 10. Its physical property values and photoelectric characteristic values measured with a liquid crystal device prepared in the same manner were as shown below.

Nematic phase upper limit temperature ($T_{N-I}$): 76.5° C.

Dielectric anisotropy ($\Delta\epsilon$): 3.2

Threshold voltage (Vth): 2.30 V

Response time ($\tau$): 40.0 msec

Birefringence ($\Delta n$): 0.085

Thus, although the threshold voltage (Vth) is a little higher as compared with (H-B), the nematic phase upper limit temperature is more than 10° C. higher, and response is also improved, although only slightly. In addition, although this (H-3) was allowed to stand for 2 weeks at −20° C., liquid crystal precipitation or phase separation was not observed.

Comparative Example 3

Nematic liquid crystal composition (H-R³) was prepared by adding 20% of 3-fluoro-4-cyanobenzene derivative (R-3):

(R-3)

having a structure in place of (I-9) in Example 40 in which the trans-decahydronaphthalene group is substituted with a cyclohexylene group, to (H-B). The physical property values of this composition along with the photoelectric characteristic values of an element prepared in the same manner are as shown below.

Nematic phase upper limit temperature ($T_{N-I}$): 58.5° C.

Dielectric anisotropy ($\Delta\epsilon$): 3.6

Threshold voltage (Vth): 2.2 V

Response time (r): 36.0 msec

Birefringence ($\Delta n$): 0.084

It can be seen that $\Delta\epsilon$ of (H-R³) has increased and Vth has been decreased more effectively. In addition, the response is also faster than (H-B). However, $T_{N-I}$ has decreased by nearly 20° C. as compared with (H-3). Thus, it can be seen that it is difficult to prepare a liquid crystal composition having both low voltage driving and a wide temperature range with a phenylcyclohexane derivative like (R-3).

Example 41

Preparation of Liquid Crystal Composition (4)

Liquid crystal composition (H-4) was prepared comprised of 80 wt % of (H-A) and 20 wt % of compound (I-23) of the present invention obtained in Example 22:

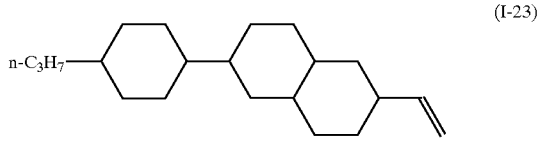

(I-23)

The $T_{N-I}$ of this composition was 116.4° C. Although this (H-4) was allowed to stand for 4 weeks at −20° C., crystal precipitation or phase separation was not observed. In addition, when this composition was crystallized by allowing to stand after cooling to −60° C. followed by measurement of $T_{C-N}$, it was found to be −3° C., indicating that it can be made to be significantly lower than (H-A), and that (I-23) dissolves easily in the host liquid crystal.

Next, (H-4) was filled into a TN cell having a cell thickness of 6.0 μm to prepare a liquid crystal device. Measurement of its photoelectric characteristics at 20° C. yielded the values indicated below.

Threshold voltage (Vth): 2.31 V
Response time (τ): 27.4 msec
Sharpness (γ): 1.29
Dielectric anisotropy (Δε): 3.2
Birefringence (Δn): 0.081

The value of Δn was able to be lowered while holding the decrease in $T_{N-I}$ to 4° C. by adding 20 wt % of (I-23). In addition, there are hardly any changes in Vth and γ, and the increase in τ was able to be held to roughly 5 msec.

In addition, although the voltage holding rates of this element at room temperature and 80° C. were measured, both were extremely favorable, indicating that this element can be adequately used for active matrix driving.

Comparative Example 4

Nematic liquid crystal composition (H-R⁴) was prepared by adding the same amount (20 wt %) of compound (R-4):

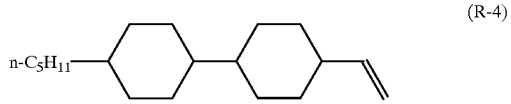

(R-4)

in place of (I-23) in Example 41, which although having a similar structure, has a trans-1,4-cyclohexylene group for the ring structure that composes the core, to (H-A). A liquid crystal device was prepared in the same manner, and the photoelectric characteristic values of this composition were as shown below.

Nematic phase upper limit temperature ($T_{N-I}$): 102.8° C.
Melting point ($T_{C-N}$): --
Threshold voltage (Vth): 2.29 V
Response time (r): 22.4 msec
Sharpness (γ): 1.21
Dielectric anisotropy (Δε): 3.6
Birefringence (Δn): 0.089

(H-R⁴) has a lower value of $T_{N-I}$ than (H-4) and a narrower nematic phase temperature range. The Δn of (H-R⁴) is larger than (H-4), Δε, Vth and γ are essentially no different from (H-4), and response is better than (H-4).

Example 42

Preparation of Liquid Crystal Composition (5)

Liquid crystal composition (M) was prepared composed of the components listed below.

4 wt % of 4-ethoxy-1-(trans-4-propylcyclohexyl)benzene
3 wt % of trans-4-pentylcyclohexylcarboxylate-4-methylphenyl
3 wt % of trans-4-propylcyclohexanecarboxylate-4-ethoxyphenyl
3 wt % of trans-4-(4-methylphenyl)-trans-4'-vinylbicyclohexane
3 wt % of trans-4-butyl-trans-4'-propylbicyclohexane
4 wt % of trans-4-pentyl-trans-4'-vinylbicyclohexane
3 wt % of 4,4-bis(3-butenyl)bicyclohexane
4 wt % of 1-(4-propylphenyl)-2-(4-methylphenyl)ethine
3 wt % of 1-(4-ethoxyphenyl)-2-(4-pentylphenyl)ethine
3 wt % of 1,2-bis[4-(3-butenyl)phenyl]ethine
4 wt % of 1-(4-ethylphenyl)ethynyl-4-(trans-4-propylcyclohexyl)benzene
3 wt % of 4-(trans-pentylcyclohexyl)-4'-ethylbiphenyl
3 wt % of 4-(trans-4-propylcyclohexyl)-1-cyanobenzene
4 wt % of 4-[trans-4-(trans-1-propenyl)cyclohexyl]-1-cyanobenzene
3 wt % of 4-[trans-4-(3-butenyl)cyclohexyl]-1-cyanobenzene
3 wt % of 4-pentyl-4-cyanobiphenyl
4 wt % of 2-(4-cyanophenyl)-5-pentylpyrimidine
3 wt % of 4-ethylbenzoate-4-cyanophenyl
3 wt % of trans-4-pentylcyclohexanecarboxylate-3,4-difluorphenyl
4 wt % of 4-butylbenzoate-3-fluoro-4-cyanophenyl
3 wt % of 4-(trans-3-penten-1-yl)benzoate-3,5-difluoro-4-cyanophenyl
3 wt % of trans-4-(3-fluoro-4-cyanophenyl)-trans-4'-(3-methoxypropyl)bicyclohexane
3 wt % of trans-4-(3,4-difluorophenyl)-trans-4'-ethylbicyclohexane
4 wt % of trans-4-(3,4-difluorophenyl)-trans-4'-vinylbicyclohexane
4 wt % of trans-4-(3,4,5-trifluorophenyl)-trans-4'-propylbicyclohexane
3 wt % of trans-4-[2-(3,4,5-trifluorophenyl)ethyl]-trans-4-propylbicyclohexane
3 wt % of 4-(trans-4-propylcyclohexyl)-4'-cyanobiphenyl
4 wt % of 4-(trans-4-propylcyclohexyl)benzoate-3-fluoro-4-cyanophenyl
3 wt % of 4-(trans-4-propylcyclohexyl)-3,4,5-trifluorobiphenyl
3 wt % of 1-(3,4,5-trifluorophenyl)ethynyl-4-(trans-4-propylcyclohexyl)benzene The $T_{N-I}$ of this (M) was 75° C., and Δn was 0.142. Liquid crystal composition (M-I) was prepared comprised of 3% of (I-10):

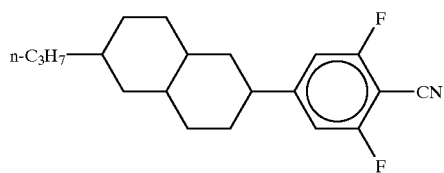
(I-10)

obtained in Example 9, 3% of (I-9):

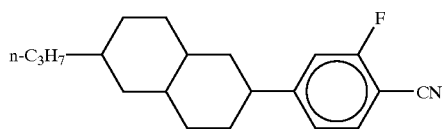
(I-9)

obtained in Example 10, and 4% of (I-3):

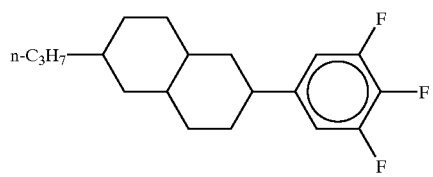
(I-3)

obtained in Example 1. The $T_{N-I}$ of this (M-I) was 70.4° C., and Δn was 0.136.

INDUSTRIAL APPLICABILITY

The novel decahydronaphthalene derivative of the present invention can be produced industrially extremely easily as shown in the examples, and by adding a small amount to a base liquid crystal, it is possible to have effects that expand the nematic phase temperature range, thereby improving its various characteristics as a nematic liquid crystal. Moreover, the novel decahydronaphthalene derivative of the present invention also has superior co-solubility with base liquid crystals generally used at present. Thus, it is suitable for various types of liquid crystal devices requiring a wide operating temperature range, and is extremely useful as a liquid crystal material.

What is claimed is:

1. A compound represented by general formula (I):

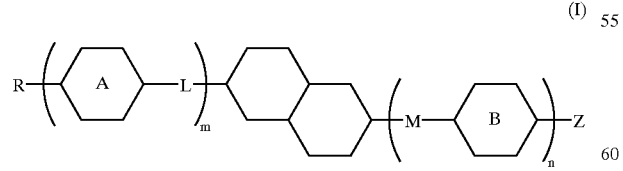
(I)

(wherein, R and Z may be substituted with a halogen and represent alkyl groups or alkoxy groups having 1–16 carbon atoms, alkenyl groups having 2–16 carbon atoms, alkenyloxy groups having 3–16 carbon atoms, alkyl groups having 1–12 carbon atoms substituted with an alkoxy group having 1–10 carbon atoms, hydrogen atoms, fluorine atoms, chlorine atoms, trifluoromethoxy groups, difluoromethoxy groups, trifluoromethyl groups, 2,2,2-trifluoroethoxy groups, cyano groups, cyanato groups, hydroxy groups or carboxy groups, m and n may be the same or different and respectively and independently represent an integer of 0–2, $1 \leq m+n \leq 3$, L and M may be the same or different and respectively and independently represent —CH$_2$CH$_2$—, —CH(CH$_3$)CH$_2$—, —CH$_2$CH(CH$_3$)$_3$—, —CH$_2$O—, —OCH$_2$—, —CF$_2$O—, —OCF$_2$—, —COO—, —OCO—, —CH═CH—, —CF═CF—, —C≡C—, —O(CH$_2$)$_3$—, —(CH$_2$)$_3$O—, —(CH$_2$)$_4$— or a single bond, rings A and B when present may be the same or different and respectively and independently represent a trans-1,4-cyclohexylene group in which one CH$_2$ group or more than one non-adjacent CH$_2$ groups in the group may be replaced by —O— or —S—, a 1,4-phenylene group in which one CH$_2$ group or more than one non-adjacent CH$_2$ groups in the group maybe replaced by —N═, a 1,4-cyclohexenylene group, 1,4-bicyclo(2,2,2)octylene group, piperidine-1,4-diyl group, naphthalene-2,6-diyl group, trans-decahydronaphthalene-trans-2,6-diyl group or 1,2,3,4-tetrahydronaphthalene-2,6-diyl group, and although these may be substituted with a cyano group or halogen, in the case m or n represents 2, at least one of the two L or M present represents a single bond; provided that the following cases are excluded:

i. case in which either m or n represents 1, the other of m or n represents 0, ring A or ring B when present represents a 1,4-cyclohexylene group, L or M when present represents a single bond, R or Z bonded to a decahydronaphthalene ring represents a non-substituted alkyl group, and R or Z bonded to a 1,4-cyclohexylene group represents a non-substituted alkyl group, alkoxy group or alkenyloxy group;

ii. case in which either m or n represents 1, the other m or n represents 0, ring A or ring B when present represents a 1,4-cyclohexylene group, L when present represents —OCO— or M when present represents —COO—, and R or Z bonded to a 1,4-cyclohexylene group represents a non-substituted alkyl group or cyano group;

iii. case in which either m or n represents 1, the other m or n represents 0, ring A or ring B when present represents a non-substituted 1,4-phenylene group, L when present represents —OCO— or M when present represents —COO—, L or M when present represents a single bond, and R or Z bonded to a 1,4-phenylene group represents a non-substituted alkyl group, alkoxy group, hydroxyl group, hydrogen atom, carboxyl group or cyano group;

iv. case in which either m or n represents 1, the other m or n represents 0, ring A or ring B when present represent a non-substituted 1,4-phenylene group, L or M when present represents a single bond, R or Z bonded to a decahydronaphthalene ring represents a non-substituted alkoxy group, and R or Z bonded to a 1,4-phenylene group represents a non-substituted alkyl group;

v. case in which either m or n represents 1, the other m or n represents 0, ring A or ring B when present represents a trans-decahydronaphthalene-trans-2,6-diyl group, L when present represents —OCO—, M when present represents —COO— or L or M when present represent a single bond, and R and Z represent non-substituted alkoxy groups;

vi. case in which either m or n represents 1, the other m or n represents 0, ring A or ring B when present represents a non-substituted naphthalene-2,6-diyl group, L when present represents —OCO— or M when present represents —COO—, R or Z bonded to a decahydronaphthalene ring represents a non-substituted alkyl group, and R or Z bonded to a naphthalene-2,6-diyl group represents a non-substituted alkyl group, bromine atom or cyano group, or the case in which R or Z bonded to a decahydronaphthalene ring represents a non-substituted alkoxy group, and R or Z bonded to a naphthalene-2,6-diyl group represents a non-substituted alkyl group or cyano group;

vii. case in which n represents 2, m represents 0, R represents a non-substituted alkyl group, M when present adjacent to a decahydronaphthalene ring represents —COO—, at least one of rings B present represents a non-substituted 1,4-phenylene group, and Z resents a non-substituted alkyl group or bromine atom, or the case in which at least one of rings B present represents a pyrimidine-2,5-diyl group, and Z represents a non-substituted alkyl group, alkoxy group or cyano group; and viii. case in which m and n represent 1, ring A represents a trans-decahydronaphthalene-trans-2,6-diyl group or a 1,4-cyclohexylene group, ring B represents a non-substituted 1,4-phenylene group or 1,4-cyclohexylene group, L represents a single bond, M represents —COO—, —OCO—, —CH$_2$O or —OCH$_2$—, and R and Z represent non-substituted alkyl groups.

2. A compound according to claim 1 wherein, ring A and ring B when present respectively and independently represent a 1,4-phenylene group, naphthalene-2,6-diyl group, 1,2,3,4-tetrahydronaphthalene-2,6-diyl group, trans-1,4-cyclohexylene group or decahydronaphthalene-2,6-diyl group that may be substituted with fluorine atom(s).

3. A compound acing to claim 1 wherein, ring A or ring B when present respectively and independently represent a 1,4-phenylene group or trans-1,4-cyclohexylene group that may be substituted with fluorine atom(s).

4. A compound according to claim 1 wherein, L and M when present represent —CH$_2$CH$_2$—, —CH$_2$O—, —OCH$_2$—, —CF$_2$O—, —OCF$_2$—, —COO—, —OCO—, —CF=CF— or a single bond.

5. A compound according to claim 1 wherein, L or M represents a single bond.

6. A compound according to claim 1 wherein, L and M represent single bonds.

7. A compound according to claim 1 wherein, 1≦m+n≦2.

8. A compound according to claim 1 wherein, R represents an alkyl group, alkoxy group, alkenyl group or alkenyloxy group having 1–12 carbon atoms.

9. A compound according to claim 1 wherein, Z represents a halogen atom or an alkyl group, alkoxy group, alkenyl group, alkenyloxy group or cyano group having 1–12 carbon atoms.

10. A compound according to claim 1 wherein, R represents an alkyl group or alkenyl group having 1–12 carbon atoms, m represents 1, n represents 1, ring A represents a trans-1,4-cyclohexylene group, ring B represents a 3-fluoro 1,4-phenylene group or 3,5-difluoro-1,4-phenylene group, L and M represent single bonds, and Z represents a fluorine atom, chlorine atom, trifluoromethoxy group, difluoromethoxy group, trifluoromethyl group, 2,2,2-trifluoroethoxy group or cyano group.

11. A compound according to claim 1 wherein, R represents an alkyl group or alkenyl group having 1–12 carbon atoms, m represents 0, n represents 1, ring B represents a 3-fluoro 1,4-phenylene group or 3,5-difluoro-1,4-phenylene group, M represents a single bond and Z represents a fluorine atom, chlorine atom, trifluoromethoxy group, difluoromethoxy group, trifluoromethyl group, 2,2,2-trifluoroethyoxy group or cyano group.

12. A compound according to claim 1 wherein, R and Z represent alkyl groups or alkenyl groups having 1–12 carbon atoms, m and n represent 1, rings A and B represent 1,4-phenylene groups or trans-1,4-cyclohexylene groups, and L and M represent single bonds.

13. A compound according to claim 1 wherein, R and Z represent alkyl groups or alkenyl groups having 1–12 carbon atoms, at least one of R or Z represents an alkenyl group, m represents 1, n represents 0, rings A and B represent 1,4-phenylene groups or trans-1,4-cyclohexylene groups, and L represents a single bond.

14. A compound represented by general formula (II):

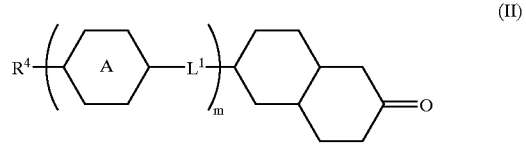

(wherein, R$^4$ represents an alkyl group, alkyoxy group, alkenyl group, alkenyloxy group or alkoxyalkyl group, L$^1$ represents —CH$_2$CH$_2$—, —CH(CH$_3$)CH$_2$—, —CH$_2$CH(CH$_3$)—, —CH$_2$O—, —OCH$_2$—, —CF$_2$O—, —OCF$_2$—, —COO—, —OCO—, —CH=CH—, —CF=CF—, —C≡C—, —O(CH$_2$)$_3$—, —(CH$_2$)$_3$O—, —(CH$_2$)$_4$—, or a single bond, R$^4$ represents an alkenyl group, alkenyloxy group or alkyoxyalkyl group when L$^1$ presents a single bond, ring A represents a trans-1,4 cyclohexylene group in which one CH$_2$ group or more than one non-adjacent CH$_2$ groups in the group may be replaced by —O— or —S—, a 1,4-phenylene group in which one CH$_2$ group or more than one non-adjacent CH$_2$ groups in the group may be replaced by —N=, a 1,4-cyclohexenylene group, 1,4-bicyclo(2,2,2) octylene group, piperidine-1,4-diyl group, naphthalene-2,6-diyl group, trans-decahydronaphthalene-trans-2,6-diyl group or 1,2,3,4-tetrahydronaphthalene-2,6-diyl group, m represents an integer of 1 or 2, and the decahydronaphthalene ring has a trans form).

15. A production method of general formula (II) according to claim 14 including: reducing a compound represented by general formula (II-A):

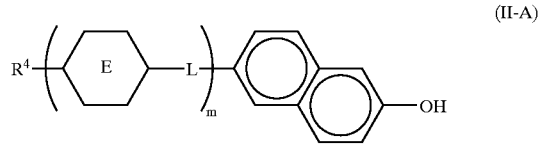

(wherein, R$^4$ is the same as previously defined in general formula (II), ring E represents a 1,4-phenyl group or trans-1,4-cyclohexylene group, L is the same as L$^1$ defined in general formula (II), and m is the same as previously defined in general formula (II), and the decahydronaphthalene ring has a trans form), and oxidizing the hydroxyl group as necessary.

16. A compound represented by general formula (V-2):

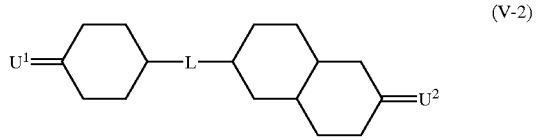
(V-2)

(wherein, $U^1$ and $U^2$ respectively and independently represent an oxygen atom or the following structure:

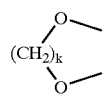

(wherein, k represents an integer from 1 to 7), L represents —$CH_2CH_2$—, —$CH(CH_3)CH_2$—, —$CH_2CH(CH_3)$—, —$CH_2O$—, —$OCH_2$—, —$CF_2O$—, —$OCF_2$—, —$COO$—, —$OCO$—, —$CH=CH$—, —$CF=CF$—, —$C\equiv C$—, —$O(CH_2)_3$—, —$(CH_2)_3O$—, —$(CH_2)_4$— or a single bond, and the decahydronaphthalene ring has a trans form).

17. A production method of general formula (V-2) according to claim 16,
including: converting a compound represented by general formula (V-2A):

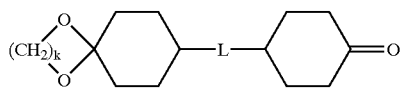
(V-2A)

(wherein, k and L are the same as previously defined in claim 16) into an enamine using a secondary amine, and reacting it with methyl vinyl ketone to obtain a compound represented by general formula (V-2B)

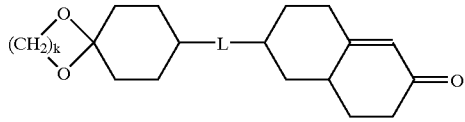
(V-2B)

as previously defined in claim 16) followed by reductive hydrogenation.

18. A production method of general formula (V-2) according to claim 16 represented by general formula (V-2C):

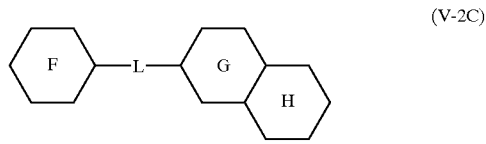
(V-2C)

(wherein, although ring G represents a cyclohexane ring or benzene ring, a single bond(s) of the cyclohexane ring may be replaced by double bond(s), and although rings F and H respectively and independently represent the following structures:

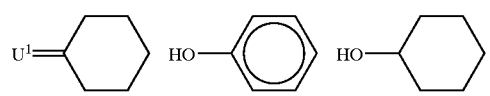

a single bond(s) of the cyclohexane ring may be replaced by double bond(s)), oxidizing the hydroxyl group as necessary, and further protecting the carbonyl group as necessary.

19. A production method of general formula (V-1a):

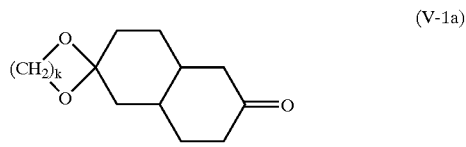
(V-1a)

(wherein k represents an integer from 1 to 7) including monoacetalation of a compound represented by general formula (V-1D):

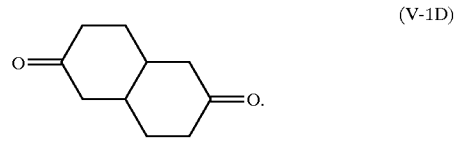
(V-1D)

20. A liquid crystal composition containing a compound according to claim 1.

21. A liquid crystal device having for its constituent feature the liquid crystal composition according to claim 20.

22. An active matrix drive, liquid crystal device that uses the liquid crystal composition according to claim 20.

23. A super twisted nematic liquid crystal device that uses the liquid crystal composition according to claim 21.

* * * * *